(12) United States Patent
Liu et al.

(10) Patent No.: US 9,770,026 B2
(45) Date of Patent: Sep. 26, 2017

(54) SUBSTITUTED PYRIMIDINE COMPOUND AND USES THEREOF

(71) Applicant: Shenyang Sinochem Agrochemicals R&D Co., Ltd., Shenyang, Liaoning (CN)

(72) Inventors: Changling Liu, Liaoning (CN); Lizeng Wang, Liaoning (CN); Yuquan Song, Liaoning (CN); Xufeng Sun, Liaoning (CN); Jie Lan, Liaoning (CN); Aiying Guan, Liaoning (CN); Junfeng Wang, Liaoning (CN); Jinbo Zhang, Liaoning (CN); Cong Feng, Liaoning (CN); Minna Zhu, Liaoning (CN); Zhinian Li, Liaoning (CN); Lanhui Ren, Liaoning (CN); Xiuhui Chang, Liaoning (CN); Fan Yang, Liaoning (CN); Qin Sun, Liaoning (CN); Wei Chen, Liaoning (CN); Shaowu Liu, Liaoning (CN); Yinping Zhou, Liaoning (CN); Zhonggang Shan, Liaoning (CN); Baoshan Chai, Liaoning (CN); Bin Wang, Liaoning (CN); Jizhong Zhou, Liaoning (CN)

(73) Assignee: Shenyang Sinochem Agrochemicals R&D Co., Ltd., Shenyang, Liaoning (CN)

( * ) Notice: Subject to any disclaimer, the term of this patent is extended or adjusted under 35 U.S.C. 154(b) by 0 days.

(21) Appl. No.: 14/423,953

(22) PCT Filed: Oct. 24, 2013

(86) PCT No.: PCT/CN2013/085879
§ 371 (c)(1),
(2) Date: Feb. 25, 2015

(87) PCT Pub. No.: WO2014/063642
PCT Pub. Date: May 1, 2014

(65) Prior Publication Data
US 2015/0257385 A1   Sep. 17, 2015

(30) Foreign Application Priority Data

Oct. 25, 2012 (CN) .......................... 2012 1 0411642
Oct. 25, 2012 (CN) .......................... 2012 1 0412048
(Continued)

(51) Int. Cl.
*C07D 401/12* (2006.01)
*C07D 401/14* (2006.01)
(Continued)

(52) U.S. Cl.
CPC ............. *A01N 43/58* (2013.01); *A01N 43/54* (2013.01); *A01N 43/56* (2013.01); *C07D 239/28* (2013.01);
(Continued)

(58) Field of Classification Search
CPC .. C07D 239/28; C07D 239/42; C07D 253/07; C07D 401/12; C07D 401/14;
(Continued)

(56) References Cited

U.S. PATENT DOCUMENTS

| 5,498,612 | A |   | 3/1996 | Obata et al. |
| 5,859,020 | A | * | 1/1999 | Preuss ................... A01N 43/54 514/266.2 |
| 5,925,644 | A | * | 7/1999 | Jakobi ................... A01N 43/54 514/256 |

FOREIGN PATENT DOCUMENTS

| CN |     103232434 A    | 8/2013 |
| WO | WO 2012/075197 A1 * | 6/2012 |

(Continued)

OTHER PUBLICATIONS

Grammenos et al., CAPLUS 159:333542 (2013) (corresponds to WO 2013/113720).*

(Continued)

*Primary Examiner* — Deepak Rao
(74) *Attorney, Agent, or Firm* — Suzannah K. Sundby, Esq.; Canady + Lortz LLP

(57) ABSTRACT

Disclosed is a substituted pyrimidine compound having a structure as represented by formula PY.

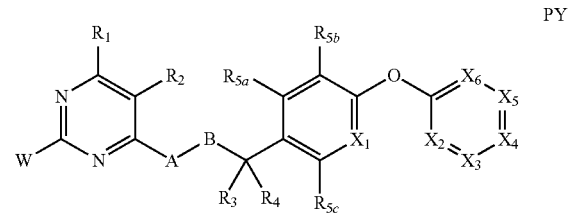

See the description for the definition of each substituent in the formula. The compound of the present invention provides broad-spectrum bactericidal, pesticidal, and acaricidal activities, provides great control effects against plant diseases such as cucumber downy mildew, corn rust, wheat powdery mildew, rice blast, and cucumber gray mold, specifically provides improved control effects against cucumber downy mildew, corn rust, wheat powdery mildew, and rice blast, provides great control effects against aphid, carmine spider mite, diamondback moth, and armyworm, and acquires great effects at a minimal dosage. The compound of the present invention also provides characteristics such as a simplified preparation method.

27 Claims, No Drawings

(30) Foreign Application Priority Data

Oct. 25, 2012 (CN) .......................... 2012 1 0412091
Oct. 25, 2012 (CN) .......................... 2012 1 0413048

(51) Int. Cl.
| | | |
|---|---|---|
| *A01N 43/58* | (2006.01) | |
| *C07D 403/12* | (2006.01) | |
| *A01N 43/54* | (2006.01) | |
| *A01N 43/56* | (2006.01) | |
| *C07D 403/14* | (2006.01) | |
| *C07D 239/28* | (2006.01) | |
| *C07D 253/07* | (2006.01) | |
| *C07D 239/42* | (2006.01) | |

(52) U.S. Cl.
CPC ......... *C07D 239/42* (2013.01); *C07D 253/07* (2013.01); *C07D 401/12* (2013.01); *C07D 401/14* (2013.01); *C07D 403/12* (2013.01); *C07D 403/14* (2013.01)

(58) Field of Classification Search
CPC .... C07D 403/12; C07D 403/14; A01N 43/54; A01N 43/56; A01N 43/58
USPC .................. 544/319, 326, 328; 514/256, 269
See application file for complete search history.

(56) References Cited

FOREIGN PATENT DOCUMENTS

| | | |
|---|---|---|
| WO | 2013113716 A1 | 8/2013 |
| WO | 2013113773 A1 | 8/2013 |
| WO | 2013113778 A1 | 8/2013 |
| WO | 2013113781 A1 | 8/2013 |
| WO | 2013113788 A1 | 8/2013 |
| WO | 2013113863 A1 | 8/2013 |
| WO | WO 2013/113720 A1 * | 8/2013 |

OTHER PUBLICATIONS

International Search Report received in PCT/CN2013/085879 dated Feb. 13, 2014.

* cited by examiner

SUBSTITUTED PYRIMIDINE COMPOUND AND USES THEREOF

FIELD OF THE INVENTION

The invention relates to fungicide, pesticide, and acaricide. Specifically to a novel substituted pyrimidine compounds and uses thereof.

BACKGROUND OF THE INVENTION

Compounds represented by following general formula and specific compound (No. 47 compound in Patent EP0370704 and No. A compound in Patent JP2009161472) were reported in Patent EP0370704 and JP2009161472, some compounds have some fungicidal and insecticidal activities. Known as a developed commercial fungicide, its English general name is diflumetorim, and Chinese name is Fumijunan. Specific compound (No. 5 compound in the literature) was also reported effective to wheat rust and barley powdery mildew in Pesticide Science. 1999 55: 896-902.

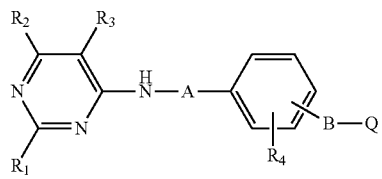

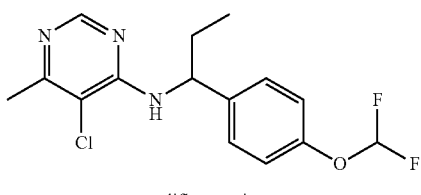

diflumetorim

The preparation method of specific compound (No. 7 compound in Patent JP11012253) were reported in Patent JP11012253, JP11049759 and EP0665225, and its English general name is flufenerim, and Chinese name is Michongan.

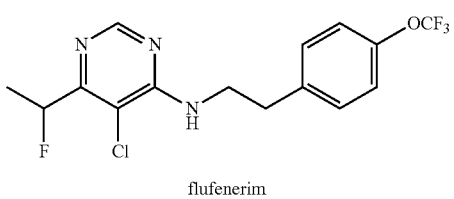 [SMILES: CC(F)c1ncnc(NCCc2ccc(OC(F)(F)F)cc2)c1Cl]

flufenerim

The preparation method of specific pyrimidinamine compounds represented by following general formula CK1, CK2, CK3 and CK4 (No. 83, 87, 101 and 41 compounds in Patent EP0665225) were reported in Patent EP0665225, JP10036355 and U.S. Pat. No. 5,498,612, their fungicidal, insecticidal and acricidal activities were also reported.

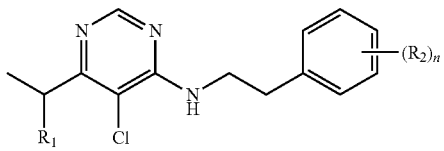
CK1

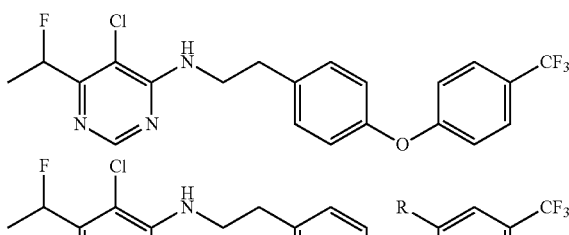

CK2 (R = Cl); CK3 (R = H)

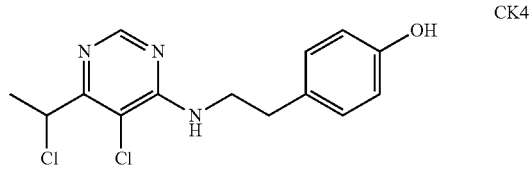
CK4

Compounds represented by following general formula and specific compound (No. 447 compound) were reported in U.S. Pat. No. 5,925,644, some compounds have some fungicidal, acricidal and nematicidal activities.

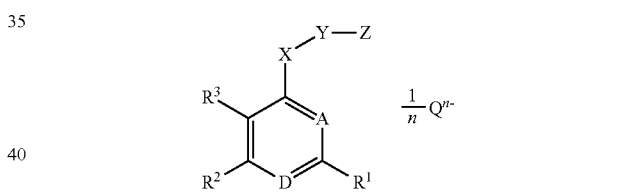

CK5

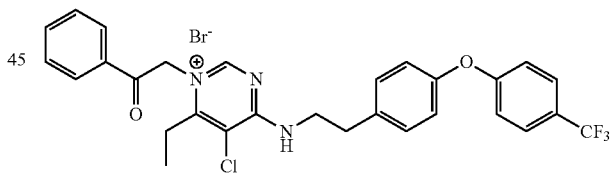

Disclosed in Patent EP264217, DE3786390, U.S. Pat. No. 4,895,849, U.S. Pat. No. 4,985,426 and JP63225364 are substituted pyrimidine benzylamine compounds having a structure as represented by following formula and the specific compound CK6 and CK7 (No. 77 and 74 compounds in Patent EP264217) applied as fungicide, insecticide and acricide.

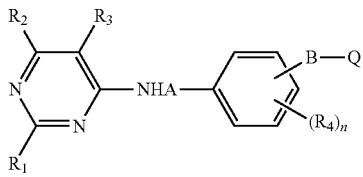

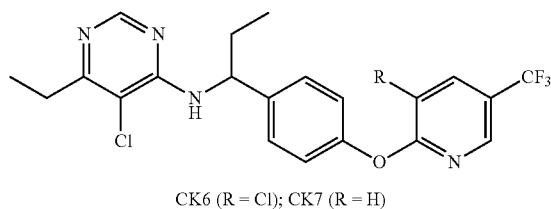

CK6 (R = Cl); CK7 (R = H)

Disclosed in Patent WO9507278 is the compound having a structure as represented by following formula with application as fungicide, acricide and/or insecticide. Thereinto, the specific compound CK8, CK9 and CK10 were listed in No. 209 line of Table 1 without any biological activity reported.

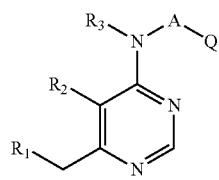

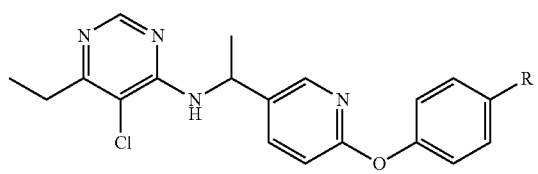

CK8 (R = H); CK9 (R = F); CK10 (R = C$_4$H$_9$-t)

Disclosed in U.S. Pat. No. 5,227,387 are the compound having a structure as represented by following formula and the specific compound CK11 (No. 81 compound in the patent) applied as nematicide.

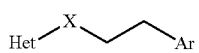

CK11

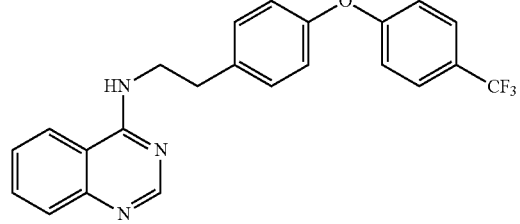

Compound represented by following formula and the specific compound CK12 (No. 29 compound in the patent) with application as fungicide and insecticide were disclosed in U.S. Pat. No. 5,326,766.

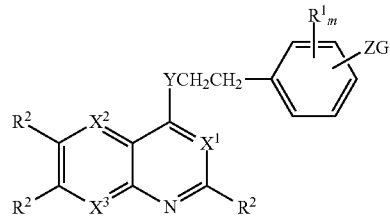

CK12

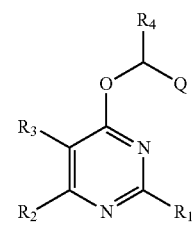

Compound represented by following formula and the specific compound CK13 (No. 98 compound in the patent), CK14 (No. 271 compound in the patent) and CK15 (No. 117 compound in the patent) with application as fungicide and insecticide were disclosed in Patent EP534341.

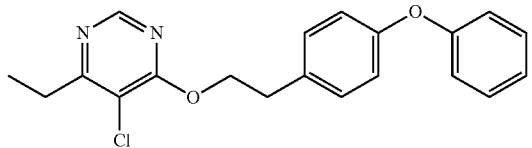

CK13

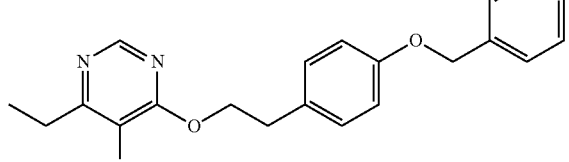

CK14

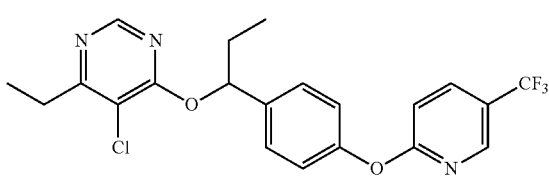

CK15

Compound represented by following general formula and the specific compound CK16 (No. 26 compound in the patent) applied as fungicide, insecticide and acricide were disclosed in Patent WO9728133.

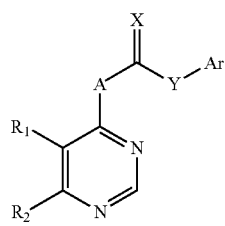

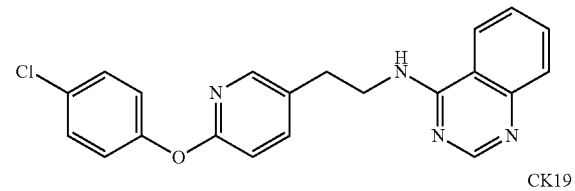

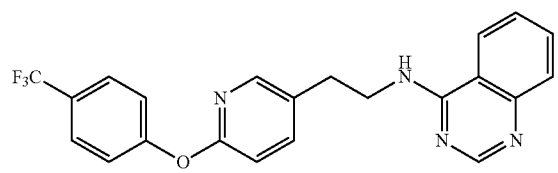

The following compound CK20 (CAS No. 203734-18-3) and CK21 (CAS No. 203734-22-9) were retrieved via Scifinder database without both specific literature and biological activity disclosed.

Compound represented by following general formula and the specific compound CK17 (No. 2.50 compound in U.S. Pat. No. 5,468,751) with application as fungicide, insecticide and acricide were disclosed in U.S. Pat. No. 5,468,751 and EP470600.

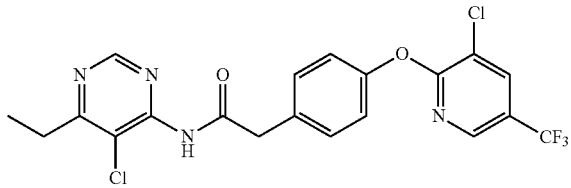

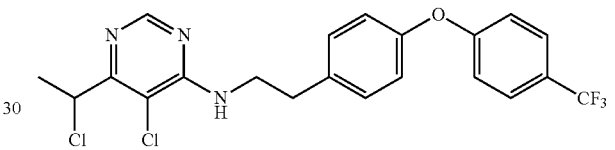

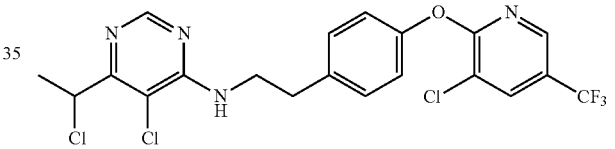

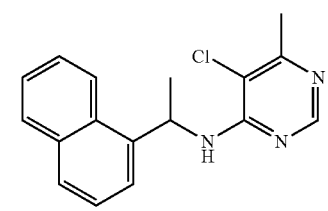

Compound represented by following general formula with application as inhibitor to treat HIV-1 was disclosed in Literature Bioorganic & Medicinal Chemistry Letters, 2007, 17: 260-265.

However, substituted pyrimidine compounds represented by general formula PY of the present invention have not been reported in prior literature.

SUMMARY OF THE INVENTION

The object of the present invention is to provide a novel substituted pyrimidine compounds, which can be used to prepare fungicides, pesticides, and acaricides against harmful fungus, bacteria, insects, and mites in agricultural or other fields.

Detailed descriptions of the invention are as follows:

The present invention provides a kind of substituted pyrimidine compounds having a structure as represented by general formula PY:

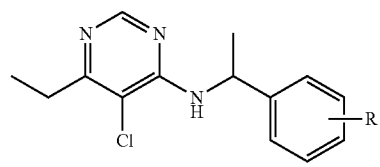

The following compound CK18 (No. 46 compound in the patent) and CK19 (No. 49 compound in the patent) were reported with good insectcidal activity at the concentration of 50 ppm and good fungicidal activity at the concentration of 400 and 100 ppm.

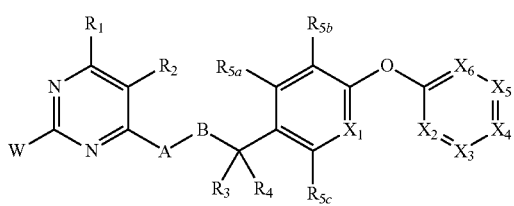

Wherein:

$R_1$ is selected from H, halo, cyano, $C_1$-$C_{12}$alkyl, $C_3$-$C_{12}$cycloalkyl, halo$C_1$-$C_{12}$alkyl, cyano$C_1$-$C_{12}$alkyl, cyano$C_1$-$C_{12}$alkoxy, $C_2$-$C_{12}$alkenyl, halo$C_2$-$C_{12}$alkenyl, $C_2$-$C_{12}$alkynyl, halo$C_2$-$C_{12}$alkynyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkoxycarbonyl$C_1$-$C_{12}$alkyl, $C_1$-$C_{12}$alkylaminocarbonyl$C_1$-$C_{12}$alkyl or di($C_1$-$C_{12}$alkyl)aminocarbonyl$C_1$-$C_{12}$alkyl;

$R_2$ is selected from H, halo, cyano, $C_3$-$C_{12}$cycloalkyl, $C_1$-$C_{12}$alkyl, $C_1$-$C_{12}$alkoxy or halo$C_1$-$C_{12}$alkoxy;

$R_3$, $R_4$ may be the same or different, selected respectively from H, halo, OH, amino, $C_1$-$C_{12}$alkyl, $C_1$-$C_{12}$alkoxy, $C_3$-$C_{12}$cycloalkyl, $C_2$-$C_{12}$alkenyl, $C_2$-$C_{12}$alkynyl, halo$C_2$-$C_{12}$alkenyl, halo$C_2$-$C_{12}$alkynyl, $C_1$-$C_{12}$alkoxy$C_1$-$C_{12}$alkyl, unsubstituted or further substituted aryl$C_1$-$C_6$alkyl or heteroaryl$C_1$-$C_6$alkyl by 1 to 5 following groups: halo, $C_1$-$C_6$alkyl, halo$C_1$-$C_6$alkyl, $C_1$-$C_6$alkoxy or halo$C_1$-$C_6$alkoxy; or $R_3$, $R_4$ and conjoint carbon can also form a $C_3$-$C_8$ cycle;

$R_{5a}$, $R_{5b}$, $R_{5c}$ may be the same or different, selected respectively from H, halo, OH, $NO_2$, cyano, $C_1$-$C_{12}$alkyl, halo$C_1$-$C_{12}$alkyl, $C_3$-$C_{12}$cycloalkyl, $C_1$-$C_{12}$alkoxy, halo$C_1$-$C_{12}$alkoxy, $C_1$-$C_{12}$alkylthio, halo$C_1$-$C_{12}$alkylthio, $C_2$-$C_{12}$alkenyl, halo$C_2$-$C_{12}$alkenyl, $C_2$-$C_{12}$alkynyl, halo$C_2$-$C_{12}$alkynyl, $C_3$-$C_{12}$alkenoxy, halo$C_3$-$C_{12}$alkenoxy, $C_3$-$C_{12}$alkynoxy, halo$C_3$-$C_{12}$alkynoxy, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylcarbonyl, halo$C_1$-$C_{12}$alkylcarbonyl, $C_1$-$C_{12}$alkylcarbonyloxy, $C_1$-$C_{12}$alkylcarbonylamino, $C_1$-$C_{12}$alkylsulfonyloxy, $C_1$-$C_{12}$alkoxycarbonyl, $C_1$-$C_{12}$alkoxycarbonyl$C_1$-$C_{12}$alkyl, $C_1$-$C_{12}$alkoxycarbonylamino, $C_1$-$C_{12}$alkoxy$C_1$-$C_{12}$alkoxy or $C_1$-$C_{12}$alkoxycarbonyl$C_1$-$C_{12}$alkoxy;

$X_1$ is selected from N or $CR_6$; $X_2$ is selected from N or $CR_7$; $X_3$ is selected from N or $CR_8$;

$X_4$ is selected from N or $CR_9$; $X_5$ is selected from N or $CR_{10}$; $X_6$ is selected from N or $CR_{11}$; however, $X_2$, $X_3$, $X_4$, $X_5$, $X_6$ are not simultaneously selected from N;

$R_6$, $R_7$, $R_8$, $R_9$, $R_{10}$, $R_{11}$ may be the same or different, selected respectively from H, halo, OH, cyano, HO(C=O), amino, $NO_2$, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_2$-$C_{12}$alkenyl, $C_2$-$C_{12}$alkynyl, $C_2$-$C_{12}$alkenoxy, halo$C_2$-$C_{12}$alkenoxy, $C_2$-$C_{12}$alkynoxy, halo$C_2$-$C_{12}$alkynoxy, $C_1$-$C_{12}$alkylthio, halo$C_1$-$C_{12}$alkylthio, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, $C_1$-$C_{12}$alkylamino, halo$C_1$-$C_{12}$alkylamino, di($C_1$-$C_{12}$alkyl)amino, halodi($C_1$-$C_{12}$alkyl)amino, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, di($C_1$-$C_{12}$alkyl)amino($C_1$-$C_{12}$alkyl), $CONH_2$, $CONHNH_2$, $CON(C_1$-$C_{12}$alkyl)$NH_2$, CONHNH($C_1$-$C_{12}$alkyl), CONHN(di($C_1$-$C_{12}$alkyl)), CONHNHCO($C_1$-$C_{12}$alkyl), $CONHNHCO_2$($C_1$-$C_{12}$alkyl), CONHNH(phenyl), $C_1$-$C_{12}$alkylaminocarbonyl, di($C_1$-$C_{12}$alkyl)aminocarbonyl, halodi($C_1$-$C_{12}$alkyl)aminocarbonyl, $C_1$-$C_{12}$alkylsulfonylamino, $C_1$-$C_{12}$alkylsulfonyl($C_1$-$C_{12}$alkyl)amino, halo$C_1$-$C_{12}$alkylsulfonylamino, $C_1$-$C_{12}$alkoxyamino, $C_1$-$C_{12}$alkoxycarbonylamino, $C_1$-$C_{12}$alkoxyaminocarbonyl, cyano$C_1$-$C_{12}$alkyl, cyano$C_1$-$C_{12}$alkoxy, $C_1$-$C_{12}$alkoxycarbonyl$C_1$-$C_{12}$alkyl, halo$C_1$-$C_{12}$alkoxycarbonyl$C_1$-$C_{12}$alkyl, $C_1$-$C_{12}$alkylaminocarbonyl$C_1$-$C_{12}$alkyl, di($C_1$-$C_{12}$alkyl)aminocarbonyl$C_1$-$C_{12}$alkyl, $C_1$-$C_{12}$alkylthiocarbonyl$C_1$-$C_{12}$alkyl, halo$C_1$-$C_{12}$alkylthiocarbonyl$C_1$-$C_{12}$alkyl, $C_1$-$C_{12}$alkylcarbonyloxy, halo$C_1$-$C_{12}$alkylcarbonyloxy, $C_1$-$C_{12}$alkoxycarbonyloxy, halo$C_1$-$C_{12}$alkoxycarbonyloxy, $C_1$-$C_{12}$alkylaminocarbonyloxy, halo$C_1$-$C_{12}$alkylaminocarbonyloxy, $C_1$-$C_{12}$alkylsulfonyloxy, halo$C_1$-$C_{12}$alkylsulfonyloxy, $C_1$-$C_{12}$alkoxy$C_1$-$C_{12}$alkoxy, halo$C_1$-$C_{12}$alkoxy$C_1$-$C_{12}$alkoxy, $C_1$-$C_{12}$alkoxycarbonyl$C_1$-$C_{12}$alkoxy or halo$C_1$-$C_{12}$alkoxycarbonyl$C_1$-$C_{12}$alkoxy;

W is selected from H, halo, $C_1$-$C_2$alkyl, $C_1$-$C_2$alkoxy, $C_1$-$C_2$alkylthio or $C_1$-$C_2$alkylsulfonyl;

A is selected from O, S or $NR_{12}$;

B is selected from —$CH_2$— or —$CH_2CH_2$—;

$R_{12}$ is selected from H, OH, H(C)=O, $C_1$-$C_{12}$alkyl, halo$C_1$-$C_{12}$alkyl, $C_1$-$C_2$alkoxy, halo$C_1$-$C_{12}$alkoxy, $C_3$-$C_{12}$cycloalkyl, $C_1$-$C_{12}$alkylthio, $C_2$-$C_{12}$alkenylthio, $C_2$-$C_{12}$alkenyl, $C_2$-$C_{12}$alkynyl, halo$C_2$-$C_{12}$alkenyl, halo$C_2$-$C_{12}$alkynyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, di($C_1$-$C_{12}$alkyl)aminosulfonyl, $C_1$-$C_{12}$alkylsulfonylaminocarbonyl, $C_1$-$C_{12}$alkylcarbonylaminosulfonyl, $C_3$-$C_{12}$cycloalkyloxycarbonyl, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, $C_1$-$C_{12}$alkylcarbonyl$C_1$-$C_{12}$alkyl, $C_1$-$C_{12}$alkoxycarbonyl$C_1$-$C_{12}$alkyl, $C_1$-$C_{12}$alkylaminocarbonyl, di($C_1$-$C_{12}$alkyl)aminocarbonyl, $C_2$-$C_{12}$alkenoxycarbonyl, $C_2$-$C_{12}$alkynoxycarbonyl, $C_1$-$C_{12}$alkoxy$C_1$-$C_{12}$alkoxycarbonyl, $C_1$-$C_{12}$alkylaminothio, di ($C_1$-$C_{12}$alkyl) aminothio, unsubstituted or further substituted (hetero)arylcarbonyl$C_1$-$C_6$alkyl, (hetero)arylcarbonyl, (hetero)aryloxycarbonyl, (hetero)aryl$C_1$-$C_6$alkyloxycarbonyl or (hetero)aryl$C_1$-$C_6$alkyl by 1 to 5 following groups: halo, $NO_2$, cyano, $C_1$-$C_6$alkyl, halo$C_1$-$C_6$alkyl, $C_1$-$C_6$alkoxy or halo$C_1$-$C_6$alkoxy;

Or the salts or complexes formed from the compounds represented by general formula PY.

The technical scheme of the present invention can be further subdivided into three optimization of technical schemes.

The first optimization of technical schemes is: the compounds represented by formula PY, wherein, $X_1$ is selected from $CR_6$, $X_2$ is selected from N or $CR_7$, $X_3$ is selected from N or $CR_8$, $X_4$ is selected from $CR_9$, $X_5$ is selected from $CR_{10}$, $X_6$ is selected from N or $CR_{11}$, within $X_2$, $X_3$ and $X_6$, at least one of which is selected from N, other substituents are defined as above, the compound having a structure as represented by formula I is as fellows.

The second optimization of technical schemes is: the compounds represented by formula PY, wherein, $X_1$ is selected from $CR_6$, $X_2$ is selected from $CR_7$, $X_3$ is selected from $CR_8$, $X_4$ is selected from $CR_9$, $X_5$ is selected from $CR_{10}$, $X_6$ is selected from $CR_{11}$, other substituents are defined as above, the compound having a structure as represented by formula II is as fellows.

The third optimization of technical schemes is: the compounds represented by formula PY, wherein, $X_1$ is selected from N, $X_2$ is selected from N or $CR_7$, $X_3$ is selected from N or $CR_8$, $X_4$ is selected from N or $CR_9$, $X_5$ is selected from $CR_{10}$, $X_6$ is selected from N or $CR_{11}$, within $X_2$, $X_3$, $X_4$ and $X_6$, at least one of which is selected from N, other substituents are defined as above, the compound having a structure as represented by formula III is as fellows.

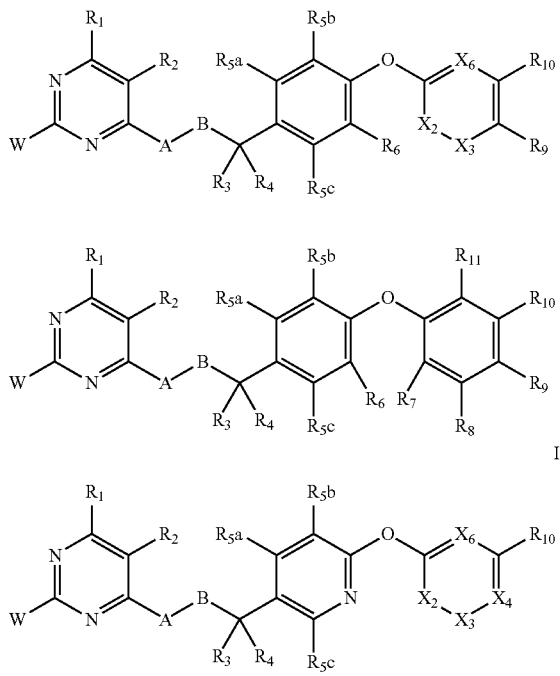

Detailed descriptions of three technical schemes of present invention are respectively disclosed.

The first optimization of technical schemes is:
the compounds having a structure as represented by formula I are as fellows.

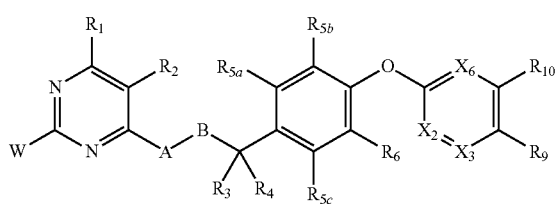

Wherein:

$R_1$ is selected from cyano, $C_3$-$C_{12}$cycloalkyl, $C_1$-$C_{12}$alkyl, halomethyl, cyano$C_1$-$C_2$alkyl, cyano$C_1$-$C_{12}$alkoxy, $C_1$-$C_{12}$alkoxycarbonyl$C_1$-$C_{12}$alkyl, $C_1$-$C_{12}$alkylaminocarbonyl$C_1$-$C_{12}$alkyl or di($C_1$-$C_{12}$alkyl)aminocarbonyl$C_1$-$C_{12}$alkyl;

$R_2$ is selected from halo, cyano, $C_3$-$C_{12}$cycloalkyl, $C_1$-$C_{12}$alkyl or $C_1$-$C_{12}$alkoxy;

$R_3$, $R_4$ may be the same or different, selected respectively from H, halo, OH, amino, $C_1$-$C_{12}$alkyl or $C_1$-$C_{12}$alkoxy;

$R_{5a}$, $R_{5b}$, $R_{5c}$ may be the same or different, selected respectively from H, halo, OH, $C_1$-$C_{12}$alkyl or $C_1$-$C_{12}$alkoxy;

$X_2$ is selected from N or $CR_7$, $X_3$ is selected from N or $CR_8$, $X_6$ is selected from N or $CR_{11}$, within $X_2$, $X_3$, $X_6$, at least one substituent is selected from N;

$R_9$ is selected from H, halo, OH, cyano, HO(C=O), amino, $NO_2$, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_2$-$C_{12}$alkenyl, $C_2$-$C_{12}$alkynyl, $C_2$-$C_{12}$alkenoxy, halo$C_2$-$C_{12}$alkenoxy, $C_2$-$C_{12}$alkynoxy, halo$C_2$-$C_{12}$alkynoxy, $C_1$-$C_{12}$alkylthio, halo$C_1$-$C_{12}$alkylthio, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, $C_1$-$C_{12}$alkylamino, halo$C_1$-$C_{12}$alkylamino, di($C_1$-$C_{12}$alkyl)amino, $C_1$-$C_{12}$alkoxycarbonyl, di($C_1$-$C_{12}$alkyl)amino($C_1$-$C_{12}$alkyl), halo$C_1$-$C_{12}$alkoxycarbonyl, $CONH_2$, $CONHNH_2$, $CON(C_1$-$C_{12}$alkyl)$NH_2$, $CONHNH(C_1$-$C_{12}$alkyl), $CONHN(di(C_1$-$C_{12}$alkyl))$, $CONHNHCO(C_1$-$C_{12}$alkyl), $CONHNHCO_2(C_1$-$C_{12}$alkyl), CONHNH(phenyl), $C_1$-$C_{12}$alkylaminocarbonyl, di($C_1$-$C_{12}$alkyl)aminocarbonyl, $C_1$-$C_{12}$alkylsulfonylamino, $C_1$-$C_{12}$alkylsulfonyl($C_1$-$C_{12}$alkyl)amino, halo$C_1$-$C_{12}$alkylsulfonylamino, $C_1$-$C_{12}$alkoxyamino, $C_1$-$C_{12}$alkoxycarbonylamino, $C_1$-$C_{12}$alkoxyaminocarbonyl, cyano$C_1$-$C_{12}$alkyl, cyano$C_1$-$C_{12}$alkoxy, $C_1$-$C_{12}$alkoxycarbonyl$C_1$-$C_{12}$alkyl, $C_1$-$C_{12}$alkylaminocarbonyl$C_1$-$C_{12}$alkyl or di($C_1$-$C_{12}$alkyl)aminocarbonyl$C_1$-$C_{12}$alkyl;

$R_6$, $R_7$, $R_8$, $R_{10}$, $R_{11}$ may be the same or different, selected respectively from H, halo, OH, cyano, HO(C=O), amino, $NO_2$, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_2$-$C_{12}$alkenyl, $C_2$-$C_{12}$alkynyl, $C_2$-$C_{12}$alkenoxy, halo$C_2$-$C_{12}$alkenoxy, $C_2$-$C_{12}$alkynoxy, halo$C_2$-$C_{12}$alkynoxy, $C_1$-$C_{12}$alkylthio, halo$C_1$-$C_{12}$alkylthio, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylamino, halo$C_1$-$C_{12}$alkylamino, di($C_1$-$C_{12}$alkyl)amino, $C_1$-$C_{12}$alkoxycarbonyl, $CONH_2$, $C_1$-$C_{12}$alkylaminocarbonyl or di($C_1$-$C_{12}$alkyl)aminocarbonyl;

W is selected from H or $C_1$-$C_{12}$alkyl;

A is selected from O, S or $NR_{12}$;

B is selected from —$CH_2$— or —$CH_2CH_2$—;

$R_{12}$ is selected from H, OH, H(C)=O, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_1$-$C_{12}$alkylthio, $C_2$-$C_{12}$alkenylthio, $C_2$-$C_{12}$alkenyl, $C_2$-$C_{12}$alkynyl, halo$C_2$-$C_{12}$alkenyl, halo$C_2$-$C_{12}$alkynyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, di($C_1$-$C_{12}$alkyl)aminosulfonyl, $C_1$-$C_{12}$alkylsulfonylaminocarbonyl, $C_1$-$C_{12}$alkylcarbonylaminosulfonyl, $C_3$-$C_{12}$cycloalkyloxycarbonyl, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, $C_1$-$C_{12}$alkylcarbonyl$C_1$-$C_{12}$alkyl, $C_1$-$C_{12}$alkoxycarbonyl$C_1$-$C_{12}$alkyl, $C_1$-$C_{12}$alkylaminocarbonyl, di($C_1$-$C_{12}$alkyl)aminocarbonyl, $C_2$-$C_{12}$alkenoxycarbonyl, $C_2$-$C_{12}$alkynoxycarbonyl, $C_1$-$C_{12}$alkoxy$C_1$-$C_{12}$alkoxycarbonyl, $C_1$-$C_{12}$alkylaminothio, di($C_1$-$C_{12}$alkyl)aminothio, unsubstituted or further substituted (hetero)arylcarbonyl$C_1$-$C_6$alkyl, (hetero)arylcarbonyl, (hetero)aryloxycarbonyl, (hetero)aryl$C_1$-$C_6$alkyloxycarbonyl or (hetero)aryl$C_1$-$C_6$alkyl by 1 to 5 following groups: halo, $NO_2$, cyano, $C_1$-$C_6$alkyl, halo$C_1$-$C_6$alkyl, $C_1$-$C_6$alkoxy or halo$C_1$-$C_6$alkoxy;

Or the salts or complexes formed from the compounds represented by general formula I.

The preferred compounds represented by general formula I of this invention are:

R$_1$ is selected from cyano, C$_3$-C$_6$cycloalkyl, C$_1$-C$_6$alkyl, halomethyl, cyanoC$_1$-C$_6$alkyl, cyanoC$_1$-C$_6$alkoxy, C$_1$-C$_6$alkoxycarbonylC$_1$-C$_6$alkyl, C$_1$-C$_6$alkylaminocarbonylC$_1$-C$_6$alkyl or di(C$_1$-C$_6$alkyl)aminocarbonylC$_1$-C$_6$alkyl;

R$_2$ is selected from halo, cyano, C$_3$-C$_6$cycloalkyl, C$_1$-C$_6$alkyl or C$_1$-C$_6$alkoxy;

R$_3$, R$_4$ may be the same or different, selected respectively from H, halo, OH, amino, C$_1$-C$_6$alkyl or C$_1$-C$_6$alkoxy;

R$_{5a}$, R$_{5b}$, R$_{5c}$ may be the same or different, selected respectively from H, halo, OH, C$_1$-C$_6$alkyl or C$_1$-C$_6$alkoxy;

X$_2$ is selected from N or CR$_7$, X$_3$ is selected from N or CR$_8$, X$_6$ is selected from N or CR$_{11}$, within X$_2$, X$_3$, X$_6$, at least one substituent is selected from N;

R$_7$ is selected from H, halo, cyano or C$_1$-C$_6$alkyl;

R$_6$, R$_8$ may be the same or different, selected respectively from H, halo, cyano, C$_1$-C$_6$alkyl or C$_1$-C$_6$alkoxy;

R$_9$ is selected from H, halo, OH, cyano, HO(C=O), amino, NO$_2$, C$_1$-C$_6$alkyl, haloC$_1$-C$_6$alkyl, C$_1$-C$_6$alkoxy, haloC$_1$-C$_6$alkoxy, C$_3$-C$_6$cycloalkyl, C$_2$-C$_6$alkenyl, C$_2$-C$_6$alkynyl, C$_2$-C$_6$alkenoxy, haloC$_2$-C$_6$alkenoxy, C$_2$-C$_6$alkynoxy, haloC$_2$-C$_6$alkynoxy, C$_1$-C$_6$alkylthio, haloC$_1$-C$_6$alkylthio, C$_1$-C$_6$alkoxyC$_1$-C$_6$alkyl, haloC$_1$-C$_6$alkoxyC$_1$-C$_6$alkyl, C$_1$-C$_6$alkylthioC$_1$-C$_6$alkyl, haloC$_1$-C$_6$alkylthioC$_1$-C$_6$alkyl, C$_1$-C$_6$alkylsulfinyl, haloC$_1$-C$_6$alkylsulfinyl, C$_1$-C$_6$alkylsulfonyl, haloC$_1$-C$_6$alkylsulfonyl, C$_1$-C$_6$alkylaminosulfonyl, C$_1$-C$_6$alkylamino, haloC$_1$-C$_6$alkylamino, di(C$_1$-C$_6$alkyl)amino, C$_1$-C$_6$alkoxycarbonyl, CONH$_2$, C$_1$-C$_6$alkylaminocarbonyl, di(C$_1$-C$_6$alkyl)aminocarbonyl, cyanoC$_1$-C$_6$alkoxy, C$_1$-C$_6$alkoxycarbonylC$_1$-C$_6$alkyl, C$_1$-C$_6$alkylaminocarbonylC$_1$-C$_6$alkyl or di(C$_1$-C$_6$alkyl)aminocarbonylC$_1$-C$_6$alkyl;

R$_{10}$ is selected from H, halo, OH, cyano, HO(C=O), amino, NO$_2$, C$_1$-C$_6$alkyl, haloC$_1$-C$_6$alkyl, C$_1$-C$_6$alkoxy, haloC$_1$-C$_6$alkoxy, C$_3$-C$_6$cycloalkyl, C$_2$-C$_6$alkenyl, C$_2$-C$_6$alkynyl, C$_2$-C$_6$alkenoxy, haloC$_2$-C$_6$alkenoxy, C$_2$-C$_6$alkynoxy, haloC$_2$-C$_6$alkynoxy, C$_1$-C$_6$alkylthio, haloC$_1$-C$_6$alkylthio, C$_1$-C$_6$alkoxyC$_1$-C$_6$alkyl, haloC$_1$-C$_6$alkoxyC$_1$-C$_6$alkyl, C$_1$-C$_6$alkylthioC$_1$-C$_6$alkyl, haloC$_1$-C$_6$alkylthioC$_1$-C$_6$alkyl, C$_1$-C$_6$alkylsulfinyl, haloC$_1$-C$_6$alkylsulfinyl, C$_1$-C$_6$alkylsulfonyl, haloC$_1$-C$_6$alkylsulfonyl, C$_1$-C$_6$alkylamino, haloC$_1$-C$_6$alkylamino, di(C$_1$-C$_6$alkyl)amino, C$_1$-C$_6$alkoxycarbonyl, CONH$_2$, C$_1$-C$_6$alkylaminocarbonyl or di(C$_1$-C$_6$alkyl)aminocarbonyl;

R$_{11}$ is selected from H, halo, OH, cyano, HO(C=O), amino, NO$_2$, C$_1$-C$_6$alkyl, haloC$_1$-C$_6$alkyl, C$_1$-C$_6$alkoxy, haloC$_1$-C$_6$alkoxy, C$_1$-C$_6$alkoxycarbonyl, CONH$_2$, C$_1$-C$_6$alkylaminocarbonyl or di(C$_1$-C$_6$alkyl)aminocarbonyl;

W is selected from H or C$_1$-C$_6$alkyl;

A is selected from O, S or NR$_{12}$;

B is selected from —CH$_2$— or —CH$_2$CH$_2$—;

R$_{12}$ is selected from H, OH, H(C)=O, C$_1$-C$_6$alkyl, C$_1$-C$_6$alkylcarbonyl or C$_1$-C$_6$alkylsulfonyl;

Or the salts formed from the compounds represented by general formula I with hydrochloric acid, sulfuric acid, nitric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid or citric acid.

In the general formula I, the preferred compounds represented by general formula I-A, I-B, I-C, I-D, I-E, I-F, I-G or I-H of this invention are:

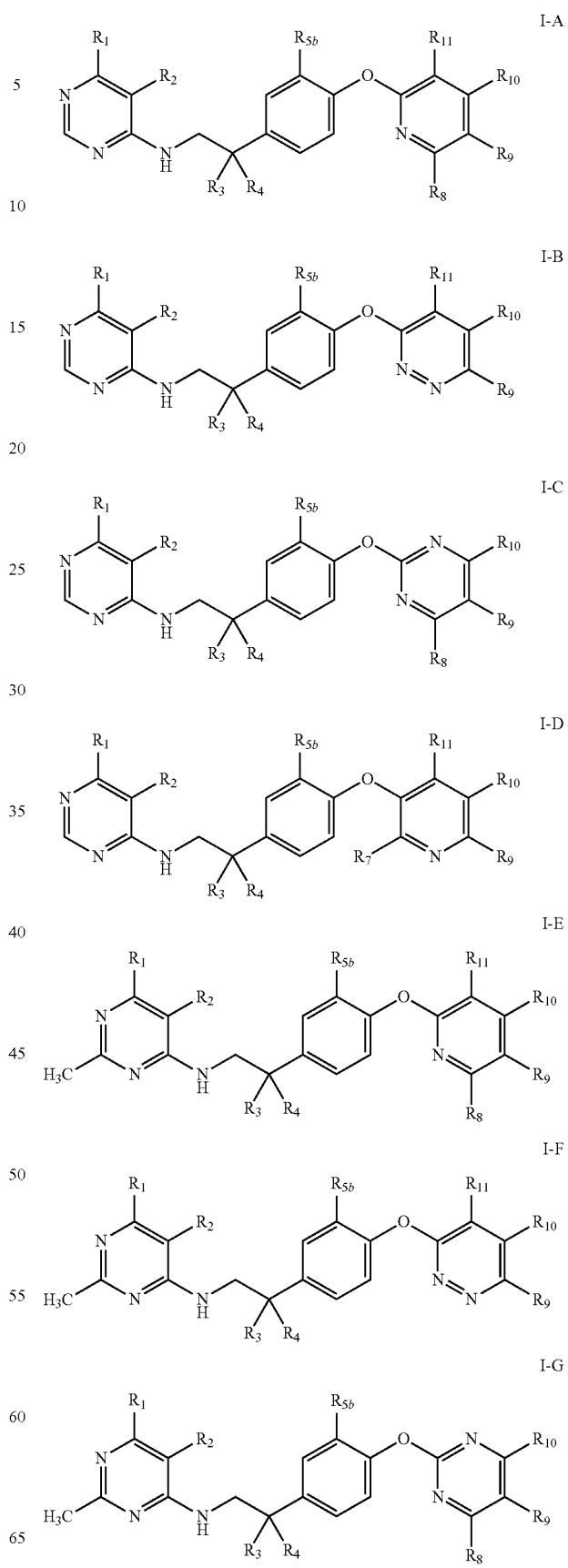

I-H

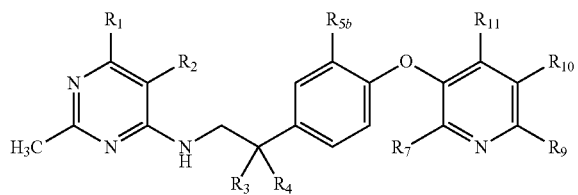

Wherein:

$R_1$ is selected from cyano, $C_1$-$C_4$alkyl or halomethyl;

$R_2$ is selected from halo, cyano, $C_3$-$C_4$cycloalkyl, $C_1$-$C_4$alkyl or $C_1$-$C_4$alkoxy;

$R_3$, $R_4$ may be the same or different, selected respectively from H, halo, OH, amino, $C_1$-$C_4$alkyl or $C_1$-$C_4$alkoxy;

$R_{5b}$ is selected from H, halo, OH, $C_1$-$C_4$alkyl or $C_1$-$C_4$alkoxy;

$R_7$ is selected from H, halo, cyano or $C_1$-$C_4$alkyl;

$R_8$ is selected from H, halo, cyano, $C_1$-$C_4$alkyl or $C_1$-$C_4$alkoxy;

$R_9$ is selected from H, halo, OH, cyano, HO(C=O), amino, $NO_2$, $C_1$-$C_4$alkyl, halo$C_1$-$C_4$alkyl, $C_1$-$C_4$alkoxy, halo$C_1$-$C_4$alkoxy, $C_1$-$C_4$alkylthio, halo$C_1$-$C_4$alkylthio, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkylsulfinyl, halo$C_1$-$C_4$alkylsulfinyl, $C_1$-$C_4$alkylsulfonyl, halo$C_1$-$C_4$alkylsulfonyl, $C_1$-$C_4$alkylaminosulfonyl, $C_1$-$C_4$alkylamino, halo$C_1$-$C_4$alkylamino, di($C_1$-$C_4$alkyl)amino, $C_1$-$C_4$alkoxycarbonyl, $CONH_2$, $C_1$-$C_4$alkylaminocarbonyl, di($C_1$-$C_4$alkyl)aminocarbonyl, cyano$C_1$-$C_4$alkoxy, $C_1$-$C_4$alkoxycarbonyl$C_1$-$C_4$alkyl, $C_1$-$C_4$alkylaminocarbonyl$C_1$-$C_4$alkyl or di($C_1$-$C_4$alkyl)aminocarbonyl$C_1$-$C_4$alkyl;

$R_{10}$ is selected from H, halo, OH, cyano, HO(C=O), amino, $NO_2$, $C_1$-$C_4$alkyl, halo$C_1$-$C_4$alkyl, $C_1$-$C_4$alkoxy, halo$C_1$-$C_4$alkoxy, $C_3$-$C_4$cycloalkyl, $C_2$-$C_4$alkenyl, $C_2$-$C_4$alkynyl, $C_2$-$C_4$alkenoxy, halo$C_2$-$C_4$alkenoxy, $C_2$-$C_4$alkynoxy, halo$C_2$-$C_4$alkynoxy, $C_1$-$C_4$alkylthio, halo$C_1$-$C_4$alkylthio, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkylsulfinyl, halo$C_1$-$C_4$alkylsulfinyl, $C_1$-$C_4$alkylsulfonyl, halo$C_1$-$C_4$alkylsulfonyl, $C_1$-$C_4$alkylamino, halo$C_1$-$C_4$alkylamino, di($C_1$-$C_4$alkyl)amino, $C_1$-$C_4$alkoxycarbonyl, $CONH_2$, $C_1$-$C_4$alkylaminocarbonyl or di($C_1$-$C_4$alkyl)aminocarbonyl;

$R_{11}$ is selected from H, halo, OH, cyano, HO(C=O), amino, $NO_2$, $C_1$-$C_4$alkyl, halo$C_1$-$C_4$alkyl, $C_1$-$C_4$alkoxy, halo$C_1$-$C_4$alkoxy, $C_1$-$C_4$alkoxycarbonyl, $CONH_2$, $C_1$-$C_4$alkylaminocarbonyl or di($C_1$-$C_4$alkyl)aminocarbonyl;

Or the salts formed from the compounds represented by general formula I-A, I-B, I-C, I-D, I-E, I-F, I-G or I-H with hydrochloric acid, sulfuric acid, nitric acid, phosphoric acid, acetic acid, trifluoroacetic acid, oxalic acid, methylsulfonic acid, p-toluenesulfonic acid, benzoic acid, maleic acid, sorbic acid, malic acid or citric acid.

In the general formula I, further more, the preferred compounds represented by general formula I-A, I-B, I-C, I-D, I-E, I-F, I-G or I-H of this invention are:

$R_1$ is selected from cyano, $CH_3$, $C_2H_5$, n-$C_3H_7$, i-$C_3H_7$, n-$C_4H_9$, s-$C_4H_9$, i-$C_4H_9$, t-$C_4H_9$, $CH_2Cl$, $CHCl_2$, $CH_2F$, $CHF_2$, $CClF_2$, $CCl_3$ or $CF_3$;

$R_2$ is selected from F, Cl, Br, cyano, $CH_3$, $C_2H_5$, $OCH_3$ or $OC_2H_5$;

$R_3$, $R_4$ may be the same or different, selected respectively from H, Cl, Br, OH, amino, $CH_3$, $C_2H_5$, $OCH_3$ or $OC_2H_5$;

$R_{5b}$ is selected from H, Cl, Br, OH, $CH_3$, $C_2H_5$, $OCH_3$ or $OC_2H_5$;

$R_7$ is selected from H, Cl or cyano;

$R_8$ is selected from H, Cl, Br, cyano, $CH_3$ or $OCH_3$;

$R_9$ is selected from H, F, Cl, Br, cyano, HO(C=O), amino, $NO_2$, $CH_3$, $C_2H_5$, $CF_3$, $CClF_2$, $OCH_3$, $OC_2H_5$, $OCF_3$, $COOCH_3$, $COOC_2H_5$, $CONH_2$, $CONHCH_3$, $CONHC_2H_5$, $CON(CH_3)_2$, $SO_2CH_3$ or $SO_2NHCH_3$;

$R_{10}$ is selected from H, Cl, cyano, $CH_3$, $C_2H_5$, $OCH_3$ or $OC_2H_5$;

$R_{11}$ is selected from H, F, Cl, Br, cyano, HO(C=O), amino, $NO_2$, $CH_3$, $C_2H_5$, $CF_3$, $CClF_2$, $OCH_3$, $OC_2H_5$, $OCF_3$, $COOCH_3$, $COOC_2H_5$, $CONH_2$, $CONHCH_3$, $CONHC_2H_5$ or $CON(CH_3)_2$;

Or the salts formed from the compounds represented by general formula I-A, I-B, I-C, I-D, I-E, I-F, I-G or I-H with hydrochloric acid, sulfuric acid, nitric acid, phosphoric acid, acetic acid, trifluoroacetic acid, oxalic acid, methylsulfonic acid, p-toluenesulfonic acid, maleic acid or benzoic acid.

Even more preferred compounds represented by general formula I of this invention are:

In the general formula I-A, $R_1$ is selected from $CH_3$, $C_2H_5$, $CH_2Cl$, $CHF_2$, $CClF_2$, $CCl_3$ or $CF_3$;

$R_2$ is selected from Cl, Br or cyano;

$R_3$, $R_4$, $R_{10}$ is selected from H;

$R_{5b}$ is selected from H, Cl, Br or $OCH_3$;

$R_8$ is selected from H or Cl;

$R_9$ is selected from H, Cl, cyano, $CF_3$, $CClF_2$, $COOCH_3$, $COOC_2H_5$ or $CONH_2$;

$R_{11}$ is selected from H, Cl, $NO_2$, $CF_3$, $COOCH_3$ or $CONHCH_3$;

Or, in the general formula I-B, $R_1$ is selected from $CH_3$, $C_2H_5$ or $CHF_2$;

$R_2$ is selected from Cl, Br or cyano;

$R_9$ is selected from Cl, Br, cyano or $CF_3$;

$R_3$, $R_4$, $R_{5b}$, $R_{10}$, $R_{11}$ is selected from H;

Or, in the general formula I-C, $R_1$ is selected from $CH_3$, $C_2H_5$ or $CHF_2$;

$R_2$ is selected from Cl, Br or cyano;

$R_3$, $R_4$, $R_{5b}$, $R_9$ is selected from H;

$R_8$, $R_{10}$ is selected from $CH_3$ or $OCH_3$;

Or, in the general formula I-E, $R_1$ is selected from $CH_3$, $C_2H_5$ or $CHF_2$;

$R_2$ is selected from Cl, Br or cyano;

$R_3$, $R_4$, $R_{5b}$, $R_8$, $R_{10}$ is selected from H;

$R_9$ is selected from H, Cl, cyano, $CF_3$, $COOCH_3$, $COOC_2H_5$ or $CONH_2$;

$R_1$ is selected from H, Cl or $CF_3$;

Or the salts formed from the compounds represented by general formula I-A, I-B, I-C or I-E with hydrochloric acid, sulfuric acid, nitric acid, phosphoric acid, acetic acid, trifluoroacetic acid, oxalic acid, methylsulfonic acid, p-toluenesulfonic acid, maleic acid or benzoic acid.

Most preferred compounds represented by general formula I of this invention are:

In the general formula I-A, $R_1$ is selected from $CH_3$, $C_2H_5$, $CH_2Cl$, $CHF_2$ or $CF_3$;

$R_2$ is selected from Cl, Br or cyano;

$R_3$, $R_4$, $R_{5b}$, $R_{10}$ is selected from H;

$R_9$ is selected from Cl, cyano or $CF_3$;

$R_8$, $R_{11}$ is selected from H or Cl;

Or, in the general formula I-B, $R_1$ is selected from $CH_3$, $C_2H_5$ or $CHF_2$;

$R_2$, $R_9$ is selected from Cl, Br or cyano;

$R_3$, $R_4$, $R_{5b}$, $R_{10}$, $R_{11}$ is selected from H;

Or the salts formed from the compounds represented by general formula I-A or I-B with hydrochloric acid, sulfuric acid, nitric acid, phosphoric acid, acetic acid, trifluoroacetic acid, oxalic acid, methylsulfonic acid, p-toluenesulfonic acid, maleic acid or benzoic acid.

The second optimization of technical schemes is:

The compounds having a structure as represented by formula II are as fellows.

II

Wherein:

$R_1$ is selected from $C_1$-$C_{12}$alkyl, $C_3$-$C_8$cycloalkyl or halomethyl;

$R_2$ is selected from halo, cyano or $C_1$-$C_4$alkoxy;

$R_3$, $R_4$ may be the same or different, selected respectively from H, halo, $C_1$-$C_{12}$alkyl, $C_1$-$C_{12}$alkoxy or $C_3$-$C_{12}$cycloalkyl; or $R_3$, $R_4$ and conjoint carbon can also form a $C_3$-$C_8$ cycle;

$R_{5a}$, $R_{5b}$, $R_{5c}$ may be the same or different, selected respectively from H, halo, OH, $C_1$-$C_{12}$alkyl or $C_1$-$C_{12}$alkoxy;

$R_6$, $R_7$, $R_8$, $R_9$, $R_{10}$, $R_{11}$ may be the same or different, selected respectively from H, halo, OH, amino, cyano, $NO_2$, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$ cycloalkyl, $C_1$-$C_{12}$alkylamino, halo$C_1$-$C_{12}$alkylamino, di($C_1$-$C_{12}$alkyl)amino, halodi($C_1$-$C_{12}$alkyl)amino, $C_1$-$C_{12}$alkylaminocarbonyl, di($C_1$-$C_{12}$alkyl)aminocarbonyl, halodi($C_1$-$C_{12}$alkyl)aminocarbonyl, $CONH_2$, $C_1$-$C_{12}$alkylthio, halo$C_1$-$C_{12}$alkylthio, $C_2$-$C_{12}$alkenyl, $C_2$-$C_{12}$alkynyl, $C_2$-$C_{12}$alkenoxy, halo$C_2$-$C_{12}$alkenoxy, $C_2$-$C_{12}$alkynoxy, halo$C_2$-$C_{12}$alkynoxy, $C_1$-$C_{12}$alkylsulfonyl, halo$C_1$-$C_{12}$alkylsulfonyl, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkoxycarbonyl$C_1$-$C_{12}$alkyl, halo$C_1$-$C_{12}$alkoxycarbonyl$C_1$-$C_{12}$alkyl, $C_1$-$C_{12}$alkylthiocarbonyl$C_1$-$C_{12}$alkyl, halo$C_1$-$C_{12}$alkylthiocarbonyl$C_1$-$C_{12}$alkyl, $C_1$-$C_{12}$alkylcarbonyloxy, halo$C_1$-$C_{12}$alkylcarbonyloxy, $C_1$-$C_{12}$alkoxycarbonyloxy, halo$C_1$-$C_{12}$alkoxycarbonyloxy, $C_1$-$C_{12}$alkylaminocarbonyloxy, halo$C_1$-$C_{12}$alkylaminocarbonyloxy, $C_1$-$C_{12}$alkylsulfonyloxy, halo$C_1$-$C_{12}$alkylsulfonyloxy, $C_1$-$C_{12}$alkoxy$C_1$-$C_{12}$alkoxy, halo$C_1$-$C_{12}$alkoxy$C_1$-$C_{12}$alkoxy, $C_1$-$C_{12}$alkoxycarbonyl$C_1$-$C_{12}$alkoxy or halo$C_1$-$C_{12}$alkoxycarbonyl$C_1$-$C_{12}$alkoxy;

W is selected from H or $C_1$-$C_{12}$alkyl;

A is selected from $NR_{12}$;

B is selected from —$CH_2$— or —$CH_2CH_2$—;

$R_{12}$ is selected from H, OH, H(C)=O, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_1$-$C_{12}$alkylthio, $C_2$-$C_{12}$alkenylthio, $C_2$-$C_{12}$alkenyl, $C_2$-$C_{12}$alkynyl, halo$C_2$-$C_{12}$alkenyl, halo$C_2$-$C_{12}$alkynyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, di($C_1$-$C_{12}$alkyl)aminosulfonyl, $C_1$-$C_{12}$alkylsulfonylaminocarbonyl, $C_1$-$C_{12}$alkylcarbonylaminosulfonyl, $C_3$-$C_{12}$cycloalkyloxycarbonyl, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, $C_1$-$C_{12}$alkylcarbonyl$C_1$-$C_{12}$alkyl, $C_1$-$C_{12}$alkoxycarbonyl$C_1$-$C_{12}$alkyl, $C_1$-$C_{12}$alkylaminocarbonyl, di($C_1$-$C_{12}$alkyl)aminocarbonyl, $C_2$-$C_{12}$alkenoxycarbonyl, $C_2$-$C_{12}$alkynoxycarbonyl, $C_1$-$C_{12}$alkoxy$C_1$-$C_{12}$alkoxycarbonyl, $C_1$-$C_{12}$alkylaminothio, di ($C_1$-$C_{12}$alkyl) aminothio, unsubstituted or further substituted (hetero)arylcarbonyl$C_1$-$C_6$alkyl, (hetero)arylcarbonyl, (hetero)aryloxycarbonyl, (hetero)aryl$C_1$-$C_6$alkyloxycarbonyl or (hetero)aryl$C_1$-$C_6$alkyl by 1 to 5 following groups: halo, $NO_2$, cyano, $C_1$-$C_6$alkyl, halo$C_1$-$C_6$alkyl, $C_1$-$C_6$alkoxy or halo$C_1$-$C_6$alkoxy;

Or the salts or complexes formed from the compounds of general formula II.

The preferred compounds represented by general formula II of this invention are:

$R_1$ is selected from $C_1$-$C_6$alkyl, $C_3$-$C_6$cycloalkyl or halomethyl;

$R_2$ is selected from halo, cyano or $C_1$-$C_4$alkoxy;

$R_3$, $R_4$ may be the same or different, selected respectively from H, halo, $C_1$-$C_6$alkyl, $C_1$-$C_6$alkoxy or $C_3$-$C_6$cycloalkyl; or $R_3$, $R_4$ and conjoint carbon can also form a $C_3$-$C_8$ cycle;

$R_{5a}$, $R_{5b}$, $R_{5c}$, $R_6$ may be the same or different, selected respectively from H, halo, OH, $C_1$-$C_6$alkyl or $C_1$-$C_6$alkoxy;

$R_7$, $R_8$, $R_9$, $R_{10}$, $R_{11}$ may be the same or different, selected respectively from H, halo, OH, amino, cyano, $NO_2$, $C_1$-$C_6$alkyl, halo$C_1$-$C_6$alkyl, $C_1$-$C_6$alkoxy, halo$C_1$-$C_6$alkoxy, $C_3$-$C_6$cycloalkyl, $C_1$-$C_6$alkylamino, halo$C_1$-$C_6$alkylamino, di($C_1$-$C_6$alkyl)amino, halodi($C_1$-$C_6$alkyl) amino, $C_1$-$C_6$alkylaminocarbonyl, di($C_1$-$C_6$alkyl)aminocarbonyl, halodi($C_1$-$C_6$alkyl)aminocarbonyl, $CONH_2$, $C_1$-$C_6$alkylthio, halo$C_1$-$C_6$alkylthio, $C_2$-$C_6$alkenyl, $C_2$-$C_6$alkynyl, $C_2$-$C_6$alkenoxy, halo$C_2$-$C_6$alkenoxy, $C_2$-$C_6$alkynoxy, halo$C_2$-$C_6$alkynoxy, $C_1$-$C_6$alkylsulfonyl, halo$C_1$-$C_6$alkylsulfonyl, $C_1$-$C_6$alkylcarbonyl, halo$C_1$-$C_6$alkylcarbonyl, $C_1$-$C_6$alkoxycarbonyl, halo$C_1$-$C_6$alkoxycarbonyl, $C_1$-$C_6$alkoxy$C_1$-$C_6$alkyl, halo$C_1$-$C_6$alkoxy$C_1$-$C_6$alkyl, $C_1$-$C_6$alkylthio$C_1$-$C_6$alkyl, halo$C_1$-$C_6$alkylthio$C_1$-$C_6$alkyl, $C_1$-$C_6$alkoxycarbonyl$C_1$-$C_6$alkyl, halo$C_1$-$C_6$alkoxycarbonyl$C_1$-$C_6$alkyl, $C_1$-$C_6$alkylthiocarbonyl$C_1$-$C_6$alkyl, halo$C_1$-$C_6$alkylthiocarbonyl$C_1$-$C_6$alkyl, $C_1$-$C_6$alkylcarbonyloxy, halo$C_1$-$C_6$alkylcarbonyloxy, $C_1$-$C_6$alkoxycarbonyloxy, halo$C_1$-$C_6$alkoxycarbonyloxy, $C_1$-$C_6$alkylaminocarbonyloxy, halo$C_1$-$C_6$alkylaminocarbonyloxy, $C_1$-$C_6$alkylsulfonyloxy, halo$C_1$-$C_6$alkylsulfonyloxy, $C_1$-$C_6$alkoxy$C_1$-$C_6$alkoxy, halo$C_1$-$C_6$alkoxy$C_1$-$C_6$alkoxy, $C_1$-$C_6$alkoxycarbonyl$C_1$-$C_6$alkoxy or halo$C_1$-$C_6$alkoxycarbonyl$C_1$-$C_6$alkoxy;

W is selected from H or $C_1$-$C_3$alkyl;

A is selected from $NR_{12}$;

B is selected from —$CH_2$— or —$CH_2CH_2$—;

$R_{12}$ is selected from H, OH, H(C)=O, $C_1$-$C_6$alkyl, $C_1$-$C_6$alkylsulfonyl or $C_1$-$C_6$alkylcarbonyl;

Or the salts formed from the compounds represented by general formula II with hydrochloric acid, sulfuric acid, nitric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid or citric acid.

Further more, the preferred compounds represented by general formula II of this invention are:

$R_1$ is selected from $C_1$-$C_4$alkyl, $C_3$-$C_4$cycloalkyl or halomethyl;

$R_2$ is selected from F, Cl, Br or cyano;

$R_3$, $R_4$ may be the same or different, selected respectively from H, halo, $C_1$-$C_4$alkyl, $C_1$-$C_4$alkoxy or $C_3$-$C_6$cycloalkyl; or $R_3$, $R_4$ and conjoint carbon can also form a $C_3$-$C_8$ cycle;

$R_{5a}$, $R_{5b}$, $R_{5c}$, $R_6$ may be the same or different, selected respectively from H, halo, OH, $C_1$-$C_4$alkyl or $C_1$-$C_4$alkoxy;

$R_7$, $R_8$, $R_9$, $R_{10}$, $R_{11}$ may be the same or different, selected respectively from H, halo, OH, amino, cyano, $NO_2$, $C_1$-$C_4$alkyl, halo$C_1$-$C_4$alkyl, $C_1$-$C_4$alkoxy, halo$C_1$-$C_4$alkoxy, $C_3$-$C_4$cycloalkyl, $C_1$-$C_4$alkylamino, halo$C_1$-$C_4$alkylamino, di($C_1$-$C_4$alkyl)amino, halodi($C_1$-$C_4$alkyl)amino, $C_1$-$C_4$alkylaminocarbonyl, di($C_1$-$C_4$alkyl)aminocarbonyl, halodi($C_1$-$C_4$alkyl)aminocarbonyl, $CONH_2$, $C_1$-$C_4$alkylthio, halo$C_1$-$C_4$alkylthio, $C_2$-$C_4$alkenyl, $C_2$-$C_4$alkynyl, $C_2$-$C_4$alkenoxy, halo$C_2$-$C_4$alkenoxy, $C_2$-$C_4$alkynoxy, halo$C_2$-$C_4$alkynoxy, $C_1$-$C_4$alkylsulfonyl, halo$C_1$-$C_4$alkylsulfonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkoxycarbonyl$C_1$-$C_4$alkyl, halo$C_1$-$C_4$alkoxycarbonyl$C_1$-$C_4$alkyl, $C_1$-$C_4$alkylthiocarbonyl$C_1$-$C_4$alkyl, halo$C_1$-$C_4$alkylthiocarbonyl$C_1$-$C_4$alkyl, $C_1$-$C_4$alkylcarbonyloxy, halo$C_1$-$C_4$alkylcarbonyloxy, $C_1$-$C_4$alkoxycarbonyloxy, halo$C_1$-$C_4$alkoxycarbonyloxy, $C_1$-$C_4$alkylaminocarbonyloxy, halo$C_1$-$C_4$alkylaminocarbonyloxy, $C_1$-$C_4$alkylsulfonyloxy, halo$C_1$-$C_4$alkylsulfonyloxy, $C_1$-$C_4$alkoxy$C_1$-$C_4$alkoxy, halo$C_1$-$C_4$alkoxy$C_1$-$C_4$alkoxy, $C_1$-$C_4$alkoxycarbonyl$C_1$-$C_4$alkoxy or halo$C_1$-$C_4$alkoxycarbonyl$C_1$-$C_4$alkoxy;

W is selected from H or $CH_3$;

A is selected from $NR_{12}$;

B is selected from —$CH_2$— or —$CH_2CH_2$—;

$R_{12}$ is selected from H, OH, H(C)=O, $C_1$-$C_4$alkyl, $C_1$-$C_4$alkylsulfonyl or $C_1$-$C_4$alkylcarbonyl;

Or the salts formed from the compounds represented by general formula II with hydrochloric acid, sulfuric acid, nitric acid, phosphoric acid, acetic acid, trifluoroacetic acid, oxalic acid, methylsulfonic acid, p-toluenesulfonic acid, benzoic acid, maleic acid, sorbic acid, malic acid or citric acid.

Even more preferred compounds represented by formula II of this invention are:

$R_1$ is selected from $CH_3$, $C_2H_5$, n-$C_3H_7$, i-$C_3H_7$, n-$C_4H_9$, s-$C_4H_9$, i-$C_4H_9$, t-$C_4H_9$, cyclopropyl, cyclobutyl, $CF_3$, $CCl_3$, $CH_2F$, $CH_2Cl$, $CH_2Br$, $CClF_2$, $CCl_2F$, $CHF_2$ or $CHCl_2$;

$R_2$ is selected from F, Cl, Br or cyano;

$R_3$, $R_4$ may be the same or different, selected respectively from H, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $OCH_3$, $OC_2H_5$, $OC_3H_7$-n, $OC_3H_7$-i, $OC_4H_9$-n, $OC_4H_9$-s, $OC_4H_9$-i or $OC_4H_9$-t;

$R_{5a}$, $R_{5b}$, $R_{5c}$, $R_6$ may be the same or different, selected respectively from H, F, Cl, Br, I, OH, $CH_3$, $C_2H_5$, n-$C_3H_7$, i-$C_3H_7$, n-$C_4H_9$, s-$C_4H_9$, i-$C_4H_9$, t-$C_4H_9$, $OCH_3$, $OC_2H_5$, $OC_3H_7$-n, $OC_3H_7$-i, $OC_4H_9$-n, $OC_4H_9$-s, $OC_4H_9$-i or $OC_4H_9$-t;

$R_7$, $R_8$, $R_9$, $R_{10}$, $R_{11}$ may be the same or different, selected respectively from H, F, Cl, Br, I, cyano, amino, $NO_2$, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CClF_2$, $CCl_2F$, $CHCl_2$, $CH_2F$, $CHF_2$, $OCH_3$, $OC_2H_5$, $OC_3H_7$-n, $OC_3H_7$-i, $OC_4H_9$-n, $OC_4H_9$-s, $OC_4H_9$-i, $OC_4H_9$-t, $OCF_3$, $OCH_2CF_3$, $COOCH_3$, $COOC_2H_5$, $CONH_2$, $CONHCH_3$, $CONHC_2H_5$, $CONH(CH_3)_2$, methylsulfonyl or trifluoromethylsulfonyl;

W is selected from H or $CH_3$;

A is selected from $NR_{12}$;

B is selected from —$CH_2$— or —$CH_2CH_2$—;

$R_{12}$ is selected from H;

Or the salts formed from the compounds represented by general formula II with hydrochloric acid, sulfuric acid, nitric acid, phosphoric acid, acetic acid, trifluoroacetic acid, oxalic acid, methylsulfonic acid, p-toluenesulfonic acid, maleic acid or benzoic acid.

Even further more preferred compounds represented by formula II of this invention are:

$R_1$ is selected from $CH_3$, $C_2H_5$, n-$C_3H_7$, i-$C_3H_7$, n-$C_4H_9$, s-$C_4H_9$, i-$C_4H_9$, t-$C_4H_9$, cyclopropyl, cyclobutyl, $CH_2Cl$, $CHCl_2$, $CH_2F$, $CHF_2$, $CClF_2$, $CCl_3$ or $CF_3$;

$R_2$ is selected from F, Cl, Br or cyano;

$R_3$, $R_4$ may be the same or different, selected respectively from H, F, Cl, Br, I, $CH_3$, $C_2H_5$, n-$C_3H_7$, i-$C_3H_7$, $OCH_3$, $OC_2H_5$, $OC_3H_7$-n or $OC_3H_7$-i;

$R_{5a}$, $R_{5b}$, $R_{5c}$, $R_6$ may be the same or different, selected respectively from H, F, Cl, Br or $OCH_3$;

$R_7$, $R_8$, $R_9$, $R_{10}$, $R_{11}$ may be the same or different, selected respectively from H, F, Cl, Br, I, cyano, $NO_2$, $CH_3$, $C_2H_5$, n-$C_3H_7$, i-$C_3H_7$, n-$C_4H_9$, s-$C_4H_9$, i-$C_4H_9$, t-$C_4H_9$, $OCH_3$, $OCF_3$, $CF_3$, $CCl_3$, $CClF_2$, $CCl_2F$, $CHCl_2$, $CH_2F$, $CHF_2$, methylsulfonyl or trifluoromethylsulfonyl;

W is selected from H or $CH_3$;

A is selected from NH;

B is selected from —$CH_2$— or —$CH_2CH_2$—;

Or the salts formed from the compounds of general formula II with hydrochloric acid, sulfuric acid, nitric acid, phosphoric acid, acetic acid, trifluoroacetic acid, oxalic acid, methylsulfonic acid, p-toluenesulfonic acid, maleic acid or benzoic acid.

Most preferred compounds represented by formula II of this invention are:

$R_1$ is selected from $CH_3$, $C_2H_5$, $CHF_2$ or $CF_3$;

$R_2$ is selected from Cl or cyano;

$R_3$, $R_4$ is selected from H;

$R_{5a}$, $R_{5b}$, $R_{5c}$, $R_6$ may be the same or different, selected respectively from H, F, Cl, Br or $OCH_3$;

W is selected from H or $CH_3$;

$R_7$, $R_8$, $R_9$, $R_{10}$, $R_{11}$ may be the same or different, selected respectively from H, F, Cl, cyano, $NO_2$, $CH_3$, $OCH_3$, $OCF_3$, $CF_3$ or methylsulfonyl;

A is selected from NH;

B is selected from —$CH_2$— or —$CH_2CH_2$—;

Or the salts formed from the compounds represented by general formula II with hydrochloric acid, sulfuric acid, nitric acid, phosphoric acid, acetic acid or trifluoroacetic acid.

The third optimization of technical schemes is:

the compounds having a structure as represented by formula III are as fellows.

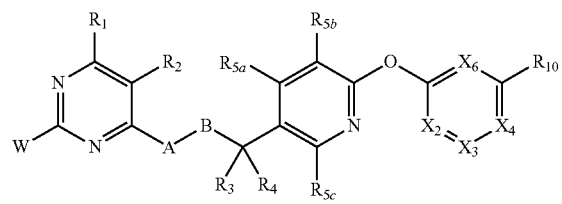

$R_1$ is selected from halo, $C_1$-$C_{12}$alkyl, $C_3$-$C_{12}$cycloalkyl, halo$C_1$-$C_{12}$alkyl, $C_2$-$C_{12}$alkenyl, halo$C_2$-$C_{12}$alkenyl, $C_2$-$C_{12}$alkynyl, halo$C_2$-$C_{12}$alkynyl, $C_1$-$C_{12}$alkoxy$C_1$-$C_{12}$alkyl or halo$C_1$-$C_{12}$alkoxy$C_1$-$C_{12}$alkyl;

$R_2$ is selected from halo, cyano, $C_1$-$C_{12}$alkyl, $C_1$-$C_{12}$alkoxy or halo$C_1$-$C_{12}$alkoxy;

W is selected from H, halo, $C_1$-$C_{12}$alkyl, $C_1$-$C_{12}$alkoxy, $C_1$-$C_{12}$alkylthio or $C_1$-$C_{12}$alkylsulfonyl;

$R_3$, $R_4$ may be the same or different, selected respectively from H, $C_1$-$C_{12}$alkyl, $C_3$-$C_{12}$cycloalkyl, $C_2$-$C_{12}$alkenyl, $C_2$-$C_{12}$alkynyl, halo$C_2$-$C_{12}$alkenyl, halo$C_2$-$C_{12}$alkynyl, $C_1$-$C_{12}$alkoxy$C_1$-$C_{12}$alkyl, unsubstituted or further substituted aryl$C_1$-$C_6$alkyl or heteroaryl$C_1$-$C_6$alkyl by 1 to 5 following groups: halo, $C_1$-$C_6$alkyl, halo$C_1$-$C_6$alkyl, $C_1$-$C_6$alkoxy or halo$C_1$-$C_6$alkoxy; or $R_3$, $R_4$ and conjoint carbon can also form a $C_3$-$C_8$ cycle;

$R_{5a}$, $R_{5b}$, $R_{5c}$ may be the same or different, selected respectively from H, halo, $NO_2$, cyano, $C_1$-$C_{12}$alkyl, halo$C_1$-$C_{12}$alkyl, $C_3$-$C_{12}$cycloalkyl, $C_1$-$C_{12}$alkoxy, halo$C_1$-$C_{12}$alkoxy, $C_1$-$C_{12}$alkylthio, halo$C_1$-$C_{12}$alkylthio, $C_2$-$C_{12}$alkenyl, halo$C_2$-$C_{12}$alkenyl, $C_2$-$C_{12}$alkynyl, halo$C_2$-$C_{12}$alkynyl, $C_3$-$C_{12}$alkenoxy, halo$C_3$-$C_{12}$alkenoxy, $C_3$-$C_{12}$alkynoxy, halo$C_3$-$C_{12}$alkynoxy, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylcarbonyl, halo$C_1$-$C_{12}$alkylcarbonyl, $C_1$-$C_{12}$alkylcarbonyloxy, $C_1$-$C_{12}$alkylcarbonylamino, $C_1$-$C_{12}$alkylsulfonyloxy, $C_1$-$C_{12}$alkoxycarbonyl, $C_1$-$C_{12}$alkoxycarbonyl$C_1$-$C_{12}$alkyl, $C_1$-$C_{12}$alkoxycarbonylamino, $C_1$-$C_{12}$alkoxy$C_1$-$C_{12}$alkoxy or $C_1$-$C_{12}$alkoxycarbonyl$C_1$-$C_{12}$alkoxy;

$X_2$ is selected from N or $CR_7$;
$X_3$ is selected from N or $CR_8$;
$X_4$ is selected from N or $CR_9$;
$X_6$ is selected from N or $CR_{11}$; however, $X_2$, $X_3$, $X_4$, $X_6$ are not simultaneously selected from N;

$R_7$, $R_8$, $R_9$, $R_1$ may be the same or different, selected respectively from H, halo, OH, cyano, HO(C=O), amino, $NO_2$, $C_1$-$C_{12}$alkyl, halo$C_1$-$C_{12}$alkyl, $C_1$-$C_{12}$alkoxy, halo$C_1$-$C_{12}$alkoxy, $C_1$-$C_{12}$alkoxycarbonyl, $CONH_2$, $C_1$-$C_{12}$alkylaminocarbonyl, di($C_1$-$C_{12}$alkyl)aminocarbonyl, $C_1$-$C_{12}$alkylsulfonyl or halo$C_1$-$C_{12}$alkylsulfonyl;

$R_{10}$ is selected from H, halo, OH, cyano, HO(C=O), amino, $NO_2$, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_2$-$C_{12}$alkenyl, $C_2$-$C_{12}$alkynyl, $C_2$-$C_{12}$alkenoxy, halo$C_2$-$C_{12}$alkenoxy, $C_2$-$C_{12}$alkynoxy, halo$C_2$-$C_{12}$alkynoxy, $C_1$-$C_{12}$alkylthio, halo$C_1$-$C_{12}$alkylthio, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, $C_1$-$C_{12}$alkylamino, halo$C_1$-$C_{12}$alkylamino, di($C_1$-$C_{12}$alkyl)amino, $C_1$-$C_{12}$alkoxycarbonyl, $CONH_2$, $C_1$-$C_{12}$alkylaminocarbonyl, di($C_1$-$C_{12}$alkyl)aminocarbonyl, cyano$C_1$-$C_{12}$alkoxy, $C_1$-$C_{12}$alkoxycarbonyl$C_1$-$C_{12}$alkyl, $C_1$-$C_{12}$alkylaminocarbonyl$C_1$-$C_{12}$alkyl or di($C_1$-$C_{12}$alkyl)aminocarbonyl$C_1$-$C_{12}$alkyl;

A is selected from O, S or $NR_{12}$;

B is selected from is selected from —$CH_2$— or —$CH_2CH_2$—;

$R_{12}$ is selected from H, OH, H(C)=O, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_1$-$C_{12}$alkylthio, $C_2$-$C_{12}$alkenylthio, $C_2$-$C_{12}$alkenyl, $C_2$-$C_{12}$alkynyl, halo$C_2$-$C_{12}$alkenyl, halo$C_2$-$C_{12}$alkynyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, di($C_1$-$C_{12}$alkyl)aminosulfonyl, $C_1$-$C_{12}$alkylsulfonylaminocarbonyl, $C_1$-$C_{12}$alkylcarbonylaminosulfonyl, $C_3$-$C_{12}$cycloalkyloxycarbonyl, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, $C_1$-$C_{12}$alkylcarbonyl$C_1$-$C_{12}$alkyl, $C_1$-$C_{12}$alkoxycarbonyl$C_1$-$C_{12}$alkyl, $C_1$-$C_{12}$alkylaminocarbonyl, di($C_1$-$C_{12}$alkyl)aminocarbonyl, $C_2$-$C_{12}$alkenoxycarbonyl, $C_2$-$C_{12}$alkynoxycarbonyl, $C_1$-$C_{12}$alkoxy$C_1$-$C_{12}$alkoxycarbonyl, $C_1$-$C_{12}$alkylaminothio, di($C_1$-$C_{12}$alkyl)aminothio, unsubstituted or further substituted (hetero)arylcarbonyl$C_1$-$C_6$alkyl, (hetero)arylcarbonyl, (hetero)aryloxycarbonyl, (hetero)aryl$C_1$-$C_6$alkyloxycarbonyl or (hetero)aryl$C_1$-$C_6$alkyl by 1 to 5 following groups: halo, $NO_2$, cyano, $C_1$-$C_6$alkyl, halo$C_1$-$C_6$alkyl, $C_1$-$C_6$alkoxy or halo$C_1$-$C_6$alkoxy;

Or the salts or complexes formed from the compounds represented by general formula III.

The preferred compounds represented by general formula III of this invention are:

$R_1$ is selected from halo, $C_1$-$C_8$alkyl, $C_3$-$C_8$cycloalkyl, halo$C_1$-$C_8$alkyl, $C_2$-$C_8$alkenyl, halo$C_2$-$C_8$alkenyl, $C_2$-$C_8$alkynyl, halo$C_2$-$C_8$alkynyl, $C_1$-$C_8$alkoxy$C_1$-$C_8$alkyl or halo$C_1$-$C_8$alkoxy$C_1$-$C_8$alkyl;

$R_2$ is selected from halo, cyano, $C_1$-$C_8$alkyl, $C_1$-$C_8$alkoxy or halo$C_1$-$C_8$alkoxy;

W is selected from H, halo, $C_1$-$C_8$alkyl, $C_1$-$C_8$alkoxy, $C_1$-$C_8$alkylthio or $C_1$-$C_8$alkylsulfonyl;

$R_3$, $R_4$ may be the same or different, selected respectively from H, $C_1$-$C_8$alkyl, $C_3$-$C_8$cycloalkyl, $C_2$-$C_8$alkenyl, $C_2$-$C_8$alkynyl, halo$C_2$-$C_8$alkenyl, halo$C_2$-$C_8$alkynyl, $C_1$-$C_8$alkoxy$C_1$-$C_8$alkyl, unsubstituted or further substituted aryl$C_1$-$C_4$alkyl or heteroaryl$C_1$-$C_4$alkyl by 1 to 3 following groups: halo, $C_1$-$C_4$alkyl, halo$C_1$-$C_4$alkyl, $C_1$-$C_4$alkoxy or halo$C_1$-$C_4$alkoxy; or $R_3$, $R_4$ and conjoint carbon can also form a $C_3$-$C_8$ cycle;

$R_{5a}$, $R_{5b}$, $R_{5c}$ may be the same or different, selected respectively from H, halo, $NO_2$, cyano, $C_1$-$C_8$alkyl, halo$C_1$-$C_8$alkyl, $C_3$-$C_6$cycloalkyl, $C_1$-$C_8$alkoxy, halo$C_1$-$C_8$alkoxy, $C_1$-$C_8$alkylthio, halo$C_1$-$C_8$alkylthio, $C_2$-$C_8$alkenyl, halo$C_2$-$C_8$alkenyl, $C_2$-$C_8$alkynyl, halo$C_2$-$C_8$alkynyl, $C_3$-$C_8$alkenoxy, halo$C_3$-$C_8$alkenoxy, $C_3$-$C_8$alkynoxy, halo$C_3$-$C_8$alkynoxy, $C_1$-$C_8$alkylsulfinyl, halo$C_1$-$C_8$alkylsulfinyl, $C_1$-$C_8$alkylsulfonyl, halo$C_1$-$C_8$alkylsulfonyl, $C_1$-$C_8$alkylcarbonyl, halo$C_1$-$C_8$alkylcarbonyl, $C_1$-$C_8$alkylcarbonyloxy, $C_1$-$C_8$alkylcarbonylamino, $C_1$-$C_8$alkylsulfonyloxy, $C_1$-$C_8$alkoxycarbonyl, $C_1$-$C_8$alkoxycarbonyl$C_1$-$C_8$alkyl, $C_1$-$C_8$alkoxycarbonylamino, $C_1$-$C_8$alkoxy$C_1$-$C_8$alkoxy or $C_1$-$C_8$alkoxycarbonyl$C_1$-$C_8$alkoxy;

$X_2$ is selected from N or $CR_7$;
$X_3$ is selected from N or $CR_8$;
$X_4$ is selected from N or $CR_9$;
$X_6$ is selected from N or $CR_{11}$; however, $X_2$, $X_3$, $X_4$, $X_6$ are not simultaneously selected from N;

$R_7$, $R_8$, $R_9$, $R_{11}$ may be the same or different, selected respectively from H, halo, OH, cyano, HO(C=O), amino, $NO_2$, $C_1$-$C_8$alkyl, halo$C_1$-$C_8$alkyl, $C_1$-$C_8$alkoxy, halo$C_1$-$C_8$alkoxy, $C_1$-$C_8$alkoxycarbonyl, $CONH_2$, $C_1$-$C_8$alkylaminocarbonyl, di($C_1$-$C_8$alkyl)aminocarbonyl, $C_1$-$C_8$alkylsulfonyl or halo$C_1$-$C_8$alkylsulfonyl;

$R_{10}$ is selected from H, halo, OH, cyano, HO(C=O), amino, $NO_2$, $C_1$-$C_8$alkyl, halo$C_1$-$C_8$alkyl, $C_1$-$C_8$alkoxy, halo$C_1$-$C_8$alkoxy, $C_3$-$C_8$cycloalkyl, $C_2$-$C_8$alkenyl, $C_2$-$C_8$alkynyl, $C_2$-$C_8$alkenoxy, halo$C_2$-$C_8$alkenoxy, $C_2$-$C_8$alkynoxy, halo$C_2$-$C_8$alkynoxy, $C_1$-$C_8$alkylthio, halo$C_1$-$C_8$alkylthio, $C_1$-$C_8$alkoxy$C_1$-$C_8$alkyl, halo$C_1$-$C_8$alkoxy$C_1$-$C_8$alkyl, $C_1$-$C_8$alkylthio$C_1$-$C_8$alkyl, halo$C_1$-$C_8$alkylthio$C_1$-$C_8$alkyl, $C_1$-$C_8$alkylsulfinyl, halo$C_1$-$C_8$alkylsulfinyl, $C_1$-$C_8$alkylsulfonyl, halo$C_1$-$C_8$alkylsulfonyl, $C_1$-$C_8$alkylaminosulfonyl, $C_1$-$C_8$alkylamino, halo$C_1$-$C_8$alkylamino, di($C_1$-$C_8$alkyl)amino, $C_1$-$C_8$alkoxycarbonyl, $CONH_2$, $C_1$-$C_8$alkylaminocarbonyl, di($C_1$-$C_8$alkyl)aminocarbonyl, cyano$C_1$-$C_8$alkoxy, $C_1$-$C_8$alkoxycarbonyl$C_1$-$C_8$alkyl, $C_1$-$C_8$alkylaminocarbonyl$C_1$-$C_8$alkyl or di($C_1$-$C_8$alkyl)aminocarbonyl$C_1$-$C_8$alkyl;

A is selected from O, S or $NR_{12}$;

B is selected from is selected from —$CH_2$— or —$CH_2CH_2$—;

$R_{12}$ is selected from H, OH, H(C)=O, $C_1$-$C_8$alkyl, halo$C_1$-$C_8$alkyl, $C_1$-$C_8$alkoxy, halo$C_1$-$C_8$alkoxy, $C_3$-$C_8$cycloalkyl, $C_1$-$C_8$alkylthio, $C_2$-$C_8$alkenylthio, $C_2$-$C_8$alkenyl, $C_2$-$C_8$alkynyl, halo$C_2$-$C_8$alkenyl, halo$C_2$-$C_8$alkynyl, $C_1$-$C_8$alkoxy$C_1$-$C_8$alkyl, halo$C_1$-$C_8$alkoxy$C_1$-$C_8$alkyl, $C_1$-$C_8$alkylthio$C_1$-$C_8$alkyl, halo$C_1$-$C_8$alkylthio$C_1$-$C_8$alkyl, $C_1$-$C_8$alkylsulfinyl, halo$C_1$-$C_8$alkylsulfinyl, $C_1$-$C_8$alkylsulfonyl, halo$C_1$-$C_8$alkylsulfonyl, $C_1$-$C_8$alkylaminosulfonyl, di($C_1$-$C_8$alkyl)aminosulfonyl, $C_1$-$C_8$alkylsulfonylaminocarbonyl, $C_1$-$C_8$alkylcarbonylaminosulfonyl, $C_3$-$C_8$cycloalkyloxycarbonyl, $C_1$-$C_8$alkylcarbonyl, halo$C_1$-$C_8$alkylcarbonyl, $C_1$-$C_8$alkoxycarbonyl, halo$C_1$-$C_8$alkoxycarbonyl, $C_1$-$C_8$alkylcarbonyl$C_1$-$C_8$alkyl, $C_1$-$C_8$alkoxycarbonyl$C_1$-$C_8$alkyl, $C_1$-$C_8$alkylaminocarbonyl, di($C_1$-$C_8$alkyl)aminocarbonyl, $C_2$-$C_8$alkenoxycarbonyl, $C_2$-$C_8$alkynoxycarbonyl, $C_1$-$C_8$alkoxy$C_1$-$C_8$alkoxycarbonyl, $C_1$-$C_8$alkylaminothio, di ($C_1$-$C_8$alkyl) aminothio, unsubstituted or further substituted (hetero)arylcarbonyl$C_1$-$C_6$alkyl, (hetero)arylcarbonyl, (hetero)aryloxycarbonyl, (hetero)aryl$C_1$-$C_6$alkyloxycarbonyl or (hetero)aryl$C_1$-$C_6$alkyl by 1 to 3 following groups: halo, $NO_2$, cyano, $C_1$-$C_4$alkyl, halo$C_1$-$C_4$alkyl, $C_1$-$C_4$alkoxy or halo$C_1$-$C_4$alkoxy;

Or the salts formed from the compounds represented by general formula III.

Further more, the preferred compounds represented by general formula III of this invention are:

$R_1$ is selected from halo, $C_1$-$C_4$alkyl, $C_3$-$C_6$cycloalkyl, halo$C_1$-$C_4$alkyl, $C_2$-$C_4$alkenyl, halo$C_2$-$C_4$alkenyl, $C_2$-$C_4$alkynyl, halo$C_2$-$C_4$alkynyl, $C_1$-$C_4$alkoxy$C_1$-$C_4$alkyl or halo$C_1$-$C_4$alkoxy$C_1$-$C_4$alkyl;

$R_2$ is selected from halo or cyano;

W is selected from H or $CH_3$;

$R_3$, $R_4$ is selected from H, $CH_3$ or $C_2H_5$;

$R_{5a}$, $R_{5b}$, $R_{5c}$ may be the same or different, selected respectively from H, halo, $NO_2$, cyano, $C_1$-$C_4$alkyl, halo$C_1$-$C_4$alkyl, $C_3$-$C_6$cycloalkyl, $C_1$-$C_4$alkoxy, halo$C_1$-$C_4$alkoxy, $C_1$-$C_4$alkylthio, halo$C_1$-$C_4$alkylthio, $C_2$-$C_4$alkenyl, $C_2$-$C_4$alkynyl, $C_1$-$C_4$alkylsulfinyl, $C_1$-$C_4$alkylsulfonyl, $C_1$-$C_4$alkylcarbonyl or $C_1$-$C_4$alkoxy$C_1$-$C_4$alkoxy;

$X_2$ is selected from N or $CR_7$;

$X_3$ is selected from N or $CR_8$;

$X_4$ is selected from N or $CR_9$;

$X_6$ is selected from N or $CR_{11}$; however, $X_2$, $X_3$, $X_4$, $X_6$ are not simultaneously selected from N;

$R_7$, $R_8$, $R_9$, $R_{11}$ may be the same or different, selected respectively from H, halo, OH, cyano, HO(C=O), amino, $NO_2$, $C_1$-$C_4$alkyl, halo$C_1$-$C_4$alkyl, $C_1$-$C_4$alkoxy, halo$C_1$-$C_4$alkoxy, $C_1$-$C_4$alkoxycarbonyl, $CONH_2$, $C_1$-$C_4$alkylaminocarbonyl, di($C_1$-$C_4$alkyl)aminocarbonyl or $C_1$-$C_4$alkylsulfonyl or halo$C_1$-$C_4$alkylsulfonyl;

$R_{10}$ is selected from H, halo, OH, cyano, HO(C=O), amino, $NO_2$, $C_1$-$C_4$alkyl, halo$C_1$-$C_4$alkyl, $C_1$-$C_4$alkoxy, halo$C_1$-$C_4$alkoxy, $C_3$-$C_4$cycloalkyl, $C_2$-$C_4$alkenyl, $C_2$-$C_4$alkynyl, $C_2$-$C_4$alkenoxy, halo$C_2$-$C_4$alkenoxy, $C_2$-$C_4$alkynoxy, halo$C_2$-$C_4$alkynoxy, $C_1$-$C_4$alkylthio, halo$C_1$-$C_4$alkylthio, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkylsulfinyl, halo$C_1$-$C_4$alkylsulfinyl, $C_1$-$C_4$alkylsulfonyl, halo$C_1$-$C_4$alkylsulfonyl, $C_1$-$C_4$alkylaminosulfonyl, $C_1$-$C_4$alkylamino, halo$C_1$-$C_4$alkylamino, di($C_1$-$C_4$alkyl)amino, $C_1$-$C_4$alkoxycarbonyl, $CONH_2$, $C_1$-$C_4$alkylaminocarbonyl, di($C_1$-$C_4$alkyl)aminocarbonyl, cyano$C_1$-$C_{12}$alkoxy, $C_1$-$C_4$alkoxycarbonyl$C_1$-$C_4$alkyl, $C_1$-$C_4$alkylaminocarbonyl$C_1$-$C_4$alkyl or di($C_1$-$C_4$alkyl)aminocarbonyl$C_1$-$C_4$alkyl;

A is selected from O, S or NH;

B is selected from —$CH_2$— or —$CH_2CH_2$—;

Or the salts formed from the compounds represented by general formula III with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid or citric acid.

In the general formula III, even more preferred compounds represented by general formula III-A, III-B, III-C, III-D, III-E, III-F, III-G, III-H, III-I or III-J of this invention are:

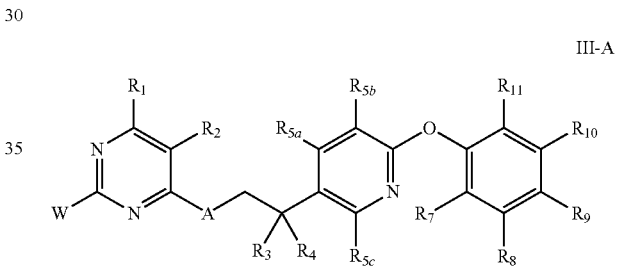

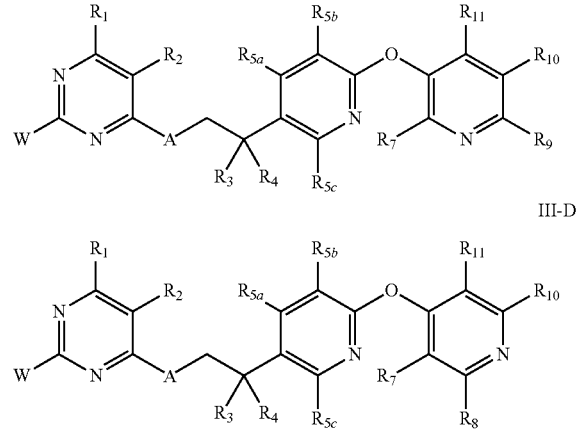

-continued

III-E
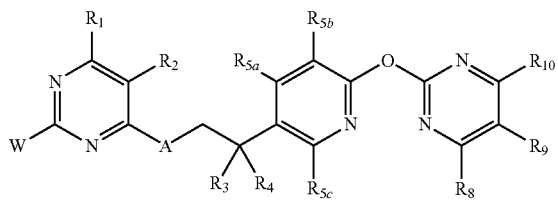

III-F
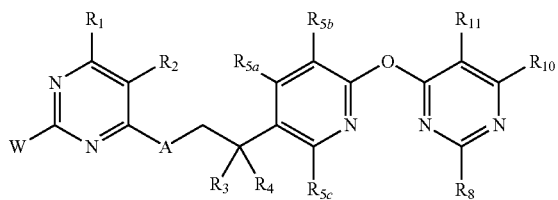

III-G
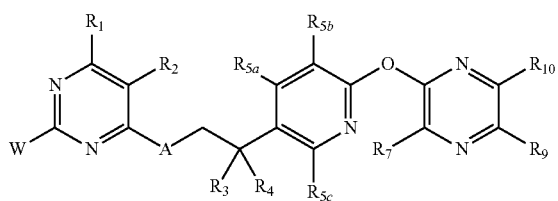

III-H
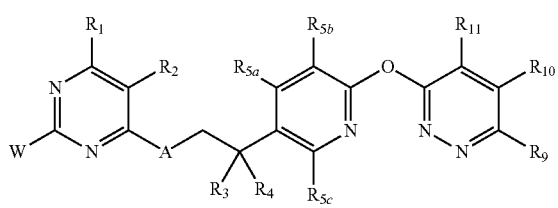

III-I
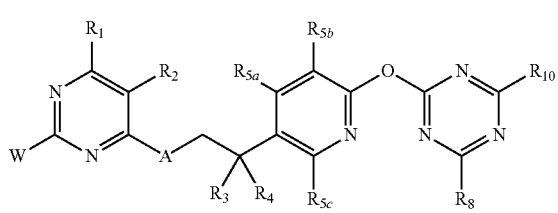

III-J
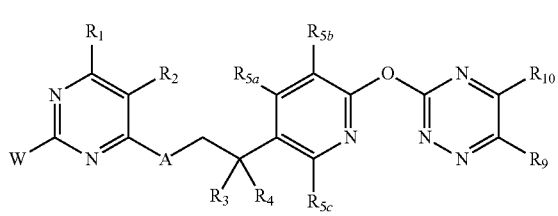

Wherein:

$R_1$ is selected from F, Cl, Br, I, $C_1$-$C_4$alkyl, $C_3$-$C_6$cycloalkyl, halo$C_1$-$C_4$alkyl, $C_2$-$C_4$alkenyl, $C_2$-$C_4$alkynyl, $C_1$-$C_4$alkoxy$C_1$-$C_4$alkyl or halo$C_1$-$C_4$alkoxy$C_1$-$C_4$alkyl;

$R_2$ is selected from halo or cyano;

W is selected from H or $CH_3$;

$R_3$, $R_4$ is selected from H, $CH_3$ or $C_2H_5$;

$R_{5a}$, $R_{5b}$, $R_{5c}$ may be the same or different, selected respectively from H, F, Cl, Br, I, $NO_2$, cyano, $C_1$-$C_4$alkyl, halo$C_1$-$C_4$alkyl, $C_1$-$C_4$alkoxy, halo$C_1$-$C_4$alkoxy or $C_1$-$C_4$alkylcarbonyl;

$R_7$, $R_8$, $R_9$, $R_{11}$ may be the same or different, selected respectively from H, F, Cl, Br, I, cyano, HO(C=O), $NO_2$, $C_1$-$C_4$alkyl, halo$C_1$-$C_4$alkyl, $C_1$-$C_4$alkoxy, halo$C_1$-$C_4$alkoxy, $C_1$-$C_4$alkoxycarbonyl, $C_1$-$C_4$alkylaminocarbonyl, di($C_1$-$C_4$alkyl)aminocarbonyl, $C_1$-$C_4$alkylsulfonyl or halo$C_1$-$C_4$alkylsulfonyl;

$R_{10}$ is selected from H, F, Cl, Br, I, cyano, $NO_2$, $C_1$-$C_4$alkyl, halo$C_1$-$C_4$alkyl, $C_1$-$C_4$alkoxy, halo$C_1$-$C_4$alkoxy, $C_1$-$C_4$alkylsulfonyl or halo$C_1$-$C_4$alkylsulfonyl;

A is selected from O, S or NH;

Or the salts formed from the compounds represented by general formula III-A, III-B, III-C, III-D, III-E, III-F, III-G, III-H, III-I or III-J with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid or citric acid.

Even further more preferred compounds represented by formula III of this invention are:

$R_1$ is selected from Cl, $CH_3$, $C_2H_5$, $CHCl_2$, $CCl_3$, $CH_2F$, $CClF_2$, $CHF_2$ or $CF_3$;

$R_2$ is selected from halo or cyano;

W is selected from H or $CH_3$;

$R_3$, $R_4$ is selected from H;

$R_{5a}$, $R_{5c}$ is selected from H;

$R_{5b}$ is selected from H, F, Cl, Br or $OCH_3$;

$R_7$, $R_8$, $R_9$, $R_{11}$ may be the same or different, selected respectively from H, F, Cl, Br, cyano, $NO_2$, $C_1$-$C_4$alkyl, halo$C_1$-$C_4$alkyl, $C_1$-$C_4$alkoxy, halo$C_1$-$C_4$alkoxy, $C_1$-$C_4$alkoxycarbonyl, $C_1$-$C_4$alkylaminocarbonyl, di($C_1$-$C_4$alkyl)aminocarbonyl, $C_1$-$C_4$alkylsulfonyl or halo$C_1$-$C_4$alkylsulfonyl;

$R_{10}$ is selected from H, F, Cl, Br, I, cyano, $NO_2$, methylsulfonyl, $C_1$-$C_4$alkyl, halo$C_1$-$C_4$alkyl, $C_1$-$C_4$alkoxy or halo$C_1$-$C_4$alkoxy;

A is selected from NH;

Or the salts formed from the compounds represented by general formula III-A with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid or citric acid.

Most preferred compounds represented by formula III of this invention are:

In the general formula III-A, $R_1$ is selected from Cl, $CH_3$, $C_2H_5$, $CHF_2$ or $CF_3$;

$R_2$ is selected from Cl or cyano;

W is selected from H or $CH_3$;

$R_3$, $R_4$ is selected from H;

$R_{5a}$, $R_{5c}$ is selected from H;

$R_{5b}$ is selected from H, Cl or $OCH_3$;

$R_7$, $R_8$, $R_9$, R may be the same or different, selected respectively from H, F, Cl, $CH_3$, cyano, $NO_2$, $CF_3$, $CClF_2$, $CCl_3$, $OCH_3$, $OCF_3$, $OCH_2CF_3$, methylsulfonyl or trifluorosulfonyl;

$R_{10}$ is selected from H, F, Cl, $CH_3$, cyano, $NO_2$, methylsulfonyl, $CF_3$, $CClF_2$, $OCH_3$, $OCF_3$ or $OCH_2CF_3$;

A is selected from NH;

Or the salts formed from the compounds represented by general formula III-A with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid or citric acid.

The terms of substitutes used above to definite the compounds represented by general formula PY are as follows:

The "halogen" or "halo" is fluorine, chlorine, bromine or iodine.

The "alkyl" stands for straight or branched chain alkyl, such as methyl, ethyl, propyl, isopropyl or tert-butyl.

The "cycloalkyl" is substituted or unsubstituted cyclic alkyl, such as cyclopropyl, cyclopentyl or cyclohexyl. The substitute(s) is(are) methyl, halogen, etc.

The "haloalkyl" stands for straight or branched chain alkyl, in which hydrogen atoms can be all or partly substituted with halogen, such as chloromethyl, dichloromethyl, trichloromethyl, fluoromethyl, difluoromethyl, trifluoromethyl, etc.

The "alkoxy" refers to straight or branched chain alkyl, which is linked to the structure by oxygen atom. The "haloalkoxy" refers to straight or branched chain alkoxy, in which hydrogen atoms may be all or partly substituted with halogen, such as chloromethoxy, dichloromethoxy, trichloromethoxy, fluoromethoxy, difluoromethoxy, trifluoromethoxy, chlorofluoromethoxy, trifluoroethoxy, etc. The "alkylthio" refers to straight or branched chain alkyl, which is linked to the structure by sulfur atom. The "haloalkylthio" refers to straight or branched chain alkylthio, in which hydrogen atoms may be all or partly substituted with halogen, such as chloromethylthio, dichloromethylthio, trichloromethylthio, fluoromethylthio, difluoromethylthio, trifluoromethylthio, chlorofluoromethylthio, etc.

The "cyanoalkyl" refers to straight or branched chain alkyl, in which hydrogen atoms may be all or partly substituted with cyano, such as —$CH_2CN$, —$CH_2CH_2CN$, —$CH_2C(CH_3)_2CN$, —$CH_2CH(CN)_2$, etc. The "cyanoalkoxy" refers to alkoxy, in which hydrogen atoms may be all or partly substituted with cyano, such as —$OCH_2CN$. The "haloalkylamino" refers to straight or branched chain alkylamino, in which hydrogen atoms may be all or partly substituted with halogen. The "dialkylamino" such as —$N(CH_3)_2$, —$N(CH_3CH_2)_2$. The "dihaloalkylamino" such as —$N(CF_3)_2$, —$N(CH_2CCl_3)_2$. The "dialkylaminoalkyl" such as —$CH_2N(CH_3)_2$.

The "alkenyl" refers to straight or branched chain alkenyl, such as ethenyl, 1-propenyl, 2-propenyl and different isomer of butenyl, pentenyl and hexenyl. Alkenyl also includes polyene, such as propa-1,2-dienyl and hexa-2,4-dienyl. The "haloalkenyl" stands for straight or branched chain alkenyl, in which hydrogen atoms can be all or partly substituted with halogen. The "alkynyl" refers to straight or branched chain alkynyl, such as ethynyl, 1-propynyl, 2-propynyl and different isomer of butynyl, pentynyl and hexynyl. Alkynyl also includes groups including more than one triple bonds, such as hexa-2,5-diynyl. The "haloalkynyl" stands for straight or branched chain alkynyl, in which hydrogen atoms can be all or partly substituted with halogen.

The alkenoxyl refers to straight or branched chain alkynes is linked to the structure by oxygen, The haloalkenoxyl stands for a straight-chain or branched alkenoxyl, in which hydrogen atoms may be all or partly substituted with halogen. The alkynoxyl refers to straight or branched chain alkynes is linked to the structure by oxygen. The haloalkynoxyl stands for a straight-chain or branched alkynoxyl, in which hydrogen atoms may be all or partly substituted with halogen.

The "alkylsulfinyl" means a straight-chain or branched alkyl is linked to the structure by (—SO—), such as methylsulfinyl.

The "haloalkylsulfinyl" stands for a straight-chain or branched alkylsulfinyl, in which hydrogen atoms may be all or partly substituted with halogen.

The "alkylsulfonyl" means a straight-chain or branched alkyl is linked to the structure by (—$SO_2$—), such as methylsulfonyl.

The "haloalkylsulfonyl" stands for a straight-chain or branched alkylsulfonyl, in which hydrogen atoms may be all or partly substituted with halogen.

The "alkylcarbonyl" means alkyl is linked to the structure by carbonyl, such as —$COCH_3$, —$COCH_2CH_3$. The "haloalkylcarbonyl" stands for a straight-chain or branched alkylcarbonyl, in which hydrogen atoms may be all or partly substituted with halogen, such as —$COCF_3$. The "alkoxyalkyl" means alkyl-O-alkyl-, such as —$CH_2OCH_3$. The "haloalkoxyalkyl" refers to alkoxyalkyl, in which hydrogen atom may be all or partyl substituted with halogen, such as —$CH_2OCH_2CH_2Cl$. The "alkylthioalkyl" means alkyl-S-alkyl-, such as —$CH_2SCH_3$. The "haloalkylthioalkyl" refers to alkylthioalkyl, in which hydrogen atom may be all or partyl substituted with halogen, such as —$CH_2SCH_2CH_2Cl$, —$CH_2SCH_2CF_3$.

The "alkoxycarbonyl" means alkoxy is linked to the structure by carbonyl, such as —$COOCH_3$, —$COOCH_2CH_3$. The "haloalkoxycarbonyl" refers to straight or branched chain alkoxycarbonyl, in which hydrogen atoms can be all or partly substituted with halogen. The "alkylaminocarbonyl" means alkyl-NH—CO—, such as —$CONHCH_3$, —$CONHCH_2CH_3$. The "dialkylaminocarbonyl" such as —$CON(CH_3)_2$, —$CON(CH_2CH_3)_2$.

The "halodialkylaminocarbonyl" such as —$CON(CF_3)_2$, —$CON(CH_2CCl_3)_2$.

The "alkoxycarbonylalkyl" such as —$CH_2COOCH_3$, —$CH_2COOCH_2CH_3$. The "haloalkoxycarbonylalkyl" such as —$CH_2COOCF_3$, —$CH_2COOCH_2CF_3$.

The "alkoxycarbonylamino" such as —$NHCOOCH_3$, —$NHCOOCH_2CH_3$. The "alkoxyaminocarbonyl" such as —$CONHOCH_3$, —$CONHOCH_2CH_3$. The "alkylaminocarbonylalkyl" such as —$CH_2CONHCH_3$, —$CH_2CONHCH_2CH_3$. "dialkylaminocarbonylalkyl" such as —$CH_2CON(CH_3)_2$, —$CH_2CON(CH_2CH_3)_2$.

The "alkenylthio" refers to straight or branched chain alkenyl, which is linked to the structure by sulfur atom. Such as —$SCH_2CH=CH_2$. The "cycloalkyloxycarbonyl" means cyclopropyloxycarbonyl, cyclohexyloxycarbonyl, etc.

The "alkenoxylcarbonyl" means $CH_2=CHCH_2OCO$—. The "alkynoxylcarbonyl" means —$COOCH_2C\equiv CH$. The "alkoxyamino": such as —$NHOCH_3$. The "alkoxyalkoxycarbonyl": such as —$COOCH_2CH_2OCH_3$, etc. The "alkylaminothio" refers to —$SNHCH_3$, —$SNHC_2H_5$. The "dialkylaminothio" refers to —$SN(CH_3)_2$, —$SN(C_2H_5)_2$.

The "alkylcarbonylalkyl" refers to alkyl-CO-alkyl-. The "alkylsulfonylamino" refers to alkyl-$SO_2$—NH—. The "haloalkylsulfonylamino" refers to straight or branched chain alkylsulfonylamino, in which hydrogen atoms can be all or partly substituted with halogen.

The "alkylsulfonylalkylamino" refers to alkyl-$SO_2$-alkyl-NH—.

The "alkylaminosulfonyl" refers to alkyl-NH—$SO_2$—. The"alkylcarbonylaminosulfonyl" refers to alkyl-CO—NH—$SO_2$—. The "dialkylaminosulfonyl" refers to (alkyl)$_2$-N—$SO_2$—.

The "alkylthiocarbonylalkyl" refers to —$CH_2COSCH_3$, —$CH_2COSCH_2CH_3$. The "haloalkylthiocarbonylalkyl" refers to —$CH_2COSCF_3$, —$CH_2COSCH_2CF_3$.

The "alkylcarbonyloxy" such as —$OCOCH_3$. The "haloalkylcarbonyloxy" such as —$OCOCF_3$.

The "alkoxycarbonyloxy" such as —OCOOCH$_3$. The "haloalkoxycarbonyloxy" such as —OCOOCF$_3$. The "alkoxyalkoxy" stands for —OCH$_2$OCH$_3$. The "haloalkoxyalkoxy" stands for —OCH$_2$OCF$_3$. The "alkoxycarbonylalkoxy" stands for —OCH$_2$COOCH$_3$. The "alkylsulfonylaminocarbonyl" refers to alkyl-SO$_2$—NH—CO—.

The "alkylcarbonylamino" refers to alkyl-CO—NH—. The "cycloalkyloxycarbonyl" means cyclopropyloxycarbonyl, cyclohexyloxycarbonyl. The "alkoxycarbonylalkoxy" stands for —OCH$_2$COOCF$_3$. The "alkylsulfonyloxy" such as alkyl-O—SO$_2$CH$_3$. The "haloalkylsulfonyloxy" such as —O—SO$_2$CF$_3$. The "alkylaminocarbonyloxy" such as —O—CONHCH$_3$. The "haloalkylaminocarbonyloxy" such as —O—CONHCF$_3$.

The "aryl" in (hetero)arylcarbonylalkyl, (hetero)arylcarbonyl, (hetero)aryloxycarbonyl, (hetero)arylalkyloxycarbonyl and (hetero)arylalkyl includes phenyl or naphthyl etc. The "heteroaryl" stands for five member ring or six member ring containing one or more N, O, S hetero atoms, such as furyl, pyrazolyl, thiazolyl, pyridinyl, pyrimidinyl, pyrazinyl, pyridazinyl, triazinyl, quinolinyl, etc.

(Hetero)arylcarbonylalkyl refers to —CH$_2$COPh, etc. (Hetero)aryloxycarbonyl such as phenoxycarbonyl, p-chlorophenoxycarbonyl, p-nitrophenoxycarbonyl, naphthyloxycarbonyl, etc. Arylalkyloxycarbonyl means benzyloxycarbonyl, p-chlorobenzyloxycarbonyl, p-trifluoromethylbenzyloxycarbonyl, etc.

(Hetero)arylcarbonyl refers to benzoyl, 4-C$_1$-benzoyl, etc. (Hetero)arylalkyloxycarbonyl refers to —COOCH$_2$Ph, —COOCH$_2$-4-Cl-Ph, etc.

(Hetero)arylalkyl means benzyl, phenylethyl, 4-chloro-benzyl, 2-chloro-5-picolyl, 2-chloro-5-methylthiazole, etc.

The present invention is also explained by the following compounds having a structure as represented by formula I listed in Table 1 to Table 118, but without being restricted thereby.

Table 1: in general formula I-A, $R_1$=CH$_3$, $R_2$=Cl, $R_3$=$R_4$=$R_{5b}$=$R_8$=$R_{10}$=$R_{11}$=H, the substituent $R_9$ refers to Table 1, the representative compounds are coded as I-1-I-58.

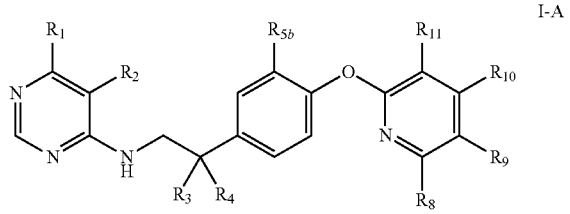

I-A

TABLE 1

| No. | $R_9$ |
|---|---|
| I-1 | H |
| I-2 | F |
| I-3 | Cl |
| I-4 | Br |
| I-5 | I |
| I-6 | CH$_3$ |
| I-7 | Et |
| I-8 | n-Pr |
| I-9 | i-Pr |
| I-10 | n-Bu |
| I-11 | s-Bu |
| I-12 | t-Bu |
| I-13 | CH$_2$F |

TABLE 1-continued

| No. | $R_9$ |
|---|---|
| I-14 | CH$_2$Cl |
| I-15 | CH$_2$Br |
| I-16 | CHF$_2$ |
| I-17 | CHCl$_2$ |
| I-18 | CHBr$_2$ |
| I-19 | CClF$_2$ |
| I-20 | CCl$_3$ |
| I-21 | CBr$_3$ |
| I-22 | CF$_3$ |
| I-23 | CN |
| I-24 | CH$_2$OCH$_3$ |
| I-25 | CH$_2$OCH$_2$CF$_3$ |
| I-26 | CH$_2$N(CH$_3$)$_2$ |
| I-27 | CH$_2$CN |
| I-28 | OCH$_3$ |
| I-29 | OCF$_3$ |
| I-30 | OCH$_2$CF$_3$ |
| I-31 | SCH$_3$ |
| I-32 | SO$_2$CH$_3$ |
| I-33 | CO$_2$H |
| I-34 | CO$_2$CH$_3$ |
| I-35 | CO$_2$C$_2$H$_5$ |
| I-36 | CO$_2$CH$_2$CF$_3$ |
| I-37 | CO$_2$-t-Bu |
| I-38 | CONH$_2$ |
| I-39 | CONHCH$_3$ |
| I-40 | CON(CH$_3$)$_2$ |
| I-41 | CON(CH$_3$)$_2$ |
| I-42 | CONHNHCH$_3$ |
| I-43 | CONHN(CH$_3$)$_2$ |
| I-44 | CONHOCH$_3$ |
| I-45 | CONHNH$_2$ |
| I-46 | CON(CH$_3$)NH$_2$ |
| I-47 | CONHNHCOCH$_3$ |
| I-48 | CONHNHCO$_2$CH$_3$ |
| I-49 | CONHNH-Ph |
| I-50 | NO$_2$ |
| I-51 | NH$_2$ |
| I-52 | NHCH$_3$ |
| I-53 | NHCH$_2$CH$_3$ |
| I-54 | NHCOCH$_3$ |
| I-55 | NHCO$_2$CH$_3$ |
| I-56 | NHSO$_2$CH$_3$ |
| I-57 | NHSO$_2$CF$_3$ |
| I-58 | N(CH$_3$)SO$_2$CH$_3$ |

Table 2: in general formula I-A, $R_1$=CH$_3$, $R_2$=$R_{5b}$=Cl, $R_3$=$R_4$=$R_8$=$R_{10}$=$R_{11}$=H, the substituent $R_9$ are consistent with those in Table 1 and corresponding to I-1-I-58 in table 1 in turn, the representative compounds are coded as I-59-I-116.

Table 3: in general formula I-A, $R_1$=CH$_3$, $R_2$=Cl, $R_{5b}$=Br, $R_3$=$R_4$=$R_8$=$R_{10}$=$R_{11}$=H, the substituent $R_9$ are consistent with those in Table 1 and corresponding to I-1-I-58 in table 1 in turn, the representative compounds are coded as I-117-I-174.

Table 4: in general formula I-A, $R_1$=CH$_3$, $R_2$=Cl, $R_{5b}$=OCH$_3$, $R_3$=$R_4$=$R_8$=$R_{10}$=$R_{11}$=H, the substituent $R_9$ are consistent with those in Table 1 and corresponding to I-1-I-58 in table 1 in turn, the representative compounds are coded as I-175-I-232.

Table 5: in general formula I-A, $R_1$=C$_2$H$_5$, $R_2$=Cl, $R_3$=$R_4$=$R_{5b}$=$R_8$=$R_{10}$=$R_{11}$=H, the substituent $R_9$ are consistent with those in Table 1 and corresponding to I-1-I-58 in table 1 in turn, the representative compounds are coded as I-233-I-290.

Table 6: in general formula I-A, $R_1$=C$_2$H$_5$, $R_2$=$R_{5b}$=Cl, $R_3$=$R_4$=$R_8$=$R_{10}$=$R_{11}$=H, the substituent $R_9$ are consistent with those in Table 1 and corresponding to I-1-I-58 in table 1 in turn, the representative compounds are coded as I-291-I-348.

Table 7: in general formula I-A, $R_1=C_2H_5$, $R_2=Cl$, $R_{5b}=Br$, $R_3=R_4=R_8=R_{10}=R_{11}=H$, the substituent $R_9$ are consistent with those in Table 1 and corresponding to I-1-I-58 in table 1 in turn, the representative compounds are coded as I-349-I-406.

Table 8: in general formula I-A, $R_1=C_2H_5$, $R_2=Cl$, $R_{5b}=OCH_3$, $R_3=R_4=R_8=R_{10}=R_{11}=H$, the substituent $R_9$ are consistent with those in Table 1 and corresponding to I-1-I-58 in table 1 in turn, the representative compounds are coded as I-407-I-464.

Table 9: in general formula I-A, $R_1=CH_3$, $R_2=R_{11}=Cl$, $R_3=R_4=R_{5b}=R_8=R_{10}=H$, the substituent $R_9$ are consistent with those in Table 1 and corresponding to I-1-I-58 in table 1 in turn, the representative compounds are coded as I-465-I-522.

Table 10: in general formula I-A, $R_1=CH_3$, $R_2=Cl$, $R_{11}=NO_2$, $R_3=R_4=R_{5b}=R_8=R_{10}=H$, the substituent $R_9$ are consistent with those in Table 1 and corresponding to I-1-I-58 in table 1 in turn, the representative compounds are coded as I-523-I-580.

Table 11: in general formula I-A, $R_1=C_2H_5$, $R_2=R_{11}=Cl$, $R_3=R_4=R_{5b}=R_8=R_{10}=H$, the substituent $R_9$ are consistent with those in Table 1 and corresponding to I-1-I-58 in table 1 in turn, the representative compounds are coded as I-581-I-638.

Table 12: in general formula I-A, $R_1=C_2H_5$, $R_2=Cl$, $R_{11}=NO_2$, $R_3=R_4=R_{5b}=R_8=R_{10}=H$, the substituent $R_9$ are consistent with those in Table 1 and corresponding to I-1-I-58 in table 1 in turn, the representative compounds are coded as I-639-I-696.

Table 13: in general formula I-A, $R_1=CH_3$, $R_2=R_8=R_{11}=Cl$, $R_3=R_4=R_{5b}=R_{10}=H$, the substituent $R_9$ are consistent with those in Table 1 and corresponding to I-1-I-58 in table 1 in turn, the representative compounds are coded as I-697-I-754.

Table 14: in general formula I-A, $R_1=CH_3$, $R_2=R_8=R_{10}=R_{11}=Cl$, $R_3=R_4=R_{5b}=H$, the substituent $R_9$ are consistent with those in Table 1 and corresponding to I-1-I-58 in table 1 in turn, the representative compounds are coded as I-755-I-812.

Table 15: in general formula I-A, $R_1=C_2H_5$, $R_2=R_8=R_1=Cl$, $R_3=R_4=R_{5b}=R_{10}=H$, the substituent $R_9$ are consistent with those in Table 1 and corresponding to I-1-I-58 in table 1 in turn, the representative compounds are coded as I-813-I-870.

Table 16: in general formula I-A, $R_1=C_2H_5$, $R_2=R_8=R_{10}=R_{11}=Cl$, $R_3=R_4=R_{5b}=H$, the substituent $R_9$ are consistent with those in Table 1 and corresponding to I-1-I-58 in table 1 in turn, the representative compounds are coded as I-871-I-928.

Table 17: in general formula I-A, $R_1=CH_3$, $R_2=Cl$, $R_{11}=CF_3$, $R_3=R_4=R_{5b}=R_8=R_{10}=H$, the substituent $R_9$ are consistent with those in Table 1 and corresponding to I-1-I-58 in table 1 in turn, the representative compounds are coded as I-929-I-986.

Table 18: in general formula I-A, $R_1=C_2H_5$, $R_2=Cl$, $R_{11}=CF_3$, $R_3=R_4=R_{5b}=R_8=R_{10}=H$, the substituent $R_9$ are consistent with those in Table 1 and corresponding to I-1-I-58 in table 1 in turn, the representative compounds are coded as I-987-I-1044.

Table 19: in general formula I-A, $R_1=CH_3$, $R_2=Cl$, $R_{11}=CO_2CH_3$, $R_3=R_4=R_{5b}=R_8=R_{10}=H$, the substituent $R_9$ are consistent with those in Table 1 and corresponding to I-1-I-58 in table 1 in turn, the representative compounds are coded as I-1045-I-1102.

Table 20: in general formula I-A, $R_1=CH_3$, $R_2=Cl$, $R_{11}=CONH_2$, $R_3=R_4=R_{5b}=R_8=R_{10}=H$, the substituent $R_9$ are consistent with those in Table 1 and corresponding to I-1-I-58 in table 1 in turn, the representative compounds are coded as I-1103-I-1160.

Table 21: in general formula I-A, $R_1=CH_3$, $R_2=Cl$, $R_1=CONHCH_3$, $R_3=R_4=R_{5b}=R_8=R_{10}=H$, the substituent $R_9$ are consistent with those in Table 1 and corresponding to I-1-I-58 in table 1 in turn, the representative compounds are coded as I-1161-I-1218.

Table 22: in general formula I-A, $R_1=C_2H_5$, $R_2=Cl$, $R_{11}=CO_2CH_3$, $R_3=R_4=R_{5b}=R_8=R_{10}=H$, the substituent $R_9$ are consistent with those in Table 1 and corresponding to I-1-I-58 in table 1 in turn, the representative compounds are coded as I-1219-I-1276.

Table 23: in general formula I-A, $R_1=C_2H_5$, $R_2=Cl$, $R_1=CONH_2$, $R_3=R_4=R_{5b}=R_8=R_{10}=H$, the substituent $R_9$ are consistent with those in Table 1 and corresponding to I-1-I-58 in table 1 in turn, the representative compounds are coded as I-1277-I-1334.

Table 24: in general formula I-A, $R_1=C_2H_5$, $R_2=Cl$, $R_{11}=CONHCH_3$, $R_3=R_4=R_{5b}=R_8=R_{10}=H$, the substituent $R_9$ are consistent with those in Table 1 and corresponding to I-1-I-58 in table 1 in turn, the representative compounds are coded as I-1335-I-1392.

Table 25: in general formula I-A, $R_1=CH_3$, $R_2=R_{5b}=R_{11}=Cl$, $R_3=R_4=R_8=R_{10}=H$, the substituent $R_9$ are consistent with those in Table 1 and corresponding to I-1-I-58 in table 1 in turn, the representative compounds are coded as I-1393-I-1450.

Table 26: in general formula I-A, $R_1=C_2H_5$, $R_2=R_{5b}=R_{11}=Cl$, $R_3=R_4=R_8=R_{10}=H$, the substituent $R_9$ are consistent with those in Table 1 and corresponding to I-1-I-58 in table 1 in turn, the representative compounds are coded as I-1451-I-1508.

Table 27: in general formula I-A, $R_1=CH_3$, $R_2=R_{11}=Cl$, $R_{5b}=Br$, $R_3=R_4=R_8=R_{10}=H$, the substituent $R_9$ are consistent with those in Table 1 and corresponding to I-1-I-58 in table 1 in turn, the representative compounds are coded as I-1509-I-1566.

Table 28: in general formula I-A, $R_1=C_2H_5$, $R_2=R_{11}=Cl$, $R_{5b}=Br$, $R_3=R_4=R_8=R_{10}=H$, the substituent $R_9$ are consistent with those in Table 1 and corresponding to I-1-I-58 in table 1 in turn, the representative compounds are coded as I-1567-I-1624.

Table 29: in general formula I-A, $R_1=CH_3$, $R_2=R_1=Cl$, $R_{5b}=OCH_3$, $R_3=R_4=R_8=R_{10}=H$, the substituent $R_9$ are consistent with those in Table 1 and corresponding to I-1-I-58 in table 1 in turn, the representative compounds are coded as I-1625-I-1682.

Table 30: in general formula I-A, $R_1=C_2H_5$, $R_2=R_1=Cl$, $R_{5b}=OCH_3$, $R_3=R_4=R_8=R_{10}=H$, the substituent $R_9$ are consistent with those in Table 1 and corresponding to I-1-I-58 in table 1 in turn, the representative compounds are coded as I-1683-I-1740.

Table 31: in general formula I-A, $R_1=CH_3$, $R_2=Br$, $R_3=R_4=R_{5b}=R_8=R_{10}=R_{11}=H$, the substituent $R_9$ are consistent with those in Table 1 and corresponding to I-1-I-58 in table 1 in turn, the representative compounds are coded as I-1741-I-1798.

Table 32: in general formula I-A, $R_1=C_2H_5$, $R_2=Br$, $R_3=R_4=R_{5b}=R_8=R_{10}=R_{11}=H$, the substituent $R_9$ are consistent with those in Table 1 and corresponding to I-1-I-58 in table 1 in turn, the representative compounds are coded as I-1799-I-1856.

Table 33: in general formula I-A, $R_1=CH_3$, $R_2=Br$, $R_{11}=Cl$, $R_3=R_4=R_{5b}=R_8=R_{10}=H$, the substituent $R_9$ are consistent with those in Table 1 and corresponding to I-1-I-58 in table 1 in turn, the representative compounds are coded as I-1857-I-1914.

Table 34: in general formula I-A, $R_1=C_2H_5$, $R_2=Br$, $R_{11}=Cl$, $R_3=R_4=R_{5b}=R_8=R_{10}=H$, the substituent $R_9$ are consistent with those in Table 1 and corresponding to I-1-I-58 in table 1 in turn, the representative compounds are coded as I-1915-I-1972.

Table 35: in general formula I-A, $R_1=CH_3$, $R_2=Br$, $R_{5b}=Cl$, $R_3=R_4=R_8=R_{10}=R_{11}=H$, the substituent $R_9$ are consistent with those in Table 1 and corresponding to I-1-I-58 in table 1 in turn, the representative compounds are coded as I-1973-I-2030.

Table 36: in general formula I-A, $R_1=C_2H_5$, $R_2=Br$, $R_{5b}=Cl$, $R_3=R_4=R_8=R_{10}=R_{11}=H$, the substituent $R_9$ are consistent with those in Table 1 and corresponding to I-1-I-58 in table 1 in turn, the representative compounds are coded as I-2031-I-2088.

Table 37: in general formula I-A, $R_1=CH_3$, $R_2=R_{5b}=Br$, $R_3=R_4=R_8=R_{10}=R_{11}=H$, the substituent $R_9$ are consistent with those in Table 1 and corresponding to I-1-I-58 in table 1 in turn, the representative compounds are coded as I-2089-I-2146.

Table 38: in general formula I-A, $R_1=C_2H_5$, $R_2=R_{5b}=Br$, $R_3=R_4=R_8=R_{10}=R_{11}=H$, the substituent $R_9$ are consistent with those in Table 1 and corresponding to I-1-I-58 in table 1 in turn, the representative compounds are coded as I-2147-I-2204.

Table 39: in general formula I-A, $R_1=CH_3$, $R_2=Br$, $R_{5b}=OCH_3$, $R_3=R_4=R_8=R_{10}=R_{11}=H$, the substituent $R_9$ are consistent with those in Table 1 and corresponding to I-1-I-58 in table 1 in turn, the representative compounds are coded as I-2205-I-2262.

Table 40: in general formula I-A, $R_1=C_2H_5$, $R_2=Br$, $R_{5b}=OCH_3$, $R_3=R_4=R_8=R_{10}=R_{11}=H$, the substituent $R_9$ are consistent with those in Table 1 and corresponding to I-1-I-58 in table 1 in turn, the representative compounds are coded as I-2263-I-2320.

Table 41: in general formula I-A, $R_1=CF_2H$, $R_2=Cl$, $R_3=R_4=R_{5b}=R_8=R_{10}=R_{11}=H$, the substituent $R_9$ are consistent with those in Table 1 and corresponding to I-1-I-58 in table 1 in turn, the representative compounds are coded as I-2321-I-2378.

Table 42: in general formula I-A, $R_1=CF_2H$, $R_2=R_{5b}=Cl$, $R_3=R_4=R_8=R_{10}=R_{11}=H$, the substituent $R_9$ are consistent with those in Table 1 and corresponding to I-1-I-58 in table 1 in turn, the representative compounds are coded as I-2379-I-2436.

Table 43: in general formula I-A, $R_1=CF_2H$, $R_2=Cl$, $R_{5b}=OCH_3$, $R_3=R_4=R_8=R_{10}=R_{11}=H$, the substituent $R_9$ are consistent with those in Table 1 and corresponding to I-1-I-58 in table 1 in turn, the representative compounds are coded as I-2437-I-2494.

Table 44: in general formula I-A, $R_1=CF_2H$, $R_2=Cl$, $R_{5b}=Br$, $R_3=R_4=R_8=R_{10}=R_{11}=H$, the substituent $R_9$ are consistent with those in Table 1 and corresponding to I-1-I-58 in table 1 in turn, the representative compounds are coded as I-2495-I-2552.

Table 45: in general formula I-A, $R_1=CF_2H$, $R_2=R_{11}=Cl$, $R_3=R_4=R_{5b}=R_8=R_{10}=H$, the substituent $R_9$ are consistent with those in Table 1 and corresponding to I-1-I-58 in table 1 in turn, the representative compounds are coded as I-2553-I-2610.

Table 46: in general formula I-A, $R_1=CF_2H$, $R_2=Cl$, $R_{11}=NO_2$, $R_3=R_4=R_{5b}=R_8=R_{10}=H$, the substituent $R_9$ are consistent with those in Table 1 and corresponding to I-1-I-58 in table 1 in turn, the representative compounds are coded as I-2611-I-2668.

Table 47: in general formula I-A, $R_1=CF_2H$, $R_2=R_{11}=Cl$, $R_{5b}=OCH_3$, $R_3=R_4=R_8=R_{10}=H$, the substituent $R_9$ are consistent with those in Table 1 and corresponding to I-1-I-58 in table 1 in turn, the representative compounds are coded as I-2669-I-2726.

Table 48: in general formula I-A, $R_1=CF_3$, $R_2=Cl$, $R_3=R_4=R_{5b}=R_8=R_{10}=R_{11}=H$, the substituent $R_9$ are consistent with those in Table 1 and corresponding to I-1-I-58 in table 1 in turn, the representative compounds are coded as I-2727-I-2784.

Table 49: in general formula I-A, $R_1=CF_3$, $R_2=R_{11}=Cl$, $R_3=R_4=R_{5b}=R_8=R_{10}=H$, the substituent $R_9$ are consistent with those in Table 1 and corresponding to I-1-I-58 in table 1 in turn, the representative compounds are coded as I-2785-I-2842.

Table 50: in general formula I-A, $R_1=CF_3$, $R_2=Cl$, $R_{11}=NO_2$, $R_3=R_4=R_{5b}=R_8=R_{10}=H$, the substituent $R_9$ are consistent with those in Table 1 and corresponding to I-1-I-58 in table 1 in turn, the representative compounds are coded as I-2843-I-2900.

Table 51: in general formula I-A, $R_1=CH_2Cl$, $R_2=Cl$, $R_3=R_4=R_{5b}=R_8=R_{10}=R_{11}=H$, the substituent $R_9$ are consistent with those in Table 1 and corresponding to I-1-I-58 in table 1 in turn, the representative compounds are coded as I-2901-I-2958.

Table 52: in general formula I-A, $R_1=CH_2Cl$, $R_2=Cl$, $R_{11}=NO_2$, $R_3=R_4=R_{5b}=R_8=R_{10}=H$, the substituent $R_9$ are consistent with those in Table 1 and corresponding to I-1-I-58 in table 1 in turn, the representative compounds are coded as I-2959-I-3016.

Table 53: in general formula I-A, $R_1=CH_2Cl$, $R_2=R_{11}=Cl$, $R_3=R_4=R_{5b}=R_8=R_{10}=H$, the substituent $R_9$ are consistent with those in Table 1 and corresponding to I-1-I-58 in table 1 in turn, the representative compounds are coded as I-3017-I-3074.

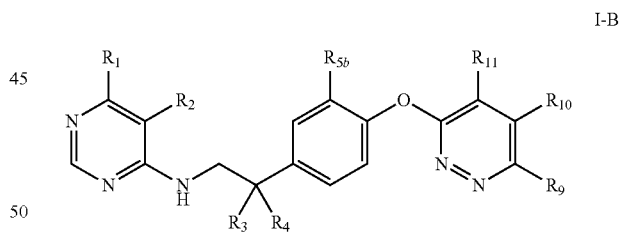

I-B

Table 54: in general formula I-B, $R_1=CH_3$, $R_2=Cl$, $R_3=R_4=R_{5b}=R_{10}=R_{11}=H$, the substituent $R_9$ are consistent with those in Table 1 and corresponding to I-1-I-58 in table 1 in turn, the representative compounds are coded as I-3075-I-3132.

Table 55: in general formula I-B, $R_1=CH_3$, $R_2=R_{5b}=Cl$, $R_3=R_4=R_{10}=R_{11}=H$, the substituent $R_9$ are consistent with those in Table 1 and corresponding to I-1-I-58 in table 1 in turn, the representative compounds are coded as I-3133-I-3190.

Table 56: in general formula I-B, $R_1=CH_3$, $R_2=Cl$, $R_{5b}=Br$, $R_3=R_4=R_{10}=R_{11}=H$, the substituent $R_9$ are consistent with those in Table 1 and corresponding to I-1-I-58 in table 1 in turn, the representative compounds are coded as I-3191-I-3248.

Table 57: in general formula I-B, $R_1=CH_3$, $R_2=Cl$, $R_{5b}=OCH_3$, $R_3=R_4=R_{10}=R_{11}=H$, the substituent $R_9$ are consistent with those in Table 1 and corresponding to I-1-I-58 in table 1 in turn, the representative compounds are coded as I-3249-I-3306.

Table 58: in general formula I-B, $R_1=C_2H_5$, $R_2=Cl$, $R_3=R_4=R_{5b}=R_{10}=R_{11}=H$, the substituent $R_9$ are consistent with those in Table 1 and corresponding to I-1-I-58 in table 1 in turn, the representative compounds are coded as I-3307-I-3364.

Table 59: in general formula I-B, $R_1=C_2H_5$, $R_2=R_{5b}=Cl$, $R_3=R_4=R_{10}=R_{11}=H$, the substituent $R_9$ are consistent with those in Table 1 and corresponding to I-1-I-58 in table 1 in turn, the representative compounds are coded as I-3365-I-3422.

Table 60: in general formula I-B, $R_1=C_2H_5$, $R_2=Cl$, $R_{5b}=Br$, $R_3=R_4=R_{10}=R_{11}=H$, the substituent $R_9$ are consistent with those in Table 1 and corresponding to I-1-I-58 in table 1 in turn, the representative compounds are coded as I-3423-I-3480.

Table 61: in general formula I-B, $R_1=C_2H_5$, $R_2=Cl$, $R_{5b}=OCH_3$, $R_3=R_4=R_{10}=R_{11}=H$, the substituent $R_9$ are consistent with those in Table 1 and corresponding to I-1-I-58 in table 1 in turn, the representative compounds are coded as I-3481-I-3538.

Table 62: in general formula I-B, $R_1=CH_3$, $R_2=R_{11}=Cl$, $R_3=R_4=R_{5b}=R_{10}=H$, the substituent $R_9$ are consistent with those in Table 1 and corresponding to I-1-I-58 in table 1 in turn, the representative compounds are coded as I-3539-I-3596.

Table 63: in general formula I-B, $R_1=CH_3$, $R_2=Cl$, $R_{11}=NO_2$, $R_3=R_4=R_{5b}=R_{10}=H$, the substituent $R_9$ are consistent with those in Table 1 and corresponding to I-1-I-58 in table 1 in turn, the representative compounds are coded as I-3597-I-3654.

Table 64: in general formula I-B, $R_1=C_2H_5$, $R_2=R_{11}=Cl$, $R_3=R_4=R_{5b}=R_{10}=H$, the substituent $R_9$ are consistent with those in Table 1 and corresponding to I-1-I-58 in table 1 in turn, the representative compounds are coded as I-3655-I-3712.

Table 65: in general formula I-B, $R_1=C_2H_5$, $R_2=Cl$, $R_{11}=NO_2$, $R_3=R_4=R_{5b}=R_{10}=H$, the substituent $R_9$ are consistent with those in Table 1 and corresponding to I-1-I-58 in table 1 in turn, the representative compounds are coded as I-3713-I-3770.

Table 66: in general formula I-B, $R_1=CH_3$, $R_2=R_{10}=Cl$, $R_3=R_4=R_{5b}=R_{11}=H$, the substituent $R_9$ are consistent with those in Table 1 and corresponding to I-1-I-58 in table 1 in turn, the representative compounds are coded as I-3771-I-3828.

Table 67: in general formula I-B, $R_1=CH_3$, $R_2=R_{10}=R_{11}=Cl$, $R_3=R_4=R_{5b}=H$, the substituent $R_9$ are consistent with those in Table 1 and corresponding to I-1-I-58 in table 1 in turn, the representative compounds are coded as I-3829-I-3886.

Table 68: in general formula I-B, $R_1=C_2H_5$, $R_2=R_{11}=Cl$, $R_3=R_4=R_{5b}=R_{10}=H$, the substituent $R_9$ are consistent with those in Table 1 and corresponding to I-1-I-58 in table 1 in turn, the representative compounds are coded as I-3887-I-3944.

Table 69: in general formula I-B, $R_1=C_2H_5$, $R_2=R_{10}=R_{11}=Cl$, $R_3=R_4=R_{5b}=H$, the substituent $R_9$ are consistent with those in Table 1 and corresponding to I-1-I-58 in table 1 in turn, the representative compounds are coded as I-3945-I-4002.

Table 70: in general formula I-B, $R_1=CH_3$, $R_2=Cl$, $R_{11}=CF_3$, $R_3=R_4=R_{5b}=R_{10}=H$, the substituent $R_9$ are consistent with those in Table 1 and corresponding to I-1-I-58 in table 1 in turn, the representative compounds are coded as I-4003-I-4060.

Table 71: in general formula I-B, $R_1=C_2H_5$, $R_2=Cl$, $R_{11}=CF_3$, $R_3=R_4=R_{5b}=R_{10}=H$, the substituent $R_9$ are consistent with those in Table 1 and corresponding to I-1-I-58 in table 1 in turn, the representative compounds are coded as I-4061-I-4118.

Table 72: in general formula I-B, $R_1=CH_3$, $R_2=Br$, $R_3=R_4=R_{5b}=R_{10}=R_{11}=H$, the substituent $R_9$ are consistent with those in Table 1 and corresponding to I-1-I-58 in table 1 in turn, the representative compounds are coded as I-4119-I-4176.

Table 73: in general formula I-B, $R_1=C_2H_5$, $R_2=Br$, $R_3=R_4=R_{5b}=R_{10}=R_{11}=H$, the substituent $R_9$ are consistent with those in Table 1 and corresponding to I-1-I-58 in table 1 in turn, the representative compounds are coded as I-4177-I-4234.

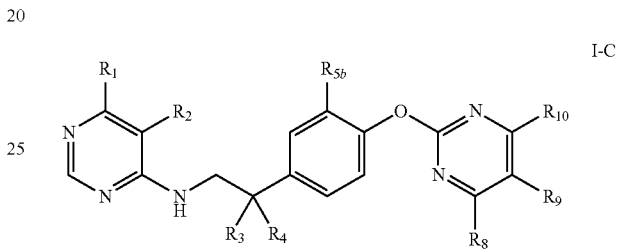

I-C

Table 74: in general formula I-C, $R_1=CH_3$, $R_2=Cl$, $R_3=R_4=R_{5b}=R_8=R_{10}=H$, the substituent $R_9$ are consistent with those in Table 1 and corresponding to I-1-I-58 in table 1 in turn, the representative compounds are coded as I-4235-I-4292.

Table 75: in general formula I-C, $R_1=CH_3$, $R_2=R_{5b}=Cl$, $R_3=R_4=R_8=R_{10}=H$, the substituent $R_9$ are consistent with those in Table 1 and corresponding to I-1-I-58 in table 1 in turn, the representative compounds are coded as I-4293-I-4350.

Table 76: in general formula I-C, $R_1=CH_3$, $R_2=Cl$, $R_{5b}=Br$, $R_3=R_4=R_8=R_{10}=H$, the substituent $R_9$ are consistent with those in Table 1 and corresponding to I-1-I-58 in table 1 in turn, the representative compounds are coded as I-4351-I-4408.

Table 77: in general formula I-C, $R_1=CH_3$, $R_2=Cl$, $R_{5b}=Br$, $R_3=R_4=R_8=R_{10}=H$, the substituent $R_9$ are consistent with those in Table 1 and corresponding to I-1-I-58 in table 1 in turn, the representative compounds are coded as I-4409-I-4466.

Table 78: in general formula I-C, $R_1=C_2H_5$, $R_2=Cl$, $R_3=R_4=R_{5b}=R_8=R_{10}=H$, the substituent $R_9$ are consistent with those in Table 1 and corresponding to I-1-I-58 in table 1 in turn, the representative compounds are coded as I-4467-I-4524.

Table 79: in general formula I-C, $R_1=C_2H_5$, $R_2=R_{5b}=Cl$, $R_3=R_4=R_8=R_{10}=H$, the substituent $R_9$ are consistent with those in Table 1 and corresponding to I-1-I-58 in table 1 in turn, the representative compounds are coded as I-4525-I-4582.

Table 80: in general formula I-C, $R_1=C_2H_5$, $R_2=Cl$, $R_{5b}=Br$, $R_3=R_4=R_8=R_{10}=H$, the substituent $R_9$ are consistent with those in Table 1 and corresponding to I-1-I-58 in table 1 in turn, the representative compounds are coded as I-4583-I-4640.

Table 81: in general formula I-C, $R_1=C_2H_5$, $R_2=Cl$, $R_{5b}=OCH_3$, $R_3=R_4=R_8=R_{10}=H$, the substituent $R_9$ are consistent with those in Table 1 and corresponding to I-1-I-58 in table 1 in turn, the representative compounds are coded as I-4641-I-4698.

Table 82: in general formula I-C, $R_1$=$CH_3$, $R_2$=Cl, $R_3$=$R_4$=$R_{5b}$=H, $R_8$=$R_{10}$=$CH_3$, the substituent $R_9$ are consistent with those in Table 1 and corresponding to I-1-I-58 in table 1 in turn, the representative compounds are coded as I-4699-I-4756.

Table 83: in general formula I-C, $R_1$=$CH_3$, $R_2$=Cl, $R_3$=$R_4$=$R_{5b}$=H, $R_8$=$R_{10}$=$OCH_3$, the substituent $R_9$ are consistent with those in Table 1 and corresponding to I-1-I-58 in table 1 in turn, the representative compounds are coded as I-4757-I-4814.

Table 84: in general formula I-C, $R_1$=$CH_3$, $R_2$=Cl, $R_3$=$R_4$=$R_{5b}$=H, $R_8$=$R_{10}$=Cl, the substituent $R_9$ are consistent with those in Table 1 and corresponding to I-1-I-58 in table 1 in turn, the representative compounds are coded as I-4815-I-4872.

Table 85: in general formula I-C, $R_1$=$CH_3$, $R_2$=Cl, $R_3$=$CH_3$, $R_4$=$R_{5b}$=$R_8$=$R_{10}$=H, the substituent $R_9$ are consistent with those in Table 1 and corresponding to I-1-I-58 in table 1 in turn, the representative compounds are coded as I-4873-I-4930.

Table 86: in general formula I-C, $R_1$=$CH_3$, $R_2$=Cl, $R_3$=$CH_3$, $R_4$=$R_{5b}$=H, $R_8$=$R_{10}$=$CH_3$, the substituent $R_9$ are consistent with those in Table 1 and corresponding to I-1-I-58 in table 1 in turn, the representative compounds are coded as I-4931-I-4988.

Table 87: in general formula I-C, $R_1$=$CH_3$, $R_2$=Cl, $R_3$=$CH_3$, $R_4$=$R_{5b}$=H, $R_8$=$R_{10}$=$OCH_3$, the substituent $R_9$ are consistent with those in Table 1 and corresponding to I-1-I-58 in table 1 in turn, the representative compounds are coded as I-4989-I-5046.

Table 88: in general formula I-C, $R_1$=$CH_3$, $R_2$=Cl, $R_3$=$CH_3$, $R_4$=$R_{5b}$=H, $R_8$=$R_{10}$=Cl, the substituent $R_9$ are consistent with those in Table 1 and corresponding to I-1-I-58 in table 1 in turn, the representative compounds are coded as I-5047-I-5104.

Table 89: in general formula I-C, $R_1$=$C_2H_5$, $R_2$=Cl, $R_3$=$CH_3$, $R_4$=$R_{5b}$=$R_8$=$R_{10}$=H, the substituent $R_9$ are consistent with those in Table 1 and corresponding to I-1-I-58 in table 1 in turn, the representative compounds are coded as I-5105-I-5162.

Table 90: in general formula I-C, $R_1$=$C_2H_5$, $R_2$=Cl, $R_3$=$R_4$=$R_{5b}$=H, $R_8$=$R_{10}$=$CH_3$, the substituent $R_9$ are consistent with those in Table 1 and corresponding to I-1-I-58 in table 1 in turn, the representative compounds are coded as I-5163-I-5220.

Table 91: in general formula I-C, $R_1$=$C_2H_5$, $R_2$=Cl, $R_3$=$R_4$=$R_{5b}$=H, $R_8$=$R_{10}$=$OCH_3$, the substituent $R_9$ are consistent with those in Table 1 and corresponding to I-1-I-58 in table 1 in turn, the representative compounds are coded as I-5221-I-5278.

Table 92: in general formula I-C, $R_1$=$C_2H_5$, $R_2$=Cl, $R_3$=$R_4$=$R_{5b}$=H, $R_8$=$R_{10}$=Cl, the substituent $R_9$ are consistent with those in Table 1 and corresponding to I-1-I-58 in table 1 in turn, the representative compounds are coded as I-5279-I-5336.

Table 93: in general formula I-C, $R_1$=$CH_3$, $R_2$=$R_8$=Cl, $R_3$=$R_4$=$R_{5b}$=$R_{10}$=H, the substituent $R_9$ are consistent with those in Table 1 and corresponding to I-1-I-58 in table 1 in turn, the representative compounds are coded as I-5337-I-5394.

Table 94: in general formula I-C, $R_1$=$CH_3$, $R_2$=Cl, $R_8$=$CH_3$, $R_3$=$R_4$=$R_{5b}$=$R_{10}$=H, the substituent $R_9$ are consistent with those in Table 1 and corresponding to I-1-I-58 in table 1 in turn, the representative compounds are coded as I-5395-I-5452.

Table 95: in general formula I-C, $R_1$=$CH_3$, $R_2$=Cl, $R_8$=$OCH_3$, $R_3$=$R_4$=$R_{5b}$=$R_{10}$=H, the substituent $R_9$ are consistent with those in Table 1 and corresponding to I-1-I-58 in table 1 in turn, the representative compounds are coded as I-5453-I-5510.

Table 96: in general formula I-C, $R_1$=$C_2H_5$, $R_2$=$R_8$=Cl, $R_3$=$R_4$=$R_{5b}$=$R_{10}$=H, the substituent $R_9$ are consistent with those in Table 1 and corresponding to I-1-I-58 in table 1 in turn, the representative compounds are coded as I-5511-I-5568.

Table 97: in general formula I-C, $R_1$=$C_2H_5$, $R_2$=Cl, $R_8$=$CH_3$, $R_3$=$R_4$=$R_{5b}$=$R_{10}$=H, the substituent $R_9$ are consistent with those in Table 1 and corresponding to I-1-I-58 in table 1 in turn, the representative compounds are coded as I-5569-I-5626.

Table 98: in general formula I-C, $R_1$=$C_2H_5$, $R_2$=Cl, $R_8$=$OCH_3$, $R_3$=$R_4$=$R_{5b}$=$R_{10}$=H, the substituent $R_9$ are consistent with those in Table 1 and corresponding to I-1-I-58 in table 1 in turn, the representative compounds are coded as I-5627-I-5684.

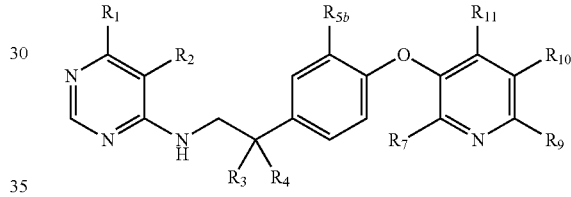

I-D

Table 99: in general formula I-D, $R_1$=$CH_3$, $R_2$=Cl, $R_3$=$R_4$=$R_{5b}$=$R_7$=$R_{10}$=$R_{11}$=H, the substituent $R_9$ are consistent with those in Table 1 and corresponding to I-1-I-58 in table 1 in turn, the representative compounds are coded as I-5685-I-5742.

Table 100: in general formula I-D, $R_1$=$CH_3$, $R_2$=$R_{5b}$=Cl, $R_3$=$R_4$=$R_7$=$R_{10}$=$R_{11}$=H, the substituent $R_9$ are consistent with those in Table 1 and corresponding to I-1-I-58 in table 1 in turn, the representative compounds are coded as I-5743-I-5800.

Table 101: in general formula I-D, $R_1$=$CH_3$, $R_2$=Cl, $R_{5b}$=Br, $R_3$=$R_4$=$R_7$=$R_{10}$=$R_{11}$=H, the substituent $R_9$ are consistent with those in Table 1 and corresponding to I-1-I-58 in table 1 in turn, the representative compounds are coded as I-5801-I-5858.

Table 102: in general formula I-D, $R_1$=$CH_3$, $R_2$=Cl, $R_{5b}$=$OCH_3$, $R_3$=$R_4$=$R_7$=$R_{10}$=$R_{11}$=H, the substituent $R_9$ are consistent with those in Table 1 and corresponding to I-1-I-58 in table 1 in turn, the representative compounds are coded as I-5859-I-5916.

Table 103: in general formula I-D, $R_1$=$C_2H_5$, $R_2$=Cl, $R_3$=$R_4$=$R_{5b}$=$R_7$=$R_{10}$=$R_{11}$=H, the substituent $R_9$ are consistent with those in Table 1 and corresponding to I-1-I-58 in table 1 in turn, the representative compounds are coded as I-5917-I-5974.

Table 104: in general formula I-D, $R_1$=$C_2H_5$, $R_2$=$R_{5b}$=Cl, $R_3$=$R_4$=$R_7$=$R_{10}$=$R_{11}$=H, the substituent $R_9$ are consistent with those in Table 1 and corresponding to I-1-I-58 in table 1 in turn, the representative compounds are coded as I-5975-I-6032.

Table 105: in general formula I-D, $R_1=C_2H_5$, $R_2=Cl$, $R_{5b}=Br$, $R_3=R_4=R_7=R_{10}=R_{11}=H$, the substituent $R_9$ are consistent with those in Table 1 and corresponding to I-1-I-58 in table 1 in turn, the representative compounds are coded as I-6033-I-6090.

Table 106: in general formula I-D, $R_1=C_2H_5$, $R_2=Cl$, $R_{5b}=OCH_3$, $R_3=R_4=R_7=R_{10}=R_{11}=H$, the substituent $R_9$ are consistent with those in Table 1 and corresponding to I-1-I-58 in table 1 in turn, the representative compounds are coded as I-6091-I-6148.

Table 107: in general formula I-D, $R_1=CH_3$, $R_2=R_{11}=Cl$, $R_3=R_4=R_{5b}=R_7=R_{10}=H$, the substituent $R_9$ are consistent with those in Table 1 and corresponding to I-1-I-58 in table 1 in turn, the representative compounds are coded as I-6149-I-6206.

Table 108: in general formula I-D, $R_1=CH_3$, $R_2=Cl$, $R_{11}=NO_2$, $R_3=R_4=R_{5b}=R_7=R_{10}=H$, the substituent $R_9$ are consistent with those in Table 1 and corresponding to I-1-I-58 in table 1 in turn, the representative compounds are coded as I-6207-I-6264.

Table 109: in general formula I-D, $R_1=C_2H_5$, $R_2=R_{11}=Cl$, $R_3=R_4=R_{5b}=R_7=R_{10}=H$, the substituent $R_9$ are consistent with those in Table 1 and corresponding to I-1-I-58 in table 1 in turn, the representative compounds are coded as I-6265-I-6322.

Table 110: in general formula I-D, $R_1=C_2H_5$, $R_2=Cl$, $R_{11}=NO_2$, $R_3=R_4=R_{5b}=R_7=R_{10}=H$, the substituent $R_9$ are consistent with those in Table 1 and corresponding to I-1-I-58 in table 1 in turn, the representative compounds are coded as I-6323-I-6380.

Table 111: in general formula I-D, $R_1=CH_3$, $R_2=R_7=R_{11}=Cl$, $R_3=R_4=R_{5b}=R_{10}=H$, the substituent $R_9$ are consistent with those in Table 1 and corresponding to I-1-I-58 in table 1 in turn, the representative compounds are coded as I-6381-I-6438.

Table 112: in general formula I-D, $R_1=CH_3$, $R_2=R_7=R_{10}=R_{11}=Cl$, $R_3=R_4=R_{5b}=H$, the substituent $R_9$ are consistent with those in Table 1 and corresponding to I-1-I-58 in table 1 in turn, the representative compounds are coded as I-6439-I-6496.

Table 113: in general formula I-D, $R_1=C_2H_5$, $R_2=R_7=R_{11}=Cl$, $R_3=R_4=R_{5b}=R_{10}=H$, the substituent $R_9$ are consistent with those in Table 1 and corresponding to I-1-I-58 in table 1 in turn, the representative compounds are coded as I-6497-I-6554.

Table 114: in general formula I-D, $R_1=C_2H_5$, $R_2=R_7=R_{10}=R_{11}=Cl$, $R_3=R_4=R_{5b}=H$, the substituent $R_9$ are consistent with those in Table 1 and corresponding to I-1-I-58 in table 1 in turn, the representative compounds are coded as I-6555-I-6612.

Table 115: in general formula I-D, $R_1=CH_3$, $R_2=Cl$, $R_{11}=CF_3$, $R_3=R_4=R_{5b}=R_7=R_{10}=H$, the substituent $R_9$ are consistent with those in Table 1 and corresponding to I-1-I-58 in table 1 in turn, the representative compounds are coded as I-6613-I-6670.

Table 116: in general formula I-D, $R_1=C_2H_5$, $R_2=Cl$, $R_{11}=CF_3$, $R_3=R_4=R_{5b}=R_7=R_{10}=H$, the substituent $R_9$ are consistent with those in Table 1 and corresponding to I-1-I-58 in table 1 in turn, the representative compounds are coded as I-6671-I-6728.

Table 117: the salts of some compounds having a structure as represented by formula I of the present invention are listed in Table 117, but without being restricted thereby.

TABLE 117

| No. | structure |
|---|---|
| I-6729 | (structure shown) |
| I-6730 | (structure shown) |
| I-6731 | (structure shown) |

TABLE 117-continued the salts of some compounds

| No. | structure |
|---|---|
| I-6732 | 5-chloro-6-methyl-pyrimidin-4-yl-NH-CH₂CH₂-(4-phenyl)-O-(5-CF₃-pyridin-2-yl) · HNO₃ |
| I-6733 | (5-chloro-6-methyl-pyrimidin-4-yl-NH-CH₂CH₂-(4-phenyl)-O-(5-CF₃-pyridin-2-yl))₂ · H₂SO₄ |
| I-6734 | (5-chloro-6-methyl-pyrimidin-4-yl-NH-CH₂CH₂-(4-phenyl)-O-(5-CF₃-pyridin-2-yl))₂ · HOOCCOOH |
| I-6735 | 5-chloro-6-methyl-pyrimidin-4-yl-NH-CH₂CH₂-(4-phenyl)-O-(5-CF₃-pyridin-2-yl) · H₃PO₄ |
| I-6736 | 5-chloro-6-ethyl-pyrimidin-4-yl-NH-CH₂CH₂-(4-phenyl)-O-(5-CF₃-pyridin-2-yl) · CF₃COOH |
| I-6737 | 5-chloro-6-methyl-pyrimidin-4-yl-NH-CH₂CH₂-(4-phenyl)-O-(5-CF₃-pyridin-2-yl) · CF₃COOH |
| I-6738 | 5-chloro-6-ethyl-pyrimidin-4-yl-NH-CH₂CH₂-(4-phenyl)-O-(5-CF₃-pyridin-2-yl) · CH₃COOH |
| I-6739 | 5-chloro-6-ethyl-pyrimidin-4-yl-NH-CH₂CH₂-(4-phenyl)-O-(5-CF₃-pyridin-2-yl) · HCl |
| I-6740 | 5-chloro-6-ethyl-pyrimidin-4-yl-NH-CH₂CH₂-(4-phenyl)-O-(5-CF₃-pyridin-2-yl) · H₃PO₄ |

TABLE 117-continued
the salts of some compounds
| No. | structure |
|---|---|
| I-6741 | 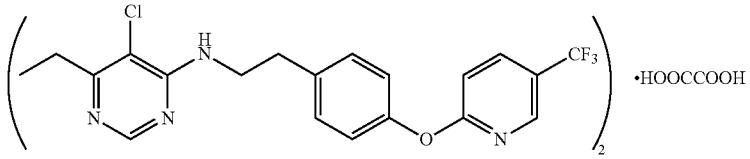 |
| I-6742 | 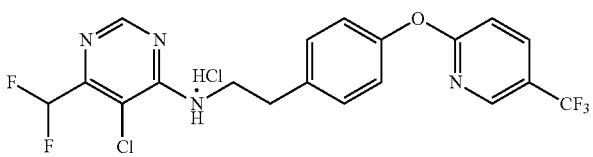 |
| I-6743 | 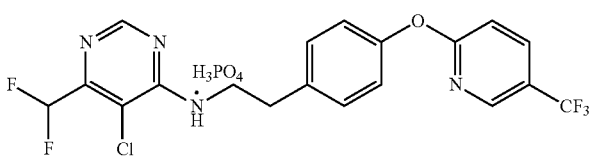 |
| I-6744 | 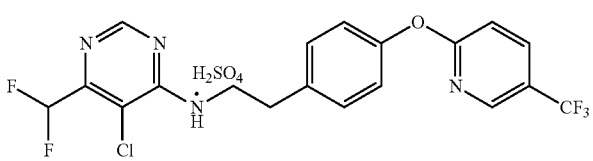 |
| I-6745 | 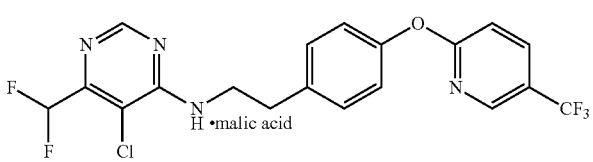 [SMILES: FC(F)c1ncnc(NCCc2ccc(Oc3ccc(C(F)(F)F)cn3)cc2)c1Cl] |
| I-6746 | 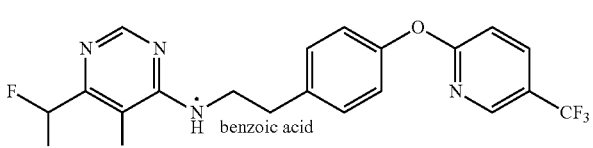 |
| I-6747 | 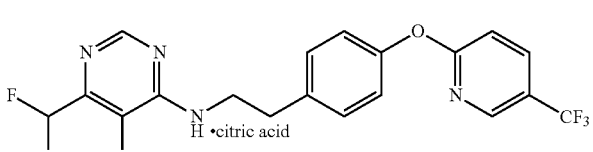 |
| I-6748 | 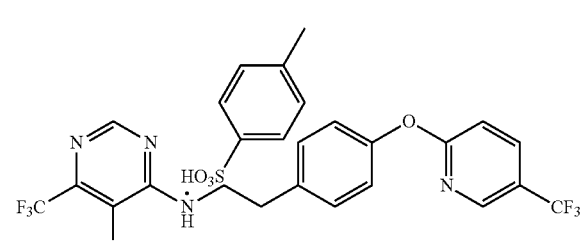 |
| I-6749 | 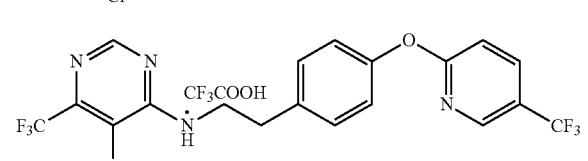 |

TABLE 117-continued
the salts of some compounds
| No. | structure |
|---|---|
| I-6750 | 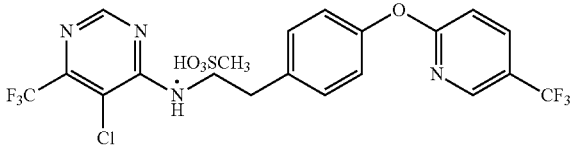 |
| I-6751 | 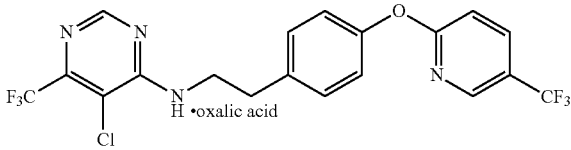 [SMILES: FC(F)(F)c1ccc(Oc2ccc(CCNc3ncnc(C(F)(F)F)c3Cl)cc2)nc1] |
| I-6752 | 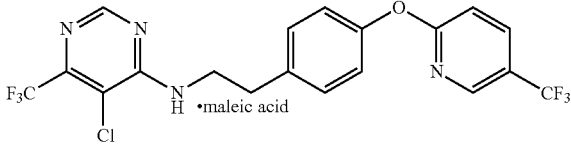 [SMILES: FC(F)(F)c1ccc(Oc2ccc(CCNc3ncnc(C(F)(F)F)c3Cl)cc2)nc1] |
| I-6753 | 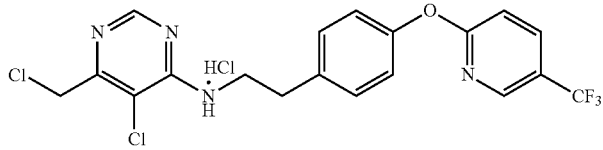 |
| I-6754 | 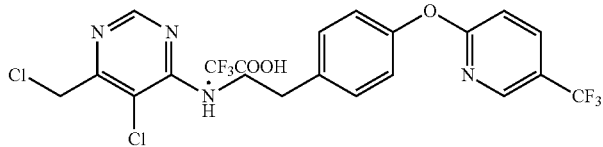 |
| I-6755 | 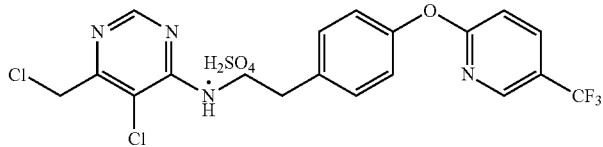 |
| I-6756 | 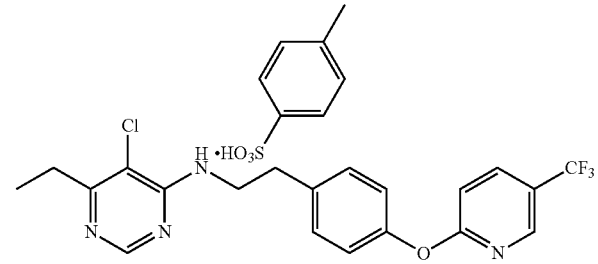 |
| I-6757 | 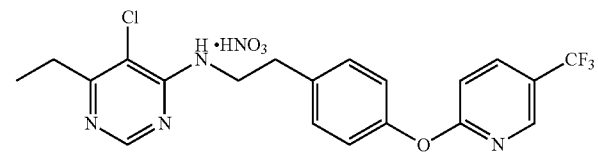 |

TABLE 117-continued the salts of some compounds

| No. | structure |
|---|---|
| I-6758 | (5-chloro-6-ethyl-pyrimidin-4-yl-NH-CH$_2$CH$_2$-C$_6$H$_4$-O-(5-CF$_3$-pyridin-2-yl))$_2$ · H$_2$SO$_4$ |
| I-6759 | 5-chloro-6-methyl-pyrimidin-4-yl-NH-CH$_2$CH$_2$-C$_6$H$_4$-O-(5-CF$_3$-pyridin-2-yl) · HO$_3$SCH$_3$ |
| I-6760 | 5-chloro-6-ethyl-pyrimidin-4-yl-NH-CH$_2$CH$_2$-C$_6$H$_4$-O-(5-CF$_3$-pyridin-2-yl) · HO$_3$SCH$_3$ |
| I-6761 | 5-chloro-6-methyl-pyrimidin-4-yl-NH-CH$_2$CH$_2$-C$_6$H$_4$-O-(5-CF$_3$-pyridin-2-yl) · malic acid |
| I-6762 | 5-chloro-6-ethyl-pyrimidin-4-yl-NH-CH$_2$CH$_2$-C$_6$H$_4$-O-(5-CF$_3$-pyridin-2-yl) · HOOC-C$_6$H$_4$-CH$_3$ |
| I-6763 | 5-chloro-6-methyl-pyrimidin-4-yl-NH-CH$_2$CH$_2$-C$_6$H$_4$-O-(5-CF$_3$-pyridin-2-yl) · maleic acid |
| I-6764 | 5-chloro-6-ethyl-pyrimidin-4-yl-NH-CH$_2$CH$_2$-C$_6$H$_4$-O-(5-CF$_3$-pyridin-2-yl) · citric acid |
| I-6765 | 5-chloro-6-ethyl-pyrimidin-4-yl-NH-CH$_2$CH$_2$-C$_6$H$_4$-O-(5-CF$_3$-pyridin-2-yl) · malic acid |
| I-6766 | 5-chloro-6-methyl-pyrimidin-4-yl-NH-CH$_2$CH$_2$-C$_6$H$_4$-O-(5-CF$_3$-pyridin-2-yl) · HOOC-C$_6$H$_4$-CH$_3$ |

TABLE 117-continued
the salts of some compounds
| No. | structure |
|---|---|
| I-6767 | 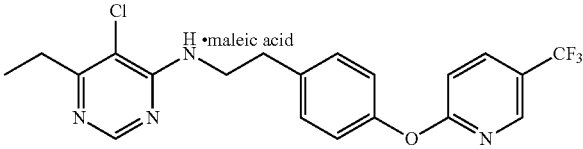 |
| I-6768 | 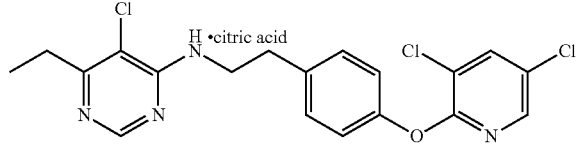 |
| I-6769 | 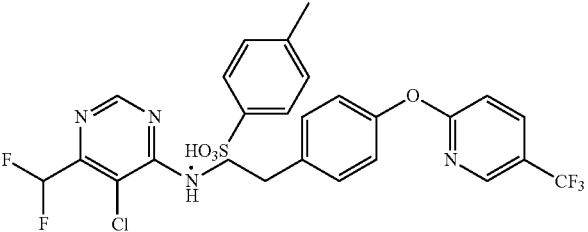 |
| I-6770 | 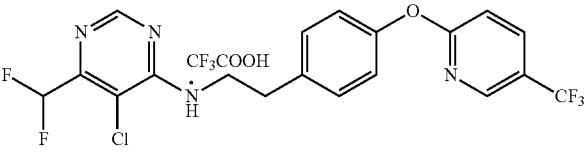 [SMILES: FC(F)c1ncnc(NCCc2ccc(Oc3ccc(C(F)(F)F)cn3)cc2)c1Cl ; "CF3COOH"] |
| I-6771 | 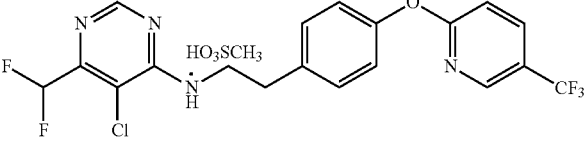 |
| I-6772 | 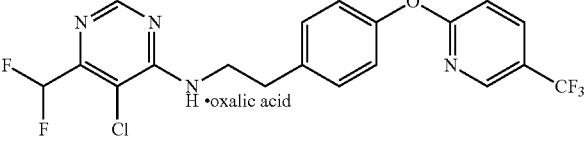 |
| I-6773 | 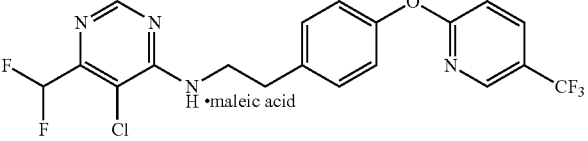 |
| I-6774 | 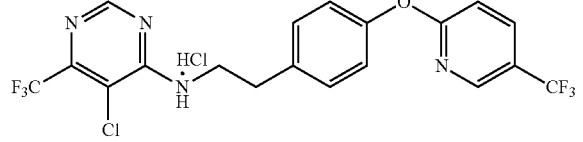 |
| I-6775 | 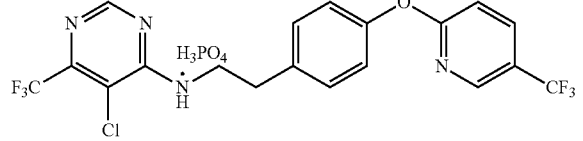 |

TABLE 117-continued the salts of some compounds

| No. | structure |
|---|---|
| I-6776 | (structure: 6-(trifluoromethyl)-5-chloropyrimidin-4-yl-NH-CH2CH2-phenyl-O-pyridyl-CF3 · H2SO4) |
| I-6777 | (structure: 6-(trifluoromethyl)-5-chloropyrimidin-4-yl-N-CH2CH2-phenyl-O-pyridyl-CF3 · malic acid) |
| I-6778 | (structure: 6-(trifluoromethyl)-5-chloropyrimidin-4-yl-N-CH2CH2-phenyl-O-pyridyl-CF3 · malic acid) |
| I-6779 | (structure: 6-(trifluoromethyl)-5-chloropyrimidin-4-yl-NH-CH2CH2-phenyl-O-pyridyl-CF3 · citric acid) |
| I-6780 | (structure: 6-(chloromethyl)-5-chloropyrimidin-4-yl-NH-CH2CH2-phenyl-O-pyridyl-CF3 · H3PO4) |
| I-6781 | (structure: 6-(chloromethyl)-5-chloropyrimidin-4-yl-NH-CH2CH2-phenyl-O-pyridyl-CF3 · p-toluenesulfonic acid (HO3S-C6H4-CH3)) |
| I-6782 | (structure: 6-(chloromethyl)-5-chloropyrimidin-4-yl-NH-CH2CH2-phenyl-O-pyridyl-CF3 · HNO3) |

Some compounds represented by general formula I-E, I-F, I-G and I-H of the present invention are listed in Table 118, but without being restricted thereby.

TABLE 118

| No. | structure |
|---|---|
| I-6783 | 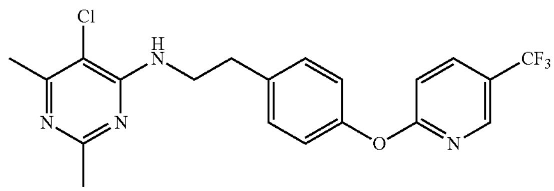 |
| I-6784 | 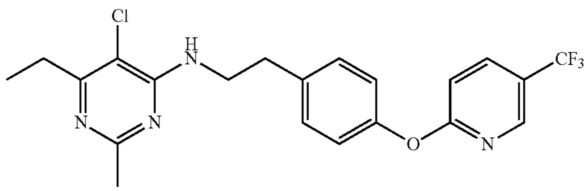 [SMILES: CCc1nc(C)nc(NCCc2ccc(Oc3ccc(C(F)(F)F)cn3)cc2)c1Cl] |
| I-6785 | 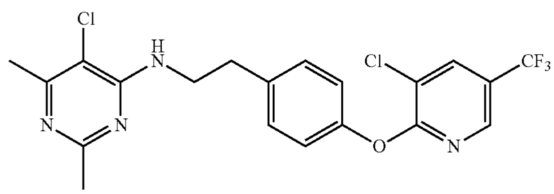 [SMILES: Cc1nc(C)c(Cl)c(NCCc2ccc(Oc3ncc(C(F)(F)F)cc3Cl)cc2)n1] |
| I-6786 | 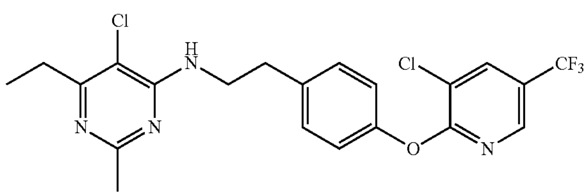 [SMILES: CCc1nc(C)nc(NCCc2ccc(Oc3ncc(C(F)(F)F)cc3Cl)cc2)c1Cl] |
| I-6787 | 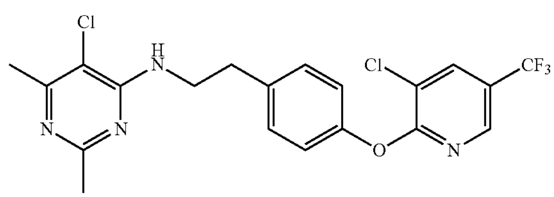 [SMILES: Cc1nc(C)c(Cl)c(NCCc2ccc(Oc3ncc(C(F)(F)F)cc3Cl)cc2)n1] |
| I-6788 | 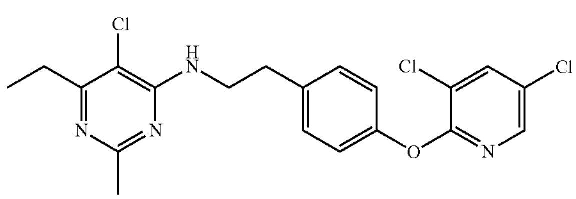 |
| I-6789 | 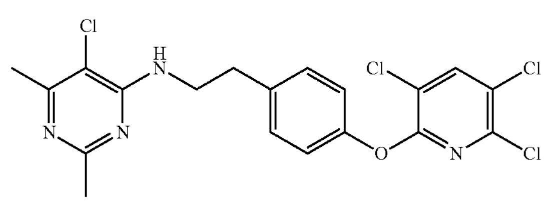 [SMILES: Cc1nc(C)c(Cl)c(NCCc2ccc(Oc3nc(Cl)c(Cl)cc3Cl)cc2)n1] |
| I-6790 | 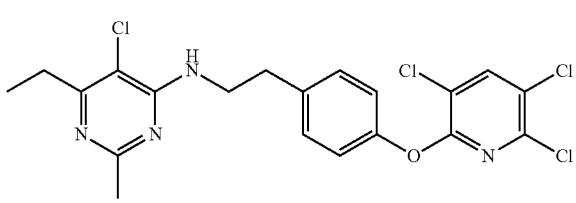 [SMILES: CCc1nc(C)nc(NCCc2ccc(Oc3nc(Cl)c(Cl)cc3Cl)cc2)c1Cl] |

TABLE 118-continued

| No. | structure |
|---|---|
| I-6791 | 3-chloro-2-(4-(2-((5-chloro-6-ethyl-2-methylpyrimidin-4-yl)amino)ethyl)phenoxy)pyridine-5-carboxamide |
| I-6792 | N-(4-(2-((5-chloro-2,6-dimethylpyrimidin-4-yl)amino)ethyl)phenoxy)-3-(trifluoromethyl)pyridine |
| I-6793 | N-(4-(2-((5-chloro-6-ethyl-2-methylpyrimidin-4-yl)amino)ethyl)phenoxy)-3-(trifluoromethyl)pyridine |
| I-6794 | 6-(4-(2-((5-chloro-2,6-dimethylpyrimidin-4-yl)amino)ethyl)phenoxy)nicotinonitrile |
| I-6795 | 6-(4-(2-((5-chloro-6-ethyl-2-methylpyrimidin-4-yl)amino)ethyl)phenoxy)nicotinonitrile |
| I-6796 | ethyl 6-(4-(2-((5-chloro-6-ethyl-2-methylpyrimidin-4-yl)amino)ethyl)phenoxy)nicotinate |
| I-6797 | methyl 6-(4-(2-((5-chloro-6-ethyl-2-methylpyrimidin-4-yl)amino)ethyl)phenoxy)nicotinate |
| I-6798 | N-(4-(2-((6-chloropyridazin-3-yl)oxy)phenethyl)-5-chloro-2,6-dimethylpyrimidin-4-amine |

TABLE 118-continued

| No. | structure |
|---|---|
| I-6799 | 5-chloro-6-ethyl-2-methyl-pyrimidin-4-yl, NH-CH2CH2-phenyl-O-(6-chloropyridazin-3-yl) |
| I-6800 | 5-chloro-2,6-dimethyl-pyrimidin-4-yl, NH-CH2CH2-phenyl-O-(6-CF3-pyridazin-3-yl) |
| I-6801 | 5-chloro-6-ethyl-2-methyl-pyrimidin-4-yl, NH-CH2CH2-phenyl-O-(6-CF3-pyridazin-3-yl) |
| I-6802 | 5-chloro-2,6-dimethyl-pyrimidin-4-yl, NH-CH2CH2-phenyl-O-(6-OCF3-pyridazin-3-yl) |
| I-6803 | 5-chloro-6-ethyl-2-methyl-pyrimidin-4-yl, NH-CH2CH2-phenyl-O-(6-OCF3-pyridazin-3-yl) |
| I-6804 | 5-chloro-2,6-dimethyl-pyrimidin-4-yl, NH-CH2CH2-phenyl-O-(6-OCH3-pyridazin-3-yl) |
| I-6805 | 5-chloro-6-ethyl-2-methyl-pyrimidin-4-yl, NH-CH2CH2-phenyl-O-(6-CN-pyridazin-3-yl) |
| I-6806 | 5-chloro-6-ethyl-2-methyl-pyrimidin-4-yl, NH-CH2CH2-(3-chlorophenyl)-O-(5-CF3-pyridin-2-yl) |

TABLE 118-continued

| No. | structure |
|---|---|
| I-6807 | (chemical structure) |
| I-6808 | (chemical structure) |
| I-6809 | (chemical structure) |
| I-6810 | (chemical structure) |
| I-6811 | (chemical structure) |
| I-6812 | (chemical structure) |
| I-6813 | (chemical structure) |
| I-6814 | (chemical structure) |

TABLE 118-continued

| No. | structure |
|---|---|
| I-6815 | (structure) |
| I-6816 | (structure) |
| I-6817 | (structure) |
| I-6818 | (structure) |
| I-6819 | (structure) |
| I-6820 | (structure) |
| I-6821 | (structure) |
| I-6822 | (structure) |

TABLE 118-continued
| No. | structure |
|---|---|
| I-6823 | 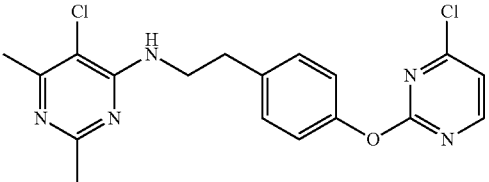 [SMILES: Cc1nc(C)c(Cl)c(NCCc2ccc(Oc3nccc(Cl)n3)cc2)n1] |
| I-6824 | 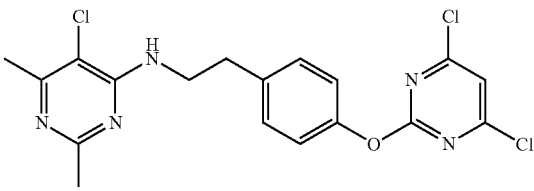 [SMILES: Cc1nc(C)c(Cl)c(NCCc2ccc(Oc3nc(Cl)cc(Cl)n3)cc2)n1] |
| I-6825 | 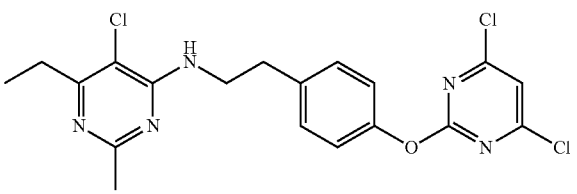 [SMILES: CCc1nc(C)nc(NCCc2ccc(Oc3nc(Cl)cc(Cl)n3)cc2)c1Cl] |
| I-6826 | 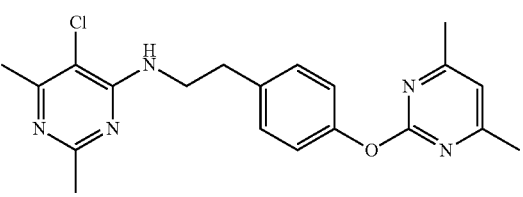 |
| I-6827 | 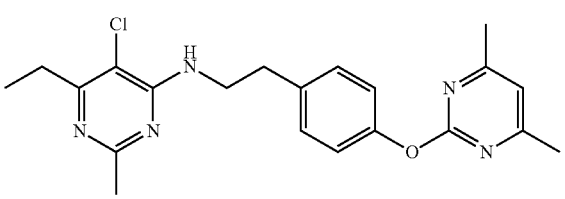 [SMILES: CCc1nc(C)nc(NCCc2ccc(Oc3nc(C)cc(C)n3)cc2)c1Cl] |
| I-6828 | 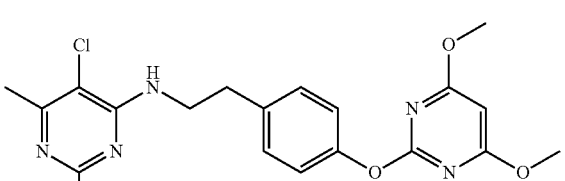 |
| I-6829 | 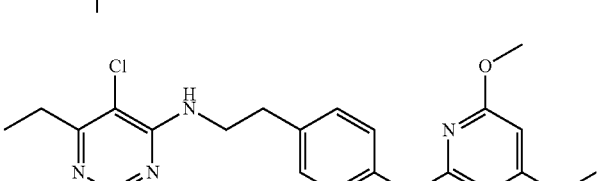 |
| I-6830 | 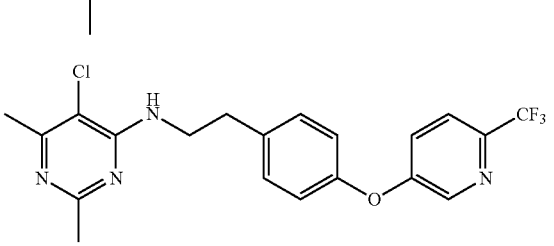 |

TABLE 118-continued

| No. | structure |
|---|---|
| I-6831 | 5-chloro-6-ethyl-2-methyl-N-(4-((6-(trifluoromethyl)pyridin-3-yl)oxy)phenethyl)pyrimidin-4-amine |
| I-6832 | 5-chloro-N-(4-((4-chloro-6-(trifluoromethyl)pyridin-3-yl)oxy)phenethyl)-2,6-dimethylpyrimidin-4-amine |
| I-6833 | 5-chloro-N-(4-((4-chloro-6-(trifluoromethyl)pyridin-3-yl)oxy)phenethyl)-6-ethyl-2-methylpyrimidin-4-amine |
| I-6834 | 5-chloro-N-(4-((4,6-dichloropyridin-3-yl)oxy)phenethyl)-2,6-dimethylpyrimidin-4-amine |
| I-6835 | 5-chloro-N-(4-((4,6-dichloropyridin-3-yl)oxy)phenethyl)-6-ethyl-2-methylpyrimidin-4-amine |
| I-6836 | 5-chloro-2,6-dimethyl-N-(4-((6-(trifluoromethoxy)pyridin-3-yl)oxy)phenethyl)pyrimidin-4-amine |
| I-6837 | 5-chloro-6-ethyl-2-methyl-N-(4-((6-(trifluoromethoxy)pyridin-3-yl)oxy)phenethyl)pyrimidin-4-amine |
| I-6838 | 5-chloro-N-(3-chloro-4-((5-(trifluoromethyl)pyridin-2-yl)oxy)phenethyl)-2,6-dimethylpyrimidin-4-amine |

TABLE 118-continued

| No. | structure |
|---|---|
| I-6839 | (chemical structure) |
| I-6840 | (chemical structure) |
| I-6841 | (chemical structure) |
| I-6842 | (chemical structure) |
| I-6843 | (chemical structure) |
| I-6844 | (chemical structure) |
| I-6845 | (chemical structure) |
| I-6846 | (chemical structure) |

In the general formula I, A=NR$_{12}$, R$_{12}$≠H, part of preferred substituents of R$_{12}$ are listed in table 119, but without being restricted thereby. The present invention is also explained by the following compounds in the general formula I listed in Table 120, but without being restricted thereby.

TABLE 119

R$_{12}$ substituents

R$_{12}$

OH
C$_2$H$_5$
i-C$_4$H$_9$
CHF$_2$
CHCl$_2$
OC$_2$H$_5$
OCH$_2$CF$_3$
SCH$_3$
CH$_2$CH=CH$_2$
CH$_2$C≡C—I
CH$_2$CH$_2$OCH$_2$CH$_3$
CH$_2$SCH$_3$
CH$_2$SCH$_2$Cl
SOC$_2$H$_5$
SO$_2$C$_2$H$_5$
SO$_2$NHCH$_3$
COC$_2$H$_5$
CO-i-C$_4$H$_9$
COOCH$_3$
COOCF$_3$
CH$_2$COOC$_2$H$_5$
CONHC$_2$H$_5$
COOCH$_2$CH=CH$_2$
SNHCH$_3$

[cyclopropyl structure]

[CO—O—cyclopropyl structure]

[benzyl structure]

[4-CF$_3$-benzyl structure]

[2,6-dichloro-4-CF$_3$-benzyl structure]

[phenylpropyl structure]

[CO—4-NO$_2$-phenyl structure]

TABLE 119-continued

R$_{12}$ substituents

R$_{12}$

[CO—O—4-CH$_3$-phenyl structure]

[CO—O—benzyl structure]

[CO—O—4-NO$_2$-benzyl structure]

[CH$_2$—C(=O)—4-Cl-phenyl structure]

—C(=O)H
n-C$_3$H$_7$
t-C$_4$H$_9$
CHBr$_2$
CCl$_3$
OCH(CH$_3$)$_2$
OCF$_2$CF$_3$
SC$_2$H$_5$
CH$_2$CH=CCl$_2$
CH$_2$OCH$_3$
CH$_2$OCH$_2$Cl
CH$_2$SCH$_2$CH$_3$
CH$_2$SCH$_2$CH$_2$Cl
SOCF$_3$
SO$_2$CF$_3$
SO$_2$N(CH$_3$)$_3$
CO-n-C$_3$H$_7$
CO-t-C$_4$H$_9$
COOC$_2$H$_5$
COOCH$_2$CH$_2$Cl
CH$_2$COCH$_3$
CONH-t-C$_4$H$_9$
COOCH$_2$C≡CH
SNHC$_2$H$_5$

[cyclobutyl structure]

[CO—O—cyclobutyl structure]

[4-Cl-benzyl structure]

[2,4-dimethyl-benzyl structure]

TABLE 119-continued
R_{12} substituents
R_{12}
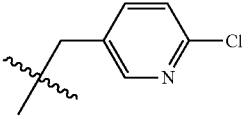
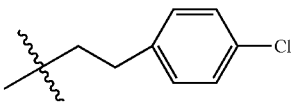 [SMILES: *CCc1ccc(Cl)cc1]
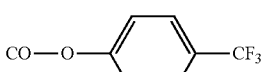
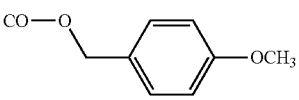
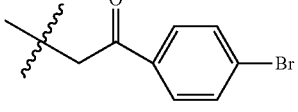
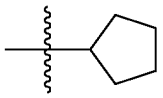 [SMILES: *C1CCCC1]
CBr_3
i-C_3H_7
CI_3
CF_3
CH_2F
OC(CH_3)_3
OCH_2F
SCH_2CH=CH_2
C≡CH
CH_2OCH_2CH_3
CH_2OCH_2CH_2Cl
CH_2CH_2SCH_3
CH_2CH_2SCH_2Cl
SOCH_2CF_3
SO_2CH_2CF_3
CONHSO_2CH_3
CO-i-C_3H_7
COCF_3
COO-n-C_3H_7
COOCH_2CF_3
CH_2COC_2H_5
CON(CH_3)_2
COOCH_2OCH_3
SN(CH_3)_2
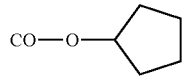
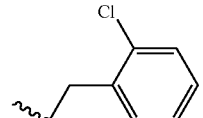
TABLE 119-continued
R_{12} substituents
R_{12}
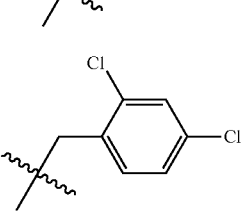
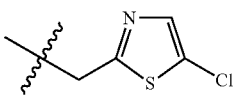 [SMILES: *Cc1ncc(Cl)s1]
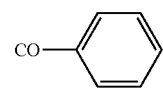
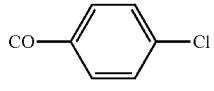
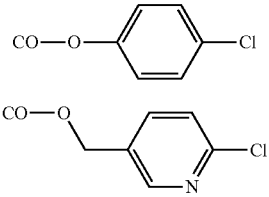
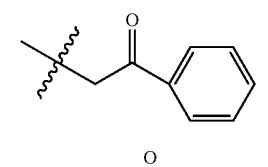
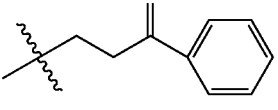
CH_3
n-C_4H_9
CH_2Br
CH_2Cl
OCH_3
OCF_3
OCHF_2
CH=CH_2
CH_2C≡CH
CH_2CH_2OCH_3
CH_2CH_2OCH_2Cl
CH_2CH_2SCH_2CH_3
SOCH_3
SO_2CH_3
SO_2NHCOCH_3
COCH_3
CO-n-C_4H_9
COCH_2Cl
COO-t-C_4H_9
CH_2COOCH_3

TABLE 119-continued

R₁₂ substituents

R₁₂

CONHCH₃
CON(C₂H₅)₂
COOCH₂CH₂OCH₃
SN(C₂H₅)₂

- —cyclohexyl
- CO—O—cyclohexyl
- —CH₂—(3-chlorophenyl)
- —CH₂—(2-chloro-4-trifluoromethylphenyl)
- —CH₂—(5-chlorothien-2-yl)
- CO—(4-methylphenyl)
- CO—O—phenyl
- CO—O—(4-nitrophenyl)
- CO—O—CH₂—(4-trifluoromethylphenyl)
- —CH₂—C(=O)—(4-methylphenyl)
- —(CH₂)₃—C(=O)—(4-chlorophenyl)

TABLE 120

| No. | structure |
|---|---|
| I-6847 | 5-chloro-6-methyl-N-methyl-N-{2-[4-(5-trifluoromethylpyridin-2-yloxy)phenyl]ethyl}pyrimidin-4-amine |
| I-6848 | 5-chloro-6-ethyl-N-methyl-N-{2-[4-(5-trifluoromethylpyridin-2-yloxy)phenyl]ethyl}pyrimidin-4-amine |
| I-6849 | 5-chloro-N-ethyl-6-methyl-N-{2-[4-(5-trifluoromethylpyridin-2-yloxy)phenyl]ethyl}pyrimidin-4-amine |
| I-6850 | 5-chloro-N-ethyl-6-ethyl-N-{2-[4-(5-trifluoromethylpyridin-2-yloxy)phenyl]ethyl}pyrimidin-4-amine |

TABLE 120-continued

| No. | structure |
|---|---|
| I-6851 | (chemical structure) |
| I-6852 | (chemical structure) |
| I-6853 | (chemical structure) |
| I-6854 | (chemical structure) |
| I-6855 | (chemical structure) |
| I-6856 | (chemical structure) |
| I-6857 | (chemical structure) |
| I-6858 | (chemical structure) |

TABLE 120-continued
| No. | structure |
|---|---|
| I-6859 | 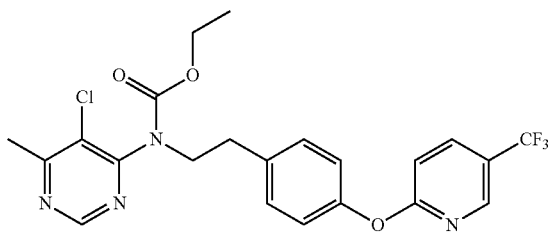 [SMILES: CCOC(=O)N(CCc1ccc(Oc2ccc(C(F)(F)F)cn2)cc1)c1ncnc(C)c1Cl] |
| I-6860 | 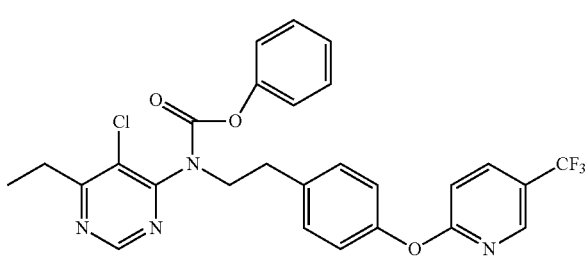 [SMILES: CCc1ncnc(N(CCc2ccc(Oc3ccc(C(F)(F)F)cn3)cc2)C(=O)Oc2ccccc2)c1Cl] |
| I-6861 | 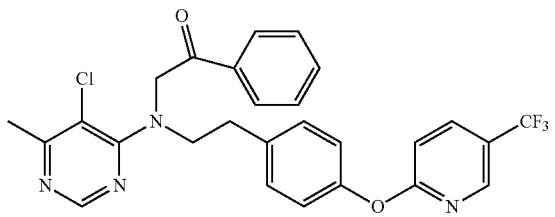 [SMILES: Cc1ncnc(N(CCc2ccc(Oc3ccc(C(F)(F)F)cn3)cc2)CC(=O)c2ccccc2)c1Cl] |
| I-6862 | 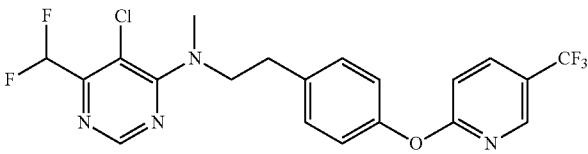 [SMILES: CN(CCc1ccc(Oc2ccc(C(F)(F)F)cn2)cc1)c1ncnc(C(F)F)c1Cl] |
| I-6863 | 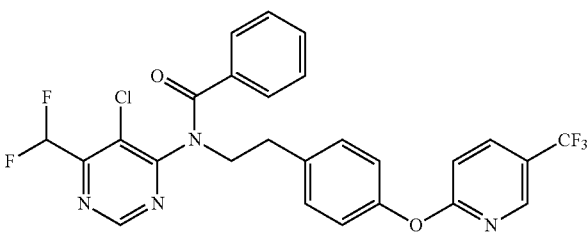 [SMILES: O=C(c1ccccc1)N(CCc1ccc(Oc2ccc(C(F)(F)F)cn2)cc1)c1ncnc(C(F)F)c1Cl] |
| I-6864 | 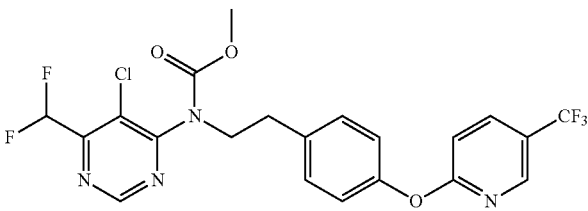 [SMILES: COC(=O)N(CCc1ccc(Oc2ccc(C(F)(F)F)cn2)cc1)c1ncnc(C(F)F)c1Cl] |
| I-6865 | 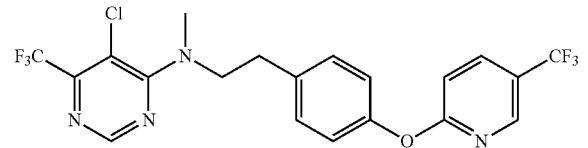 [SMILES: CN(CCc1ccc(Oc2ccc(C(F)(F)F)cn2)cc1)c1ncnc(C(F)(F)F)c1Cl] |

TABLE 120-continued

| No. | structure |
|---|---|
| I-6866 | (structure) |
| I-6867 | (structure) |
| I-6868 | (structure) |
| I-6869 | (structure) |
| I-6870 | (structure) |
| I-6871 | (structure) |
| I-6872 | (structure) |
| I-6873 | (structure) |

TABLE 120-continued

| No. | structure |
|---|---|
| I-6874 | (structure) |
| I-6875 | (structure) |
| I-6876 | (structure) |
| I-6877 | (structure) |
| I-6878 | (structure) |
| I-6879 | (structure) |
| I-6880 | (structure) |

TABLE 120-continued

| No. | structure |
|---|---|
| I-6881 | 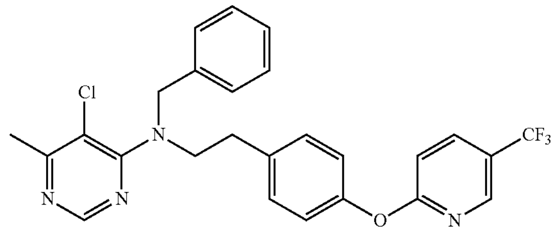 [SMILES: Cc1ncnc(N(CCc2ccc(Oc3ccc(C(F)(F)F)cn3)cc2)Cc2ccccc2)c1Cl] |
| I-6882 | 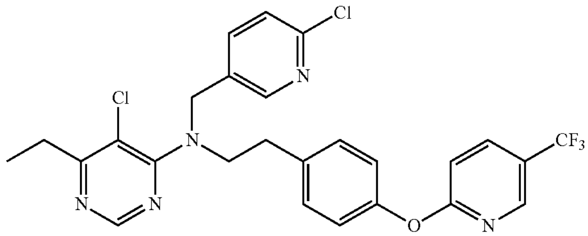 [SMILES: CCc1ncnc(N(CCc2ccc(Oc3ccc(C(F)(F)F)cn3)cc2)Cc2ccc(Cl)nc2)c1Cl] |
| I-6883 | 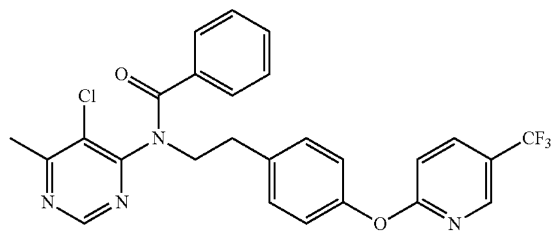 [SMILES: Cc1ncnc(N(CCc2ccc(Oc3ccc(C(F)(F)F)cn3)cc2)C(=O)c2ccccc2)c1Cl] |
| I-6884 | 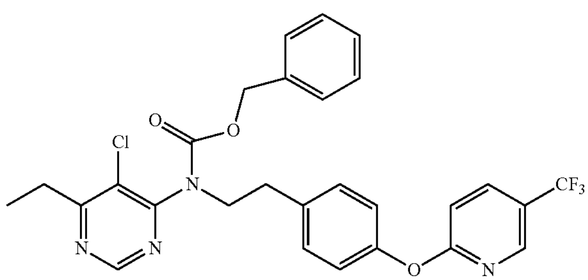 [SMILES: CCc1ncnc(N(CCc2ccc(Oc3ccc(C(F)(F)F)cn3)cc2)C(=O)OCc2ccccc2)c1Cl] |
| I-6885 | 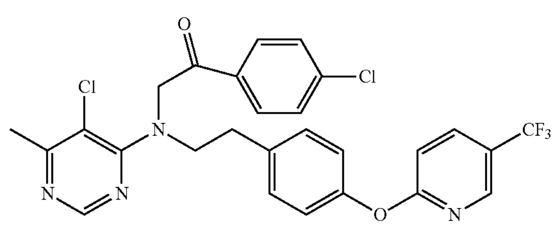 [SMILES: Cc1ncnc(N(CCc2ccc(Oc3ccc(C(F)(F)F)cn3)cc2)CC(=O)c2ccc(Cl)cc2)c1Cl] |
| I-6886 | 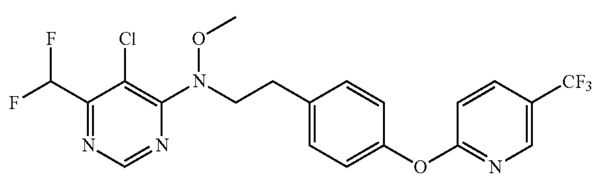 [SMILES: CON(CCc1ccc(Oc2ccc(C(F)(F)F)cn2)cc1)c1ncnc(C(F)F)c1Cl] |
| I-6887 | 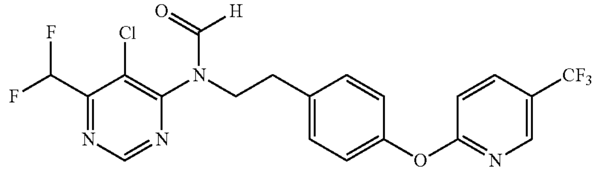 [SMILES: O=CN(CCc1ccc(Oc2ccc(C(F)(F)F)cn2)cc1)c1ncnc(C(F)F)c1Cl] |

TABLE 120-continued

| No. | structure |
|---|---|
| I-6888 | (chemical structure) |
| I-6889 | (chemical structure) |
| I-6890 | (chemical structure) |
| I-6891 | (chemical structure) |
| I-6892 | (chemical structure) |
| I-6893 | (chemical structure) |
| I-6894 | (chemical structure) |

In the general formula II, part of preferred substituents of $R_1$, $R_2$, $R_3(R_4)$, $R_{5a}(R_{5b}, R_{5c})$, $R_6(R_7, R_8, R_9, R_{10}, R_{11})$ and $R_{12}$ are separately listed in table 121, table 122, table 123, table 124, table 125 and table 126, but without being restricted thereby.

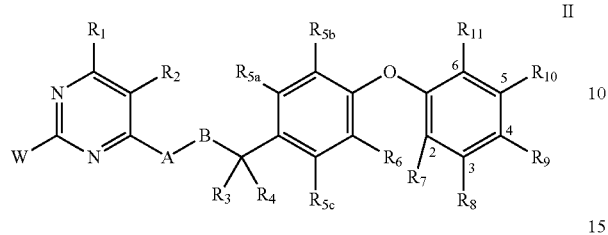

II

TABLE 121

R₁ substituents

R₁

CH₃
n-C₄H₉
CF₃
CH₂Br
CF₂H

[cyclopropyl structure]

C₂H₅
s-C₄H₉
CCl₃
CClF₂
CBr₂H

[cyclobutyl structure]

n-C₃H₇
i-C₄H₉
CH₂F
CFCl₂
CBr₃

[cyclopentyl-methyl structure]

i-C₃H₇
t-C₄H₉
CH₂Cl
CCl₂H
CClBr₂

[cyclohexyl-methyl structure]

TABLE 122

R₂ substituents

| R₂ | R₂ | R₂ | R₂ |
|---|---|---|---|
| F | Cl | Br | I |
| CN | OCH₃ | OC₂H₅ | OC₃H₇-n |
| OC₃H₇-i | OC₄H₉-n | OC₄H₉-i | OC₄H₉-t |

TABLE 123

R₃(R₄) substituents

R₃(R₄)

H
i-C₃H₇
F
t-C₄H₉
OCH₃
CH₃
n-C₄H₉
Cl

[cyclopropyl structure]

OC₂H₅
C₂H₅
s-C₄H₉
Br

[cyclopentyl structure]

OC₃H₇-n
n-C₃H₇
i-C₄H₉
I

[cyclohexyl structure]

OC₃H₇-i

CR₃(R₄)

[cyclopropyl structure]

[cyclobutyl structure]

[cyclopentyl structure]

[cyclohexyl structure]

TABLE 124

$R_{5a}$ ($R_{5b}$, $R_{5c}$) substituents

| $R_{5a}$ ($R_{5b}$, $R_{5c}$) | $R_{5a}$ ($R_{5b}$, $R_{5c}$) | $R_{5a}$ ($R_{5b}$, $R_{5c}$) | $R_{5a}$ ($R_{5b}$, $R_{5c}$) |
|---|---|---|---|
| H | CH$_3$ | i-C$_4$H$_9$ | OC$_4$H$_9$-n |
| F | C$_2$H$_5$ | t-C$_4$H$_9$ | OC$_4$H$_9$-i |
| Cl | n-C$_3$H$_7$ | OCH$_3$ | OC$_4$H$_9$-t |
| Br | i-C$_3$H$_7$ | OC$_2$H$_5$ | OCF$_3$ |

TABLE 124-continued

$R_{5a}$ ($R_{5b}$, $R_{5c}$) substituents

| $R_{5a}$ ($R_{5b}$, $R_{5c}$) | $R_{5a}$ ($R_{5b}$, $R_{5c}$) | $R_{5a}$ ($R_{5b}$, $R_{5c}$) | $R_{5a}$ ($R_{5b}$, $R_{5c}$) |
|---|---|---|---|
| I | n-C$_4$H$_9$ | OC$_3$H$_7$-n | OCH$_2$CF$_3$ |
| OH | s-C$_4$H$_9$ | OC$_3$H$_7$-i | OCF$_2$CF$_3$ |

TABLE 125

$R_6$ ($R_7$, $R_8$, $R_9$, $R_{10}$, $R_{11}$) substituents

| $R_6$ ($R_7$, $R_8$, $R_9$, $R_{10}$, $R_{11}$) | $R_6$ ($R_7$, $R_8$, $R_9$, $R_{10}$, $R_{11}$) | $R_6$ ($R_7$, $R_8$, $R_9$, $R_{10}$, $R_{11}$) | $R_6$ ($R_7$, $R_8$, $R_9$, $R_{10}$, $R_{11}$) | $R_6$ ($R_7$, $R_8$, $R_9$, $R_{10}$, $R_{11}$) |
|---|---|---|---|---|
| H | 4-CH$_3$ | 3-CH$_2$OCH$_3$ | 2,6-2Cl-4-CONH$_2$ | 2-CF$_3$-4-Br-6-NO$_2$ |
| 2-F | 2,3-2CH$_3$ | 4-CH$_2$OCH$_3$ | 2,4-2Cl-6-NO$_2$ | 3-NO$_2$-4-CF$_3$ |
| 3-F | 2,4-2CH$_3$ | 2-OCOCH$_3$ | 2,4-2Cl-6-CN | 2-NO$_2$-4-CN-5-CF$_3$ |
| 4-F | 2,5-2CH$_3$ | 3-OCOCH$_3$ | 2,4-2Cl-6-CF$_3$ | 2-NO$_2$-4-CF$_3$-5-CN |
| 2,3-2F | 2,6-2CH$_3$ | 4-OCOCH$_3$ | 2,4-2F-6-NO$_2$ | 4-OCF$_3$-2,6-2Br |
| 2,4-2F | 3,4-2CH$_3$ | 2-OCOCH$_2$CH$_3$ | 2,6-2F-4-NO$_2$ | 2-CH$_3$-4-Cl-5-CH$_2$CO$_2$C$_2$H$_5$ |
| 2,5-2F | 3,5-2CH$_3$ | 3-OCOCH$_2$CH$_3$ | 2-NO$_2$-4-F | 2,4-2Cl-3-CH$_3$ |
| 2,6-2F | 2-C$_2$H$_5$ | 4-OCOCH$_2$CH$_3$ | 2-NO$_2$-4-Br | 2,4-2Cl-3-CH$_3$-6-NO$_2$ |
| 3,4-2F | 3-C$_2$H$_5$ | 2-OCO$_2$CH$_3$ | 2-NO$_2$-4-CF$_3$ | 2-Cl-3-CH$_3$ |
| 3,5-2F | 4-C$_2$H$_5$ | 3-OCO$_2$CH$_3$ | 2-NO$_2$-4-CN | 2-CH$_3$-3-Cl |
| 2,3,4-3F | 2-CF$_3$ | 4-OCO$_2$CH$_3$ | 2-NO$_2$-4-COCH$_3$ | 2-CH$_3$-3-Cl-4,6-2NO$_2$ |
| 2,3,5-3F | 3-CF$_3$ | 2-OCH$_2$OCH$_3$ | 2-NO$_2$-4-CONH$_2$ | 2-CH$_3$-3-Cl-4-NO$_2$ |
| 2,4,5-3F | 4-CF$_3$ | 3-OCH$_2$OCH$_3$ | 2-NO$_2$-4-CH$_3$ | 2-CH$_3$-3-Cl-6-NO$_2$ |
| 2,3,6-3F | 2-OCH$_3$ | 4-OCH$_2$OCH$_3$ | 2-NO$_2$-4-OCH$_3$ | 2-Cl-3-CH$_3$-4,6-2NO$_2$ |
| 2,4,6-3F | 3-OCH$_3$ | 2-OCF$_2$OCF$_3$ | 2-NO$_2$-4-SCH$_3$ | 2-Cl-3-CH$_3$-4-NO$_2$ |
| 3,4,5-3F | 4-OCH$_3$ | 3-OCF$_2$OCF$_3$ | 2-NO$_2$-4-NCH$_3$ | 2-Cl-3-CH$_3$-6-NO$_2$ |
| 2-Cl | 2-SCH$_3$ | 4-OCF$_2$OCF$_3$ | 2-F-4-NO$_2$ | 2-Br-4-NO$_2$-6-CN |
| 3-Cl | 3-SCH$_3$ | 2-COPh | 2-Br-4-NO$_2$ | 3-Cl-4-CF$_3$-2,6-2NO$_2$ |
| 4-Cl | 4-SCH$_3$ | 3-COPh | 2-CF$_3$-4-NO$_2$ | 2NO$_2$-4,5-2Cl |
| 2,3-2Cl | 2-OCF$_3$ | 4-COPh | 2-CN-4-NO$_2$ | 2-NO$_2$-3,5-2Cl |
| 2,4-2Cl | 3-OCF$_3$ | 2-COCH$_2$Ph | 2-COCH$_3$-4-NO$_2$ | 2,5-2Cl-4-NO$_2$ |
| 2,5-2Cl | 4-OCF$_3$ | 3-COCH$_2$Ph | 2-CONH$_2$-4-NO$_2$ | 2,5-2Cl-6-NO$_2$ |
| 2,6-2Cl | 2-SCF$_3$ | 4-COCH$_2$Ph | 2-CH$_3$-4-NO$_2$ | 2,3-2Cl-4-NO$_2$ |
| 3,4-2Cl | 3-SCF$_3$ | 2-NHPh | 2-Cl-4-F-6-NO$_2$ | 2,3-2Cl-6-NO$_2$ |
| 3,5-2Cl | 4-SCF$_3$ | 3-NHPh | 2-Cl-4-Br-6-NO$_2$ | 3,4-2Cl-2,6-2NO$_2$ |
| 2,3,4-3Cl | 2-OC$_2$H$_5$ | 4-NHPh | 2-Cl-4-CH$_3$-6-NO$_2$ | 2,5-2Cl-4,6-2NO$_2$ |
| 2,3,5-3Cl | 3-OC$_2$H$_5$ | 2-OPh | 2-Cl-4-CF$_3$-6-NO$_2$ | 2,4,5-3Cl-6-NO$_2$ |
| 2,4,5-3Cl | 4-OC$_2$H$_5$ | 3-OPh | 2-Cl-4,6-2NO$_2$ | 2,3,4-3Cl-5-NO$_2$ |
| 2,3,6-3Cl | 2-NHCH$_3$ | 4-OPh | 2-Cl-4-CN-6-NO$_2$ | 2,3,4-3Cl-6-NO$_2$ |
| 2,4,6-3Cl | 3-NHCH$_3$ | 2-CONHPh | 2-Cl-4-OCF$_3$-6-NO$_2$ | 2,3,5-3Cl-4,6-2CN |
| 3,4,5-3Cl | 4-NHCH$_3$ | 3-CONHPh | 2-F-4-Cl-6-NO$_2$ | 2,5-2Cl-4-OCF$_2$OCF$_3$ |
| 2-Br | 2-N(CH$_3$)$_2$ | 4-CONHPh | 2-Br-4-Cl-6-NO$_2$ | 2,6-2Br-4-NO$_2$ |
| 3-Br | 3-N(CH$_3$)$_2$ | 2-CO$_2$Ph | 2-CH$_3$-4-Cl-6-NO$_2$ | 2-F-4-NO$_2$-6-Cl |
| 4-Br | 4-N(CH$_3$)$_2$ | 3-CO$_2$Ph | 2-CF$_3$-4-Cl-6-NO$_2$ | 2-Cl-4-NO$_2$-6-SCN |
| 2,3-2Br | 2-COCH$_3$ | 4-CO$_2$Ph | 4-Cl-2,6-2NO$_2$ | 2-Br-4-NO$_2$-6-Cl |
| 2,4-2Br | 3-COCH$_3$ | 2-CONH$_2$ | 2-F-4-CN | 2-Cl-4-NO$_2$-6-OCH$_3$ |
| 2,5-2Br | 4-COCH$_3$ | 3-CONH$_2$ | 2-CN-4-CF$_3$ | 2-Cl-4-NO$_2$-6-SCH$_3$ |
| 2,6-2Br | 2-COC$_2$H$_5$ | 4-CONH$_2$ | 4-CF$_3$-2,6-2NO$_2$ | 2-Cl-4-NO$_2$-6-NHCH$_3$ |
| 3,4-2Br | 3-COC$_2$H$_5$ | 2-Cl-4-F | 4-CN-2,6-2NO$_2$ | 2-Cl-4-NO$_2$-6-SO$_2$CH$_3$ |
| 3,5-2Br | 4-COC$_2$H$_5$ | 2-Cl-4-Br | 4-CH$_3$-2,6-2NO$_2$ | 2-Cl-4-SO$_2$CH$_3$ |
| 2,3,4-3Br | 2-SO$_2$CH$_3$ | 2-Cl-4-CH$_3$ | 4-OCF$_3$-2,6-2NO$_2$ | 2,6-2Cl-4-SO$_2$CH$_3$ |
| 2,3,5-3Br | 3-SO$_2$CH$_3$ | 2-Cl-4-CF$_3$ | 4-OCH$_3$-2,6-2NO$_2$ | 2,6-2Cl-4-CH$_3$ |
| 2,4,5-3Br | 4-SO$_2$CH$_3$ | 4-SCH$_3$-2,6-2NO$_2$ | 2,6-2Cl-4-CO$_2$CH$_3$ |
| 2,3,6-3Br | 2-OCHF$_2$ | 2-Cl-4-CN | 4-NHCH$_3$-2,6-2NO$_2$ | 2,6-2Cl-4-CONHCH$_3$ |
| 2,4,6-3Br | 3-OCHF$_2$ | 2-Cl-4-OCF$_3$ | 4-F-2,6-2NO$_2$ | 2,6-2Cl-4-CON(CH$_3$)$_2$ |
| 3,4,5-3Br | 4-OCHF$_2$ | 2-F-4-Cl | 2-CF$_3$-4,6-2NO$_2$ | 2,6-2Cl-4-CF(CF$_3$)$_2$ |
| 2-CN | 2-SO$_2$C$_2$H$_5$ | 2-Br-4-Cl | 2-CN-4,6-2NO$_2$ | 2-Cl-4-CF(CF$_3$)$_2$-6-Br |
| 3-CN | 3-SO$_2$C$_2$H$_5$ | 2-CH$_3$-4-Cl | 2-CH$_3$-4,6-2NO$_2$ | 2-F-4-CF(CF$_3$)$_2$-6-Br |
| 4-CN | 4-SO$_2$C$_2$H$_5$ | 2-CF$_3$-4-Cl | 2-F-4,6-2NO$_2$ | 2-F-4-CF(CF$_3$)$_2$-6-Cl |
| 2-NO$_2$ | 2-CO$_2$CH$_3$ | 2-NO$_2$-4-Cl | 2-OCF$_3$-4,6-2NO$_2$ | 2,4,5-3Cl-3,6-2CN |
| 3-NO$_2$ | 3-CO$_2$CH$_3$ | 2-CN-4-Cl | 2-CF$_3$-4-Br | 2,3,5-3F-4,6-2CN |
| 4-NO$_2$ | 4-CO$_2$CH$_3$ | 2-OCF$_3$-4-Cl | 3-CF$_3$-4-NO$_2$ | 2-SO$_2$NH$_2$ |
| 2,4-2NO$_2$ | 2-CO$_2$C$_2$H$_5$ | 2,6-2Cl-4-NO$_2$ | 2-CN-4-Cl-6-NO$_2$ | 3-SO$_2$NH$_2$ |
| 2,4,6-3NO$_2$ | 3-CO$_2$C$_2$H$_5$ | 2,6-2Cl-4-CF$_3$ | 2-OCF$_3$-4-Cl-6-NO$_2$ | 4-SO$_2$NH$_2$ |
| 2-CH$_3$ | 4-CO$_2$C$_2$H$_5$ | 2,6-2Cl-4-CN | 3-CF$_3$-4-CN | |
| 3-CH$_3$ | 2-CH$_2$OCH$_3$ | 2,6-2Cl-4-COCH$_3$ | 3-CN-4-CF$_3$ | |

TABLE 126

| $R_{12}$ substituents | | | |
|---|---|---|---|
| $R_{12}$ | $R_{12}$ | $R_{12}$ | $R_{12}$ |
| H | OH | $CH_3$ | $C_2H_5$ |
| n-$C_3H_7$ | i-$C_3H_7$ | n-$C_4H_9$ | s-$C_4H_9$ |
| i-$C_4H_9$ | t-$C_4H_9$ | HCO | $CH_3CO$ |
| $CH_3CH_2CO$ | n-$C_3H_7CO$ | i-$C_3H_7CO$ | $CH_3SO_2$ |
| $CH_3CH_2SO_2$ | n-$C_3H_7SO_2$ | n-$C_4H_9SO_2$ | |

The present invention is also explained by the following compounds having a structure as represented by formula II listed in Table 127 to Table 202, Compounds having a structure as represented by formula II-A are listed in Table 127 to Table 190, Compounds having a structure as represented by formula II-B are listed in Table 191 to Table 201, but without being restricted thereby.

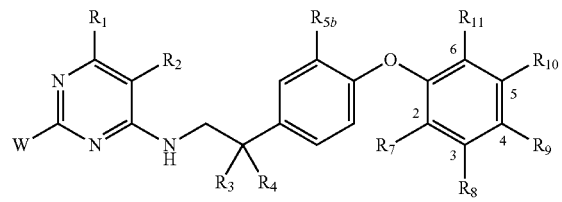

II-A

In general formula II-A, W=H, $R_1$=$CH_3$, $R_2$=Cl, $R_3$=$R_4$=$R_{5b}$=H, the substituents $R_7$, $R_8$, $R_9$, $R_{10}$ and $R_{11}$ refer to Table 127, the representative compounds are coded as II-1-II-2780

TABLE 127

| No. | $R_7$ | $R_8$ | $R_9$ | $R_{10}$ | $R_{11}$ |
|---|---|---|---|---|---|
| II-1 | H | H | H | H | H |
| II-2 | F | H | H | H | H |
| II-3 | H | F | H | H | H |
| II-4 | H | H | F | H | H |
| II-5 | F | F | H | H | H |
| II-6 | F | H | F | H | H |
| II-7 | F | H | H | F | H |
| II-8 | F | H | H | H | F |
| II-9 | H | F | F | H | H |
| II-10 | H | F | H | F | H |
| II-11 | F | F | F | H | H |
| II-12 | F | F | H | F | H |
| II-13 | F | H | F | F | H |
| II-14 | F | F | H | H | F |
| II-15 | F | H | F | H | F |
| II-16 | H | F | F | F | H |
| II-17 | Cl | H | H | H | H |
| II-18 | H | Cl | H | H | H |
| II-19 | H | H | Cl | H | H |
| II-20 | Cl | Cl | H | H | H |
| II-21 | Cl | H | Cl | H | H |
| II-22 | Cl | H | H | Cl | H |
| II-23 | Cl | H | H | H | Cl |
| II-24 | H | Cl | Cl | H | H |
| II-25 | H | Cl | H | Cl | H |
| II-26 | Cl | Cl | Cl | H | H |
| II-27 | Cl | Cl | H | Cl | H |
| II-28 | Cl | H | Cl | Cl | H |
| II-29 | Cl | Cl | H | H | Cl |
| II-30 | Cl | H | Cl | H | Cl |
| II-31 | H | Cl | Cl | Cl | H |
| II-32 | Br | H | H | H | H |
| II-33 | H | Br | H | H | H |
| II-34 | H | H | Br | H | H |
| II-35 | Br | Br | H | H | H |
| II-36 | Br | H | Br | H | H |
| II-37 | Br | H | H | Br | H |
| II-38 | Br | H | H | H | Br |
| II-39 | H | Br | Br | H | H |
| II-40 | H | Br | H | Br | H |
| II-41 | Br | Br | Br | H | H |
| II-42 | Br | Br | H | Br | H |
| II-43 | Br | H | Br | Br | H |
| II-44 | Br | Br | H | H | Br |
| II-45 | Br | H | Br | H | Br |
| II-46 | H | Br | Br | Br | H |
| II-47 | CN | H | H | H | H |
| II-48 | H | CN | H | H | H |
| II-49 | H | H | CN | H | H |
| II-50 | $NO_2$ | H | H | H | H |
| II-51 | H | $NO_2$ | H | H | H |
| II-52 | H | H | $NO_2$ | H | H |
| II-53 | $NO_2$ | H | $NO_2$ | H | H |
| II-54 | $NO_2$ | H | $NO_2$ | H | $NO_2$ |
| II-55 | $CH_3$ | H | H | H | H |

TABLE 127-continued

| No. | R$_7$ | R$_8$ | R$_9$ | R$_{10}$ | R$_{11}$ |
|---|---|---|---|---|---|
| II-56 | H | CH$_3$ | H | H | H |
| II-57 | H | H | CH$_3$ | H | H |
| II-58 | CH$_3$ | CH$_3$ | H | H | H |
| II-59 | CH$_3$ | H | CH$_3$ | H | H |
| II-60 | CH$_3$ | H | H | CH$_3$ | H |
| II-61 | CH$_3$ | H | H | H | CH$_3$ |
| II-62 | H | CH$_3$ | CH$_3$ | H | H |
| II-63 | H | CH$_3$ | H | CH$_3$ | H |
| II-64 | C$_2$H$_5$ | H | H | H | H |
| II-65 | H | C$_2$H$_5$ | H | H | H |
| II-66 | H | H | C$_2$H$_5$ | H | H |
| II-67 | CF$_3$ | H | H | H | H |
| II-68 | H | CF$_3$ | H | H | H |
| II-69 | H | H | CF$_3$ | H | H |
| II-70 | OCH$_3$ | H | H | H | H |
| II-71 | H | OCH$_3$ | H | H | H |
| II-72 | H | H | OCH$_3$ | H | H |
| II-73 | SCH$_3$ | H | H | H | H |
| II-74 | H | SCH$_3$ | H | H | H |
| II-75 | H | H | SCH$_3$ | H | H |
| II-76 | OCF$_3$ | H | H | H | H |
| II-77 | H | OCF$_3$ | H | H | H |
| II-78 | H | H | OCF$_3$ | H | H |
| II-79 | SCF$_3$ | H | H | H | H |
| II-80 | H | SCF$_3$ | H | H | H |
| II-81 | H | H | SCF$_3$ | H | H |
| II-82 | OC$_2$H$_5$ | H | H | H | H |
| II-83 | H | OC$_2$H$_5$ | H | H | H |
| II-84 | H | H | OC$_2$H$_5$ | H | H |
| II-85 | NHCH$_3$ | H | H | H | H |
| II-86 | H | NHCH$_3$ | H | H | H |
| II-87 | H | H | NHCH$_3$ | H | H |
| II-88 | N(CH$_3$)$_2$ | H | H | H | H |
| II-89 | H | N(CH$_3$)$_2$ | H | H | H |
| II-90 | H | H | N(CH$_3$)$_2$ | H | H |
| II-91 | COCH$_3$ | H | H | H | H |
| II-92 | H | COCH$_3$ | H | H | H |
| II-93 | H | H | COCH$_3$ | H | H |
| II-94 | COC$_2$H$_5$ | H | H | H | H |
| II-95 | H | COC$_2$H$_5$ | H | H | H |
| II-96 | H | H | COC$_2$H$_5$ | H | H |
| II-97 | SO$_2$CH$_3$ | H | H | H | H |
| II-98 | H | SO$_2$CH$_3$ | H | H | H |
| II-99 | H | H | SO$_2$CH$_3$ | H | H |
| II-100 | OCHF$_2$ | H | H | H | H |
| II-101 | H | OCHF$_2$ | H | H | H |
| II-102 | H | H | OCHF$_2$ | H | H |
| II-103 | SO$_2$C$_2$H$_5$ | H | H | H | H |
| II-104 | H | SO$_2$C$_2$H$_5$ | H | H | H |
| II-105 | H | H | SO$_2$C$_2$H$_5$ | H | H |
| II-106 | CO$_2$CH$_3$ | H | H | H | H |
| II-107 | H | CO$_2$CH$_3$ | H | H | H |
| II-108 | H | H | CO$_2$CH$_3$ | H | H |
| II-109 | CO$_2$C$_2$H$_5$ | H | H | H | H |
| II-110 | H | CO$_2$C$_2$H$_5$ | H | H | H |
| II-111 | H | H | CO$_2$C$_2$H$_5$ | H | H |
| II-112 | CH$_2$OCH$_3$ | H | H | H | H |
| II-113 | H | CH$_2$OCH$_3$ | H | H | H |
| II-114 | H | H | CH$_2$OCH$_3$ | H | H |
| II-115 | OCOCH$_3$ | H | H | H | H |
| II-116 | H | OCOCH$_3$ | H | H | H |
| II-117 | H | H | OCOCH$_3$ | H | H |
| II-118 | OCOCH$_2$CH$_3$ | H | H | H | H |
| II-119 | H | OCOCH$_2$CH$_3$ | H | H | H |
| II-120 | H | H | OCOCH$_2$CH$_3$ | H | H |
| II-121 | OCO$_2$CH$_3$ | H | H | H | H |
| II-122 | H H | OCO$_2$CH$_3$ | H | H | H |
| II-123 | H | H | OCO$_2$CH$_3$ | H | H |
| II-124 | OCH$_2$OCH$_3$ | H | H | H | H |
| II-125 | H | OCH$_2$OCH$_3$ | H | H | H |
| II-126 | H | H | OCH$_2$OCH$_3$ | H | H |
| II-127 | OCF$_2$OCF$_3$ | H | H | H | H |
| II-128 | H | OCF$_2$OCF$_3$ | H | H | H |
| II-129 | H | H | OCF$_2$OCF$_3$ | H | H |
| II-130 | COPh | H | H | H | H |
| II-131 | H | COPh | H | H | H |
| II-132 | H | H | COPh | H | H |
| II-133 | COCH$_2$Ph | H | H | H | H |

TABLE 127-continued

| No. | R_7 | R_8 | R_9 | R_10 | R_11 |
|---|---|---|---|---|---|
| II-134 | H | COCH_2Ph | H | H | H |
| II-135 | H | H | COCH_2Ph | H | H |
| II-136 | NHPh | H | H | H | H |
| II-137 | H | NHPh | H | H | H |
| II-138 | H | H | NHPh | H | H |
| II-139 | OPh | H | H | H | H |
| II-140 | H | OPh | H | H | H |
| II-141 | H | H | OPh | H | H |
| II-142 | CONHPh | H | H | H | H |
| II-143 | H | CONHPh | H | H | H |
| II-144 | H | H | CONHPh | H | H |
| II-145 | CO_2Ph | H | H | H | H |
| II-146 | H | CO_2Ph | H | H | H |
| II-147 | H | H | CO_2Ph | H | H |
| II-148 | CONH_2 | H | H | H | H |
| II-149 | H | CONH_2 | H | H | H |
| II-150 | H | H | CONH_2 | H | H |
| II-151 | Cl | H | F | H | H |
| II-152 | Cl | H | Br | H | H |
| II-153 | Cl | H | CH_3 | H | H |
| II-154 | Cl | H | CF_3 | H | H |
| II-155 | Cl | H | NO_2 | H | H |
| II-156 | Cl | H | CN | H | H |
| II-157 | Cl | H | OCF_3 | H | H |
| II-158 | F | H | Cl | H | H |
| II-159 | Br | H | Cl | H | H |
| II-160 | CH_3 | H | Cl | H | H |
| II-161 | CF_3 | H | Cl | H | H |
| II-162 | NO_2 | H | Cl | H | H |
| II-163 | CN | H | Cl | H | H |
| II-164 | OCF_3 | H | Cl | H | H |
| II-165 | Cl | H | NO_2 | H | Cl |
| II-166 | Cl | H | CF_3 | H | Cl |
| II-167 | Cl | H | CN | H | Cl |
| II-168 | Cl | H | COCH_3 | H | Cl |
| II-169 | Cl | H | CONH_2 | H | Cl |
| II-170 | Cl | H | Cl | H | NO_2 |
| II-171 | Cl | H | Cl | H | CN |
| II-172 | Cl | H | Cl | H | CF_3 |
| II-173 | F | H | F | H | NO_2 |
| II-174 | F | H | NO_2 | H | F |
| II-175 | NO_2 | H | F | H | H |
| II-176 | NO_2 | H | Br | H | H |
| II-177 | NO_2 | H | CF_3 | H | H |
| II-178 | NO_2 | H | CN | H | H |
| II-179 | NO_2 | H | COCH_3 | H | H |
| II-180 | NO_2 | H | CONH_2 | H | H |
| II-181 | NO_2 | H | CH_3 | H | H |
| II-182 | NO_2 | H | OCH_3 | H | H |
| II-183 | NO_2 | H | SCH_3 | H | H |
| II-184 | NO_2 | H | NCH_3 | H | H |
| II-185 | F | H | NO_2 | H | H |
| II-186 | Br | H | NO_2 | H | H |
| II-187 | CF_3 | H | NO_2 | H | H |
| II-188 | CN | H | NO_2 | H | H |
| II-189 | COCH_3 | H | NO_2 | H | H |
| II-190 | CONH_2 | H | NO_2 | H | H |
| II-191 | CH_3 | H | NO_2 | H | H |
| II-192 | Cl | H | F | H | NO_2 |
| II-193 | Cl | H | Br | H | NO_2 |
| II-194 | Cl | H | CH_3 | H | NO_2 |
| II-195 | Cl | H | CF_3 | H | NO_2 |
| II-196 | Cl | H | NO_2 | H | NO_2 |
| II-197 | Cl | H | CN | H | NO_2 |
| II-198 | Cl | H | OCF_3 | H | NO_2 |
| II-199 | F | H | Cl | H | NO_2 |
| II-200 | Br | H | Cl | H | NO_2 |
| II-201 | CH_3 | H | Cl | H | NO_2 |
| II-202 | CF_3 | H | Cl | H | NO_2 |
| II-203 | NO_2 | H | Cl | H | NO_2 |
| II-204 | F | H | CN | H | H |
| II-205 | CN | H | CF_3 | H | H |
| II-206 | NO_2 | H | CF_3 | H | NO_2 |
| II-207 | NO_2 | H | CN | H | NO_2 |
| II-208 | NO_2 | H | CH_3 | H | NO_2 |
| II-209 | NO_2 | H | OCF_3 | H | NO_2 |
| II-210 | NO_2 | H | OCH_3 | H | NO_2 |
| II-211 | NO_2 | H | SCH_3 | H | NO_2 |

TABLE 127-continued

| No. | $R_7$ | $R_8$ | $R_9$ | $R_{10}$ | $R_{11}$ |
|---|---|---|---|---|---|
| II-212 | $NO_2$ | H | $NHCH_3$ | H | $NO_2$ |
| II-213 | $NO_2$ | H | F | H | $NO_2$ |
| II-214 | $CF_3$ | H | $NO_2$ | H | $NO_2$ |
| II-215 | CN | H | $NO_2$ | H | $NO_2$ |
| II-216 | $CH_3$ | H | $NO_2$ | H | $NO_2$ |
| II-217 | F | H | $NO_2$ | H | $NO_2$ |
| II-218 | $OCF_3$ | H | $NO_2$ | H | $NO_2$ |
| II-219 | $CF_3$ | H | Br | H | H |
| II-220 | H | $CF_3$ | $NO_2$ | H | H |
| II-221 | CN | H | Cl | H | $NO_2$ |
| II-222 | $OCF_3$ | H | Cl | H | $NO_2$ |
| II-223 | H | $CF_3$ | CN | H | H |
| II-224 | H | CN | $CF_3$ | H | H |
| II-225 | $CF_3$ | H | Br | H | $NO_2$ |
| II-226 | H | $NO_2$ | $CF_3$ | H | H |
| II-227 | $NO_2$ | H | CN | $CF_3$ | H |
| II-228 | $NO_2$ | H | $CF_3$ | CN | H |
| II-229 | Br | H | $OCF_3$ | H | Br |
| II-230 | $CH_3$ | H | Cl | $CH_2CO_2C_2H_5$ | H |
| II-231 | Cl | $CH_3$ | Cl | H | $OCF_2OCF_3$ |
| II-232 | Cl | $CH_3$ | Cl | H | $NO_2$ |
| II-233 | Cl | $CH_3$ | H | H | H |
| II-234 | $CH_3$ | Cl | H | H | H |
| II-235 | $CH_3$ | Cl | $NO_2$ | H | $NO_2$ |
| II-236 | $CH_3$ | Cl | $NO_2$ | H | H |
| II-237 | $CH_3$ | Cl | H | H | $NO_2$ |
| II-238 | Cl | $CH_3$ | $NO_2$ | H | $NO_2$ |
| II-239 | Cl | $CH_3$ | $NO_2$ | H | H |
| II-240 | Cl | $CH_3$ | H | H | $NO_2$ |
| II-241 | Br | H | $NO_2$ | H | CN |
| II-242 | $NO_2$ | Cl | $CF_3$ | H | $NO_2$ |
| II-243 | $NO_2$ | H | Cl | Cl | H |
| II-244 | $NO_2$ | Cl | H | Cl | H |
| II-245 | Cl | H | $NO_2$ | Cl | H |
| II-246 | Cl | H | H | Cl | $NO_2$ |
| II-247 | Cl | Cl | $NO_2$ | H | H |
| II-248 | Cl | Cl | H | H | $NO_2$ |
| II-249 | $NO_2$ | Cl | Cl | H | $NO_2$ |
| II-250 | Cl | H | $NO_2$ | Cl | $NO_2$ |
| II-251 | Cl | H | Cl | Cl | $NO_2$ |
| II-252 | Cl | Cl | Cl | $NO_2$ | H |
| II-253 | Cl | Cl | Cl | H | $NO_2$ |
| II-254 | Cl | Cl | CN | Cl | CN |
| II-255 | Cl | H | $OCF_2OCF_3$ | Cl | H |
| II-256 | Br | H | $NO_2$ | H | Br |
| II-257 | F | H | $NO_2$ | H | Cl |
| II-258 | Cl | H | $NO_2$ | H | SCN |
| II-259 | Br | H | $NO_2$ | H | Cl |
| II-260 | Cl | H | $NO_2$ | H | $OCH_3$ |
| II-261 | Cl | H | $NO_2$ | H | $SCH_3$ |
| II-262 | Cl | H | $NO_2$ | H | $NHCH_3$ |
| II-263 | Cl | H | $NO_2$ | H | $SO_2CH_3$ |
| II-264 | Cl | H | $SO_2CH_3$ | H | H |
| II-265 | Cl | H | $SO_2CH_3$ | H | Cl |
| II-266 | Cl | H | $CH_3$ | H | Cl |
| II-267 | Cl | H | $CO_2CH_3$ | H | Cl |
| II-268 | Cl | H | $CONHCH_3$ | H | Cl |
| II-269 | Cl | H | $CON(CH_3)_2$ | H | Cl |
| II-270 | Cl | H | $CF(CF_3)_2$ | H | Cl |
| II-271 | Cl | H | $CF(CF_3)_2$ | H | Br |
| II-272 | F | H | $CF(CF_3)_2$ | H | Br |
| II-273 | F | H | $CF(CF_3)_2$ | H | Cl |
| II-274 | Cl | CN | Cl | Cl | CN |
| II-275 | F | F | CN | F | CN |
| II-276 | $SO_2NH_2$ | H | H | H | H |
| II-277 | H | $SO_2NH_2$ | H | H | H |
| II-278 | H | H | $SO_2NH_2$ | H | H |

Table 128: in general formula II-A, W=H, $R_1=C_2H_5$, $R_2=Cl$, $R_3=R_4=R_{5b}=H$, the substituents $R_7$, $R_8$, $R_9$, $R_{10}$ and $R_{11}$ are consistent with those in Table 127 and corresponding to II-1-II-278 in table 127 in turn, the representative compounds are coded as II-279-II-556.

Table 129: in general formula II-A, W=H, $R_1=CH_3$, $R_2=R_{5b}=Cl$, $R_3=R_4=H$, the substituents $R_7$, $R_8$, $R_9$, $R_{10}$ and $R_{11}$ are consistent with those in Table 127 and corresponding to II-1-II-278 in table 127 in turn, the representative compounds are coded as II-557-II-834.

Table 130: in general formula II-A, W=H, $R_1=C_2H_5$, $R_2=R_{5b}=Cl$, $R_3=R_4=H$, the substituents $R_7$, $R_8$, $R_9$, $R_{10}$ and $R_{11}$ are consistent with those in Table 127 and corresponding to II-1-II-278 in table 127 in turn, the representative compounds are coded as II-835-II-1112.

Table 131: in general formula II-A, W=H, $R_1$=$CH_3$, $R_2$=Cl, $R_3$=$R_4$=H, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-1113-II-1390.

Table 132: in general formula II-A, W=H, $R_1$=$C_2H_5$, $R_2$=Cl, $R_3$=$R_4$=H, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-1391-II-1668.

Table 133: in general formula II-A, W=H, $R_1$=$CH_3$, $R_2$=Cl, $R_3$=$R_4$=H, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-1669-II-1946.

Table 134: in general formula II-A, W=H, $R_1$=$C_2H_5$, $R_2$=Cl, $R_3$=$R_4$=H, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-1947-II-2224.

Table 135: in general formula II-A, W=H, $R_1$=$CH_3$, $R_2$=Cl, $R_3$=$R_{5b}$=H, $R_4$=$CH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-2225-II-2502.

Table 136: in general formula II-A, W=H, $R_1$=$C_2H_5$, $R_2$=Cl, $R_3$=$R_{5b}$=H, $R_4$=$CH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-2503-II-2780.

Table 137: in general formula II-A, W=H, $R_1$=$CH_3$, $R_2$=Cl, $R_3$=H, $R_4$=$CH_3$, $R_{5b}$=Cl, the substituents $R_7$, $R_8$, $R_9$, $R_{10}$ and $R_{11}$ are consistent with those in Table 127 and corresponding to II-1-II-278 in table 127 in turn, the representative compounds are coded as II-2781-II-3058.

Table 138: in general formula II-A, W=H, $R_1$=$C_2H_5$, $R_2$=Cl, $R_3$=H, $R_4$=$CH_3$, $R_{5b}$=Cl, the substituents $R_7$, $R_8$, $R_9$, $R_{10}$ and $R_{11}$ are consistent with those in Table 127 and corresponding to II-1-II-278 in table 127 in turn, the representative compounds are coded as II-3059-II-3336.

Table 139: in general formula II-A, W=H, $R_1$=$CH_3$, $R_2$=Cl, $R_3$=H, $R_4$=$CH_3$, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-3337-II-3614.

Table 140: in general formula II-A, W=H, $R_1$=$C_2H_5$, $R_2$=Cl, $R_3$=H, $R_4$=$CH_3$, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-3615-II-3892.

Table 141: in general formula II-A, W=H, $R_1$=$CH_3$, $R_2$=Cl, $R_3$=H, $R_4$=$CH_3$, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-3893-II-4170.

Table 142: in general formula II-A, W=H, $R_1$=$C_2H_5$, $R_2$=Cl, $R_3$=H, $R_4$=$CH_3$, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-4171-II-4448.

Table 143: in general formula II-A, W=$CH_3$, $R_1$=$CH_3$, $R_2$=Cl, $R_3$=$R_4$=$R_{5b}$=H, the substituents $R_7$, $R_8$, $R_9$, $R_{10}$ and $R_{11}$ are consistent with those in Table 127 and corresponding to II-1-II-278 in table 127 in turn, the representative compounds are coded as II-4449-II-4726.

Table 144: in general formula II-A, W=$CH_3$, $R_1$=$C_2H_5$, $R_2$=Cl, $R_3$=$R_4$=$R_{5b}$=H, the substituents $R_7$, $R_8$, $R_9$, $R_{10}$ and $R_{11}$ are consistent with those in Table 127 and corresponding to II-1-II-278 in table 127 in turn, the representative compounds are coded as II-4727-II-5004.

Table 145: in general formula II-A, W=$CH_3$, $R_1$=$CH_3$, $R_2$=$R_{5b}$=Cl, $R_3$=$R_4$=H, the substituents $R_7$, $R_8$, $R_9$, $R_{10}$ and $R_{11}$ are consistent with those in Table 127 and corresponding to II-1-II-278 in table 127 in turn, the representative compounds are coded as II-5005-II-5282.

Table 146: in general formula II-A, W=$CH_3$, $R_1$=$C_2H_5$, $R_2$=$R_{5b}$=Cl, $R_3$=$R_4$=H, the substituents $R_7$, $R_8$, $R_9$, $R_{10}$ and $R_{11}$ are consistent with those in Table 127 and corresponding to II-1-II-278 in table 127 in turn, the representative compounds are coded as II-5283-II-5560.

Table 147: in general formula II-A, W=$CH_3$, $R_1$=$CH_3$, $R_2$=Cl, $R_3$=$R_4$=H, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-5561-II-5838.

Table 148: in general formula II-A, W=$CH_3$, $R_1$=$C_2H_5$, $R_2$=Cl, $R_3$=$R_4$=H, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-5839-II-6116.

Table 149: in general formula II-A, W=$CH_3$, $R_1$=$CH_3$, $R_2$=Cl, $R_3$=$R_4$=H, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-6117-II-6394.

Table 150: in general formula II-A, W=$CH_3$, $R_1$=$C_2H_5$, $R_2$=Cl, $R_3$=$R_4$=H, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-6395-II-6672.

Table 151: in general formula II-A, W=$CH_3$, $R_1$=$CH_3$, $R_2$=Cl, $R_3$=$R_{5b}$=H, $R_4$=$CH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-6673-II-6950.

Table 152: in general formula II-A, W=$CH_3$, $R_1$=$C_2H_5$, $R_2$=Cl, $R_3$=$R_{5b}$=H, $R_4$=$CH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-6951-II-7228.

Table 153: in general formula II-A, W=$CH_3$, $R_1$=$CH_3$, $R_2$=Cl, $R_3$=H, $R_4$=$CH_3$, $R_{5b}$=Cl, the substituents $R_7$, $R_8$, $R_9$, $R_{10}$ and $R_{11}$ are consistent with those in Table 127 and corresponding to II-1-II-278 in table 127 in turn, the representative compounds are coded as II-7229-II-7506.

Table 154: in general formula II-A, W=$CH_3$, $R_1$=$C_2H_5$, $R_2$=Cl, $R_3$=H, $R_4$=$CH_3$, $R_{5b}$=Cl, the substituents $R_7$, $R_8$, $R_9$, $R_{10}$ and $R_{11}$ are consistent with those in Table 127 and corresponding to II-1-II-278 in table 127 in turn, the representative compounds are coded as II-7507-II-7784.

Table 155: in general formula II-A, W=$CH_3$, $R_1$=$CH_3$, $R_2$=Cl, $R_3$=H, $R_4$=$CH_3$, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-7785-II-8062.

Table 156: in general formula II-A, W=$CH_3$, $R_1$=$C_2H_5$, $R_2$=Cl, $R_3$=H, $R_4$=$CH_3$, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-8063-II-8340.

Table 157: in general formula II-A, W=$CH_3$, $R_1$=$CH_3$, $R_2$=Cl, $R_3$=H, $R_4$=$CH_3$, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-8341-II-8618.

Table 158: in general formula II-A, W=$CH_3$, $R_1$=$C_2H_5$, $R_2$=Cl, $R_3$=H, $R_4$=$CH_3$, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-8619-II-8896.

Table 159: in general formula II-A, W=H, $R_1$=$CHF_2$, $R_2$=Cl, $R_3$=$R_4$=$R_{5b}$=H, the substituents $R_7$, $R_8$, $R_9$, $R_{10}$ and $R_{11}$ are consistent with those in Table 127 and corresponding to II-1-II-278 in table 127 in turn, the representative compounds are coded as II-8897-II-9174.

Table 160: in general formula II-A, W=H, $R_1$=$CF_3$, $R_2$=Cl, $R_3$=$R_4$=$R_{5b}$=H, the substituents $R_7$, $R_8$, $R_9$, $R_{10}$ and $R_{11}$ are consistent with those in Table 127 and corresponding to II-1-II-278 in table 127 in turn, the representative compounds are coded as II-9175-II-9452.

Table 161: in general formula II-A, W=H, $R_1$=$CHF_2$, $R_2$=$R_{5b}$=Cl, $R_3$=$R_4$=H, the substituents $R_7$, $R_8$, $R_9$, $R_{10}$ and $R_{11}$ are consistent with those in Table 127 and corresponding to II-1-II-278 in table 127 in turn, the representative compounds are coded as II-9453-II-9730.

Table 162: in general formula II-A, W=H, $R_1$=$CF_3$, $R_2$=$R_{5b}$=Cl, $R_3$=$R_4$=H, the substituents $R_7$, $R_8$, $R_9$, $R_{10}$ and $R_{11}$ are consistent with those in Table 127 and corresponding to II-1-II-278 in table 127 in turn, the representative compounds are coded as II-9731-II-10008.

Table 163: in general formula II-A, W=H, $R_1$=$CHF_2$, $R_2$=Cl, $R_3$=$R_4$=H, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-10009-II-10286.

Table 164: in general formula II-A, W=H, $R_1$=$CF_3$, $R_2$=Cl, $R_3$=$R_4$=H, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-10287-II-10564.

Table 165: in general formula II-A, W=H, $R_1$=$CHF_2$, $R_2$=Cl, $R_3$=$R_4$=H, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-10565-II-10842.

Table 166: in general formula II-A, W=H, $R_1$=$CF_3$, $R_2$=Cl, $R_3$=$R_4$=H, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-10843-II-11120.

Table 167: in general formula II-A, W=H, $R_1$=$CHF_2$, $R_2$=Cl, $R_3$=$R_{5b}$=H, $R_4$=$CH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-11121-II-11398.

Table 168: in general formula II-A, W=H, $R_1$=$CF_3$, $R_2$=Cl, $R_3$=$R_{5b}$=H, $R_4$=$CH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-11399-II-11676.

Table 169: in general formula II-A, W=H, $R_1$=$CHF_2$, $R_2$=Cl, $R_3$=H, $R_4$=$CH_3$, $R_{5b}$=Cl, the substituents $R_7$, $R_8$, $R_9$, $R_{10}$ and $R_{11}$ are consistent with those in Table 127 and corresponding to II-1-II-278 in table 127 in turn, the representative compounds are coded as II-11677-II-11954.

Table 170: in general formula II-A, W=H, $R_1$=$CF_3$, $R_2$=Cl, $R_3$=H, $R_4$=$CH_3$, $R_{5b}$=Cl, the substituents $R_7$, $R_8$, $R_9$, $R_{10}$ and $R_{11}$ are consistent with those in Table 127 and corresponding to II-1-II-278 in table 127 in turn, the representative compounds are coded as II-11955-II-12232.

Table 171: in general formula II-A, W=H, $R_1$=$CHF_2$, $R_2$=Cl, $R_3$=H, $R_4$=$CH_3$, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-12233-II-12510.

Table 172: in general formula II-A, W=H, $R_1$=$CF_3$, $R_2$=Cl, $R_3$=H, $R_4$=$CH_3$, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-12511-II-12788.

Table 173: in general formula II-A, W=H, $R_1$=$CHF_2$, $R_2$=Cl, $R_3$=H, $R_4$=$CH_3$, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-12789-II-13066.

Table 174: in general formula II-A, W=H, $R_1$=$CF_3$, $R_2$=Cl, $R_3$=H, $R_4$=$CH_3$, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-13067-II-13344.

Table 175: in general formula II-A, W=$CH_3$, $R_1$=$CHF_2$, $R_2$=Cl, $R_3$=$R_4$=$R_{5b}$=H, the substituents $R_7$, $R_8$, $R_9$, $R_{10}$ and $R_{11}$ are consistent with those in Table 127 and corresponding to II-1-II-278 in table 127 in turn, the representative compounds are coded as II-13345-II-13622.

Table 176: in general formula II-A, W=$CH_3$, $R_1$=$CF_3$, $R_2$=Cl, $R_3$=$R_4$=$R_{5b}$=H, the substituents $R_7$, $R_8$, $R_9$, $R_{10}$ and $R_{11}$ are consistent with those in Table 127 and corresponding to II-1-II-278 in table 127 in turn, the representative compounds are coded as II-13623-II-13900.

Table 177: in general formula II-A, W=$CH_3$, $R_1$=$CHF_2$, $R_2$=$R_{5b}$=Cl, $R_3$=$R_4$=H, the substituents $R_7$, $R_8$, $R_9$, $R_{10}$ and $R_{11}$ are consistent with those in Table 127 and corresponding to II-1-II-278 in table 127 in turn, the representative compounds are coded as II-13901-II-14178.

Table 178: in general formula II-A, W=$CH_3$, $R_1$=$CF_3$, $R_2$=$R_{5b}$=Cl, $R_3$=$R_4$=H, the substituents $R_7$, $R_8$, $R_9$, $R_{10}$ and $R_{11}$ are consistent with those in Table 127 and corresponding to II-1-II-278 in table 127 in turn, the representative compounds are coded as II-14179-II-14456.

Table 179: in general formula II-A, W=$CH_3$, $R_1$=$CHF_2$, $R_2$=Cl, $R_3$=$R_4$=H, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-14457-II-14734.

Table 180: in general formula II-A, W=$CH_3$, $R_1$=$CF_3$, $R_2$=Cl, $R_3$=$R_4$=H, $R_{5b}$=Br, the substituents $R_7$, $R_8$, $R_9$, $R_{10}$ and $R_{11}$ are consistent with those in Table 127 and corresponding to II-1-II-278 in table 127 in turn, the representative compounds are coded as II-14735-II-15012.

Table 181: in general formula II-A, W=$CH_3$, $R_1$=$CHF_2$, $R_2$=Cl, $R_3$=$R_4$=H, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-15013-II-15290.

Table 182: in general formula II-A, W=$CH_3$, $R_1$=$CF_3$, $R_2$=Cl, $R_3$=$R_4$=H, $R_{5b}$=$OCH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-15291-II-15568.

Table 183: in general formula II-A, W=$CH_3$, $R_1$=$CHF_2$, $R_2$=Cl, $R_3$=$R_{5b}$=H, $R_4$=$CH_3$, the substituents $R_7$, $R_8$, $R_9$, $R_{10}$ and $R_{11}$ are consistent with those in Table 127 and corresponding to II-1-II-278 in table 127 in turn, the representative compounds are coded as II-15569-II-15846.

Table 184: in general formula II-A, W=CH$_3$, R$_1$=CF$_3$, R$_2$=Cl, R$_3$=R$_{5b}$=H, R$_4$=CH$_3$, the substituents R$_7$, R$_8$, R$_9$, R$_{10}$ and R$_{11}$ are consistent with those in Table 127 and corresponding to II-1-II-278 in table 127 in turn, the representative compounds are coded as II-15847-II-16124.

Table 185: in general formula II-A, W=CH$_3$, R$_1$=CHF$_2$, R$_2$=Cl, R$_3$=H, R$_4$=CH$_3$, R$_{5b}$=Cl, the substituents R$_7$, R$_8$, R$_9$, R$_{10}$ and R$_{11}$ are consistent with those in Table 127 and corresponding to II-1-II-278 in table 127 in turn, the representative compounds are coded as II-16125-II-16402.

Table 186: in general formula II-A, W=CH$_3$, R$_1$=CF$_3$, R$_2$=Cl, R$_3$=H, R$_4$=CH$_3$, R$_{5b}$=Cl, the substituents R$_7$, R$_8$, R$_9$, R$_{10}$ and R$_{11}$ are consistent with those in Table 127 and corresponding to II-1-II-278 in table 127 in turn, the representative compounds are coded as II-16403-II-16680.

Table 187: in general formula II-A, W=CH$_3$, R$_1$=CHF$_2$, R$_2$=Cl, R$_3$=H, R$_4$=CH$_3$, R$_{5b}$=Br, the substituents R$_7$, R$_8$, R$_9$, R$_{10}$ and R$_{11}$ are consistent with those in Table 127 and corresponding to II-1-II-278 in table 127 in turn, the representative compounds are coded as II-16681-II-16958.

Table 188: in general formula II-A, W=CH$_3$, R$_1$=CF$_3$, R$_2$=Cl, R$_3$=H, R$_4$=CH$_3$, R$_{5b}$=Br, the substituents R$_7$, R$_8$, R$_9$, R$_{10}$ and R$_{11}$ are consistent with those in Table 127 and corresponding to II-1-II-278 in table 127 in turn, the representative compounds are coded as II-16959-II-17236.

Table 189: in general formula II-A, W=CH$_3$, R$_1$=CHF$_2$, R$_2$=Cl, R$_3$=H, R$_4$=CH$_3$, R$_{5b}$=OCH$_3$, the substituents R$_7$, R$_8$, R$_9$, R$_{10}$ and R$_{11}$ are consistent with those in Table 127 and corresponding to II-1-II-278 in table 127 in turn, the representative compounds are coded as II-17237-II-17514.

Table 190: in general formula II-A, W=CH$_3$, R$_1$=C$_2$H$_5$, R$_2$=Cl, R$_3$=H, R$_4$=CH$_3$, R$_{5b}$=OCH$_3$, the substituents R$_7$, R$_8$, R$_9$, R$_{10}$ and R$_{11}$ are consistent with those in Table 127 and corresponding to II-1-II-278 in table 127 in turn, the representative compounds are coded as II-17515-II-17792.

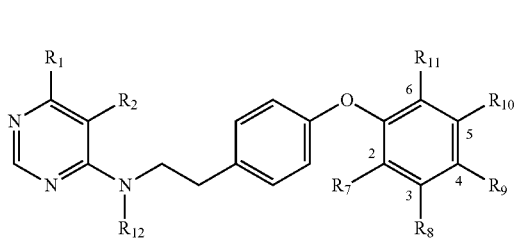

II-B

In general formula II-B, R$_1$=CH$_3$, R$_2$=Cl, R$_7$=R$_8$=R$_{10}$=R$_{11}$=H, R$_9$=CF$_3$, the substituent R$_{12}$ refers to Table 191, the representative compounds are coded as II-17793-II-17932.

TABLE 191

| No. | R$_{12}$ |
|---|---|
| II-17793 | S-i-C$_3$H$_7$ |
| II-17794 | OH |
| II-17795 | —C(═O)H |
| II-17796 | CBr$_3$ |
| II-17797 | CH$_3$ |
| II-17798 | C$_2$H$_5$ |
| II-17799 | n-C$_3$H$_7$ |
| II-17800 | i-C$_3$H$_7$ |
| II-17801 | n-C$_4$H$_9$ |
| II-17802 | i-C$_4$H$_9$ |
| II-17803 | t-C$_4$H$_9$ |
| II-17804 | CI$_3$ |

TABLE 191-continued

| No. | R$_{12}$ |
|---|---|
| II-17805 | CH$_2$Br |
| II-17806 | CHF$_2$ |
| II-17807 | CHBr$_2$ |
| II-17808 | CF$_3$ |
| II-17809 | CH$_2$Cl |
| II-17810 | CHCl$_2$ |
| II-17811 | CCl$_3$ |
| II-17812 | CH$_2$F |
| II-17813 | OCH$_3$ |
| II-17814 | OC$_2$H$_5$ |
| II-17815 | OCH(CH$_3$)$_2$ |
| II-17816 | OC(CH$_3$)$_3$ |
| II-17817 | OCF$_3$ |
| II-17818 | OCH$_2$CF$_3$ |
| II-17819 | OCH$_2$F |
| II-17820 | OCHF$_2$ |
| II-17821 | SCH$_3$ |
| II-17822 | SC$_2$H$_5$ |
| II-17823 | SCH$_2$CH═CH$_2$ |
| II-17824 | CH═CH$_2$ |
| II-17825 | CH$_2$CH═CH$_2$ |
| II-17826 | CH$_2$CH═CCl$_2$ |
| II-17827 | C≡CH |
| II-17828 | CH$_2$C≡CH |
| II-17829 | CH$_2$C≡C—I |
| II-17830 | CH$_2$OCH$_3$ |
| II-17831 | CH$_2$OCH$_2$CH$_3$ |
| II-17832 | CH$_2$CH$_2$OCH$_3$ |
| II-17833 | CH$_2$CH$_2$OCH$_2$CH$_3$ |
| II-17834 | CH$_2$OCH$_2$Cl |
| II-17835 | CH$_2$OCH$_2$CH$_2$Cl |
| II-17836 | CH$_2$CH$_2$OCH$_2$Cl |
| II-17837 | CH$_2$SCH$_3$ |
| II-17838 | CH$_2$SCH$_2$CH$_3$ |
| II-17839 | CH$_2$CH$_2$SCH$_3$ |
| II-17840 | CH$_2$CH$_2$SCH$_2$CH$_3$ |
| II-17841 | CH$_2$SCH$_2$Cl |
| II-17842 | CH$_2$SCH$_2$CH$_2$Cl |
| II-17843 | CH$_2$CH$_2$SCH$_2$Cl |
| II-17844 | SOCH$_3$ |
| II-17845 | SOC$_2$H$_5$ |
| II-17846 | SOCF$_3$ |
| II-17847 | SOCH$_2$CF$_3$ |
| II-17848 | SO$_2$CH$_3$ |
| II-17849 | SO$_2$C$_2$H$_5$ |
| II-17850 | SO$_2$CF$_3$ |
| II-17851 | SO$_2$CH$_2$CF$_3$ |
| II-17852 | SO$_2$NHCOCH$_3$ |
| II-17853 | SO$_2$NHCH$_3$ |
| II-17854 | SO$_2$N(CH$_3$)$_3$ |
| II-17855 | CONHSO$_2$CH$_3$ |
| II-17856 | COCH$_3$ |
| II-17857 | COC$_2$H$_5$ |
| II-17858 | CO—n-C$_3$H$_7$ |
| II-17859 | CO—i-C$_3$H$_7$ |
| II-17860 | CO—n-C$_4$H$_9$ |
| II-17861 | CO—i-C$_4$H$_9$ |
| II-17862 | CO—t-C$_4$H$_9$ |
| II-17863 | COCF$_3$ |
| II-17864 | COCH$_2$Cl |
| II-17865 | COOCH$_3$ |
| II-17866 | COOC$_2$H$_5$ |
| II-17867 | COO—n-C$_3$H$_7$ |
| II-17868 | COO—t-C$_4$H$_9$ |
| II-17869 | COOCF$_3$ |
| II-17870 | COOCH$_2$CH$_2$Cl |
| II-17871 | COOCH$_2$CF$_3$ |
| II-17872 | CH$_2$COOCH$_3$ |
| II-17873 | CH$_2$COOC$_2$H$_5$ |
| II-17874 | CH$_2$COCH$_3$ |
| II-17875 | CH$_2$COC$_2$H$_5$ |
| II-17876 | CONHCH$_3$ |
| II-17877 | CONHC$_2$H$_5$ |
| II-17878 | CONH—t-C$_4$H$_9$ |
| II-17879 | CON(CH$_3$)$_2$ |
| II-17880 | CON(C$_2$H$_5$)$_2$ |
| II-17881 | COOCH$_2$CH═CH$_2$ |
| II-17882 | COOCH$_2$C≡CH |

TABLE 191-continued
| No. | R₁₂ |
|---|---|
| II-17883 | COOCH₂OCH₃ |
| II-17884 | COOCH₂CH₂OCH₃ |
| II-17885 | SNHCH₃ |
| II-17886 | SNHC₂H₅ |
| II-17887 | SN(CH₃)₂ |
| II-17888 | SN(C₂H₅)₂ |
| II-17889 | 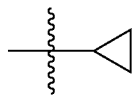 [SMILES: *C1CC1] |
| II-17890 | 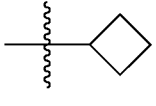 |
| II-17891 | 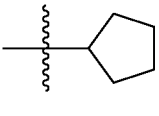 |
| II-17892 | 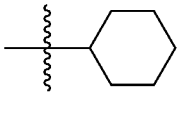 |
| II-17893 | 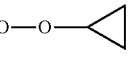 |
| II-17894 | 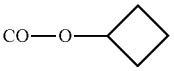 |
| II-17895 | 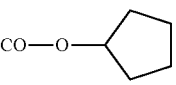 |
| II-17896 | 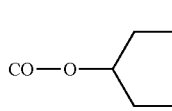 |
| II-17897 | 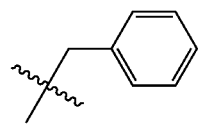 [SMILES: *Cc1ccccc1] |
| II-17898 | 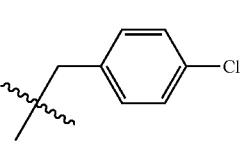 |
| II-17899 | 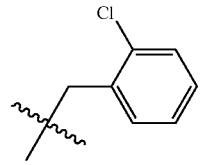 [SMILES: *Cc1ccccc1Cl] |
| II-17900 | 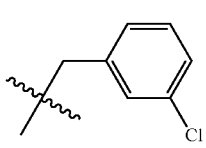 [SMILES: *Cc1cccc(Cl)c1] |
| II-17901 |  |
| II-17902 |  |
| II-17903 |  |
| II-17904 |  |
| II-17905 |  |
| II-17906 |  |
| II-17907 |  |
| II-17908 |  |
| II-17909 |  |
| II-17910 |  |
| II-17911 |  |

TABLE 191-continued

| No. | R$_{12}$ |
|---|---|
| II-17912 | CO—C$_6$H$_4$—CH$_3$ (para) |
| II-17913 | CO—C$_6$H$_4$—NO$_2$ (para) |
| II-17914 | CO—C$_6$H$_4$—CF$_3$ (para) |
| II-17915 | CO—C$_6$H$_4$—Cl (para) |
| II-17916 | CO—O—C$_6$H$_5$ |
| II-17917 | CO—O—C$_6$H$_4$—CH$_3$ (para) |
| II-17918 | CO—O—C$_6$H$_4$—CF$_3$ (para) |
| II-17919 | CO—O—C$_6$H$_4$—Cl (para) |
| II-17920 | CO—O—C$_6$H$_4$—NO$_2$ (para) |
| II-17921 | CO—O—CH$_2$—C$_6$H$_5$ |
| II-17922 | CO—O—CH$_2$—C$_6$H$_4$—CH$_3$ (para) |
| II-17923 | CO—O—CH$_2$—(2-chloropyridin-5-yl) |
| II-17924 | CO—O—CH$_2$—C$_6$H$_4$—CF$_3$ (para) |
| II-17925 | CO—O—CH$_2$—C$_6$H$_4$—NO$_2$ (para) |
| II-17926 | CO—O—CH$_2$—C$_6$H$_4$—OCH$_3$ (para) |
| II-17927 | CH$_2$—CO—C$_6$H$_5$ |
| II-17928 | CH$_2$—CO—C$_6$H$_4$—CH$_3$ (para) |
| II-17929 | CH$_2$—CO—C$_6$H$_4$—Cl (para) |
| II-17930 | CH$_2$—CO—C$_6$H$_4$—Br (para) |
| II-17931 | CH$_2$CH$_2$—CO—C$_6$H$_5$ |
| II-17932 | CH$_2$CH$_2$—CO—C$_6$H$_4$—Cl (para) |

Table 192: in general formula II-B, R$_1$=C$_2$H$_5$, R$_2$=Cl, R$_7$=R$_8$=R$_{10}$=R$_{11}$=H, R$_9$=CF$_3$, the substituent R$_{12}$ are consistent with those in Table 191 and corresponding to II-17793-II-17932 in table 191 in turn, the representative compounds are coded as II-17933-II-18072.

Table 193: in general formula II-B, R$_1$=CH$_3$, R$_2$=R$_9$=Cl, R$_7$=R$_8$=R$_{10}$=R$_{11}$=H, the substituent R$_{12}$ are consistent with those in Table 191 and corresponding to II-17793-II-17932 in table 191 in turn, the representative compounds are coded as II-18073-II-18212.

Table 194: in general formula II-B, R$_1$=C$_2$H$_5$, R$_2$=R$_9$=Cl, R$_7$=R$_8$=R$_{10}$=R$_{11}$=H, the substituent R$_{12}$ are consistent with those in Table 191 and corresponding to II-17793-II-17932 in table 191 in turn, the representative compounds are coded as II-18213-II-18352.

Table 195: in general formula II-B, R$_1$=CH$_3$, R$_2$=R$_7$=R$_9$=Cl, R$_8$=R$_{10}$=R$_{11}$=H, the substituent R$_{12}$ are consistent with those in Table 191 and corresponding to II-17793-II-17932 in table 191 in turn, the representative compounds are coded as II-18353-II-18492.

Table 196: in general formula II-B, R$_1$=C$_2$H$_5$, R$_2$=R$_7$=R$_9$=Cl, R$_8$=R$_{10}$=R$_{11}$=H, the substituent R$_{12}$ are consistent with those in Table 191 and corresponding to II-17793-II-17932 in table 191 in turn, the representative compounds are coded as II-18493-II-18632.

Table 197: in general formula II-B, R$_1$=CH$_3$, R$_2$=R$_7$=R$_{11}$=Cl, R$_8$=R$_{10}$=H, R$_9$=NO$_2$, the substituent R$_{12}$ are consistent with those in Table 191 and corresponding to II-17793-II-17932 in table 191 in turn, the representative compounds are coded as II-18633-II-18772.

Table 198: in general formula II-B, R$_1$=C$_2$H$_5$, R$_2$=R$_7$=R$_{11}$=Cl, R$_8$=R$_{10}$=H, R$_9$=NO$_2$, the substituent R$_{12}$ are consistent with those in Table 191 and corresponding to II-17793-II-17932 in table 191 in turn, the representative compounds are coded as II-18773-II-18912.

Table 199: in general formula II-B, $R_1$=CHF$_2$, $R_2$=$R_9$=Cl, $R_7$=$R_8$=$R_{10}$=$R_{11}$=H, the substituent $R_{12}$ are consistent with those in Table 191 and corresponding to II-17793-II-17932 in table 191 in turn, the representative compounds are coded as II-18913-II-19052.

Table 200: in general formula II-B, $R_1$=CHF$_2$, $R_2$=Cl, $R_7$=$R_8$=$R_{10}$=$R_{11}$=H, $R_9$=CF$_3$, the substituent $R_{12}$ are consistent with those in Table 191 and corresponding to II-17793-II-17932 in table 191 in turn, the representative compounds are coded as II-19053-II-19192.

Table 201: in general formula II-B, $R_1$=CHF$_2$, $R_2$=$R_7$=$R_9$=Cl, $R_8$=$R_{10}$=$R_{11}$=H, the substituent $R_{12}$ are consistent with those in Table 191 and corresponding to II-17793-II-17932 in table 191 in turn, the representative compounds are coded as II-19193-II-19332.

The salts of some compounds having a structure as represented by formula II of the present invention are listed in Table 202, but without being restricted thereby.

TABLE 202

| No. | structure |
|---|---|
| II-19333 | 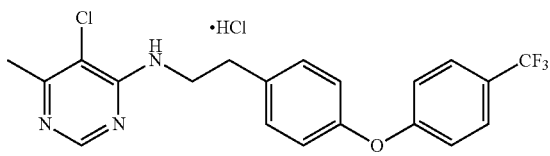 [SMILES: Cc1ncnc(NCCc2ccc(Oc3ccc(C(F)(F)F)cc3)cc2)c1Cl ; Cl] |
| II-19334 | 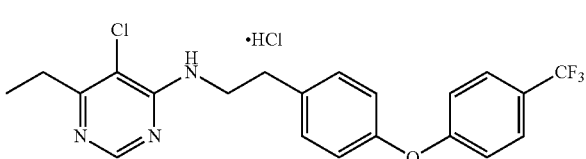 |
| II-19335 | 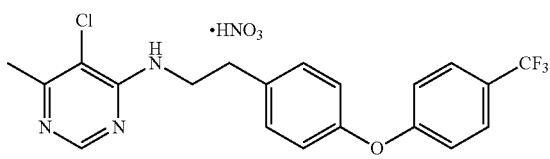 [SMILES: Cc1ncnc(NCCc2ccc(Oc3ccc(C(F)(F)F)cc3)cc2)c1Cl ; "·HNO3"] |
| II-19336 | 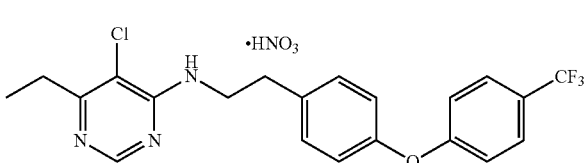 |
| II-19337 | 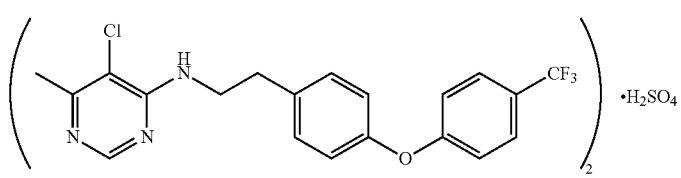 |
| II-19338 | 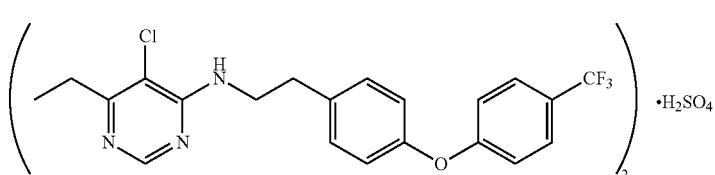 |
| II-19339 | 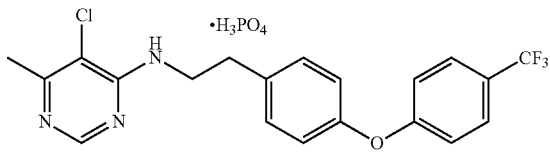 [SMILES: Cc1ncnc(NCCc2ccc(Oc3ccc(C(F)(F)F)cc3)cc2)c1Cl ; "·H3PO4"] |

TABLE 202-continued
the salts of some compounds
| No. | structure |
|---|---|
| II-19340 | 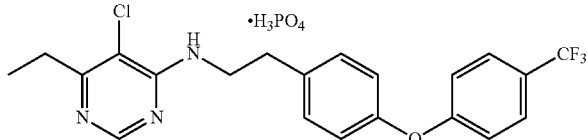 |
| II-19341 | 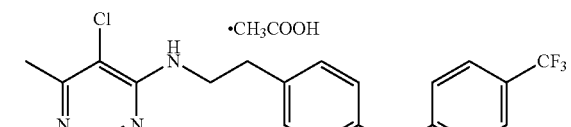 |
| II-19342 | 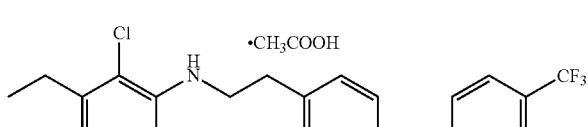 |
| II-19343 | 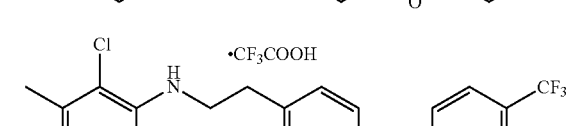 |
| II-19344 | 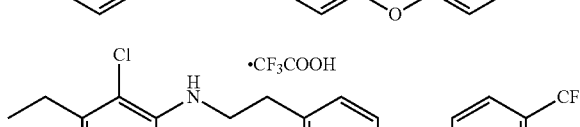 |
| II-19345 | 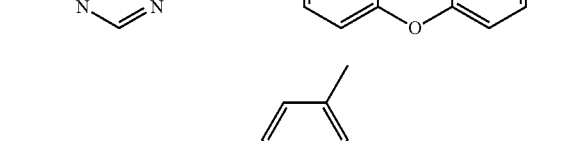 |
| II-19346 | 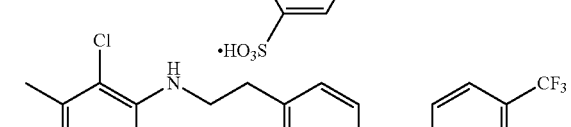 |
| II-19347 | 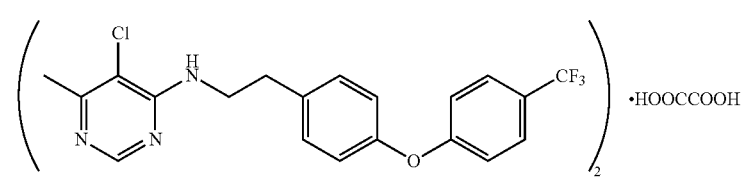 |

TABLE 202-continued
the salts of some compounds
| No. | structure |
|---|---|
| II-19348 | 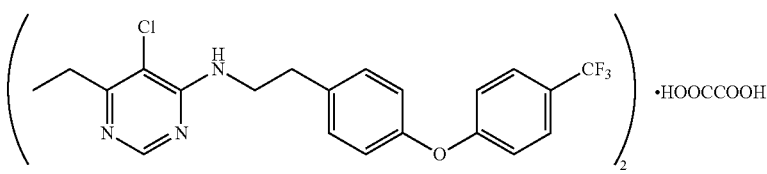 |
| II-19349 | 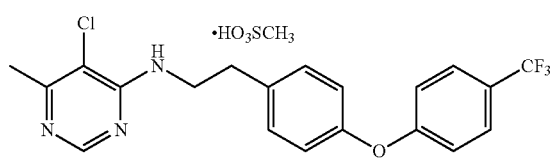 |
| II-19350 | 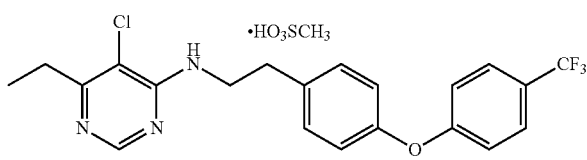 |
| II-19351 | 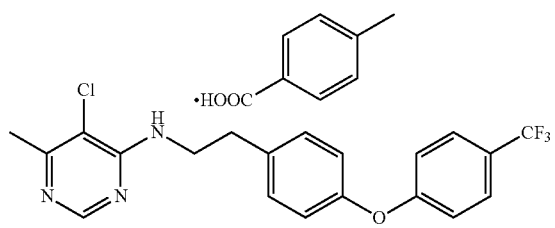 |
| II-19352 | 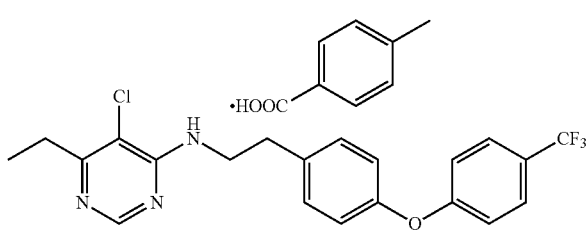 |
| II-19353 | 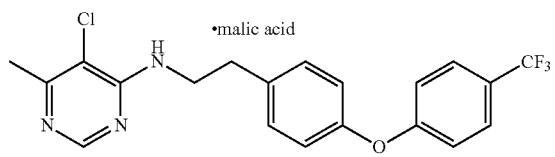 |
| II-19354 | 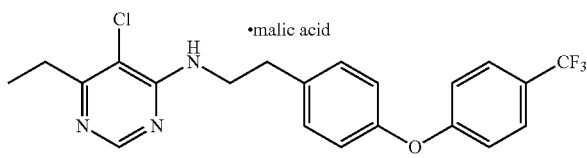 |
| II-19355 | 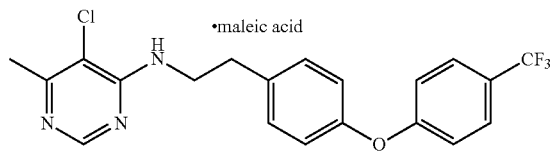 |

TABLE 202-continued
the salts of some compounds
| No. | structure |
|---|---|
| II-19356 | 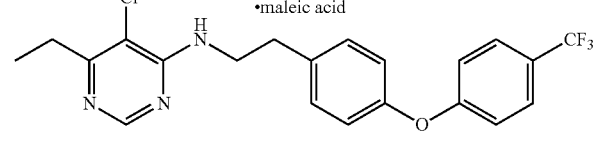 ·maleic acid |
| II-19357 | 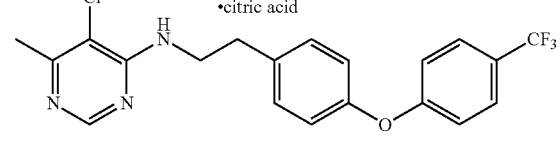 ·citric acid |
| II-19358 | 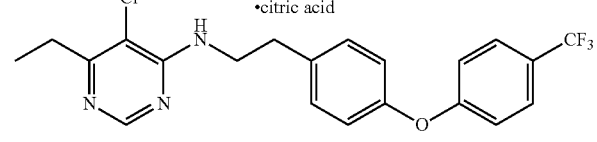 ·citric acid |
| II-19359 | 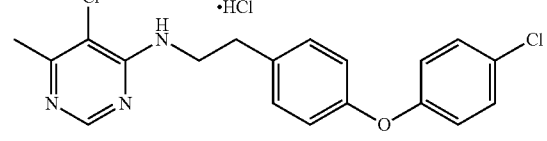 ·HCl |
| II-19360 | 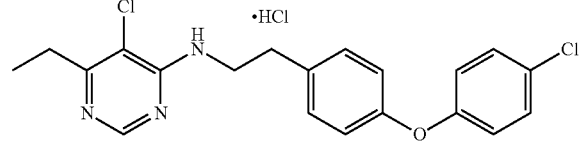 [SMILES: CCc1ncnc(NCCc2ccc(Oc3ccc(Cl)cc3)cc2)c1Cl ; Cl] ·HCl |
| II-19361 | 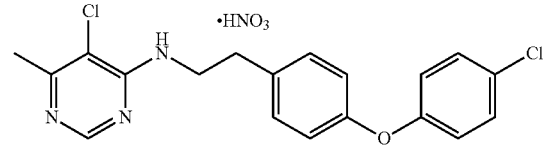 [SMILES: Cc1ncnc(NCCc2ccc(Oc3ccc(Cl)cc3)cc2)c1Cl ; "·HNO3"] ·HNO$_3$ |
| II-19362 | 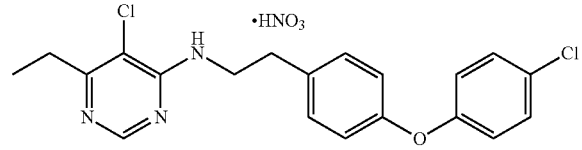 [SMILES: CCc1ncnc(NCCc2ccc(Oc3ccc(Cl)cc3)cc2)c1Cl ; "·HNO3"] ·HNO$_3$ |
| II-19363 | 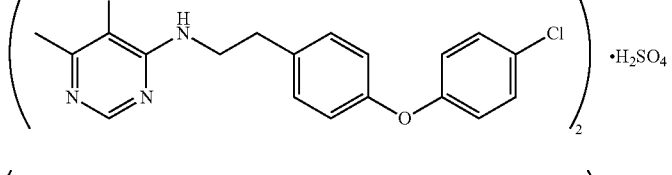 ·H$_2$SO$_4$ |
| II-19364 | 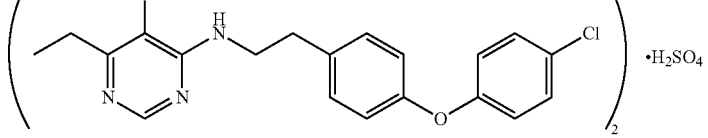 ·H$_2$SO$_4$ |

TABLE 202-continued
the salts of some compounds
| No. | structure |
|---|---|
| II-19365 | 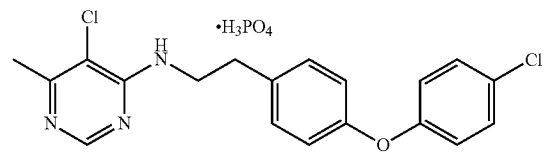 [SMILES: Cc1ncnc(NCCc2ccc(Oc3ccc(Cl)cc3)cc2)c1Cl ; "·H3PO4"] |
| II-19366 | 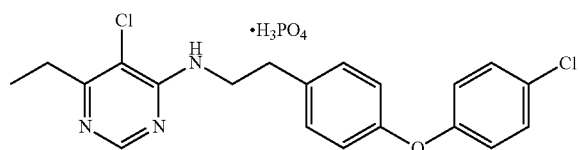 |
| II-19367 | 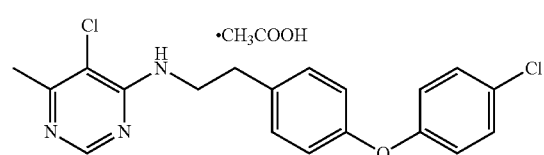 |
| II-19368 | 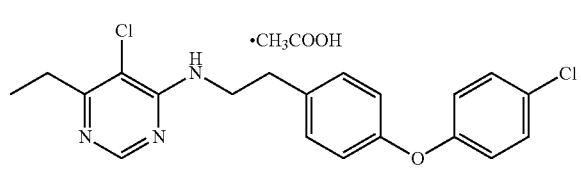 [SMILES: CCc1ncnc(NCCc2ccc(Oc3ccc(Cl)cc3)cc2)c1Cl ; "·CF3COOH"] |
| II-19369 | 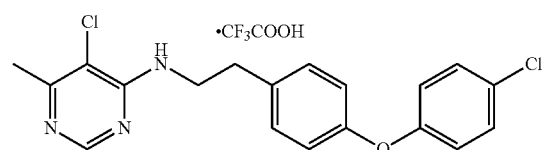 |
| II-19370 | 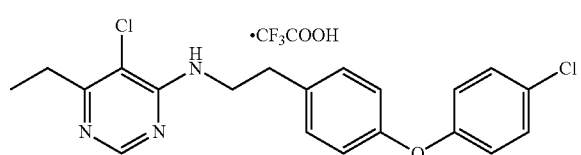 |
| II-19371 | 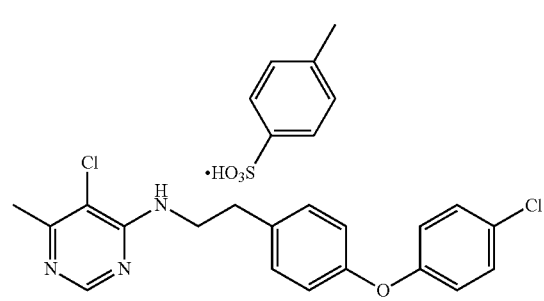 |
| II-19372 | 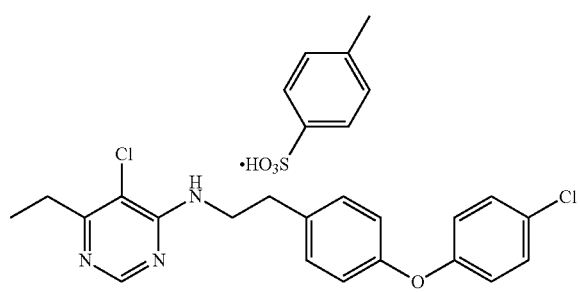 |

TABLE 202-continued the salts of some compounds

| No. | structure |
|---|---|
| II-19373 | (5-chloro-6-methyl-pyrimidin-4-yl)-NH-CH₂CH₂-(4-phenyl)-O-(4-chlorophenyl) )₂ ·HOOCCOOH |
| II-19374 | (5-chloro-6-ethyl-pyrimidin-4-yl)-NH-CH₂CH₂-(4-phenyl)-O-(4-chlorophenyl) )₂ ·HOOCCOOH |
| II-19375 | (5-chloro-6-methyl-pyrimidin-4-yl)-NH-CH₂CH₂-(4-phenyl)-O-(4-chlorophenyl) ·HO₃SCH₃ |
| II-19376 | (5-chloro-6-ethyl-pyrimidin-4-yl)-NH-CH₂CH₂-(4-phenyl)-O-(4-chlorophenyl) ·HO₃SCH₃ |
| II-19377 | (5-chloro-6-methyl-pyrimidin-4-yl)-NH-CH₂CH₂-(4-phenyl)-O-(4-chlorophenyl) ·HOOC-(4-methylphenyl) |
| II-19378 | (5-chloro-6-ethyl-pyrimidin-4-yl)-NH-CH₂CH₂-(4-phenyl)-O-(4-chlorophenyl) ·HOOC-(4-methylphenyl) |
| II-19379 | (5-chloro-6-methyl-pyrimidin-4-yl)-NH-CH₂CH₂-(4-phenyl)-O-(4-chlorophenyl) ·malic acid |
| II-19380 | (5-chloro-6-ethyl-pyrimidin-4-yl)-NH-CH₂CH₂-(4-phenyl)-O-(4-chlorophenyl) ·malic acid |

TABLE 202-continued
the salts of some compounds
| No. | structure |
|---|---|
| II-19381 | 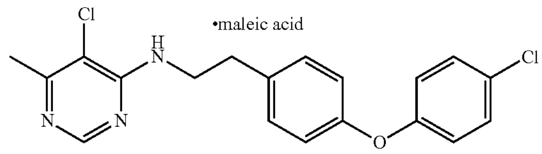 |
| II-19382 | 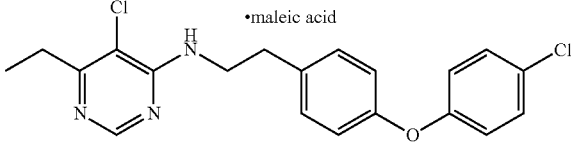 |
| II-19383 | 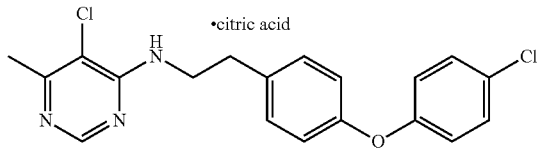 |
| II-19384 | 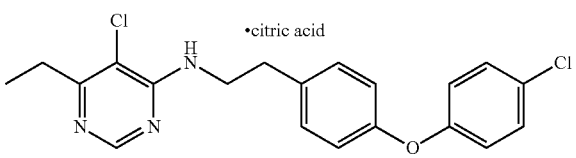 |
| II-19385 | 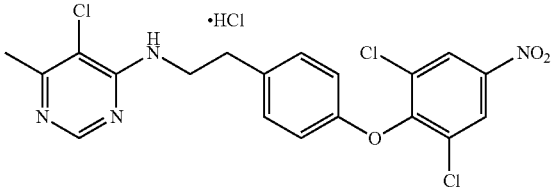 [SMILES: Cc1ncnc(NCCc2ccc(Oc3c(Cl)cc([N+](=O)[O-])cc3Cl)cc2)c1Cl ; Cl] |
| II-19386 | 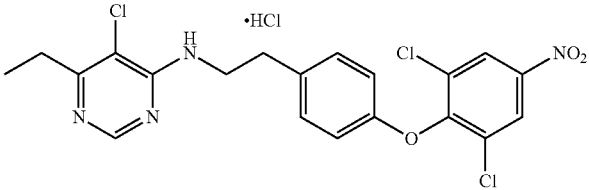 [SMILES: CCc1ncnc(NCCc2ccc(Oc3c(Cl)cc([N+](=O)[O-])cc3Cl)cc2)c1Cl ; Cl] |
| II-19387 | 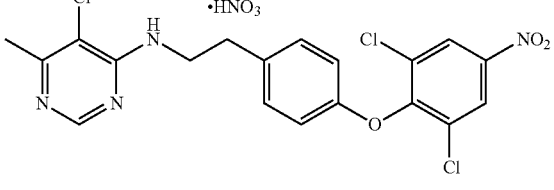 |
| II-19388 | 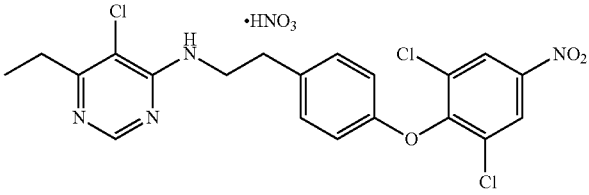 [SMILES: CCc1ncnc(NCCc2ccc(Oc3c(Cl)cc([N+](=O)[O-])cc3Cl)cc2)c1Cl ; "·HNO3"] |

TABLE 202-continued
the salts of some compounds
| No. | structure |
|---|---|
| II-19389 | 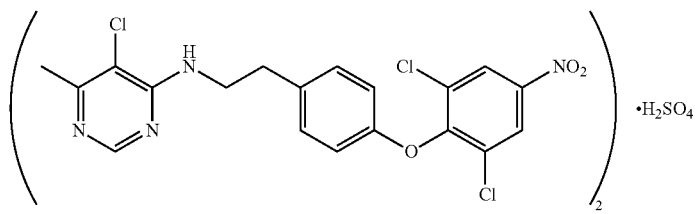 |
| II-19390 | 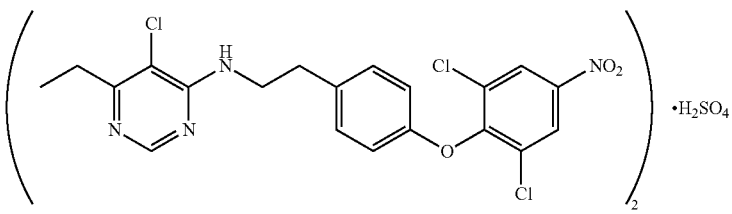 |
| II-19391 | 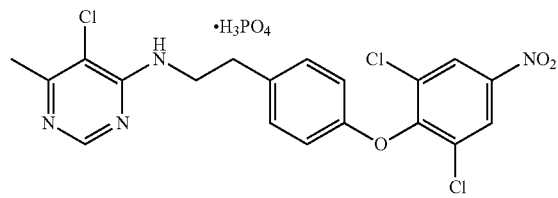 [SMILES: Cc1ncnc(NCCc2ccc(Oc3c(Cl)cc([N+](=O)[O-])cc3Cl)cc2)c1Cl ; "·H3PO4"] |
| II-19392 | 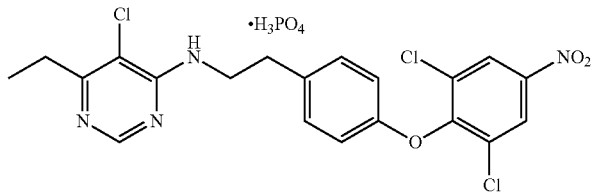 [SMILES: CCc1ncnc(NCCc2ccc(Oc3c(Cl)cc([N+](=O)[O-])cc3Cl)cc2)c1Cl ; "·H3PO4"] |
| II-19393 | 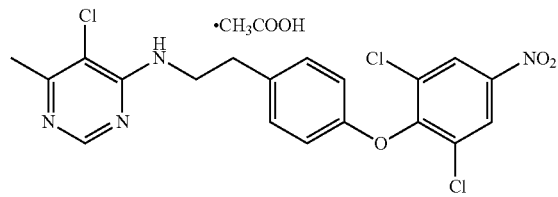 [SMILES: Cc1ncnc(NCCc2ccc(Oc3c(Cl)cc([N+](=O)[O-])cc3Cl)cc2)c1Cl ; "·CH3COOH"] |
| II-19394 | 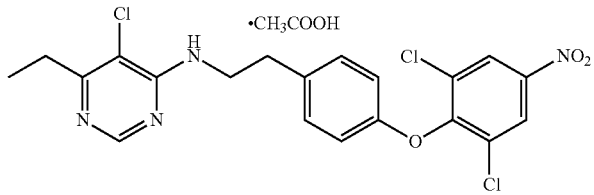 [SMILES: CCc1ncnc(NCCc2ccc(Oc3c(Cl)cc([N+](=O)[O-])cc3Cl)cc2)c1Cl ; "·CH3COOH"] |
| II-19395 | 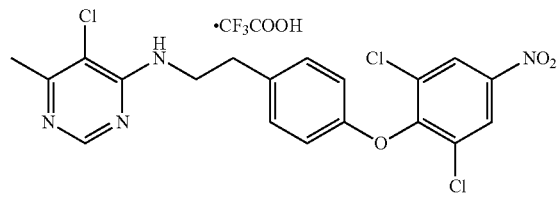 [SMILES: Cc1ncnc(NCCc2ccc(Oc3c(Cl)cc([N+](=O)[O-])cc3Cl)cc2)c1Cl ; "·CF3COOH"] |

TABLE 202-continued the salts of some compounds

| No. | structure |
|---|---|
| II-19396 | 5-chloro-6-ethyl-N-(4-(2,6-dichloro-4-nitrophenoxy)phenethyl)pyrimidin-4-amine · CF₃COOH |
| II-19397 | 5-chloro-6-methyl-N-(4-(2,6-dichloro-4-nitrophenoxy)phenethyl)pyrimidin-4-amine · HO₃S-C₆H₄-CH₃ (p-toluenesulfonate) |
| II-19398 | 5-chloro-6-ethyl-N-(4-(2,6-dichloro-4-nitrophenoxy)phenethyl)pyrimidin-4-amine · HO₃S-C₆H₄-CH₃ (p-toluenesulfonate) |
| II-19399 | (5-chloro-6-methyl-N-(4-(2,6-dichloro-4-nitrophenoxy)phenethyl)pyrimidin-4-amine)₂ · HOOCCOOH |
| II-19400 | (5-chloro-6-ethyl-N-(4-(2,6-dichloro-4-nitrophenoxy)phenethyl)pyrimidin-4-amine)₂ · HOOCCOOH |
| II-19401 | 5-chloro-6-methyl-N-(4-(2,6-dichloro-4-nitrophenoxy)phenethyl)pyrimidin-4-amine · HO₃SCH₃ |

TABLE 202-continued the salts of some compounds

| No. | structure |
|---|---|
| II-19402 | (structure: 5-chloro-6-ethyl-pyrimidin-4-yl-NH-CH₂CH₂-phenyl-O-(2,6-dichloro-4-nitrophenyl) · HO₃SCH₃) |
| II-19403 | (structure: 5-chloro-6-methyl-pyrimidin-4-yl-NH-CH₂CH₂-phenyl-O-(2,6-dichloro-4-nitrophenyl) · HOOC-C₆H₄-CH₃) |
| II-19404 | (structure: 5-chloro-6-ethyl-pyrimidin-4-yl-NH-CH₂CH₂-phenyl-O-(2,6-dichloro-4-nitrophenyl) · HOOC-C₆H₄-CH₃) |
| II-19405 | (structure: 5-chloro-6-methyl-pyrimidin-4-yl-NH-CH₂CH₂-phenyl-O-(2-fluoro-4-cyanophenyl) · HO₃S-C₆H₄-CH₃) |
| II-19406 | (structure: 5-chloro-6-ethyl-pyrimidin-4-yl-NH-CH₂CH₂-phenyl-O-(2-fluoro-4-cyanophenyl) · HO₃S-C₆H₄-CH₃) |

TABLE 202-continued
the salts of some compounds
| No. | structure |
|---|---|
| II-19407 | 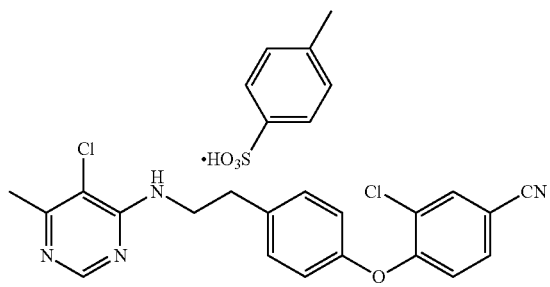 |
| II-19408 | 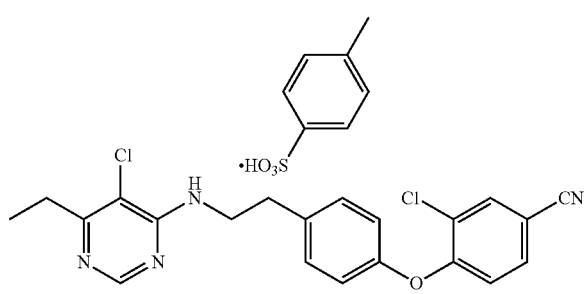 |
| II-19409 | 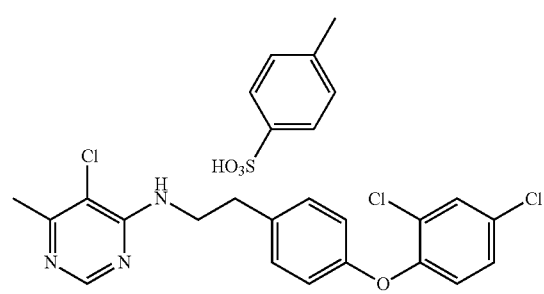 |
| II-19410 | 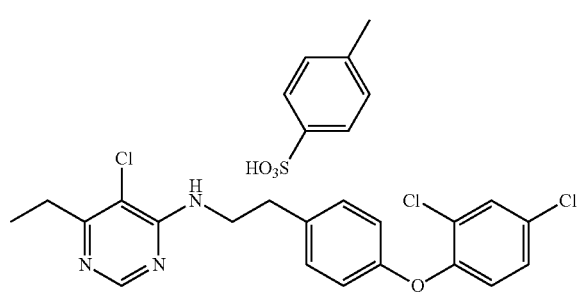 |
| II-19411 | 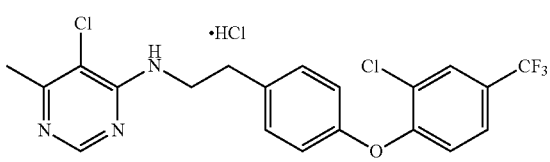 [SMILES: Cc1ncnc(NCCc2ccc(Oc3ccc(C(F)(F)F)cc3Cl)cc2)c1Cl ; Cl] |
| II-19412 | 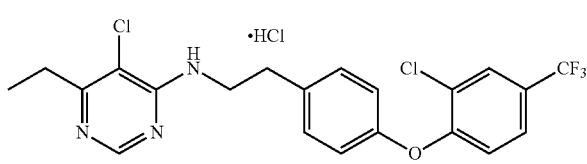 [SMILES: CCc1ncnc(NCCc2ccc(Oc3ccc(C(F)(F)F)cc3Cl)cc2)c1Cl ; Cl] |

TABLE 202-continued
the salts of some compounds
| No. | structure |
|---|---|
| II-19413 | 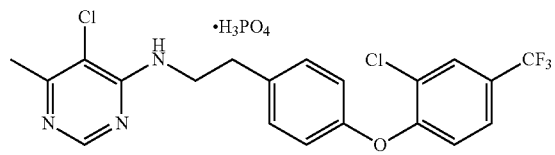 [SMILES: Cc1ncnc(NCCc2ccc(Oc3ccc(C(F)(F)F)cc3Cl)cc2)c1Cl ; "·H3PO4"] |
| II-19414 | 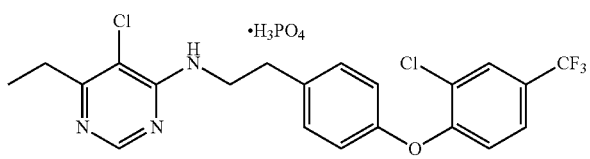 [SMILES: CCc1ncnc(NCCc2ccc(Oc3ccc(C(F)(F)F)cc3Cl)cc2)c1Cl ; "·H3PO4"] |
| II-19415 | 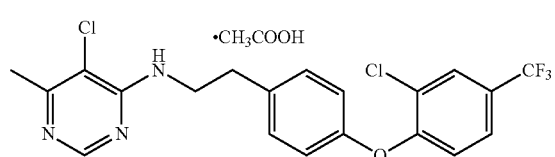 |
| II-19416 | 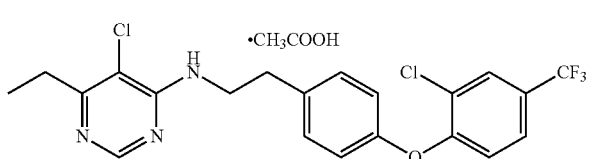 |
| II-19417 | 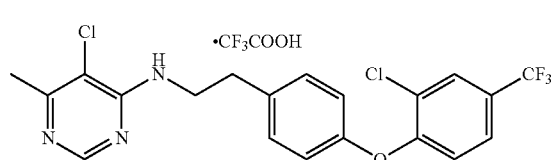 |
| II-19418 | 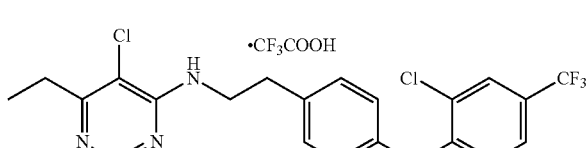 |
| II-19419 | 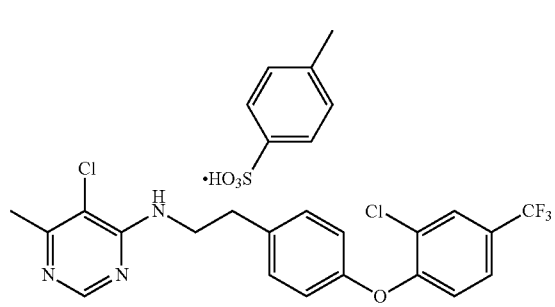 |
| II-19420 | 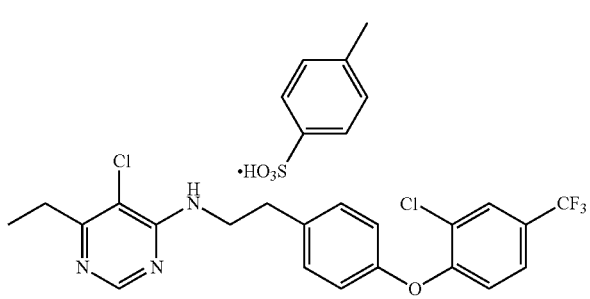 |

TABLE 202-continued
the salts of some compounds
| No. | structure |
|---|---|
| II-19421 | 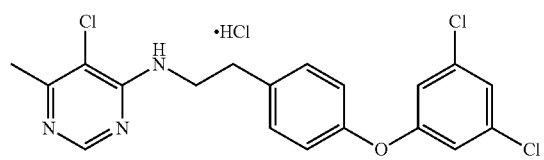 [SMILES: Cc1ncnc(NCCc2ccc(Oc3cc(Cl)cc(Cl)c3)cc2)c1Cl ; Cl] |
| II-19422 | 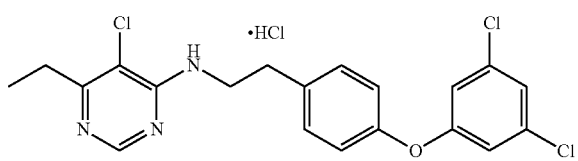 [SMILES: CCc1ncnc(NCCc2ccc(Oc3cc(Cl)cc(Cl)c3)cc2)c1Cl ; Cl] |
| II-19423 | 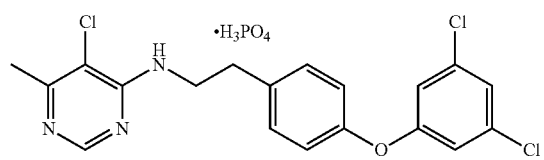 [SMILES: Cc1ncnc(NCCc2ccc(Oc3cc(Cl)cc(Cl)c3)cc2)c1Cl ; "·H3PO4"] |
| II-19424 | 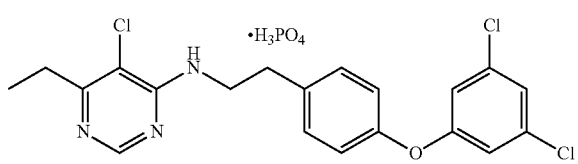 [SMILES: CCc1ncnc(NCCc2ccc(Oc3cc(Cl)cc(Cl)c3)cc2)c1Cl ; "·H3PO4"] |
| II-19425 | 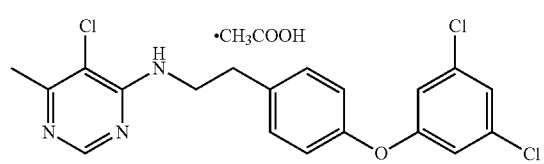 [SMILES: Cc1ncnc(NCCc2ccc(Oc3cc(Cl)cc(Cl)c3)cc2)c1Cl ; "·CH3COOH"] |
| II-19426 | 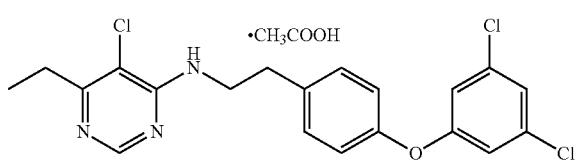 [SMILES: CCc1ncnc(NCCc2ccc(Oc3cc(Cl)cc(Cl)c3)cc2)c1Cl ; "·CH3COOH"] |
| II-19427 | 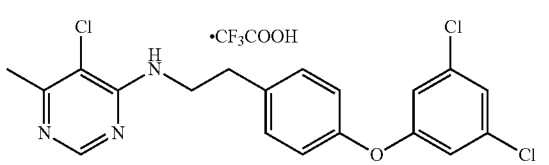 [SMILES: Cc1ncnc(NCCc2ccc(Oc3cc(Cl)cc(Cl)c3)cc2)c1Cl ; "·CF3COOH"] |
| II-19428 | 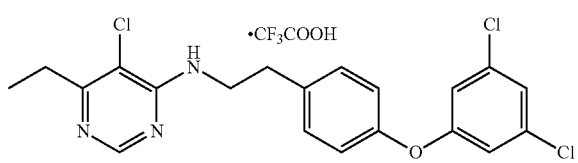 |

TABLE 202-continued
| the salts of some compounds | |
|---|---|
| No. | structure |
II-19429
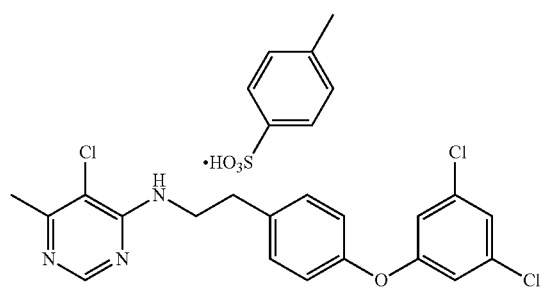
II-19430
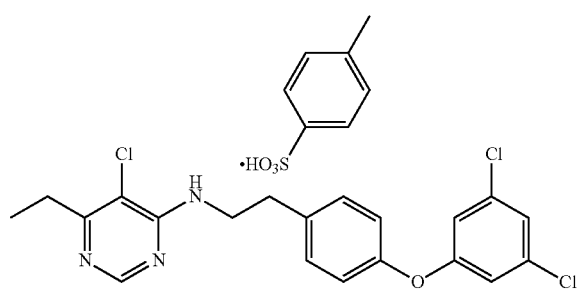
II-19431
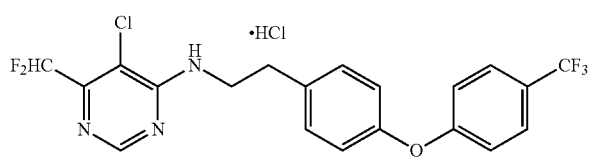 [SMILES: FC(F)c1ncnc(NCCc2ccc(Oc3ccc(C(F)(F)F)cc3)cc2)c1Cl ; Cl]
II-19432
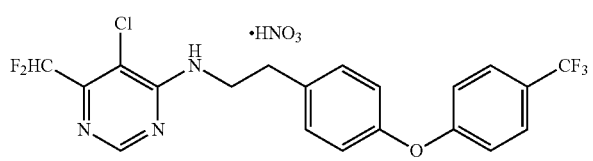 [SMILES: FC(F)c1ncnc(NCCc2ccc(Oc3ccc(C(F)(F)F)cc3)cc2)c1Cl ; "·HNO3"]
II-19433
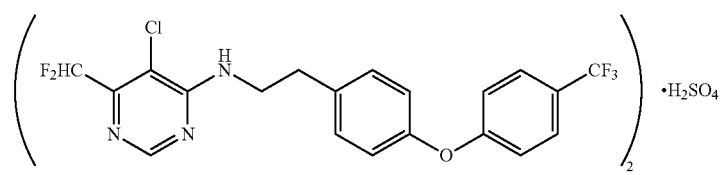
II-19434
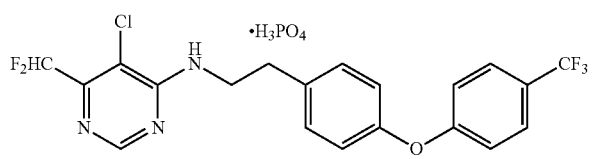 [SMILES: FC(F)c1ncnc(NCCc2ccc(Oc3ccc(C(F)(F)F)cc3)cc2)c1Cl ; "·H3PO4"]
II-19435
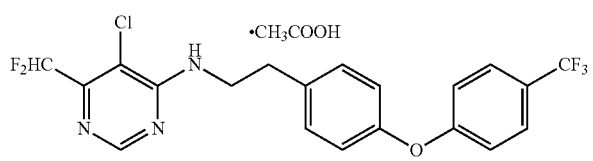 [SMILES: FC(F)c1ncnc(NCCc2ccc(Oc3ccc(C(F)(F)F)cc3)cc2)c1Cl ; "·CH3COOH"]

TABLE 202-continued the salts of some compounds

| No. | structure |
|---|---|
| II-19436 | 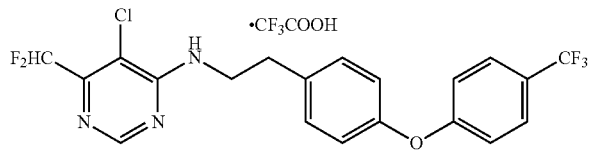 [SMILES: FC(F)c1ncnc(NCCc2ccc(Oc3ccc(C(F)(F)F)cc3)cc2)c1Cl ; "·CF3COOH"] |

In the general formula III, part of preferred substituents of $R_1$, $R_2$, W, $R_3$ and $R_4$ are separately listed in table 203 to table 206, but without being restricted thereby. The definitions of other substituents are defined as above.

TABLE 203

$R_1$ substituents $R_1$

H
F
Cl
Br
I
$CH_3$
$C_2H_5$
n-$C_3H_7$
i-$C_3H_7$
n-$C_4H_9$
i-$C_4H_9$
t-$C_4H_9$

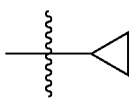 [SMILES: *C1CC1]

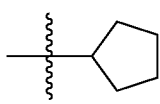 [SMILES: *C1CCCC1]

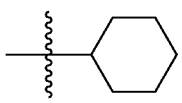

$CH_2Cl$
$CHCl_2$
$CH_2CH=CH_2$
$CCl_3$
$CHF_2$
$CHBr_2$
$CF_3$
$CH(CH_3)F$
$CH(CH_3)Cl$
$CH(CH_3)Br$
$C(CH_3)_2F$
$OCH_3$
$OC_2H_5$
$OCF_3$
$OCH_2CH=CH_2$
$OCH_2CH=CHCl$
$OCH_2C\equiv CH$
$OCH_2C\equiv C-I$
$OCH_2C\equiv CCH_3$
$OSO_2CH_3$
$CH_2C\equiv CH$
$SCH_3$
$SOCH_3$

TABLE 203-continued $R_1$ substituents $R_1$ $SO_2CH_3$
COOH
$COOCH_3$
$COOC_2H_5$
$CONH_2$
$CONHCH_3$
CONHCN
$CONHCH_2CN$
$CON(CH_3)_2$
$NH_2$
$NHCH_3$
$NHC_2H_5$
$N(CH_3)_2$
$N(C_2H_5)_2$
$NHCH_2CN$
$CH_2OCH_2Cl$
$NHOCH_3$
$NHOC_2H_5$
$NHCOCH_3$
$NHCOC_2H_5$
$NHCOOCH_3$
$NHCOOC_2H_5$
$N(CH_3)NH_2$
$NHN(CH_3)_2$
$CH_2OCH_3$
$CH_2OCH_2CH_3$
$CH_2CH_2OCH_3$
$CH_2CH_2OCH_2CH_3$
$CH(CH_3)SCH_3$
$CH(CH_3)SOCH_3$
$CH(CH_3)SO_2CH_3$
$CH(CH_3)OH$
$CH(CH_3)OCOCH_3$
$CH_2OCH_2CH_2Cl$

TABLE 204

$R_2$ substituents

| $R_2$ | $R_2$ | $R_2$ | $R_2$ |
|---|---|---|---|
| H | $NO_2$ | t-$C_4H_9$ | $OC_4H_9$-i |
| F | $CH_3$ | $OCH_3$ | $OC_4H_9$-t |
| Cl | $C_2H_5$ | $OC_2H_5$ | $OCH_2F$ |
| Br | n-$C_3H_7$ | $OC_3H_7$-n | $OCHF_2$ |
| I | i-$C_3H_7$ | $OC_3H_7$-i | $OCF_3$ |
| CN | n-$C_4H_9$ | $OC_4H_9$-n | $OCH_2CF_3$ |

TABLE 205

W substituents

W

H
F
Cl
Br
I
CH₃
C₂H₅
n-C₃H₇
i-C₃H₇
n-C₄H₉
t-C₄H₉

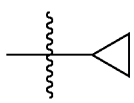 [SMILES: *C1CC1]

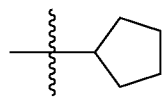 [SMILES: *C1CCCC1]

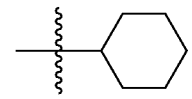

CHCl₂
CCl₃
CHF₂
CHBr₂
CF₃
CH(CH₃)F
CH(CH₃)Cl
CH(CH₃)Br
CH(n-C₄H₉)F
C(CH₃)₂F
OCH₃
OC₂H₅
OC₃H₇-n
OC₃H₇-i
OC₄H₉-n
OC₄H₉-i
OC₄H₉-t
OCF₃
OCH₂CF₃
SCH₃
SC₂H₅
SC₃H₇-n
SC₃H₇-i
SC₄H₉-n
SC₄H₉-i
SC₄H₉-t

TABLE 206

R₃(R₄) substituents

R₃(R₄)

H
CH₃
C₂H₅
n-C₃H₇
i-C₃H₇
n-C₄H₉
i-C₄H₉

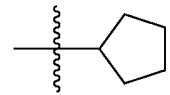 [SMILES: *C1CCCC1]

TABLE 206-continued

R₃(R₄) substituents

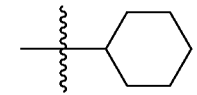

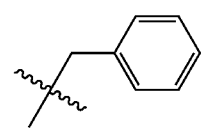 [SMILES: *Cc1ccccc1]

t-C₄H₉
CH=CH₂
C≡CH
CH₂CH=CH₂
CH₂C≡CH
CH₂CH=CCl₂
CH₂C≡C—I
CH₂OCH₃
CH₂OCH₂CH₃
CH₂CH₂OCH₃
CH₂CH₂OCH₂CH₃

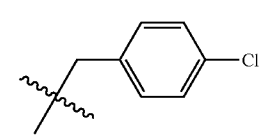 [SMILES: *Cc1ccc(Cl)cc1]

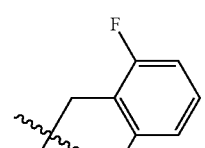

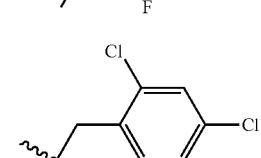

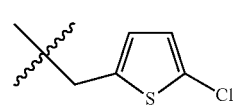

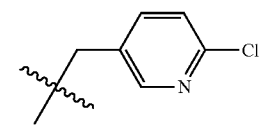 [SMILES: *Cc1ccc(Cl)nc1]

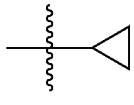

CR₃R₄

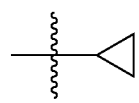 [SMILES: *C1CC1]

TABLE 206-continued

R₃(R₄)substituents

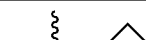
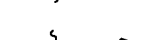

The present invention is also explained by the following compounds having a structure as represented by formula III listed in Table 207 to Table 304, but without being restricted thereby. The compounds having a structure as represented by formula III-A, III-B, III-C, III-D, III-E, III-F, III-G and III-H refer to Table 207 to Table 304, $R_{5a}=R_{5c}=H$.

In general formula III-A,

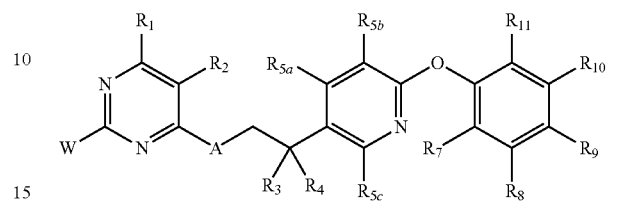

III-A $A=NH$, $R_1=CH_3$, $R_2=Cl$, $W=R_3=R_4=R_{5b}=H$, the substituents $R_7$, $R_8$, $R_9$, $R_{10}$ and $R_{11}$ refer to Table 207, the representative compounds are coded as III-1-III-180.

TABLE 207

| No. | $R_7$ | $R_8$ | $R_9$ | $R_{10}$ | $R_{11}$ |
|---|---|---|---|---|---|
| III-1 | H | H | H | H | H |
| III-2 | F | H | H | H | H |
| III-3 | H | F | H | H | H |
| III-4 | H | H | F | H | H |
| III-5 | Cl | H | H | H | H |
| III-6 | H | Cl | H | H | H |
| III-7 | H | H | Cl | H | H |
| III-8 | Br | H | H | H | H |
| III-9 | H | Br | H | H | H |
| III-10 | H | H | Br | H | H |
| III-11 | I | H | H | H | H |
| III-12 | H | I | H | H | H |
| III-13 | H | H | I | H | H |
| III-14 | CH₃ | H | H | H | H |
| III-15 | H | CH₃ | H | H | H |
| III-16 | H | H | CH₃ | H | H |
| III-17 | OCH₃ | H | H | H | H |
| III-18 | H | OCH₃ | H | H | H |
| III-19 | H | H | OCH₃ | H | H |
| III-20 | CF₃ | H | H | H | H |
| III-21 | H | CF₃ | H | H | H |
| III-22 | H | H | CF₃ | H | H |
| III-23 | OCF₃ | H | H | H | H |
| III-24 | H | OCF₃ | H | H | H |
| III-25 | H | H | OCF₃ | H | H |
| III-26 | NO₂ | H | H | H | H |
| III-27 | H | NO₂ | H | H | H |
| III-28 | H | H | NO₂ | H | H |
| III-29 | CN | H | H | H | H |
| III-30 | H | CN | H | H | H |
| III-31 | H | H | CN | H | H |
| III-32 | CH(CH₃)₂ | H | H | H | H |
| III-33 | H | CH(CH₃)₂ | H | H | H |
| III-34 | H | H | CH(CH₃)₂ | H | H |
| III-35 | H | H | t-Bu | H | H |
| III-36 | SCH₃ | H | H | H | H |
| III-37 | H | SCH₃ | H | H | H |
| III-38 | H | H | SCH₃ | H | H |
| III-39 | SCF₃ | H | H | H | H |
| III-40 | H | SCF₃ | H | H | H |
| III-41 | H | H | SCF₃ | H | H |
| III-42 | COCH₃ | H | H | H | H |
| III-43 | H | COCH₃ | H | H | H |
| III-44 | H | H | COCH₃ | H | H |
| III-45 | SOCH₃ | H | H | H | H |
| III-46 | H | SOCH₃ | H | H | H |
| III-47 | H | H | SOCH₃ | H | H |
| III-48 | SO₂CH₃ | H | H | H | H |
| III-49 | H | SO₂CH₃ | H | H | H |
| III-50 | H | H | SO₂CH₃ | H | H |
| III-51 | OCHF₂ | H | H | H | H |
| III-52 | H | OCHF₂ | H | H | H |

TABLE 207-continued

| No. | $R_7$ | $R_8$ | $R_9$ | $R_{10}$ | $R_{11}$ |
|---|---|---|---|---|---|
| III-53 | H | H | OCHF$_2$ | H | H |
| III-54 | CO$_2$CH$_3$ | H | H | H | H |
| III-55 | H | CO$_2$CH$_3$ | H | H | H |
| III-56 | H | H | CO$_2$CH$_3$ | H | H |
| III-57 | N(CH$_3$)$_2$ | H | H | H | H |
| III-58 | H | N(CH$_3$)$_2$ | H | H | H |
| III-59 | H | H | N(CH$_3$)$_2$ | H | H |
| III-60 | N(C$_2$H$_5$)$_2$ | H | H | H | H |
| III-61 | H | N(C$_2$H$_5$)$_2$ | H | H | H |
| III-62 | H | H | N(C$_2$H$_5$)$_2$ | H | H |
| III-63 | NHCOCH$_3$ | H | H | H | H |
| III-64 | H | NHCOCH$_3$ | H | H | H |
| III-65 | H | H | NHCOCH$_3$ | H | H |
| III-66 | NHSO$_2$CH$_3$ | H | H | H | H |
| III-67 | H | NHSO$_2$CH$_3$ | H | H | H |
| III-68 | H | H | NHSO$_2$CH$_3$ | H | H |
| III-69 | OCH$_2$CH=CH$_2$ | H | H | H | H |
| III-70 | H | OCH$_2$CH=CH$_2$ | H | H | H |
| III-71 | H | H | OCH$_2$CH=CH$_2$ | H | H |
| III-72 | OCH$_2$C≡CH | H | H | H | H |
| III-73 | H | OCH$_2$C≡CH | H | H | H |
| III-74 | H | H | OCH$_2$C≡CH | H | H |
| III-75 | F | F | H | H | H |
| III-76 | F | H | F | H | H |
| III-77 | F | H | H | F | H |
| III-78 | F | H | H | H | F |
| III-79 | H | F | F | H | H |
| III-80 | H | F | H | F | H |
| III-81 | Cl | Cl | H | H | H |
| III-82 | Cl | H | Cl | H | H |
| III-83 | Cl | H | H | Cl | H |
| III-84 | Cl | H | H | H | Cl |
| III-85 | H | Cl | Cl | H | H |
| III-86 | H | Cl | H | Cl | H |
| III-87 | NO$_2$ | H | NO$_2$ | H | H |
| III-88 | NO$_2$ | H | H | NO$_2$ | H |
| III-89 | NO$_2$ | H | H | H | NO$_2$ |
| III-90 | H | NO$_2$ | H | NO$_2$ | H |
| III-91 | CN | H | CN | H | H |
| III-92 | CN | H | H | CN | H |
| III-93 | CN | H | H | H | CN |
| III-94 | H | CN | H | CN | H |
| III-95 | CH$_3$ | CH$_3$ | H | H | H |
| III-96 | CH$_3$ | H | CH$_3$ | H | H |
| III-97 | CH$_3$ | H | H | CH$_3$ | H |
| III-98 | CH$_3$ | H | H | H | CH$_3$ |
| III-99 | H | CH$_3$ | CH$_3$ | H | H |
| III-100 | H | CH$_3$ | H | CH$_3$ | H |
| III-101 | CF$_3$ | H | CF$_3$ | H | H |
| III-102 | CF$_3$ | H | H | CF$_3$ | H |
| III-103 | CF$_3$ | H | H | H | CF$_3$ |
| III-104 | H | CF$_3$ | H | CF$_3$ | H |
| III-105 | OCF$_3$ | H | OCF$_3$ | H | H |
| III-106 | OCF$_3$ | H | H | OCF$_3$ | H |
| III-107 | OCF$_3$ | H | H | H | OCF$_3$ |
| III-108 | H | OCF$_3$ | H | OCF$_3$ | H |
| III-109 | CH$_3$ | Cl | H | H | H |
| III-110 | CH$_3$ | H | Cl | H | H |
| III-111 | H | Cl | CH$_3$ | H | H |
| III-112 | Cl | H | CH$_3$ | H | H |
| III-113 | CH$_3$ | H | H | Cl | H |
| III-114 | CH$_3$ | H | H | H | Cl |
| III-115 | Br | CH$_3$ | H | H | H |
| III-116 | H | CH$_3$ | Cl | H | H |
| III-117 | CH$_3$ | NO$_2$ | H | H | H |
| III-118 | CH$_3$ | H | NO$_2$ | H | H |
| III-119 | CH$_3$ | H | OCH$_3$ | H | H |
| III-120 | CH$_3$ | H | H | NO$_2$ | H |
| III-121 | Cl | H | CF$_3$ | H | H |
| III-122 | Cl | H | H | CF$_3$ | H |
| III-123 | Cl | H | NO$_2$ | H | H |
| III-124 | Cl | H | H | NO$_2$ | H |
| III-125 | CF$_3$ | H | Br | H | H |
| III-126 | CF$_3$ | H | NO$_2$ | H | H |
| III-127 | H | CF$_3$ | NO$_2$ | H | H |
| III-128 | H | CF$_3$ | Cl | H | H |
| III-129 | CF$_3$ | H | CN | H | H |
| III-130 | Cl | H | CN | H | H |

TABLE 207-continued

| No. | R$_7$ | R$_8$ | R$_9$ | R$_{10}$ | R$_{11}$ |
|---|---|---|---|---|---|
| III-131 | NO$_2$ | H | CN | H | H |
| III-132 | NO$_2$ | H | CH$_3$ | H | H |
| III-133 | NO$_2$ | H | CF$_3$ | H | H |
| III-134 | NO$_2$ | H | Cl | H | H |
| III-135 | NO$_2$ | H | H | Cl | H |
| III-136 | H | NO$_2$ | CH$_3$ | H | H |
| III-137 | H | NO$_2$ | Cl | H | H |
| III-138 | CN | F | H | H | H |
| III-139 | CN | H | NO$_2$ | H | H |
| III-140 | CN | H | Cl | H | H |
| III-141 | CN | H | H | CH$_3$ | H |
| III-142 | Cl | Cl | Cl | H | H |
| III-143 | Cl | Cl | H | Cl | H |
| III-144 | Cl | H | Cl | Cl | H |
| III-145 | Cl | H | Cl | H | Cl |
| III-146 | H | Cl | Cl | Cl | H |
| III-147 | CH$_3$ | H | CH$_3$ | H | CH$_3$ |
| III-148 | OCH$_3$ | H | OCH$_3$ | H | OCH$_3$ |
| III-149 | Cl | Cl | Br | H | H |
| III-150 | F | H | F | H | Cl |
| III-151 | CH$_3$ | H | Br | H | Br |
| III-152 | CF$_3$ | H | Cl | H | Cl |
| III-153 | CF$_3$ | H | Br | H | Br |
| III-154 | F | H | Cl | H | Br |
| III-155 | Cl | H | NO$_2$ | H | Cl |
| III-156 | Br | H | NO$_2$ | H | Br |
| III-157 | Cl | H | CN | H | Cl |
| III-158 | Cl | H | CF$_3$ | H | Cl |
| III-159 | Br | H | CF$_3$ | H | Br |
| III-160 | Cl | CH$_3$ | H | H | Cl |
| III-161 | Cl | H | CONH$_2$ | H | Cl |
| III-162 | Cl | H | CO$_2$CH$_3$ | H | Cl |
| III-163 | Cl | H | NHCOCH$_3$ | H | Cl |
| III-164 | Cl | H | OCF$_3$ | H | Cl |
| III-165 | Br | H | F | H | Br |
| III-166 | Br | H | CH$_3$ | H | Br |
| III-167 | Cl | H | COCH$_3$ | H | Cl |
| III-168 | Cl | H | NO$_2$ | Cl | H |
| III-169 | F | H | F | H | Cl |
| III-170 | Cl | H | CF$_3$ | H | Br |
| III-171 | CH$_3$ | H | NO$_2$ | H | Cl |
| III-172 | CH$_3$ | H | NO$_2$ | H | Br |
| III-173 | CH$_3$ | H | Cl | H | NO$_2$ |
| III-174 | CH$_3$ | H | Br | H | NO$_2$ |
| III-175 | NO$_2$ | H | CF$_3$ | H | Cl |
| III-176 | NO$_2$ | H | CF$_3$ | H | Br |
| III-177 | F | H | Br | H | Br |
| III-178 | CN | H | Cl | H | Cl |
| III-179 | CN | H | Br | H | Br |
| III-180 | F | H | CN | H | H |

Table 208: A=NH, R$_1$=C$_2$H$_5$, R$_2$=Cl, W=R$_3$=R$_4$=R$_{5b}$=H, the substituents R$_7$, R$_8$, R$_9$, R$_{10}$ and R$_{11}$ are consistent with those in Table 207 and corresponding to III-1-III-180 in table 207 in turn, the representative compounds are coded as III-181-III-360.

Table 209: A=NH, R$_1$=CF$_3$, R$_2$=Cl, W=R$_3$=R$_4$=R$_{5b}$=H, the s substituents R$_7$, R$_8$, R$_9$, R$_{10}$ and R$_{11}$ are consistent with those in Table 207 and corresponding to III-1-III-180 in table 207 in turn, the representative compounds are coded as III-361-III-540.

Table 210: A=NH, R$_1$=CHF$_2$, R$_2$=Cl, W=R$_3$=R$_4$=R$_{5b}$=H, the substituents R$_7$, R$_8$, R$_9$, R$_{10}$ and R$_{11}$ are consistent with those in Table 207 and corresponding to III-1-III-180 in table 207 in turn, the representative compounds are coded as III-541-III-720.

Table 211: A=NH, R$_1$=CH$_3$, R$_2$=Cl, W=R$_3$=R$_4$=H, R$_{5b}$=Cl, the substituents R$_7$, R$_8$, R$_9$, R$_{10}$ and R$_{11}$ are consistent with those in Table 207 and corresponding to III-1-III-180 in table 207 in turn, the representative compounds are coded as III-721-III-900.

Table 212: A=NH, R$_1$=C$_2$H$_5$, R$_2$=Cl, W=R$_3$=R$_4$=H, R$_{5b}$=Cl, the substituents R$_7$, R$_8$, R$_9$, R$_{10}$ and R$_{11}$ are consistent with those in Table 207 and corresponding to III-1-III-180 in table 207 in turn, the representative compounds are coded as III-901-III-1080.

Table 213: A=NH, R$_1$=CF$_3$, R$_2$=Cl, W=R$_3$=R$_4$=H, R$_{5b}$=Cl, the substituents R$_7$, R$_8$, R$_9$, R$_{10}$ and R$_{11}$ are consistent with those in Table 207 and corresponding to III-1-III-180 in table 207 in turn, the representative compounds are coded as III-1081-III-1260.

Table 214: A=NH, R$_1$=CHF$_2$, R$_2$=Cl, W=R$_3$=R$_4$=H, R$_{5b}$=Cl, the substituents R$_7$, R$_8$, R$_9$, R$_{10}$ and R$_{11}$ are consistent with those in Table 207 and corresponding to III-1-III-180 in table 207 in turn, the representative compounds are coded as III-1261-III-1440.

Table 215: A=NH, R$_1$=CH$_3$, R$_2$=Cl, W=CH$_3$, R$_3$=R$_4$=R$_{5b}$=H, the substituents R$_7$, R$_8$, R$_9$, R$_{10}$ and R$_{11}$ are consistent with those in Table 207 and corresponding to III-1-III-180 in table 207 in turn, the representative compounds are coded as III-1441-III-1620.

Table 216: A=NH, R$_1$=C$_2$H$_5$, R$_2$=Cl, W=CH$_3$, R$_3$=R$_4$=R$_{5b}$=H, the substituents R$_7$, R$_8$, R$_9$, R$_{10}$ and R$_{11}$ are consistent with those in Table 207 and corresponding to III-1-III-180 in table 207 in turn, the representative compounds are coded as III-1621-III-1800.

Table 217: A=NH, $R_1$=$CF_3$, $R_2$=Cl, W=$CH_3$, $R_3$=$R_4$=$R_{5b}$=H, the substituents $R_7$, $R_8$, $R_9$, $R_{10}$ and $R_{11}$ are consistent with those in Table 207 and corresponding to III-1-III-180 in table 207 in turn, the representative compounds are coded as III-1801-III-1980.

Table 218: A=NH, $R_1$=$CHF_2$, $R_2$=Cl, W=$CH_3$, $R_3$=$R_4$=$R_{5b}$=H, the substituents $R_7$, $R_8$, $R_9$, $R_{10}$ and $R_{11}$ are consistent with those in Table 207 and corresponding to III-1-III-180 in table 207 in turn, the representative compounds are coded as III-1981-III-2160.

Table 219: A=NH, $R_1$=$CH_3$, $R_2$=Cl, W=$CH_3$, $R_3$=$R_4$=H, $R_{5b}$=Cl, the substituents $R_7$, $R_8$, $R_9$, $R_{10}$ and $R_{11}$ are consistent with those in Table 207 and corresponding to III-1-III-180 in table 207 in turn, the representative compounds are coded as III-2161-III-2340.

Table 220: A=NH, $R_1$=$C_2H_5$, $R_2$=Cl, W=$CH_3$, $R_3$=$R_4$=H, $R_{5b}$=Cl, the substituents $R_7$, $R_8$, $R_9$, $R_{10}$ and $R_{11}$ are consistent with those in Table 207 and corresponding to III-1-III-180 in table 207 in turn, the representative compounds are coded as III-2341-III-2520.

Table 221: A=NH, $R_1$=Cl, $R_2$=Cl, W=$CH_3$, $R_3$=$R_4$=$R_{5b}$=H, the substituents $R_7$, $R_8$, $R_9$, $R_{10}$ and $R_{11}$ are consistent with those in Table 207 and corresponding to III-1-III-180 in table 207 in turn, the representative compounds are coded as III-2521-III-2700.

Table 222: A=NH, $R_1$=$CHF_2$, $R_2$=Cl, W=$CH_3$, $R_3$=$R_4$=H, $R_{5b}$=Cl, the substituents $R_7$, $R_8$, $R_9$, $R_{10}$ and $R_{11}$ are consistent with those in Table 207 and corresponding to III-1-III-180 in table 207 in turn, the representative compounds are coded as III-2701-III-2880.

Table 223: A=NH, $R_1$=$CH_3$, $R_2$=Cl, W=$R_4$=$R_{5b}$=H, $R_3$=$CH_3$, the substituents $R_7$, $R_8$, $R_9$, $R_{10}$ and $R_{11}$ are consistent with those in Table 207 and corresponding to III-1-III-180 in table 207 in turn, the representative compounds are coded as III-2881-III-3060.

Table 224: A=NH, $R_1$=$C_2H_5$, $R_2$=Cl, W=$R_4$=$R_{5b}$=H, $R_3$=$CH_3$, the substituents $R_7$, $R_8$, $R_9$, $R_{10}$ and $R_{11}$ are consistent with those in Table 207 and corresponding to III-1-III-180 in table 207 in turn, the representative compounds are coded as III-3061-III-3240.

Table 225: A=NH, $R_1$=$CH_3$, $R_2$=Cl, W=$R_4$=H, $R_3$=$CH_3$, $R_{5b}$=Cl, the substituents $R_7$, $R_8$, $R_9$, $R_{10}$ and $R_{11}$ are consistent with those in Table 207 and corresponding to III-1-III-180 in table 207 in turn, the representative compounds are coded as III-3241-III-3420.

Table 226: A=NH, $R_1$=$C_2H_5$, $R_2$=Cl, W=$R_4$=H, $R_3$=$CH_3$, $R_{5b}$=Cl, the substituents $R_7$, $R_8$, $R_9$, $R_{10}$ and $R_{11}$ are consistent with those in Table 207 and corresponding to III-1-III-180 in table 207 in turn, the representative compounds are coded as III-3421-III-3600.

Table 227: A=NH, $R_1$=$CH_3$, $R_2$=Cl, W=$R_{5b}$=H, $R_3$=$R_4$=$CH_3$, the substituents $R_7$, $R_8$, $R_9$, $R_{10}$ and $R_{11}$ are consistent with those in Table 207 and corresponding to III-1-III-180 in table 207 in turn, the representative compounds are coded as III-3601-III-3780.

Table 228: A=NH, $R_1$=$C_2H_5$, $R_2$=Cl, W=$R_{5b}$=H, $R_3$=$R_4$=$CH_3$, the substituents $R_7$, $R_8$, $R_9$, $R_{10}$ and $R_{11}$ are consistent with those in Table 207 and corresponding to III-1-III-180 in table 207 in turn, the representative compounds are coded as III-3781-III-3960.

Table 229: A=NH, $R_1$=$CH_3$, $R_2$=Cl, W=H, $R_3$=$R_4$=$CH_3$, $R_{5b}$=Cl, the substituents $R_7$, $R_8$, $R_9$, $R_{10}$ and $R_{11}$ are consistent with those in Table 207 and corresponding to III-1-III-180 in table 207 in turn, the representative compounds are coded as III-3961-III-4140.

Table 230: A=NH, $R_1$=$C_2H_5$, $R_2$=Cl, W=H, $R_3$=$R_4$=$CH_3$, $R_{5b}$=Cl, the substituents $R_7$, $R_8$, $R_9$, $R_{10}$ and $R_{11}$ are consistent with those in Table 207 and corresponding to III-1-III-180 in table 207 in turn, the representative compounds are coded as III-4141-III-4320.

Table 231: A=O, $R_1$=$CH_3$, $R_2$=Cl, W=$R_3$=$R_4$=$R_{5b}$=H, the substituents $R_7$, $R_8$, $R_9$, $R_{10}$ and $R_{11}$ are consistent with those in Table 207 and corresponding to III-1-III-180 in table 207 in turn, the representative compounds are coded as III-4321-III-4500.

Table 232: A=O, $R_1$=$C_2H_5$, $R_2$=Cl, W=$R_3$=$R_4$=$R_{5b}$=H, the substituents $R_7$, $R_8$, $R_9$, $R_{10}$ and $R_{11}$ are consistent with those in Table 207 and corresponding to III-1-III-180 in table 207 in turn, the representative compounds are coded as III-4501-III-4680.

Table 233: A=O, $R_1$=$CH_3$, $R_2$=Cl, W=$R_3$=$R_4$=H, $R_{5b}$=Cl, the substituents $R_7$, $R_8$, $R_9$, $R_{10}$ and $R_{11}$ are consistent with those in Table 207 and corresponding to III-1-III-180 in table 207 in turn, the representative compounds are coded as III-4681-III-4860.

Table 234: A=O, $R_1$=$C_2H_5$, $R_2$=Cl, W=$R_3$=$R_4$=H, $R_{5b}$=Cl, the substituents $R_7$, $R_8$, $R_9$, $R_{10}$ and $R_{11}$ are consistent with those in Table 207 and corresponding to III-1-III-180 in table 207 in turn, the representative compounds are coded as III-4861-III-5040.

Table 235: A=S, $R_1$=$CH_3$, $R_2$=Cl, W=$R_3$=$R_4$=$R_{5b}$=H, the substituents $R_7$, $R_8$, $R_9$, $R_{10}$ and $R_{11}$ are consistent with those in Table 207 and corresponding to III-1-III-180 in table 207 in turn, the representative compounds are coded as III-5041-III-5220.

Table 236: A=S, $R_1$=$C_2H_5$, $R_2$=Cl, W=$R_3$=$R_4$=$R_{5b}$=H, the substituents $R_7$, $R_8$, $R_9$, $R_{10}$ and $R_{11}$ are consistent with those in Table 207 and corresponding to III-1-III-180 in table 207 in turn, the representative compounds are coded as III-5221-III-5400.

Table 237: A=S, $R_1$=$CH_3$, $R_2$=Cl, W=$R_3$=$R_4$=H, $R_{5b}$=Cl, the substituents $R_7$, $R_8$, $R_9$, $R_{10}$ and $R_{11}$ are consistent with those in Table 207 and corresponding to III-1-III-180 in table 207 in turn, the representative compounds are coded as III-5401-III-5580.

Table 238: A=S, $R_1$=$C_2H_5$, $R_2$=Cl, W=$R_3$=$R_4$=H, $R_{5b}$=Cl, the substituents $R_7$, $R_8$, $R_9$, $R_{10}$ and $R_{11}$ are consistent with those in Table 207 and corresponding to III-1-III-180 in table 207 in turn, the representative compounds are coded as III-5581-III-5760.

In general formula III-B,

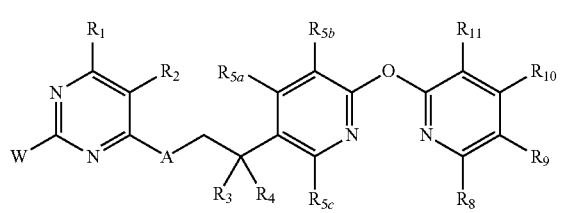

III-B

A=NH, $R_1$=$CH_3$, $R_2$=Cl, W=$R_3$=$R_4$=$R_{5b}$=H, the substituents $R_8$, $R_9$, $R_{10}$ and $R_{11}$ refer to Table 239, the representative compounds are coded as III-5761-III-5802.

TABLE 239

| No. | $R_8$ | $R_9$ | $R_{10}$ | $R_{11}$ |
|---|---|---|---|---|
| III-5761 | H | H | H | H |
| III-5762 | H | H | H | F |

TABLE 239-continued

| No. | $R_8$ | $R_9$ | $R_{10}$ | $R_{11}$ |
| --- | --- | --- | --- | --- |
| III-5763 | H | H | H | Cl |
| III-5764 | H | H | H | Br |
| III-5765 | H | H | Cl | H |
| III-5766 | H | Cl | H | H |
| III-5767 | H | Br | H | H |
| III-5768 | Cl | H | H | H |
| III-5769 | H | H | H | $NO_2$ |
| III-5770 | H | H | $NO_2$ | H |
| III-5771 | H | $NO_2$ | H | H |
| III-5772 | H | CN | H | H |
| III-5773 | H | $OCF_3$ | H | H |
| III-5774 | H | H | H | $CH_3$ |
| III-5775 | H | H | $CH_3$ | H |
| III-5776 | H | $CH_3$ | H | H |
| III-5777 | $CH_3$ | H | H | H |
| III-5778 | H | H | H | $CF_3$ |
| III-5779 | H | H | $CF_3$ | H |
| III-5780 | H | $CF_3$ | H | H |
| III-5781 | H | H | H | $OCH_3$ |
| III-5782 | H | H | $OCH_3$ | H |
| III-5783 | H | $OCH_3$ | H | H |
| III-5784 | $OCH_3$ | H | H | H |
| III-5785 | H | Cl | H | Cl |
| III-5786 | Cl | H | Cl | H |
| III-5787 | H | $NO_2$ | H | Cl |
| III-5788 | H | CN | H | Cl |
| III-5789 | H | $CF_3$ | H | Cl |
| III-5790 | H | $NO_2$ | H | Br |
| III-5791 | H | H | Cl | $NO_2$ |
| III-5792 | H | Cl | H | $NO_2$ |
| III-5793 | H | CN | H | $CH_3$ |
| III-5794 | H | Br | $CH_3$ | H |
| III-5795 | H | $NO_2$ | $CH_3$ | H |
| III-5796 | $CH_3$ | H | $CH_3$ | H |
| III-5797 | H | Cl | H | $CF_3$ |
| III-5798 | Cl | H | H | $CF_3$ |
| III-5799 | $CH_3$ | Cl | $CH_3$ | Cl |
| III-5800 | Cl | Cl | H | Cl |
| III-5801 | Cl | $CF_3$ | H | Br |
| III-5802 | H | Br | $CH_3$ | Br |

Table 240: A=NH, $R_1=C_2H_5$, $R_2=Cl$, $W=R_3=R_4=R_{5b}=H$, the substituents $R_8$, $R_9$, $R_{10}$ and $R_{11}$ are consistent with those in Table 239 and corresponding to III-5761-III-5802 in table 239 in turn, the representative compounds are coded as III-5803-III-5844.

Table 241: A=NH, $R_1=CF_3$, $R_2=Cl$, $W=R_3=R_4=R_{5b}=H$, the substituents $R_8$, $R_9$, $R_{10}$ and $R_{11}$ are consistent with those in Table 239 and corresponding to III-5761-III-5802 in table 239 in turn, the representative compounds are coded as III-5845-III-5886.

Table 242: A=NH, $R_1=CHF_2$, $R_2=Cl$, $W=R_3=R_4=R_{5b}=H$, the substituents $R_8$, $R_9$, $R_{10}$ and $R_{11}$ are consistent with those in Table 239 and corresponding to III-5761-III-5802 in table 239 in turn, the representative compounds are coded as III-5887-III-5928.

Table 243: A=NH, $R_1=CH_3$, $R_2=Cl$, $W=R_3=R_4=H$, $R_{5b}=Cl$, the substituents $R_8$, $R_9$, $R_{10}$ and $R_{11}$ are consistent with those in Table 239 and corresponding to III-5761-III-5802 in table 239 in turn, the representative compounds are coded as III-5929-III-5970.

Table 244: A=NH, $R_1=C_2H_5$, $R_2=Cl$, $W=R_3=R_4=H$, $R_{5b}=Cl$, the substituents $R_8$, $R_9$, $R_{10}$ and $R_{11}$ are consistent with those in Table 239 and corresponding to III-5761-III-5802 in table 239 in turn, the representative compounds are coded as III-5971-III-6012.

Table 245: A=NH, $R_1=CH_3$, $R_2=Cl$, $W=CH_3$, $R_3=R_4=R_{5b}=H$, the substituents $R_8$, $R_9$, $R_{10}$ and $R_{11}$ are consistent with those in Table 239 and corresponding to III-5761-III-5802 in table 239 in turn, the representative compounds are coded as III-6013-III-6054.

Table 246: A=NH, $R_1=C_2H_5$, $R_2=Cl$, $W=CH_3$, $R_3=R_4=R_{5b}=H$, the substituents $R_8$, $R_9$, $R_{10}$ and $R_{11}$ are consistent with those in Table 239 and corresponding to III-5761-III-5802 in table 239 in turn, the representative compounds are coded as III-6055-III-6096.

Table 247: A=NH, $R_1=C_2H_5$, $R_2=Cl$, $W=CH_3$, $R_3=R_4=R_{5b}=H$, the substituents $R_8$, $R_9$, $R_{10}$ and $R_{11}$ are consistent with those in Table 239 and corresponding to III-5761-III-5802 in table 239 in turn, the representative compounds are coded as III-6097-III-6138.

Table 248: A=O, $R_1=C_2H_5$, $R_2=Cl$, $W=R_3=R_4=R_{5b}=H$, the substituents $R_8$, $R_9$, $R_{10}$ and $R_{11}$ are consistent with those in Table 239 and corresponding to III-5761-III-5802 in table 239 in turn, the representative compounds are coded as III-6139-III-6180.

Table 249: A=S, $R_1=CH_3$, $R_2=Cl$, $W=R_3=R_4=R_{5b}=H$, the substituents $R_8$, $R_9$, $R_{10}$ and $R_{11}$ are consistent with those in Table 239 and corresponding to III-5761-III-5802 in table 239 in turn, the representative compounds are coded as III-6181-III-6222.

Table 250: A=S, $R_1=C_2H_5$, $R_2=Cl$, $W=R_3=R_4=R_{5b}=H$, the substituents $R_8$, $R_9$, $R_{10}$ and $R_{11}$ are consistent with those in Table 239 and corresponding to III-5761-III-5802 in table 239 in turn, the representative compounds are coded as III-6223-III-6264.

In general formula III-C,

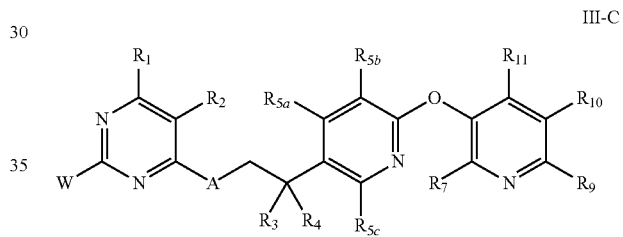

III-C

A=NH, $R_1=CH_3$, $R_2=Cl$, $W=R_3=R_4=R_{5b}=H$, the substituents $R_7$, $R_9$, $R_{10}$ and $R_{11}$ refer to Table 251, the representative compounds are coded as III-6265-III-6282.

TABLE 251

| No. | $R_7$ | $R_9$ | $R_{10}$ | $R_{11}$ |
| --- | --- | --- | --- | --- |
| III-6265 | H | H | H | H |
| III-6266 | Cl | H | H | H |
| III-6267 | $OCH_3$ | H | H | H |
| III-6268 | $OCH_2CF_3$ | H | H | H |
| III-6269 | H | H | H | $CH_3$ |
| III-6270 | H | H | H | $CF_3$ |
| III-6271 | H | Br | H | H |
| III-6272 | H | $CF_3$ | H | H |
| III-6273 | H | $OCH_3$ | H | H |
| III-6274 | Cl | H | Cl | H |
| III-6275 | Cl | Cl | H | H |
| III-6276 | Cl | Cl | Cl | H |
| III-6277 | Cl | H | H | $CH_3$ |
| III-6278 | Cl | H | $CH_3$ | H |
| III-6279 | Cl | $CH_3$ | H | H |
| III-6280 | Cl | Cl | H | $CF_3$ |
| III-6281 | H | $NHCH_3$ | Cl | H |
| III-6282 | H | $SO_2CH_3$ | Cl | H |

Table 252: A=NH, $R_1=C_2H_5$, $R_2=Cl$, $W=R_3=R_4=R_{5b}=H$, the substituents $R_7$, $R_9$, $R_{10}$ and $R_{11}$ are consistent with those in Table 251 and corresponding to III-6265-III-6282 in table 251 in turn, the representative compounds are coded as III-6283-III-6300.

Table 253: A=NH, $R_1$=CH$_3$, $R_2$=Cl, W=$R_3$=$R_4$=H, $R_{5b}$=Cl, the substituents $R_7$, $R_9$, $R_{10}$ and $R_{11}$ are consistent with those in Table 251 and corresponding to III-6265-III-6282 in table 251 in turn, the representative compounds are coded as III-6301-III-6318.

Table 254: A=NH, $R_1$=C$_2$H$_5$, $R_2$=Cl, W=$R_3$=$R_4$=H, $R_{5b}$=Cl, the substituents $R_7$, $R_9$, $R_{10}$ and $R_{11}$ are consistent with those in Table 251 and corresponding to III-6265-III-6282 in table 251 in turn, the representative compounds are coded as III-6319-III-6336.

Table 255: A=NH, $R_1$=CH$_3$, $R_2$=Cl, W=CH$_3$, $R_3$=$R_4$=$R_{5b}$=H, the substituents $R_7$, $R_9$, $R_{10}$ and $R_{11}$ are consistent with those in Table 251 and corresponding to III-6265-III-6282 in table 251 in turn, the representative compounds are coded as III-6337-III-6354.

Table 256: A=NH, $R_1$=C$_2$H$_5$, $R_2$=Cl, W=CH$_3$, $R_3$=$R_4$=$R_{5b}$=H, the substituents $R_7$, $R_9$, $R_{10}$ and $R_{11}$ are consistent with those in Table 251 and corresponding to III-6265-III-6282 in table 251 in turn, the representative compounds are coded as III-6355-III-6372.

In general formula III-D,

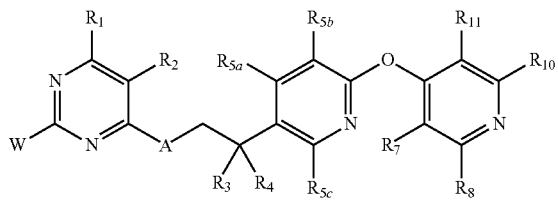

III-D

A=NH, $R_1$=CH$_3$, $R_2$=Cl, W=$R_3$=$R_4$=$R_{5b}$=H, the substituents $R_7$, $R_8$, $R_{10}$ and $R_{11}$ refer to Table 257, the representative compounds are coded as III-6373-III-6380.

TABLE 257

| No. | $R_7$ | $R_8$ | $R_{10}$ | $R_{11}$ |
|---|---|---|---|---|
| III-6373 | H | H | Cl | H |
| III-6374 | H | H | H | Br |
| III-6375 | Cl | H | H | Cl |
| III-6376 | H | H | OCH$_3$ | H |
| III-6377 | H | OCH$_3$ | OCH$_3$ | H |
| III-6378 | H | Cl | OCH$_3$ | H |
| III-6379 | H | Cl | NHCH$_3$ | H |
| III-6380 | Cl | Cl | Cl | Cl |

Table 258: A=NH, $R_1$=C$_2$H$_5$, $R_2$=Cl, W=$R_3$=$R_4$=$R_{5b}$=H, the substituents $R_7$, $R_8$, $R_{10}$ and $R_{11}$ are consistent with those in Table 257 and corresponding to III-6373-III-6380 in table 257 in turn, the representative compounds are coded as III-6381-III-6388.

Table 259: A=NH, $R_1$=CH$_3$, $R_2$=Cl, W=$R_3$=$R_4$=H, $R_{5b}$=Cl, the substituents $R_7$, $R_8$, $R_{10}$ and $R_{11}$ are consistent with those in Table 257 and corresponding to III-6373-III-6380 in table 257 in turn, the representative compounds are coded as III-6389-III-6396.

Table 260: A=NH, $R_1$=C$_2$H$_5$, $R_2$=Cl, W=$R_3$=$R_4$=H, $R_{5b}$=Cl, the substituents $R_7$, $R_8$, $R_{10}$ and $R_{11}$ are consistent with those in Table 257 and corresponding to III-6373-III-6380 in table 257 in turn, the representative compounds are coded as III-6397-III-6404.

Table 261: A=NH, $R_1$=CH$_3$, $R_2$=Cl, W=CH$_3$, $R_3$=$R_4$=$R_{5b}$=H, the substituents $R_7$, $R_8$, $R_{10}$ and $R_{11}$ are consistent with those in Table 257 and corresponding to III-6373-III-6380 in table 257 in turn, the representative compounds are coded as III-6405-III-6412.

Table 262: A=NH, $R_1$=C$_2$H$_5$, $R_2$=Cl, W=CH$_3$, $R_3$=$R_4$=$R_{5b}$=H, the substituents $R_7$, $R_8$, $R_{10}$ and $R_{11}$ are consistent with those in Table 257 and corresponding to III-6373-III-6380 in table 257 in turn, the representative compounds are coded as III-6413-III-6420.

In general formula III-E,

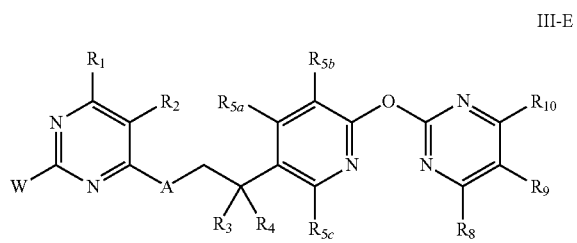

III-E

A=NH, $R_1$=CH$_3$, $R_2$=Cl, W=$R_3$=$R_4$=$R_{5b}$=H, the substituents $R_8$, $R_9$, $R_{10}$ and $R_{11}$ refer to Table 263, the representative compounds are coded as III-6421-III-6424.

TABLE 263

| No. | $R_8$ | $R_9$ | $R_{10}$ |
|---|---|---|---|
| III-6421 | H | H | H |
| III-6422 | CH$_3$ | H | CH$_3$ |
| III-6423 | OCH$_3$ | H | OCH$_3$ |
| III-6424 | CO$_2$C$_2$H$_5$ | H | CF$_3$ |

Table 264: A=NH, $R_1$=C$_2$H$_5$, $R_2$=Cl, W=$R_3$=$R_4$=$R_{5b}$=H, the substituents $R_8$, $R_9$, $R_{10}$ and $R_{11}$ are consistent with those in Table 263 and corresponding to III-6421-III-6424 in table 263 in turn, the representative compounds are coded as III-6425-III-6428.

Table 265: A=NH, $R_1$=CH$_3$, $R_2$=Cl, W=$R_3$=$R_4$=H, $R_{5b}$=Cl, the substituents $R_8$, $R_9$, $R_{10}$ and $R_{11}$ are consistent with those in Table 263 and corresponding to III-6421-III-6424 in table 263 in turn, the representative compounds are coded as III-6429-III-6432.

Table 266: A=NH, $R_1$=C$_2$H$_5$, $R_2$=Cl, W=$R_3$=$R_4$=H, $R_{5b}$=Cl, the substituents $R_8$, $R_9$, $R_{10}$ and $R_{11}$ are consistent with those in Table 263 and corresponding to III-6421-III-6424 in table 263 in turn, the representative compounds are coded as III-6433-III-6436.

Table 267: A=NH, $R_1$=CH$_3$, $R_2$=Cl, W=CH$_3$, $R_3$=$R_4$=$R_{5b}$=H, the substituents $R_8$, $R_9$, $R_{10}$ and $R_{11}$ are consistent with those in Table 263 and corresponding to III-6421-III-6424 in table 263 in turn, the representative compounds are coded as III-6437-III-6440.

Table 268: A=NH, $R_1$=C$_2$H$_5$, $R_2$=Cl, W=CH$_3$, $R_3$=$R_4$=$R_{5b}$=H, the substituents $R_8$, $R_9$, $R_{10}$ and $R_{11}$ are consistent with those in Table 263 and corresponding to III-6421-III-6424 in table 263 in turn, the representative compounds are coded as III-6441-III-6444.

In general formula III-F,

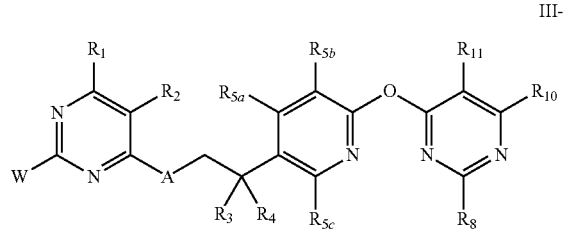

III-F

A=NH, R$_1$=CH$_3$, R$_2$=Cl, W=R$_3$=R$_4$=R$_{5b}$=H, the substituents R$_8$, R$_{10}$ and R refer to Table 269, the representative compounds are coded as III-6445-III-6448.

TABLE 269

| No. | R$_8$ | R$_{10}$ | R$_{11}$ |
|---|---|---|---|
| III-6445 | H | H | H |
| III-6446 | H | Cl | H |
| III-6447 | CH$_3$ | Cl | H |
| III-6448 | H | Cl | Cl |

Table 270: A=NH, R$_1$=C$_2$H$_5$, R$_2$=Cl, W=R$_3$=R$_4$=R$_{5b}$=H, the substituents R$_8$, R$_{10}$ and R$_{11}$ are consistent with those in Table 269 and corresponding to III-6445-III-6448 in table 269 in turn, the representative compounds are coded as III-6449-III-6452.

Table 271: A=NH, R$_1$=CH$_3$, R$_2$=Cl, W=R$_3$=R$_4$=H, R$_{5b}$=Cl, the substituents R$_8$, R$_{10}$ and R$_{11}$ are consistent with those in Table 269 and corresponding to III-6445-III-6448 in table 269 in turn, the representative compounds are coded as III-6453-III-6456.

Table 272: A=NH, R$_1$=C$_2$H$_5$, R$_2$=Cl, W=R$_3$=R$_4$=H, R$_{5b}$=Cl, the substituents R$_8$, R$_{10}$ and R$_{11}$ are consistent with those in Table 269 and corresponding to III-6445-III-6448 in table 269 in turn, the representative compounds are coded as III-6457-III-6460.

Table 273: A=NH, R$_1$=CH$_3$, R$_2$=Cl, W=CH$_3$, R$_3$=R$_4$=R$_{5b}$=H, the substituents R$_8$, R$_{10}$ and R$_{11}$ are consistent with those in Table 269 and corresponding to III-6445-III-6448 in table 269 in turn, the representative compounds are coded as III-6461-III-6464.

Table 274: A=NH, R$_1$=C$_2$H$_5$, R$_2$=Cl, W=CH$_3$, R$_3$=R$_4$=R$_{5b}$=H, the substituents R$_8$, R$_{10}$ and R$_{11}$ are consistent with those in Table 269 and corresponding to III-6445-III-6448 in table 269 in turn, the representative compounds are coded as III-6465-III-6468.

In general formula III-G,

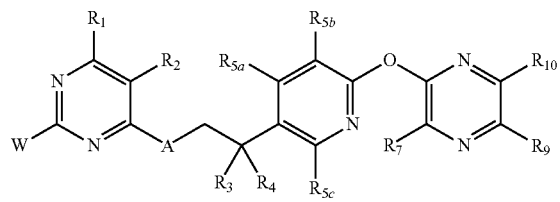

III-G

A=NH, R$_1$=CH$_3$, R$_2$=Cl, W=R$_3$=R$_4$=R$_{5b}$=H, the substituents R$_7$, R$_9$ and R$_{10}$ refer to Table 275, the representative compounds are coded as III-6469-III-6470.

TABLE 275

| No. | R$_7$ | R$_9$ | R$_{10}$ |
|---|---|---|---|
| III-6469 | H | H | H |
| III-6470 | H | H | Cl |

Table 276: A=NH, R$_1$=C$_2$H$_5$, R$_2$=Cl, W=R$_3$=R$_4$=R$_{5b}$=H, the substituents R$_7$, R$_9$ and R$_{10}$ are consistent with those in Table 275 and corresponding to III-6469-III-6470 in table 275 in turn, the representative compounds are coded as III-6471-III-6472.

Table 277: A=NH, R$_1$=CH$_3$, R$_2$=Cl, W=R$_3$=R$_4$=H, R$_{5b}$=Cl, the substituents R$_7$, R$_9$ and R$_{10}$ are consistent with those in Table 275 and corresponding to III-6469-III-6470 in table 275 in turn, the representative compounds are coded as III-6473-III-6474.

Table 278: A=NH, R$_1$=C$_2$H$_5$, R$_2$=Cl, W=R$_3$=R$_4$=H, R$_{5b}$=Cl, the substituents R$_7$, R$_9$ and R$_{10}$ are consistent with those in Table 275 and corresponding to III-6469-III-6470 in table 275 in turn, the representative compounds are coded as III-6475-III-6476.

Table 279: A=NH, R$_1$=CH$_3$, R$_2$=Cl, W=CH$_3$, R$_3$=R$_4$=R$_{5b}$=H, the substituents R$_7$, R$_9$ and R$_{10}$ are consistent with those in Table 275 and corresponding to III-6469-III-6470 in table 275 in turn, the representative compounds are coded as III-6477-III-6478.

Table 280: A=NH, R$_1$=C$_2$H$_5$, R$_2$=Cl, W=CH$_3$, R$_3$=R$_4$=R$_{5b}$=H, the substituents R$_7$, R$_9$ and R$_{10}$ are consistent with those in Table 275 and corresponding to III-6469-III-6470 in table 275 in turn, the representative compounds are coded as III-6479-III-6480.

In general formula III-H,

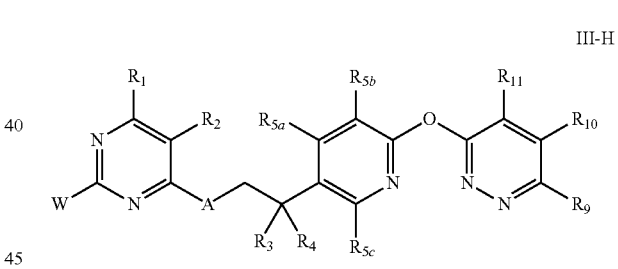

III-H

A=NH, R$_1$=CH$_3$, R$_2$=Cl, W=R$_3$=R$_4$=R$_{5b}$=H, the substituents R$_9$, R$_{10}$ and R refer to Table 281, the representative compounds are coded as III-6481-III-6482.

TABLE 281

| No. | R$_9$ | R$_{10}$ | R$_{11}$ |
|---|---|---|---|
| III-6481 | H | H | H |
| III-6482 | Cl | H | H |

Table 284: A=NH, R$_1$=C$_2$H$_5$, R$_2$=Cl, W=R$_3$=R$_4$=H, R$_{5b}$=Cl, the substituents R$_9$, R$_{10}$ and R$_{11}$ are consistent with those in Table 281 and corresponding to III-6481-III-6482 in table 281 in turn, the representative compounds are coded as III-6487-III-6488.

Table 285: A=NH, R$_1$=CH$_3$, R$_2$=Cl, W=CH$_3$, R$_3$=R$_4$=R$_{5b}$=H, the substituents R$_9$, R$_{10}$ and R$_{11}$ are consistent with those in Table 281 and corresponding to III-6481-III-6482 in table 281 in turn, the representative compounds are coded as III-6489-III-6490

Table 286: A=NH, $R_1=C_2H_5$, $R_2=Cl$, $W=CH_3$, $R_3=R_4=R_{5b}=H$, the substituents $R_9$, $R_{10}$ and $R_{11}$ are consistent with those in Table 281 and corresponding to III-6481-III-6482 in table 281 in turn, the representative compounds are coded as III-6491-III-6492.

In general formula III-A, $A=NR_{12}$, $R_1=CH_3$, $R_2=Cl$, $W=R_3=R_4=R_{5b}=R_7=R_8=R_{10}=R_{11}=H$, $R_9=Cl$, the substituents $R_{12}$ refer to Table 287, the representative compounds are coded as III-6493-III-6632.

TABLE 287

| No. | $R_{12}$ |
|---|---|
| III-6493 | S—i-$C_3H_7$ |
| III-6494 | OH |
| III-6495 | —C(=O)H |
| III-6496 | $CBr_3$ |
| III-6497 | $CH_3$ |
| III-6498 | $C_2H_5$ |
| III-6499 | n-$C_3H_7$ |
| III-6500 | i-$C_3H_7$ |
| III-6501 | n-$C_4H_9$ |
| III-6502 | i-$C_4H_9$ |
| III-6503 | t-$C_4H_9$ |
| III-6504 | $CI_3$ |
| III-6505 | $CH_2Br$ |
| III-6506 | $CHF_2$ |
| III-6507 | $CHBr_2$ |
| III-6508 | $CF_3$ |
| III-6509 | $CH_2Cl$ |
| III-6510 | $CHCl_2$ |
| III-6511 | $CCl_3$ |
| III-6512 | $CH_2F$ |
| III-6513 | $OCH_3$ |
| III-6514 | $OC_2H_5$ |
| III-6515 | $OCH(CH_3)_2$ |
| III-6516 | $OC(CH_3)_3$ |
| III-6517 | $OCF_3$ |
| III-6518 | $OCH_2CF_3$ |
| III-6519 | $OCH_2F$ |
| III-6520 | $OCHF_2$ |
| III-6521 | $SCH_3$ |
| III-6522 | $SC_2H_5$ |
| III-6523 | $SCH_2CH=CH_2$ |
| III-6524 | $CH=CH_2$ |
| III-6525 | $CH_2CH=CH_2$ |
| III-6526 | $CH_2CH=CCl_2$ |
| III-6527 | $C\equiv CH$ |
| III-6528 | $CH_2C\equiv CH$ |
| III-6529 | $CH_2C\equiv C-I$ |
| III-6530 | $CH_2OCH_3$ |
| III-6531 | $CH_2OCH_2CH_3$ |
| III-6532 | $CH_2CH_2OCH_3$ |
| III-6533 | $CH_2CH_2OCH_2CH_3$ |
| III-6534 | $CH_2OCH_2Cl$ |
| III-6535 | $CH_2OCH_2CH_2Cl$ |
| III-6536 | $CH_2CH_2OCH_2Cl$ |
| III-6537 | $CH_2SCH_3$ |
| III-6538 | $CH_2SCH_2CH_3$ |
| III-6539 | $CH_2CH_2SCH_3$ |
| III-6540 | $CH_2CH_2SCH_2CH_3$ |
| III-6541 | $CH_2SCH_2Cl$ |
| III-6542 | $CH_2SCH_2CH_2Cl$ |
| III-6543 | $CH_2CH_2SCH_2Cl$ |
| III-6544 | $SOCH_3$ |
| III-6545 | $SOC_2H_5$ |
| III-6546 | $SOCF_3$ |
| III-6547 | $SOCH_2CF_3$ |
| III-6548 | $SO_2CH_3$ |
| III-6549 | $SO_2C_2H_5$ |
| III-6550 | $SO_2CF_3$ |
| III-6551 | $SO_2CH_2CF_3$ |
| III-6552 | $SO_2NHCOCH_3$ |
| III-6553 | $SO_2NHCH_3$ |
| III-6554 | $SO_2N(CH_3)_3$ |
| III-6555 | $CONHSO_2CH_3$ |
| III-6556 | $COCH_3$ |
| III-6557 | $COC_2H_5$ |
| III-6558 | CO—n-$C_3H_7$ |

TABLE 287-continued

| No. | $R_{12}$ |
|---|---|
| III-6559 | CO—i-$C_3H_7$ |
| III-6560 | CO—n-$C_4H_9$ |
| III-6561 | CO—i-$C_4H_9$ |
| III-6562 | CO—t-$C_4H_9$ |
| III-6563 | $COCF_3$ |
| III-6564 | $COCH_2Cl$ |
| III-6565 | $COOCH_3$ |
| III-6566 | $COOC_2H_5$ |
| III-6567 | COO—n-$C_3H_7$ |
| III-6568 | COO—t-$C_4H_9$ |
| III-6569 | $COOCF_3$ |
| III-6570 | $COOCH_2CH_2Cl$ |
| III-6571 | $COOCH_2CF_3$ |
| III-6572 | $CH_2COOCH_3$ |
| III-6573 | $CH_2COOC_2H_5$ |
| III-6574 | $CH_2COCH_3$ |
| III-6575 | $CH_2COC_2H_5$ |
| III-6576 | $CONHCH_3$ |
| III-6577 | $CONHC_2H_5$ |
| III-6578 | CONH—t-$C_4H_9$ |
| III-6579 | $CON(CH_3)_2$ |
| III-6580 | $CON(C_2H_5)_2$ |
| III-6581 | $COOCH_2CH=CH_2$ |
| III-6582 | $COOCH_2C\equiv CH$ |
| III-6583 | $COOCH_2OCH_3$ |
| III-6584 | $COOCH_2CH_2OCH_3$ |
| III-6585 | $SNHCH_3$ |
| III-6586 | $SNHC_2H_5$ |
| III-6587 | $SN(CH_3)_2$ |
| III-6588 | $SN(C_2H_5)_2$ |
| III-6589 | 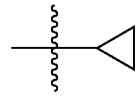 [SMILES: *C1CC1] |
| III-6590 | 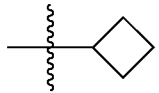 [SMILES: *C1CCC1] |
| III-6591 | 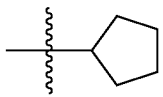 [SMILES: *C1CCCC1] |
| III-6592 | 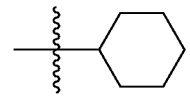 |
| III-6593 | 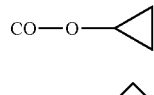 |
| III-6594 | CO—O—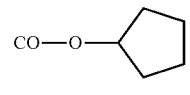 |
| III-6595 | CO—O—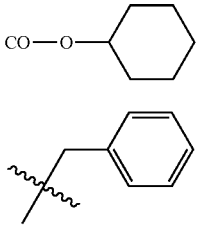 |
| III-6596 | CO—O— |
| III-6597 | |

TABLE 287-continued
| No. | R₁₂ |
|---|---|
| III-6598 | 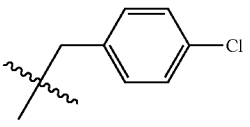 |
| III-6599 | 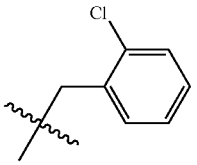 [SMILES: *Cc1ccccc1Cl] |
| III-6600 | 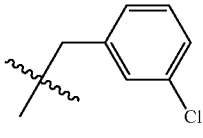 |
| III-6601 | 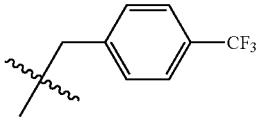 [SMILES: *Cc1ccc(C(F)(F)F)cc1] |
| III-6602 | 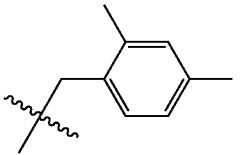 [SMILES: *Cc1ccc(C)cc1C] |
| III-6603 | 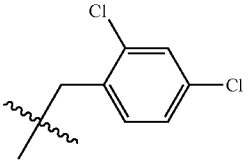 [SMILES: *Cc1ccc(Cl)cc1Cl] |
| III-6604 | 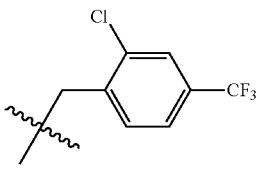 [SMILES: *Cc1ccc(C(F)(F)F)cc1Cl] |
| III-6605 | 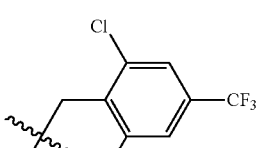 |
| III-6606 | 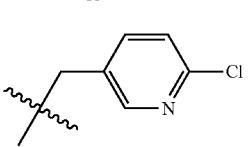 |
| III-6607 | 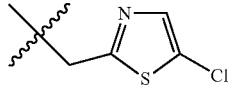 [SMILES: *Cc1ncc(Cl)s1] |
| III-6608 | 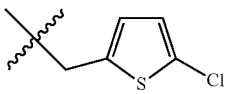 |
| III-6609 | 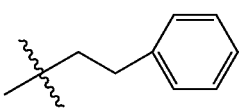 [SMILES: *CCc1ccccc1] |
| III-6610 | 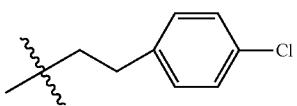 [SMILES: *CCc1ccc(Cl)cc1] |
| III-6611 | 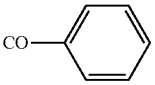 |
| III-6612 |  |
| III-6613 |  |
| III-6614 | 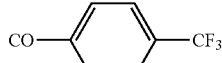 |
| III-6615 | 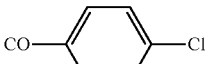 |
| III-6616 | 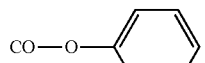 |
| III-6617 | 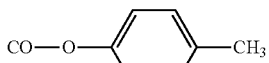 |
| III-6618 | 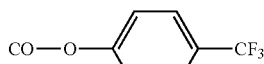 |
| III-6619 | 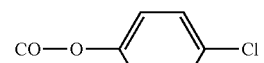 |
| III-6620 | 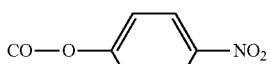 |
| III-6621 | 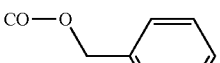 |
| III-6622 | 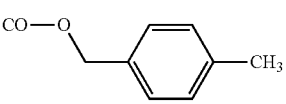 |

TABLE 287-continued

| No. | $R_{12}$ |
|---|---|
| III-6623 | 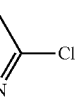 |
| III-6624 | 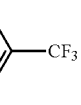 |
| III-6625 | 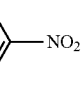 |
| III-6626 | 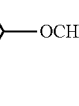 |
| III-6627 |  |
| III-6628 | 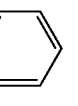 |
| III-6629 | 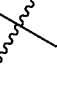 |
| III-6630 | 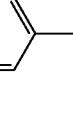 |
| III-6631 | 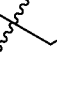 |
| III-6632 | 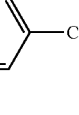 |

Table 288: in general formula III-A, A=$NR_{12}$, $R_1$=$CH_3$, $R_2$=Cl, W=$R_3$=$R_4$=$R_{5b}$=$R_8$=$R_{10}$=$R_{11}$=H, $R_7$=$R_9$=Cl, the substituent $R_{12}$ are consistent with those in Table 287 and corresponding to III-6493-III-6632 in table 287 in turn, the representative compounds are coded as III-6633-III-6772.

Table 289: in general formula Ill-A, A=$NR_{12}$, $R_1$=$CH_3$, $R_2$=Cl, W=$R_3$=$R_4$=$R_{5b}$=$R_7$=$R_8$=$R_{10}$=$R_{11}$=H, $R_9$=$CF_3$, the substituent $R_{12}$ are consistent with those in Table 287 and corresponding to III-6493-III-6632 in table 287 in turn, the representative compounds are coded as III-6773-III-6912.

Table 290: in general formula III-B, A=$NR_{12}$, $R_1$=$CH_3$, $R_2$=Cl, W=$R_3$=$R_4$=$R_{5b}$=$R_8$=$R_{10}$=$R_{11}$=H, $R_9$=Cl, the substituent $R_{12}$ are consistent with those in Table 287 and corresponding to III-6493-III-6632 in table 287 in turn, the representative compounds are coded as III-6913-III-7052.

Table 291: in general formula III-B, A=$NR_{12}$, $R_1$=$CH_3$, $R_2$=Cl, W=$R_3$=$R_4$=$R_{5b}$=$R_8$=$R_{10}$=$R_{11}$=H, $R_9$=$CF_3$, the substituent $R_{12}$ are consistent with those in Table 287 and corresponding to III-6493-III-6632 in table 287 in turn, the representative compounds are coded as III-7053-III-7192.

Table 292: in general formula III-B, A=$NR_{12}$, $R_1$=$CH_3$, $R_2$=Cl, W=$R_3$=$R_4$=$R_{5b}$=$R_8$=$R_{10}$=H, $R_9$=$CF_3$, $R_{11}$=Cl, the substituent $R_{12}$ are consistent with those in Table 287 and corresponding to III-6493-III-6632 in table 287 in turn, the representative compounds are coded as III-7193-III-7332.

Table 293: in general formula III-B, A=$NR_{12}$, $R_1$=$CH_3$, $R_2$=Cl, W=$R_3$=$R_4$=$R_{5b}$=$R_8$=$R_{10}$=H, $R_9$=$R_{11}$=Cl, the substituent $R_{12}$ are consistent with those in Table 287 and corresponding to III-6493-III-6632 in table 287 in turn, the representative compounds are coded as III-7333-III-7472.

Table 294: in general formula III-C, A=$NR_{12}$, $R_1$=$CH_3$, $R_2$=Cl, W=$R_3$=$R_4$=$R_{5b}$=$R_9$=$R_{10}$=$R_{11}$=H, $R_7$=Cl, the substituent $R_{12}$ are consistent with those in Table 287 and corresponding to III-6493-III-6632 in table 287 in turn, the representative compounds are coded as III-7473-III-7612.

Table 295: in general formula III-D, A=$NR_{12}$, $R_1$=$CH_3$, $R_2$=Cl, W=$R_3$=$R_4$=$R_{5b}$=$R_7$=$R_{11}$=H, $R_8$=$R_{10}$=Cl, the substituent $R_{12}$ are consistent with those in Table 287 and corresponding to III-6493-III-6632 in table 287 in turn, the representative compounds are coded as III-7613-III-7752.

Table 296: in general formula III-E, A=$NR_{12}$, $R_1$=$CH_3$, $R_2$=Cl, W=$R_3$=$R_4$=$R_{5b}$=$R_9$=H, $R_8$=$R_{10}$=$OCH_3$, the substituent $R_{12}$ are consistent with those in Table 287 and corresponding to III-6493-III-6632 in table 287 in turn, the representative compounds are coded as III-7753-III-7892.

Table 297: in general formula III-E, A=$NR_{12}$, $R_1$=$C_2H_5$, $R_2$=Cl, W=$R_3$=$R_4$=$R_{5b}$=$R_9$=H, $R_8$=$R_{10}$=$CH_3$, the substituent $R_{12}$ are consistent with those in Table 287 and corresponding to III-6493-III-6632 in table 287 in turn, the representative compounds are coded as III-7893-III-8032.

Table 298: in general formula III-F, A=$NR_{12}$, $R_1$=$CH_3$, $R_2$=Cl, W=$R_3$=$R_4$=$R_{5b}$=$R_8$=H, $R_{10}$=$CH_3$, $R_{11}$=Cl, the substituent $R_{12}$ are consistent with those in Table 287 and corresponding to III-6493-III-6632 in table 287 in turn, the representative compounds are coded as III-8033-III-8172.

Table 299: in general formula III-G, A=$NR_{12}$, $R_1$=$CH_3$, $R_2$=Cl, W=$R_3$=$R_4$=$R_{5b}$=$R_7$=$R_9$=H, $R_{10}$=Cl, the substituent $R_{12}$ are consistent with those in Table 287 and corresponding to III-6493-III-6632 in table 287 in turn, the representative compounds are coded as III-8173-III-83122.

Table 300: in general formula Ill-H, A=$NR_{12}$, $R_1$=$CH_3$, $R_2$=Cl, W=$R_3$=$R_4$=$R_{5b}$=$R_{10}$=$R_{11}$=H, $R_7$=Cl, the substituent $R_{12}$ are consistent with those in Table 287 and corresponding to III-6493-III-6632 in table 287 in turn, the representative compounds are coded as III-8313-III-8452.

The salts of some compounds having a structure as represented by formula III of the present invention are listed in Table 301, but without being restricted thereby.

TABLE 301
the salts of some compounds
| No. | structure |
|---|---|
| III-8453 | 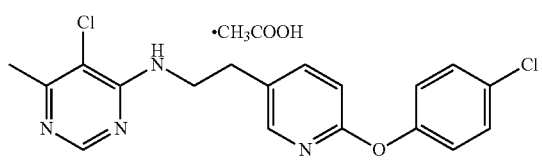 |
| III-8454 | 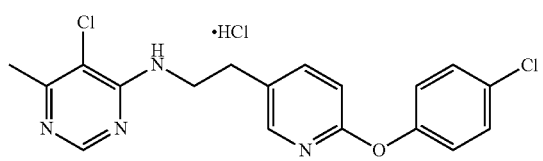 [SMILES: Cc1ncnc(NCCc2ccc(Oc3ccc(Cl)cc3)nc2)c1Cl ; Cl] |
| III-8455 | 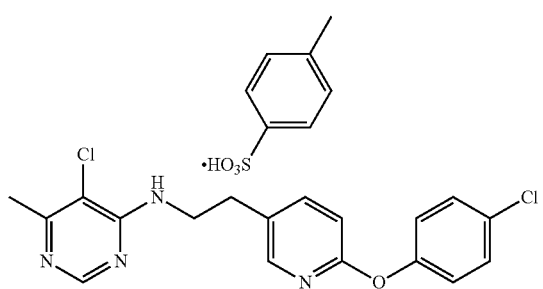 |
| III-8456 | 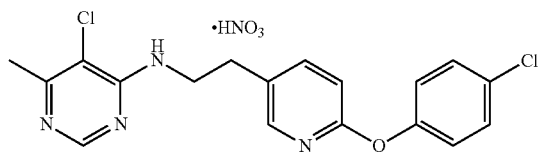 |
| III-8457 | 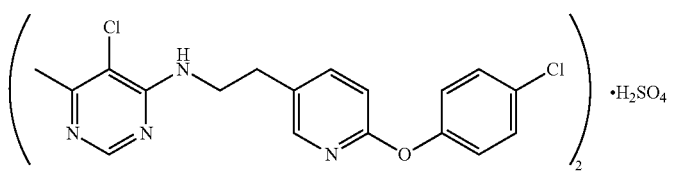 |
| III-8458 | 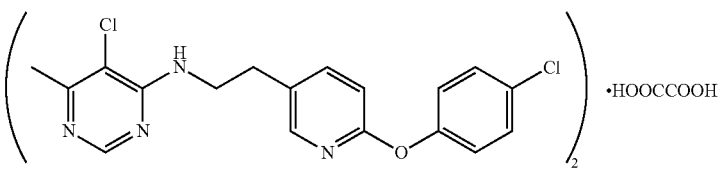 |
| III-8459 | 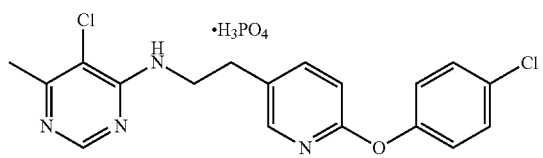 |
| III-8460 | 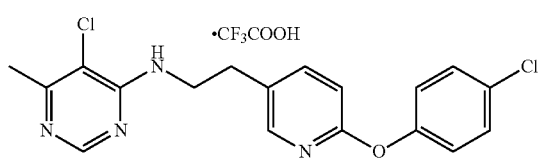 [SMILES: Cc1ncnc(NCCc2ccc(Oc3ccc(Cl)cc3)nc2)c1Cl ; "·CF3COOH"] |

TABLE 301-continued
the salts of some compounds
| No. | structure |
|---|---|
| III-8461 | 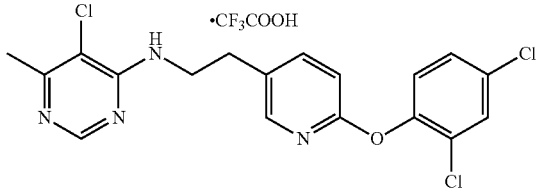 |
| III-8462 | 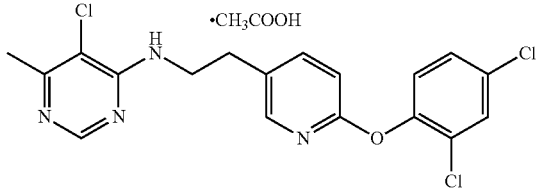 [SMILES: Cc1ncnc(NCCc2ccc(Oc3ccc(Cl)cc3Cl)nc2)c1Cl ; "·CF3COOH"] |
| III-8463 | 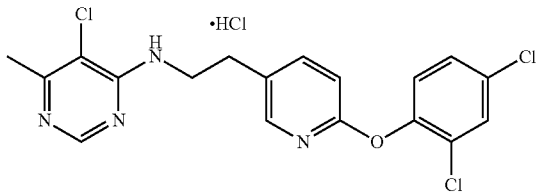 [SMILES: Cc1ncnc(NCCc2ccc(Oc3ccc(Cl)cc3Cl)nc2)c1Cl ; Cl] |
| III-8464 | 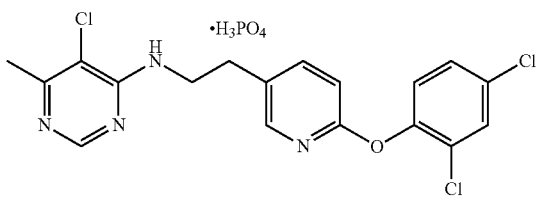 [SMILES: Cc1ncnc(NCCc2ccc(Oc3ccc(Cl)cc3Cl)nc2)c1Cl ; "·H3PO4"] |
| III-8465 | 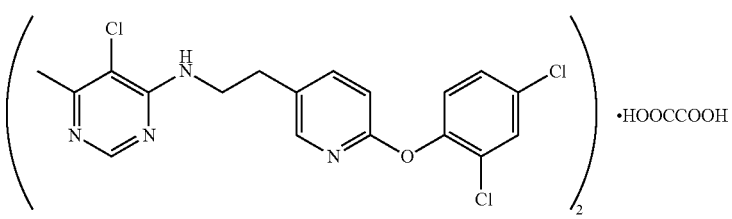 |
| III-8466 | 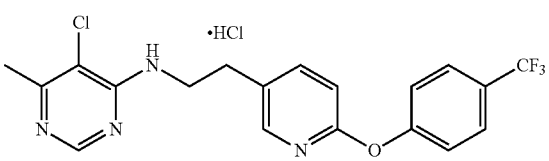 [SMILES: Cc1ncnc(NCCc2ccc(Oc3ccc(C(F)(F)F)cc3)nc2)c1Cl ; Cl] |
| III-8467 | 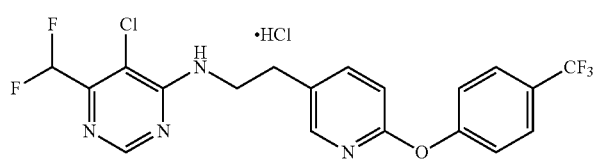 [SMILES: FC(F)c1ncnc(NCCc2ccc(Oc3ccc(C(F)(F)F)cc3)nc2)c1Cl ; Cl] |
| III-8468 | 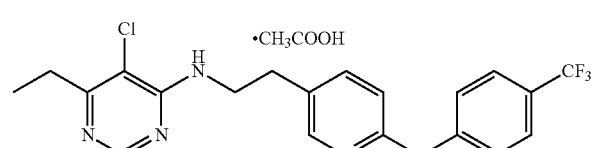 |

TABLE 301-continued the salts of some compounds

| No. | structure |
|---|---|
| III-8469 | 5-chloro-6-ethyl-N-(2-(6-(4-(trifluoromethyl)phenoxy)pyridin-3-yl)ethyl)pyrimidin-4-amine · p-toluenesulfonic acid salt |
| III-8470 | 5-chloro-6-(difluoromethyl)-N-(2-(6-(4-(trifluoromethyl)phenoxy)pyridin-3-yl)ethyl)pyrimidin-4-amine · p-toluenesulfonic acid salt |
| III-8471 | 5-chloro-6-ethyl-N-(2-(6-(2-chloro-4-(trifluoromethyl)phenoxy)pyridin-3-yl)ethyl)pyrimidin-4-amine · HCl |
| III-8472 | 5-chloro-6-methyl-N-(2-(6-(2-chloro-4-(trifluoromethyl)phenoxy)pyridin-3-yl)ethyl)pyrimidin-4-amine · CH₃COOH |
| III-8473 | 5-chloro-6-(difluoromethyl)-N-(2-(6-(2-chloro-4-(trifluoromethyl)phenoxy)pyridin-3-yl)ethyl)pyrimidin-4-amine · CH₃COOH |
| III-8474 | 5-chloro-6-methyl-N-(2-(6-(2-chloro-4-(trifluoromethyl)phenoxy)pyridin-3-yl)ethyl)pyrimidin-4-amine · p-toluenesulfonic acid salt |

TABLE 301-continued
the salts of some compounds
| No. | structure |
|---|---|
| III-8475 | 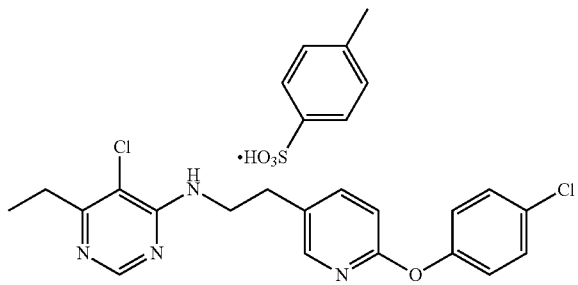 |
| III-8476 | 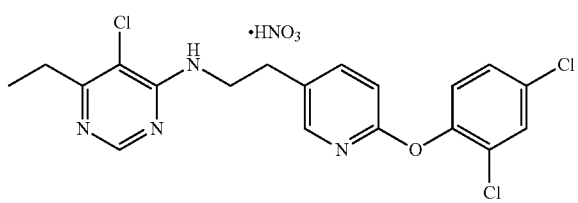 [SMILES: CCc1ncnc(NCCc2ccc(Oc3ccc(Cl)cc3Cl)nc2)c1Cl ; "·HNO3"] |
| III-8477 | 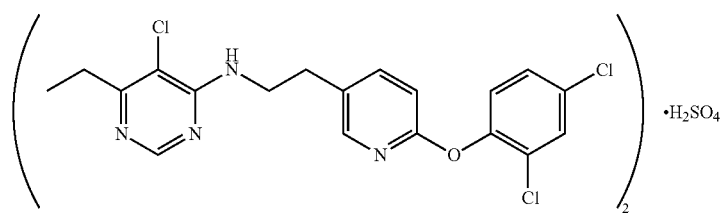 |
| III-8478 | 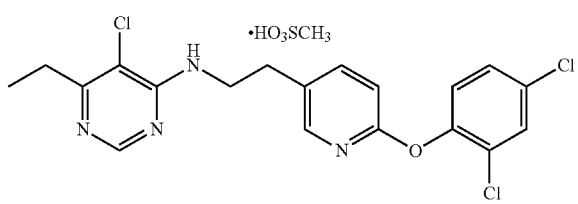 |
| III-8479 | 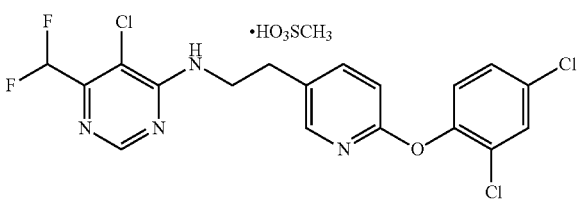 |
| III-8480 | 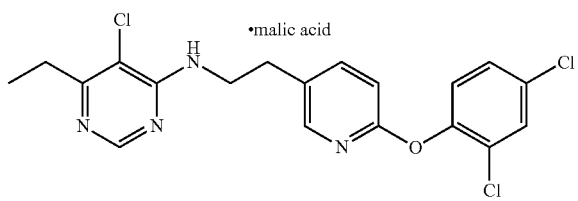 |
| III-8481 | 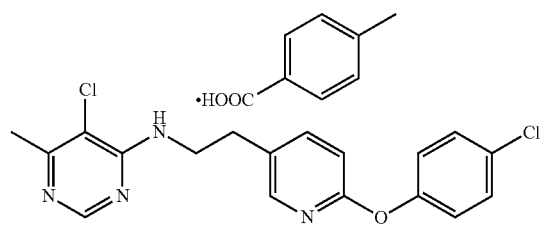 |

TABLE 301-continued
the salts of some compounds
| No. | structure |
|---|---|
| III-8482 | 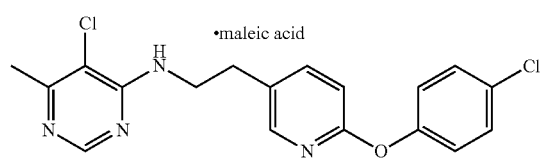 |
| III-8483 | 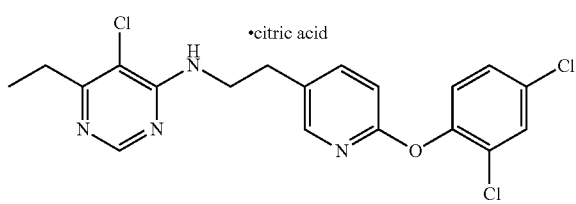 |
| III-8484 | 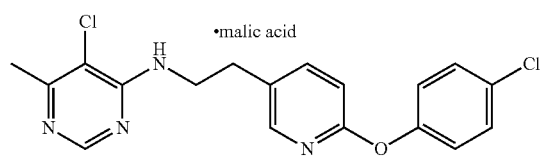 |
| III-8485 | 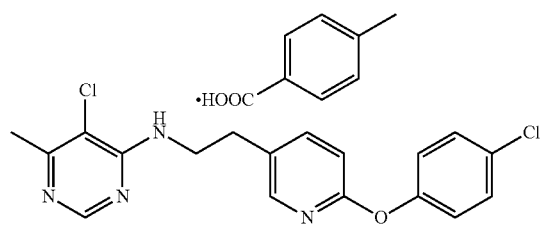 |
| III-8486 | 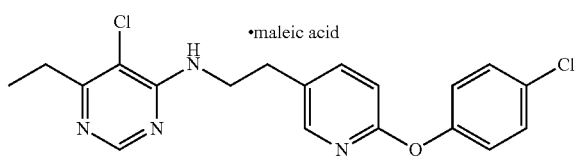 |
| III-8487 | 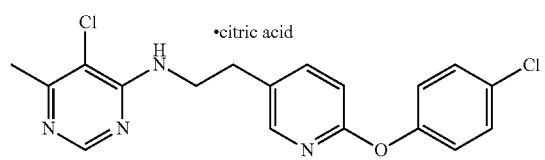 |
| III-8488 | 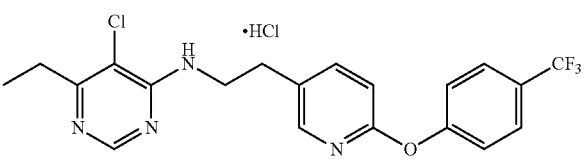 [SMILES: CCc1ncnc(NCCc2ccc(Oc3ccc(C(F)(F)F)cc3)nc2)c1Cl ; Cl] |
| III-8489 | 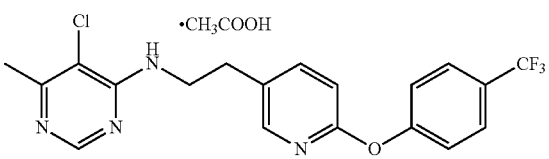 [SMILES: Cc1ncnc(NCCc2ccc(Oc3ccc(C(F)(F)F)cc3)nc2)c1Cl ; "·CH3COOH"] |

TABLE 301-continued
the salts of some compounds
| No. | structure |
|---|---|
| III-8490 | 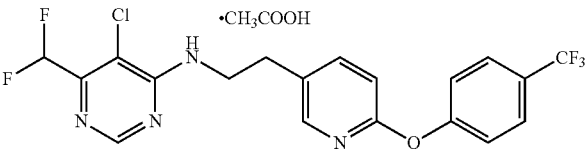 [SMILES: FC(F)c1ncnc(NCCc2ccc(Oc3ccc(C(F)(F)F)cc3)nc2)c1Cl ; "·CH3COOH"] |
| III-8491 | 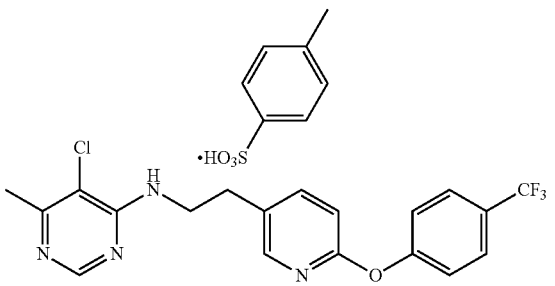 |
| III-8492 | 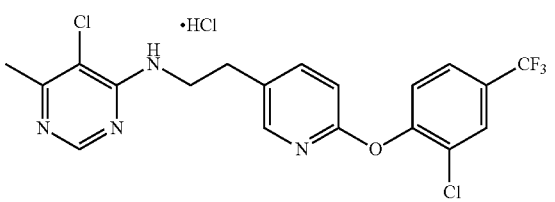 [SMILES: Cc1ncnc(NCCc2ccc(Oc3ccc(C(F)(F)F)cc3Cl)nc2)c1Cl ; Cl] |
| III-8493 | 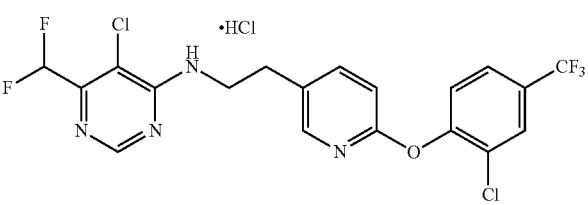 [SMILES: FC(F)c1ncnc(NCCc2ccc(Oc3ccc(C(F)(F)F)cc3Cl)nc2)c1Cl ; Cl] |
| III-8494 | 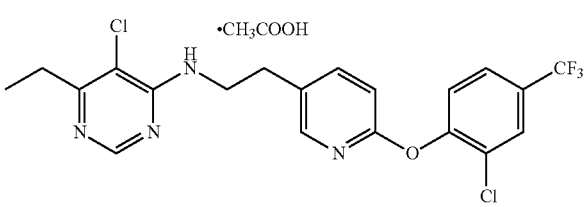 [SMILES: CCc1ncnc(NCCc2ccc(Oc3ccc(C(F)(F)F)cc3Cl)nc2)c1Cl ; "·CH3COOH"] |
| III-8495 | 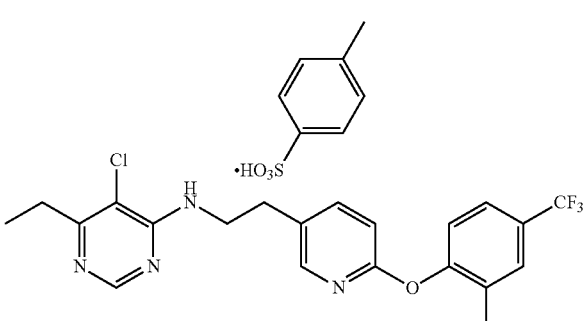 |

TABLE 301-continued the salts of some compounds

| No. | structure |
|---|---|
| III-8496 | 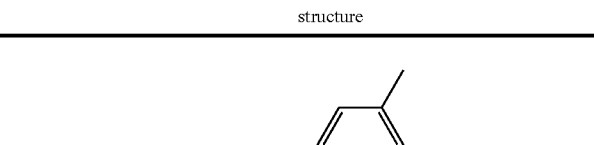 |

The compounds represented by general formula PY of the invention can be prepared according to three schemes in which Substituent A can be defined as different substituents, the definitions of each substituent is defined as above:

Scheme 1 to prepare the compounds represented by general formula PY: when A=NH, the compounds represented by general formula PY-1 can be prepared according to the following two schemes.

Method 1: the compounds represented by general formula PY-1 can be prepared by reaction of intermediates i and ii in the presence of proper base, the preparation methods are shown as follows.

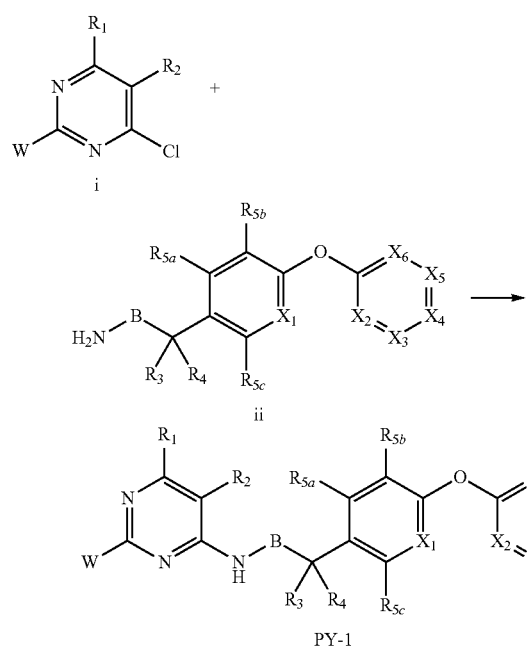

PY-1

The reaction was carried out in proper solvent and the proper solvent mentioned may be selected from benzene, toluene, xylene, acetone, butanone, methylisobutylketone, tetrahydrofuran, acetonitrile, 1,4-dioxane, DMF, N-methyl pyrrolidone, DMSO, pyridine, dichloromethane, chloroform, dichloroethane, methyl acetate or ethyl acetate and so on.

The reaction above can be carried out in the presence or absence of base, the reaction is promoted in the presence of base. Proper base mentioned may be selected from alkali metal hydride such as sodium hydride; alkali metal hydroxides such as sodium hydroxide or potassium hydroxide; alkali metal carbonate such as sodium carbonate or potassium carbonate; organic amine such as pyridine or triethylamine.

The proper temperature mentioned is from room temperature to boiling point of the solvent, normal temperature is from 20 to 100° C.

The reaction time is in the range of 30 minutes to 20 hours, generally being 1-10 hours.

The detailed operation refers to the methods described in EP0370704, EP0356158, EP0264217, EP0665225, JP10036355 or U.S. Pat. No. 4,985,426.

Intermediates I are commercially available, or prepared according to the methods described in JP2000007662, U.S. Pat. No. 4,977,264, U.S. Pat. No. 6,090,815, US20040092402, JP09124613, U.S. Pat. No. 5,468,751, U.S. Pat. No. 4,985,426, U.S. Pat. No. 4,845,097, Recueil des Travaux Chimiques des Pays-Bas (1978), 97(11), Pages 288-92, Journal of the American Chemical Society, 79, 1455(1957) or Journal of Chemical Society, p. 3478-3481 (1955).

Intermediates ii are commercially available, or prepared according to the methods described in U.S. Pat. No. 4,895,849, JP10036355, EP665225, US20070093498, WO2007046809, U.S. Pat. No. 5,783,522A, WO02083647A1, CN1927860A, WO9404527, US20110054173, WO2011025505, WO2004093800A, WO 2012075917, US20050648509, US2002082454, Organic Syntheses, Coll. Vol. 10, p. 501 (2004); Vol. 75, p. 61 (1998) or Organic Syntheses, Coll. Vol. 10, p. 102 (2004); Vol. 75, p. 53 (1998).

Method 2: the compounds represented by general formula iv can be prepared by reaction of intermediates i and iii in proper solvent, then the compounds represented by general formula PY-1 can be prepared by reaction of intermediates iv and v in the presence of proper base, the preparation methods are shown as follows. Wherein, L is a leaving group, selected from halogen, boric acid, methyl methanesulfonate or p-toluenesulfonates.

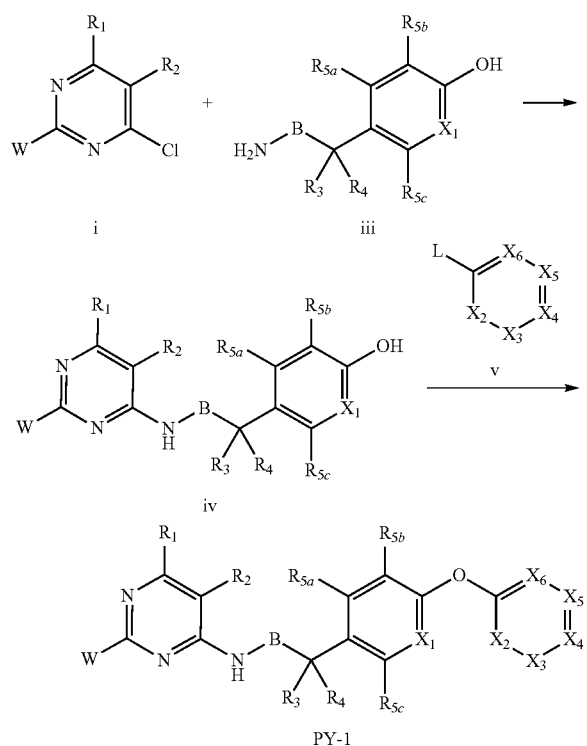

PY-1

The reaction was carried out between the intermediates represented by general formula i and iii in proper solvent and the proper solvent mentioned may be selected from benzene, toluene, xylene, acetone, butanone, methylisobutylketone, tetrahydrofuran, acetonitrile, 1,4-dioxane, DMF, N-methyl pyrrolidone, DMSO, pyridine, dichloromethane, chloroform, dichloroethane, methyl acetate or ethyl acetate and so on. The reaction above can be carried out in the presence or absence of base, the reaction is promoted in the presence of base. Proper base mentioned may be selected from alkali metal hydride such as sodium hydride; alkali metal hydroxides such as sodium hydroxide or potassium hydroxide; alkali metal carbonate such as sodium carbonate or potassium carbonate; organic amine such as pyridine or triethylamine.

The proper temperature mentioned is from room temperature to boiling point of the solvent, normal temperature is from 20 to 100° C. The reaction time is in the range of 30 minutes to 20 hours, generally being 1-10 hours.

The reaction was carried out between the intermediates represented by general formula iv and v in proper solvent and the proper solvent mentioned may be selected from benzene, toluene, xylene, acetone, butanone, methylisobutylketone, tetrahydrofuran, acetonitrile, 1,4-dioxane, DMF, N-methyl pyrrolidone, DMSO, pyridine, dichloromethane, chloroform, dichloroethane, methyl acetate or ethyl acetate and so on. The reaction above can be carried out in the presence of base. Proper base mentioned may be selected from alkali metal hydride such as sodium hydride; alkali metal hydroxides such as sodium hydroxide or potassium hydroxide; alkali metal carbonate such as sodium carbonate or potassium carbonate; organic amine such as pyridine or triethylamine.

The proper temperature mentioned is from room temperature to boiling point of the solvent, normal temperature is from 20 to 200° C. The reaction time is in the range of 30 minutes to 20 hours, generally being 1-10 hours.

The detailed operation refers to the methods described in JP11049759, EP0370704, EPO 196524 or U.S. Pat. No. 4,895,849.

Other materials, such as the compounds represented by general formula iii and v, used to prepare the compounds represented by general formula PY-1, are commercially available.

The intermediate represented by general formula ii is one of key intermediate, some compounds are commercially available, or are prepared according to the known method described above, also can be prepared according to the following two schemes in which Substituent $X_1$ can be defined as different substituents.

Method 1: when $X_1$=$CR_6$, the intermediate ii used to prepare the compounds represented by the general formula I and II (wherein A=NH) can be prepared according to the following two schemes. Relevant intermediates are commercially available, or prepared according to the methods described in U.S. Pat. No. 4,895,849, JP10036355, EP665225, US20070093498, WO2007046809, U.S. Pat. No. 5,783,522A, WO02083647A1, CN1927860A, Organic Syntheses, Coll. Vol. 10, p. 501 (2004); Vol. 75, p. 61 (1998) or Organic Syntheses, Coll. Vol. 10, p. 102 (2004); Vol. 75, p. 53 (1998).

(1) Reduction of Cyano:

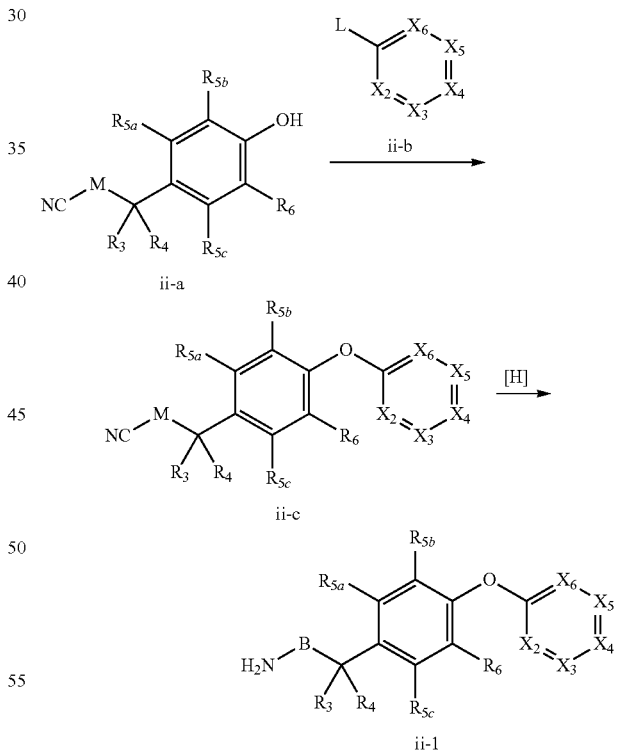

Wherein, L is a leaving group, selected from halogen, boric acid, methyl methanesulfonate or p-toluenesulfonates. B is a alkyl chain with one more carbon than M.

The compounds represented by general formula ii-c can be prepared by reaction of intermediates ii-a and ii-b in proper solvent in the presence of proper base. The detailed operation refers to the methods described in US2002082454 and Fine Chemicals, 2005, 22(12): 944-960. The proper temperature mentioned is from room temperature to boiling point of the solvent, normal temperature is from 20 to 100° C. The reaction time is in the range of 30 minutes to 20 hours, generally being 1-10 hours. The proper solvent mentioned may be selected from acetone, butanone, tetrahydrofuran, acetonitrile, toluene, xylene, benzene, DMF, DMSO, methanol or ethanol and so on. Proper base mentioned may be selected from potassium hydroxide, sodium hydroxide, sodium carbonate, potassium carbonate, sodium bicarbonate, triethylamine, pyridine or sodium hydride.

When L refers to boric acid group, the compounds represented by general formula ii-c can also be prepared by reaction of intermediates ii-a and ii-b at 0-100° C. in proper solvent in the presence of proper base and catalyst. The proper solvent mentioned may be selected from benzene, toluene, xylene, chloroform, dichloromethane, acetone, butanone, tetrahydrofuran, acetonitrile, 1,4-dioxane, DMF, N-methyl pyrrolidone or DMSO and so on. Proper base mentioned may be selected from pyridine or triethylamine and so on. Proper catalyst mentioned may be selected from copper acetate, copper chloride or copper sulfate and so on.

The intermediates represented by general formula ii-1 can be prepared by reaction of intermediates represented by general formula ii-c and ammonia water in the presence of proper catalyst by using hydrogenation reduction. The detailed operation refers to the methods described in J. Am. Chem. Soc, 70, 3788 (1948); 82, 681 (1960); 82, 2386 (1960); Can. J. Chem, 49, 2990 (1971); J. Org. Chem, 37, 335 (1972); Organic Syntheses, Coll. Vol. 3, p. 229, p. 720 (1955), Vol. 23, p. 71 (1943) or Vol. 27, p. 18 (1947). The proper temperature mentioned is from room temperature to boiling point of the solvent, normal temperature is from 20 to 100° C. The reaction time is in the range of 30 minutes to 20 hours, generally being 1-10 hours. The proper solvent mentioned may be selected from methanol, ethanol, isopropanol, benzene, toluene, xylene, acetone, butanone, methylisobutylketone, chloroform, dichloroethane, methyl acetate, ethyl acetate, tetrahydrofuran, 1,4-dioxane, DMF, N-methyl pyrrolidone or DMSO, etc. The proper catalysts mentioned may be selected from Raney-nickel, palladium carbon or platinum oxide, etc.

(2) The method to prepare the substituted amine and its salts by reaction of the substituted 4-hydroxyphenylalkyl amine

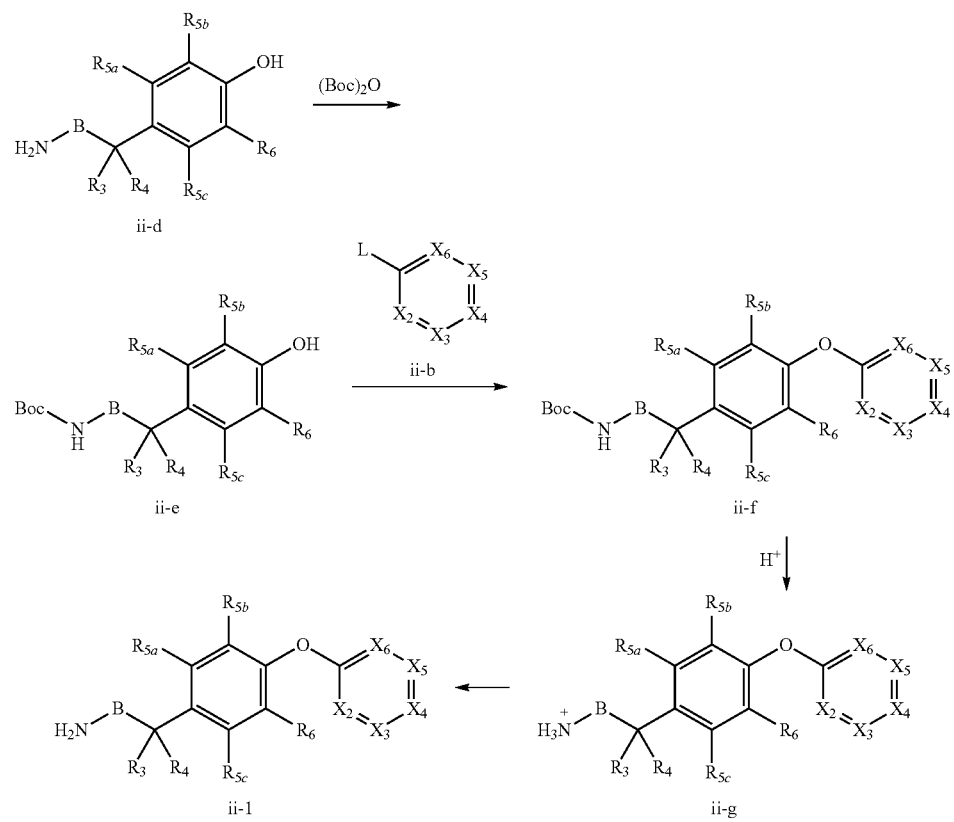

Wherein, Boc$_2$O refers to di-tert-butyl dicarbonate.

Firstly, the compounds represented by general formula ii-e can be prepared by reaction of intermediates ii-d and di-tert-butyl dicarbonate at 0-100° C. in proper solvent in the presence of proper base. The preferred temperature is 0-50° C. The reaction time is in the range of 30 minutes to 20 hours, generally being 0.5-10 hours. The proper solvent mentioned may be selected from benzene, toluene, xylene, chloroform, dichloromethane, tetrahydrofuran, acetonitrile, 1,4-dioxane, DMF, N-methyl pyrrolidone or DMSO and so on. Proper base mentioned may be selected from alkali metal carbonate such as sodium carbonate, sodium bicarbonate, potassium carbonate or potassium bicarbonate.

Then the compounds represented by general formula ii-f can be prepared by reaction of intermediates ii-e and ii-b at 0-100° C. in proper solvent in the presence of proper base. The reaction time is in the range of 30 minutes to 20 hours, generally being 0.5-10 hours. The proper solvent mentioned may be selected from benzene, toluene, xylene, chloroform, dichloromethane, acetone, butanone, tetrahydrofuran, acetonitrile, 1,4-dioxane, DMF, N-methyl pyrrolidone or DMSO and so on. Proper base mentioned may be selected from alkali metal hydride such as sodium hydride; alkali metal hydroxides such as sodium hydroxide or potassium hydroxide; alkali carbonate such as sodium carbonate or potassium carbonate; organic amine such as pyridine or triethylamine.

When L refers to boric acid group. The method to prepare the compounds represented by general formula ii-f refers to the method to prepare the compounds represented by general formula ii-c with method of cyano reduction.

The salts represented by general formula ii-g can be prepared by deprotection reaction of intermediates represented by general formula ii-f and proper acid in proper solvent, and then alkalized to obtain ii-1. The preferred temperature is 0-50° C. The reaction time is in the range of detailed operation refers to the methods described in WO2004093800A and US20050096485.

Other materials mentioned above, such as the compounds represented by general formula ii-a, ii-b, ii-d and Boc$_2$O, used to prepare the compounds represented by general formula ii-1, are commercially available.

Method 2: when X$_1$=N, the intermediate ii used to prepare the compounds represented by the general formula III (wherein A=NH) can be prepared according to the following two schemes in which B is selected from different substituent.

(1) When B=—CH$_2$—, the detailed operation refers to the methods described in WO9404527, US20110054173 or WO2011025505. The compounds also can be prepared according to the following method.

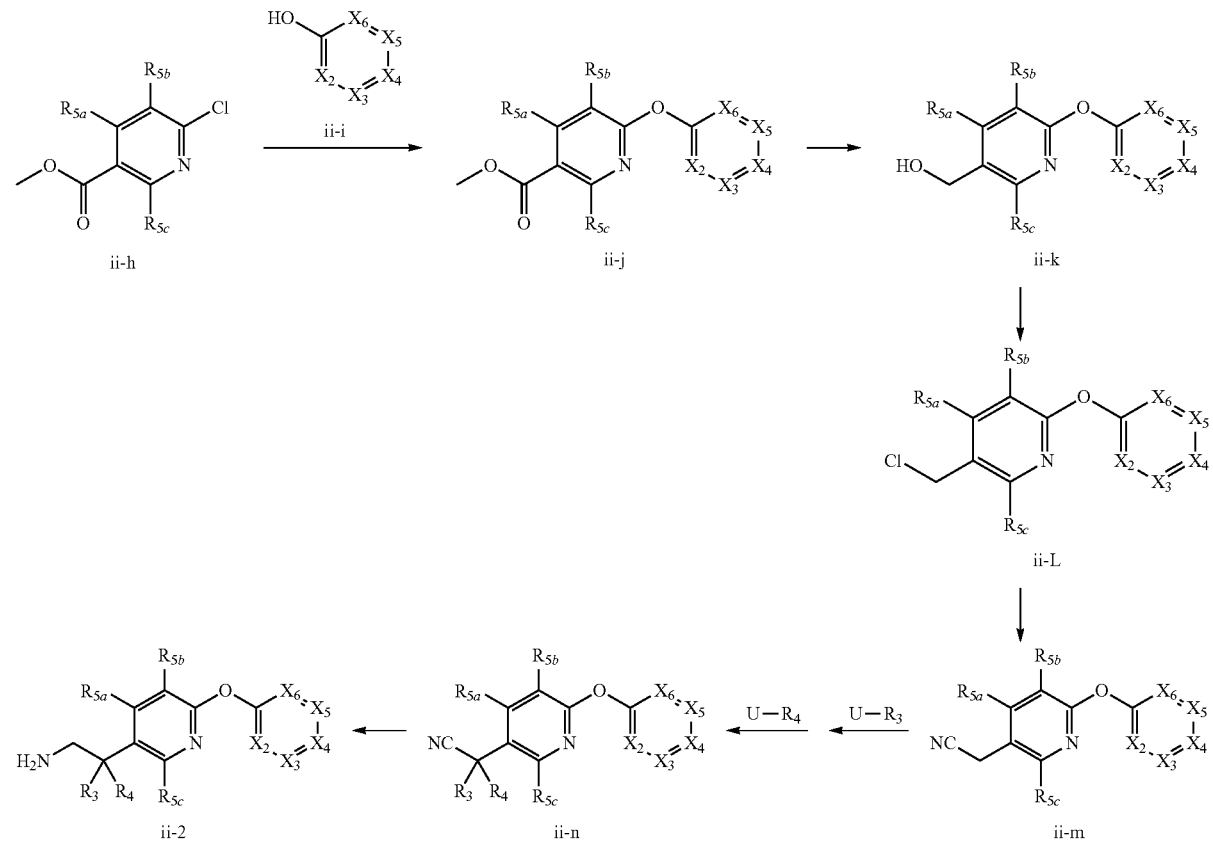

30 minutes to 20 hours, generally being 0.5-10 hours. The proper solvent mentioned may be selected from ethyl acetate, methyl acetate, methyl formate, benzene, toluene, xylene, chloroform, dichloromethane, water, tetrahydrofuran, acetonitrile, 1,4-dioxane, DMF, N-methyl pyrrolidone or DMSO and so on, the proper acid mentioned may be selected from hydrochloric acid, trifluoroacetic acid, sulfuric acid, acetic acid, propionic acid, butyric acid, oxalic acid, adipic acid, dodecanedioic acid, lauric acid, stearic acid, fumaric acid, maleic acid, benzoic acid or phthalic acid, etc. the proper base mentioned may be selected from alkali metal hydride such as sodium hydride; alkali metal hydroxides such as sodium hydroxide or potassium hydroxide; alkali carbonate, such as sodium carbonate or potassium carbonate; organic amine, such as pyridine or triethylamine. The Wherein, U is a leaving group, selected from halogen or hydroxy, etc.

The intermediates represented by general formula ii-j can be prepared by reaction of intermediates represented by general formula ii-h and ii-i in proper solvent and temperature in the presence of proper base. The reaction time is in the range of 30 minutes to 20 hours, generally being 0.5-10 hours. The intermediates represented by general formula ii-k can be prepared by reduction reaction of intermediates represented by general formula ii-j and Red-Al, the detailed operation refers to the methods described in EP1840128. The intermediates represented by general formula ii-L can be prepared by reaction of intermediates represented by general formula ii-k and sulfoxide chloride according to known methods. The intermediates represented by general formula ii-m can be prepared by reaction of intermediates represented by general formula ii-L and sodium cyanide according to the methods described in WO2007045989 and WO2009115257. According to the methods described in Journal of Organic Chemistry, 71(21), 8023-8027; 2006, Synthesis, (24), 4242-4250, 2010, Heterocycles, 56(1-2), 443-455, 2002 or ARKIVOC (Gainesville, Fla., United States) [online computer file], (10), 40-51, 2002, The intermediates represented by general formula ii-n can be prepared via intermediate ii-m. Finally, the intermediates represented by general formula ii-2 can be prepared by reaction of intermediates represented by general formula ii-n and ammonia water in the presence of proper catalyst by using hydrogenation reduction. The detailed operation refers to the methods described in J. Am. Chem. Soc, 70, 3788(1948); 82, 681(1960); 82, 2386(1960); Can. J. Chem, 49, 2990(1971); J. Org. Chem, 37, 335(1972); Organic Syntheses, Coll. Vol. 3, p. 229, p. 720 (1955), Vol. 23, p. 71 (1943) or Vol. 27, p. 18 (1947). The proper catalysts mentioned may be selected from Raney-nickel, palladium carbon or platinum oxide, etc.

The sources of intermediates are as follows: the intermediate represented by general formula ii-h and ii-I are commercially available, or can be prepared according to the conventional method.

The proper base mentioned may be selected from potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide and so on.

The reaction was carried out in proper solvent and the proper solvent mentioned may be selected from tetrahydrofuran, 1,4-dioxane, acetonitrile, toluene, xylene, benzene, DMF, N-methyl pyrrolidone, DMSO, acetone or butanone and so on.

The proper temperature mentioned is from room temperature to boiling point of the solvent, normal temperature is from 20 to 100° C.

The reaction time is in the range of 30 minutes to 20 hours, generally being 1-10 hours.

(2) When B=—CH$_2$CH$_2$—, the preparation method is as follows:

The compounds represented by general formula ii-o can be prepared by reaction of the compounds represented by general formula ii-n according to the methods described in Synthesis, (9), 727-9; 1983 or Tetrahedron Letters, 39(51), 9455-9456; 1998; the compounds having general formula ii-3 can be prepared by reaction of the compounds having general formula ii-o according to the methods in which B=—CH$_2$—.

The second method to prepare the compounds represented by general formula PY: when A=NR$_{12}$ (R$_{12}$≠H), the compounds represented by general formula PY-2 can be prepared by reaction of the compounds represented by general formula PY-1 with U-R1 according to the conventional method (U defined as above); or can be prepared according to the methods described in JP08269021, JP3543411, JP1995-72621, JP1995-96669, JP3511729, JP08291149, EP530149, WO9208704 and WO2004093800A.

The third method to prepare the compounds represented by general formula PY: when A=O or S, the compounds represented by general formula PY-3, PY-4 can be prepared according to the methods described in WO2012075917 and EP534341.

The structural formula of the compounds represented by general formula PY-2, PY-3 and PY-4 are shown as follows

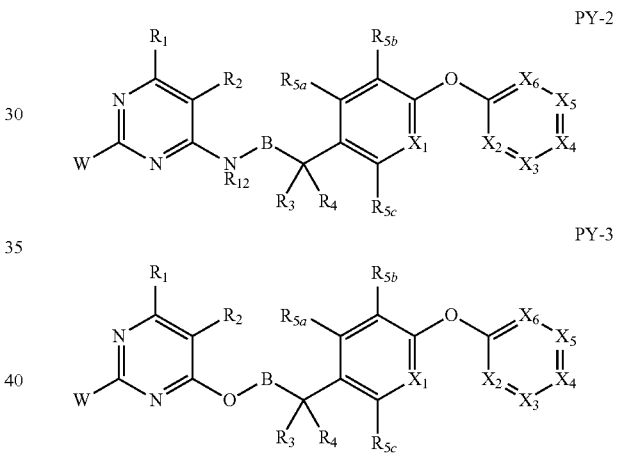

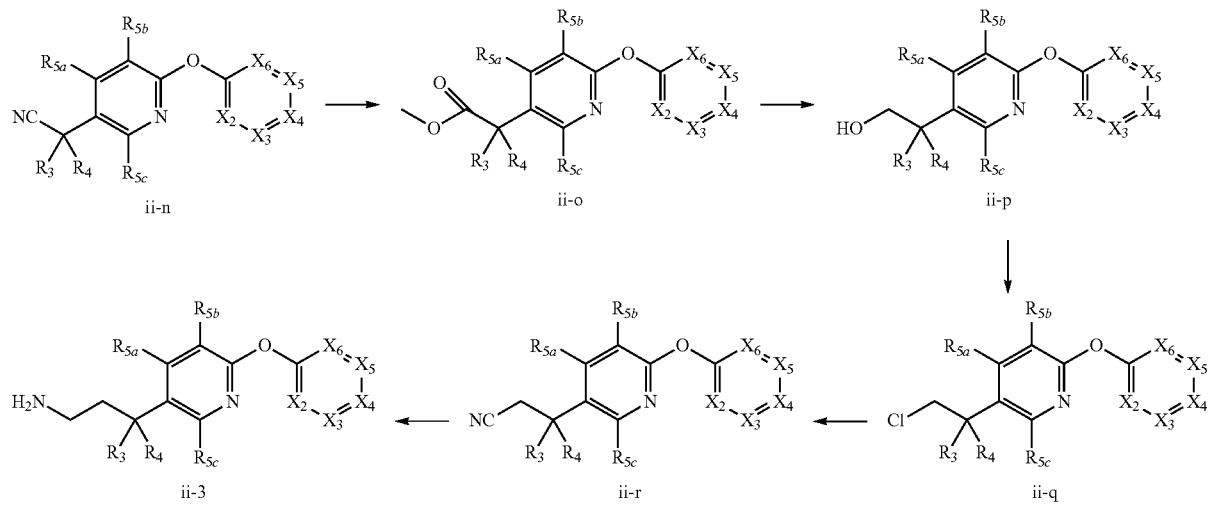

-continued

PY-4

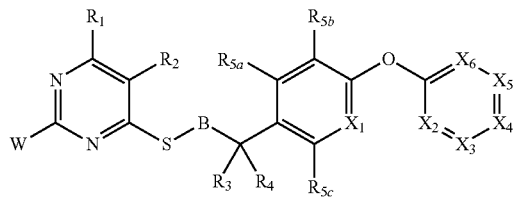

In general formula PY, the corresponding salts represented by general formula PY-5A can be prepared by reaction of the compounds represented by general formula PY-5 (when A=NR$_{12}$) with corresponding organic acids or inorganic acids, as shown in the following.

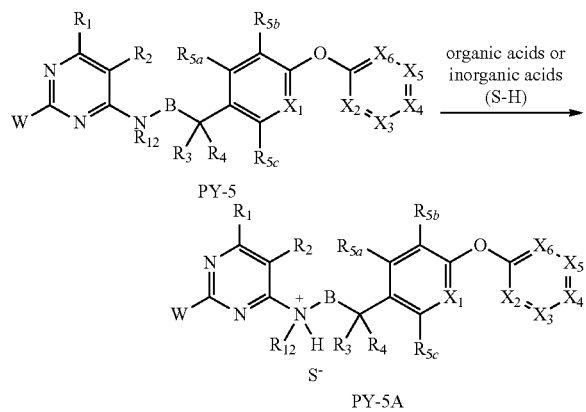

In addition, in general formula PY, the salts can also formed based on nitrogen atom of pyrimidine ring, the preparation method refers to DE19647317, JP2001504473, U.S. Pat. No. 5,925,644, WO9822446 and ZA9710187, etc.

The reaction forming salts of compounds represented by general formula PY-5 with organic acids or inorganic acids can be carried out at room temperature to boiling point of the solvent, normal temperature is from 20 to 100° C. The reaction time is in the range of 30 minutes to 20 hours, generally being 1-10 hours. The proper solvent mentioned may be selected from water, methanol, ethanol, isopropanol, benzene, toluene, xylene, acetone, ethyl methyl ketone, methyl isobutyl ketone, chloroform, dichloromethane, methyl acetate, ethyl acetate, tetrahydrofuran, 1,4-dioxane, DMF, N-methyl pyrrolidone or DMSO and so on.

The acids, which can be used to form salts with compounds represented by general formula PY-5, includes carboxylic acid, such as formic acid, acetic acid, propanoic acid, butyric acid, oxalic acid, trifluoroacetic acid, adipic acid, dodecanedioic acid, lauric acid, stearic acid, fumaric acid, maleic acid, sorbic acid, malic acid, citric acid, benzoic acid, p-toluylic acid or phthalic acid, etc. sulfonic acid, such as methanesulfonic acid, 1, 3-propylene sulfonic acid, p-toluenesulfonic acid or dodecylbenzene sulfonic acid, etc. inorganic acid, such as hydrochloric acid, sulphuric acid, nitric acid, phosphorous acid or carbonic acid, etc. The further preferred acids are hydrochloric acid, sulphuric acid, nitric acid, phosphorous acid, acetic acid, trifluoroacetic acid, oxalic acid, methanesulfonic acid, p-toluenesulfonic acid or benzoic acid.

Although the compounds represented by general formula PY and some compounds reported in prior art are both belong to substituted pyrimidine compounds, there are still some obvious differences in structure between them. It is due to these differences in structure that lead to compounds of present invention with better fungicidal and/or insecticidal/acaricidal activities.

The compounds represented by general formula PY show excellent activity against both many plant pathogens/diseases in agricultural and other fields, and insects/mites. Therefore the technical scheme of the present invention also includes the uses of the compounds represented by general formula PY or their salts/complexes to prepare fungicides, insecticides/acaricides in agricultural, forestry or public health fields. The further preferred technical scheme of the present invention also includes the uses of the compounds represented by general formula I, II or III or their salts/complexes to prepare fungicides, insecticides/acaricides in agricultural, forestry or public health fields.

The present invention is explained by the following examples of plant disease and insect pests, but without being restricted thereby.

The compounds represented by general formula PY can be used to control these plant diseases: Oomycete diseases, such as downy mildew (cucumber downy mildew, rape downy mildew, soybean downy mildew, downy mildew of beet, downy mildew of sugarcane, tobacco downy mildew, pea downy mildew, vegetable sponge downy mildew, chinese wax gourd downy mildew, muskmelon downy mildew, chinese cabbage downy mildew, spinach downy mildew, radish downy mildew, grape downy mildew, onion downy mildew), white rust (rape white rust, chinese cabbage white rust), damping-off disease (rape damping-off, tobacco damping-off, tomato damping-off, pepper damping-off, eggplant damping-off, cucumber damping-off, cotton damping-off), *pythium* rot (pepper soft stale disease, vegetable sponge cottony leak, chinese wax gourd cottony leak), blight (broad bean *phytophthora* blight, cucumber *phytophthora* blight, pumpkin *phytophthora* rot, chinese wax gourd *phytophthora* blight, watermelon *phytophthora* blight, muskmelon *phytophthora* blight, pepper *phytophthora* blight, chinese chives *phytophthora* blight, carlic *phytophthora* blight, cotton *phytophthora* blight), late blight (potato late blight, tomato late blight) and so on; diseases caused by Deuteromycotina, such as wilt disease (sweet potato *fusarium* wilt, cotton *fusarium* wilt disease, sesame wilt disease, *fusarium* wilt disease of costarbean, tomato *fusarium* wilt, bean *fusarium* wilt, cucumber *fusarium* wilt, vegetable sponge *fusarium* wilt, pumpkin *fusarium* wilt, chinese wax gourd *fusarium* wilt, watermelon *fusarium* wilt, muskmelon *fusarium* wilt, pepper *fusarium* wilt, broad bean *fusarium* wilt, *fusarium* wilt disease of rape, *fusarium* wilt disease of soybean), root rot (pepper root rot, eggplant root rot, bean *fusarium* root-rot, cucumber *fusarium* root rot, balsam pear *fusarium* root rot, cotton black root rot, broad bean *thielaviopsis* root rot), drooping disease (cotton soreshin, sesame soreshin, pepper *rhizoctonia* rot, cucumber *rhizoctonia* rot, chinese cabbage *rhizoctonia* rot), anthracnose (sorghum anthracnose, cotton anthracnose, kenaf anthracnose, jute anthracnose, flax anthracnose, tobacco anthracnose, mulberry anthracnose, pepper anthracnose, eggplant anthracnose, bean anthracnose, cucumber anthracnose, balsam pear anthracnose, summer squash anthracnose, chinese wax gourd anthracnose, watermelon anthracnose, muskmelon anthracnose, litchi anthracnose), *verticillium* wilt (cotton *verticillium* wilt, *verticillium* wilt of sunflower, tomato *verticillium* wilt, pepper *verticillium* wilt, eggplant *verticillium* wilt), scab (summer squash scab, chinese wax gourd scab, muskmelon scab), gray mold (cotton boll gray mold, kenaf gray mold, tomato gray mold, pepper gray mold, bean gray mold, celery gray mold, spinach gray mold, kiwi fruit gray mold rot), brown spot (cotton brown spot, jute brown spot, beet sercospora leaf spot, peanut brown spot, pepper brown leaf spot, chinese wax gourd *corynespora* leaf spot, soybean brown spot, sunflower brown spot, pea *ascochyta* blight, broad bean brown spot), black spot (flax black spot, rape *alternaria* leaf spot, sesame black spot, sunflower *alternaria* leaf spot, costarbean *alternaria* leaf spot, tomato nail head spot, pepper black fruit spot, eggplant black spot, bean leaf spot, cucumber *alternaria* blight, celery *alternaria* black leaf spot, carrot *alternaria* black rot, carrot leaf blight, apple *alternaria* rot, peanut brown spot), spot blight (tomato *septoria* leaf spot, pepper *septoria* leaf spot, celery late blight), early blight (tomato early blight, pepper early blight, eggplant early blight, potato early blight, celery early blight), ring spot (soybean zonate spot, sesame ring spot, bean zonate spot), leaf blight (sesame leaf blight, sunflower leaf blight, watermelon *alternaria* blight, muskmelon *alternaria* spot), basal stem rot (tomato basal stem rot, bean *rhizoctonia* rot), and others (corn northern leaf spot, kenaf damping-off, rice blast, millet black sheath, sugarcane eye spot, cotton *aspergillus* boll rot, peanut crown rot, soybean stem blight, soybean black spot, muskmelon *alternaria* leaf blight, peanut web blotch, tea red leaf spot, pepper *phyllosticta* blight, chinese wax gourd *phyllosticta* leaf spot, celery black rot, spinach heart rot, kenaf leaf mold, kenaf brown leaf spot, Jute stem blight, soybean *cercospora* spot, sesame leaf spot, costarbean gray leaf spot, tea brown leaf spot, eggplant *cercospora* leaf spot, bean *cercospora* leaf spot, balsam pear *cercospora* leaf spot, watermelon *cercospora* leaf spot, jute dry rot, sunflower root and stem rot, bean charcoal rot, soybean target spot, eggplant *corynespora* leaf spot, cucumber *corynespora* target leaf spot, tomato leaf mold, eggplant *fulvia* leaf mold, broad bean chocolate spot) and so on; diseases caused by Basidiomycete, such as rust (wheat stripe rust, wheat stem rust, wheat leaf rust, peanut rust, sunflower rust, sugarcane rust, chinese chives rust, onion rust, millet rust, soybean rust), smut (corn head smut, corn smut, sorghum silk smut, sorghum loose kernel smut, sorghum hard smut, sorghum smut, millet kernel smut, sugarcane smut, bean rust), and others (for example, wheat sheath blight and rice sheath blight) and so on; diseases caused by Ascomycete, such as powdery mildew (wheat powdery mildew, rape powdery mildew, powdery mildew of sesame, powdery mildew of sunflower, beet powdery mildew, eggplant powdery mildew, pea powdery mildew, vegetable sponge powdery mildew, pumpkin powdery mildew, summer squash powdery mildew, chinese wax gourd, muskmelon powdery mildew, grape powdery mildew, broad bean powdery mildew), *sclerotinia* rot (flax sclertiniose, rape sclertiniose, soybean sclertiniose, peanut sclertiniose, tobacco *sclerotinia* rot, pepper *sclerotinia* rot, eggplant *sclerotinia* rot, bean *sclerotinia* rot, pea *sclerotinia* rot, cucumber *sclerotinia* rot, balsam pear *sclerotinia* rot, chinese wax gourd *sclerotinia* rot, watermelon *sclerotinia* disease, celery stem rot), scab (apple scab, pear scab) and so on. Especially, the compounds of the present invention exhibit very good control against corn southern rust, rice blast, cucumber gray mold and cucumber downy mildew at very low doses.

The compounds represented by general formula PY can be used to control these insect pests: Coleoptera, such as *Acanthoscelides* spp., *Acanthoscelides obtectus*, *Agrilus planipennis*, *Agriotes* spp., *Anoplophora glabripennis*, *Anthonomus* spp., *Anthonomus grandis*, *Aphidius* spp., *Apion* spp., *Apogonia* spp., *Atacnius sprctulus*, *Atomaria linearis*, pygmy mangold beetle, *Aulacophore* spp., *Bothynoderes punctiventris*, *Bruchus* spp., *Bruchus pisorum*, *Cacoesia*, *Cacoesia* spp., *Callosobruchus maculatus*, *Carpophilus hemipteras*, *Cassida vittata*, *Cerosterna* spp., *Ccrotoma*, *Ccrotoma* spp., *Cerotoma trifur cata*, *Ceutorhynchus* spp., *Ceutorhynchus assimilis*, cabbage seedpod weevil, *Ceutorhynchus napi*, cabbage curculio, *Chaetocnema* spp., *Colaspis* spp., *Conoderus scalaris*, *Conoderus stigmosus*, *Conotrachelus nenuphar*, *Cotinus nitidis*, Green June beetle, *Crioceris asparagi*, *Cryptolestes ferrugincus*, rusty grainbeetle, *Cryptolestes pusillus*, *Cryptolestes turcicus* Turkish grain beetle, *Ctenicera* spp., *Curculio* spp., *Cyclocephala* spp., *Cylindrocpturus adspersus*, sunflower stem weevil, *Deporaus marginatus*, mango leaf-cutting weevil, *Dermestes lardarius*, *Dermestes maculates*, *Diabrotica* spp., *Epilachna varivcstis*, *raustinus cubae*, *Hylobius pales*, pales weevil, *Hypera* spp., *Hypera postica*, *Hyperdoes* spp., *Hyperodes* weevil, *Hypothenemus hampei*, *Ips* spp., engravers, *Lasioderma serricorne*, *Leptinotarsa decemlineata*, *Liogenys fuscus*, *Liogenys suturalis*, *Lissorhoptrus oryzophilus*, *Lyctus* spp., powder post beetles, *Maecolaspis joliveti*, *Megascelis* spp., *Melanotus communis*, *Meligethes* spp., *Meligethes aeneus*, blossom beetle, *Melolontha melolontha*, *Oberea brevis*, *Oberea linearis*, *Oryctes rhinoceros*, date palm beetle, *Oryzaephilus mercator*, merchant grain beetle, *Oryzaephilus surinamensis*, sawtoothed grain beetle, *Otiorhynchus* spp., *Oulema melanopus*, cereal leafbeetle, *Oulema oryzae*, *Pantomorus* spp., *Phyllophaga* spp., *Phyllophaga cuyabana*, *Phyllotreta* spp., *Phynchites* spp., *Popillia japonica*, *Prostephanus truncates*, larger grain borer, *Rhizopertha dominica*, lesser grain borer, *Rhizotrogus* spp., *Euroopean chafer*, *Rhynchophorus* spp., *Scolytus* spp., *Shenophorus* spp. *Sitona lincatus*, pca leaf weevil, *Sitophilus* spp., *Sitophilus granaries*, granary weevil, *Sitophilus oryzae*, rice weevil, *Stegobium paniceum*, drugstore beetle, *Tribolium* spp., *Tribolium castaneum*, red flour beetle, *Tribolium confusum*, confused flour beetle, *Trogoderma variabile*, warehouse beetle and *Zabrus tenebioides*.

Dermaptera.

Dictyoptera, such as *Blattella germanica*, German cockroach, *Blatta orientalis*, *Parcoblatta pennylvanica*, *Periplaneta americana*, American cockroach, *Periplaneta australoasiae*, Australian cockroach, *Periplancta brunnca*, brown cockroach, *Periplaneta fuliginosa*, smokybrown cockroach, *Pyncoselus suninamensis*, Surinam cockroach and *Supella longipalpa*, brownbanded cockroach.

Diptera, such as *Aedes* spp., *Agromyza frontella*, alfalfa blotch leafminer, *Agromyza* spp., *Anastrepha* spp., *Anastrepha suspensa*, Caribbean fruit fly, *Anopheles* spp., *Batrocera* spp., *Bactrocera cucurbitae*, *Bactrocera dorsalis*, *Ceratitis* spp., *Ceratitis capitata*, *Chrysops* spp., *Cochliomyia* spp., *Contarinia* spp., *Culex* spp., *Dasineura* spp., *Dasineura brassicae*, *Delia* spp., *Delia platura*, seedcom maggot, *Drosophila* spp., *Fannia* spp., *Fannia canicularis*, little house fly, *Fannia scalaris*, *Gasterophilus intestinalis*, *Gracillia perseae*, *Haematobia irritans*, *Hylemyia* spp., root maggot, *Hypoderma lineatum*, common cattle grub, *Liriomyza* spp., *Liriomyza brassica*, serpentine leafminer, *Melophagus ovinus*, *Musca* spp., muscid fly, *Musca autumnalis*, face fly, *Vusca domestica*, house fly, *Oestrus ovis*, sheep bot fly, *Oscinella frit*, *Pegomyia betae*, beet leafminer, *Phorbia* spp., *Psila rosae*, carrotrust fly, *Rhagoletis cerasi*, cherry fruit fly, *Rhagoletis pomonella*, apple maggot, *Sitodiplosis mosellana*, orange wheat blossom midge, *stomoxys* calcitruns, stable fly, *Tahanus* spp. and *Tipula* spp.

Hemiptera, such as *Acrosternum hilare*, green stink bug, *Blissus leucopterus*, chinch bug, *Calocoris norvegicus*, potato mirid, *Cimex hemipterus*, tropical bed bug, *Cimex lectularius*, bed hug, *Daghertus fasciatus*, *Dichelops furcatus*, *Dysdercus suturellus*, cotton stainer, *Edessa meditabunda*, *Eurygaster maura*, cereal bug, *Euschistus heros*, *Euschistus servus*, brown stink bug, *Helopeltis antonii*, *Helopeltis theivora*, tea blight plantbug, *Lagynotomus* spp., *Leptocorisa oratorius*, *Leptocorisa varicomi*, *Lygus* spp., plant bug, *Lygus hesperus*, western tarnished plant bug, *Maconellicoccus hirsutus*, *Neurocolpus longirostris*, *Nezara viridula*, southern green stink bug, *PhyLocoris* spp., *Phytocoris californicus*, *Phytocoris relativus*, *Piezodorus guildingi*, *Poecilocapsus lineatus*, fourlined plant bug, *Psallus vaccinicola*, *Pseudacysta perseae*, *Scaptocoris castanea* and *Triatoma* spp., bloodsuckingconenose bug, kissing bug.

Homoptera, such as *Acrythosiphonpisum*, pea aphid, *Adelges* spp., adelgids, *Aleurodes proletella*, *Aleurodicus disperses*, *Aleurothrixus flccosus*, woolly whitefly, *Aluacaspis* spp., *Amrasca bigutella bigutella*, *Aphrophora* spp., leafhopper, *Aonidiella aurantii*, California red scale, *Aphis* spp., *Aphis gossypii*, cotton aphid, *Aphis pomi*, apple aphid, *Aulacorthitm solan*, foxglove aphid, *Bemisia* spp., *Bemisia argentifolii*, *Bemisia tabaci*, sweetpotato whitefly, *Brachycolus noxius*, Russian aphid, *Brachycorynclia asparagi*, asparagus aphid, *Brevennia rehi*, *Brevicoryne brassicae*, *Ceroplastes* spp., *Ceroplastes rubens*, red wax scale, *Chionaspis* spp., *Chrysomphalus* spp., *Coccus* spp., *Dysaphis plantaginea*, rosy apple aphid, *Empoasca* spp., *Eriosoma lanigerum*, woolly apple aphid, *Icerya purchasi*, cottony cushion scale, *Idioscopus nitidulus*, mango leafhopper, *Laodelphax striatellus*, smaller brown planthopper, *Lepidosaphes* spp., *Macrosiphum* spp., *Macrosiphum euphorbiae*, potato aphid, *Macrosiphum granarium*, English grain aphid, *Macrosiphum rosae*, rose aphid, *Macrosteles quadrilineatus*, aster leafhopper, *Mahanarva frimbiolata*, *Metopolophium dirhodum*, rose grain aphid, *Midis longicornis*, *Myzus persicae*, green peach aphid, *Nephotettix* spp., *Nephotettix cinctipes*, green leafhopper, *Nilaparvata lugens*, brown planthopper, *Parlatoria pergandii*, chaff scale, *Parlatoria ziziphi*, ebony scale, *Peregrinus maidis*, corn delphacid, *Philaenus* spp., *Phylloxera vitifoliae*, grape phylloxera, *Physokermes piceae*, spruce bud scale, *Planococcus* spp., *Pseudococcus* spp., *Pseudococcus brevipes*, pine apple mealybug, *Quadraspidiotus perniciosus*, San Jose scale, *Rhapalosiphum* spp., *Rhapalosiphum maida*, corn leaf aphid, *Rhapalosiphum padi*, oatbird-cherry aphid, *Saissetia* spp., *Saissetia oleae*, *Schizaphis graminum*, greenbug, *Sitobion avenge*, *Sogatella furcifera*, white-backed planthopper, *Therioaphis* spp., *Toumeyella* spp., *Toxoptera* spp., *Trialeurodes* spp., *Trialeurodes vaporariorum*, greenhouse whitefly, *Trialeurodes abutiloneus*, bandedwing whitefly, *Unaspis* spp., *Unaspis yanonensis*, arrowhead scale and *Zulia entreriana*.

Hymenoptera, such as *Acromyrrmex* spp., *Athalia rosae*, *Atta* spp., leafcutting ants, *Camponotus* spp., carpenter ant, *Diprion* spp., sawfly, *Formica* spp., *Iridomyrmex humilis*, Argentineant, *Monomorium* ssp., *Monomorium minumum*, little black ant, *Monomorium pharaonis*, haraoh ant, *Neodiprion* spp., *Pogonomyrmex* spp., *Polistes* spp., paper wasp, *Solenopsis* spp., *Tapoinoma sessile*, odorous house ant, *Tetranomorium* spp., pavement ant, *Vespula* spp., yellow jacket and *Xylocopa* spp., carpenter bee.

Isoptera, such as *Coptotermes* spp., *Coptotermes* curvignathus, *Coptotermes* frenchii, *Coptotermes formosanus*, Formosan subterranean termite, *Cornitermes* spp., nasute termite, *Cryptotermes* spp., *Heterotermes* spp., desert subterranean termite, *Ileterotermes aureus*, *Kalotermes* spp., *Incistitermes* spp., *Macrotermes* spp., fungus growing termite, *Marginitermes* spp., *Microcerotermes* spp., harvester termite, *Microtermes obesi*, *Procornitermes* spp., *Reticulitermes* spp., *Reticulitermes banyulensis*, *Reticulitermes grassei*, *Reticulitermes flavipes*, *Reticulitermes hageni*, *Reticulitermes hesperus*, *Reticulitermes santonensis*, *Reticulitermes speratus*, *Reticulitermes tibialis*, *Reticulitermes virginicus*, *Schedorhinotermes* spp. and *Zootermopsis* spp.

Lepidoptera, such as *Achoea janata*, *Adoxophyes* spp., *Adoxophyes orana*, *Agrotis* spp., *Agrotis ipsilon*, *Alabama argillacea*, cotton leafworm, *Amorbia cuneana*, *Amyelosis transitella*, navel orangeworm, *Anacamptodes defectaria*, *Anarsia lineatella*, peach twig borer, *Anomis sabulijera*, jute looper, *Anticarsia gemmatalis*, velvetbean caterpillar, *Archips argyrospila*)(fruit tree leafroller, *Archips rosana*, rose leaf roller, *Ar gyrotaenia* spp., tortricid moths, *Argyrotaenia citrana*, orange tortrix, *Autographa gamma*, *Bonagota cranaodcs*, *Borbo cinnara*, rice leaf folder, *Bucculatrix thurberiella*, cotton leafperforator, *Caloptilia* spp., *Capua reticulana*, *Carposina niponensis*, peach fruit moth, *Chilo* spp., *Chlumetia transversa*, mango shoot borer, *Choristoneura rosaceana*, oblique banded leaf roller, *Chrysodeixis* spp., *Cnaphalocerus medinalis*, grass leafroller, *Colias* spp., *Conpomorpha cramerella*, *Cossus cossus*, *Crambus* spp., Sod webworms, *Cydia funebrana*, plum fruit moth, *Cydia molesta*, oriental fruit moth, *Cydia nignicana*, pea moth, *Cydia pomonella*, codling moth, *Darna diducta*, *Diaphania* spp., stem borer, *Diatr aea* spp., stalk bor er, *Diatraea saccharalis*, sugarcane borer, *Diatraea graniosella*, southwester corn borer, *Earias* spp., *Earias insulata*, Egyptian bollworm, *Earias vit.ella*, rough northern bollworm, *Ecdytopopha aurantianum*, *Elasmopalpus lignosellus*, lesser cornstalk borer, *Epiphysias postruttana*, light brown, apple moth, *Ephestia* spp., *Ephestia cautella*, almond moth, *Ephestia elutella*, tobbaco moth, *Ephestia kuehniella*, Mediterranean flour moth, *Epimeces* spp, *Epinotia aporema*, *Erionota thrax*, banana skipper, *Eupoecilia ambiguella*, grape berry moth, *Euxoa auxiliaris*, army cutworm, *Feltia* spp., *Gortyna* spp., *Grapholita molesta*, oriental fruit moth, *Hedylepta indicata*, bean leaf webber, *Helicoverpa* spp., *Helicoverpa armigera*, cotton bollworm, *Helicoverpa zea*, *Heliothis* spp., *Heliothis virescens*, tobacco budworm, *Hellula undalis*, cabbage webworm, *Indarbela* spp. *Keiferia lycopersicella*, tomato pinworm, *Leucinodes orbonalis*, eggplant fruit borer, *Leucoptera malifoliella*, *Lithocollectis* spp., *Lobesia botrana*, grape fruit moth, *Loxagrotis* spp., *Loxagrotis albicosta*, western bean cutworm, *Lymantria dispar*, gypsy moth, *Lyonetiaclerkella*, apple leafminer, *Mahasena corbetti*, oil palm bagworm, *Malacosoma* spp., tent caterpillars, *Mamestra brassicae*, cabbage armyworm, *Maruca testulalis*, *Metisa plana*, *Mythimna unipuncta*, true armyworm, *Neoleucinodes elegantalis*, small tomato borer, *Nymphula depunctalis*, rice caseworm, *Operophthera brumata*, winter moth, *Ostrinia nubilalis*, European corn borer, *Oxydia vesulia*, *Pandemis cerasana*, common currant tortrix, *Pandemis heparana*, brown apple tortrix, *Papilio demodocus*, *Pectinophora gossypiella*, pink bollworm, *Peridroma* spp., *Peridroma saucia*, variegated cutworm, *Perileucoptera coffeella*, white coffee leafminer, *Phthorimaea operculella*, potato tuber moth, *Phyllocnisitis citrella*, *Phyllonorycter* spp., *Pieris rapae*, imported cabbageworm, *Plathypena scabra*, *Plodia interpunctella*, Indian meal moth, *Plutella xylostella*, diamondback moth, *Polychrosis viteana*, grape berry moth, *Prays endocarps*, *Prsys oleae*, olive moth, *Pseudaletia* spp., *Pseudaletia unipunctata*, *Pseudoplusia includens*, soybean looper, *Rachiplusia nu*, *Scirpophaga incertulas*, *Sesamia* spp., *Sesamia inferens*, pink rice stemborer, *Sesamia nonagrioides*, *Setora*

*nitens, Sitotroga cerealella, Angoumois* grain moth, *Sparganothis pilleriana, Spodoptera* spp., *Spodoptera exigua,* beet armyworm, *Spodoptera fugiperda,* fall armyworm, *Spodoptera oridania,* southern armyworm, *Synanthedon* spp., *Thecla basilides, Thermisia gemmatalis, Tineola bisselliella,* webbing clothes moth, *Trichoplusia ni,* cabbage looper, *Tuts absoluta, Yponomeuta* spp., *Zeuzeracoffeae,* red branch borer and *Zeuzera pyrina,* eopard moth.

Mallophaga, chewing lice, such as *Bovicola ovis,* sheep biting louse, *Menacanthus stramineus,* chicken body louse and *Menopon gallinea,* common hen house, Orthoptera, such as *Anabrus simplex,* Mormon cricket, Gryllotalpidae, mole cricket, *Locusta migratoria, Melanoplus* spp., *Microcentrum retinerve,* angular winged katydid, *Pterophylla* spp., *histocerca gregaria, Scudderia furcata,* fork tailed bush katydid and *Valanga nigricorni,* sucking louse, such as *Haematopinus* spp., *Linognathus ovillus,* sheep louse, *Pediculus humanus capitis, Pediculus humanus humanus* and *Pthirus pubis,* crab louse.

Siphonaptera, such as *Ctenocephal ides canis,* dog flea, *Ctenocephalides felis,* cat flea and *Pulex irritanshuman* flea.

Thysanoptera, such as *Frankliniella fusca,* tobacco thrip, *Frankliniella occidentalis,* western flower thrips, *Frankliniella shultzei, Frankliniella williamsi,* corn thrip, *Heliothrips haemorrhaidalis,* greenhouse thrip, *Riphiphorothrips cruentatus, Scirtothrips* spp, *Scirtothrips cirri,* citrus thrip, *Scirtothrips dorsalis,* yellow tea thrips, *Taeniothrips rhopalantennalis* and *Thrips* spp.

Thysanura, bristletail, such as *Lepisma* spp, silverfish and *Thermobia* spp.

Acarina, mite and tick, such as *Acarapsis woodi,* tracheal mite of honeybee, *Acarus* spp., *Acarus siro,* grain mite, *Aceria mangiferae,* mango bud mite, *Aculops* spp., *Aculops lycopersici,* tomato russet mite, *Aculops pelekasi, Aculus pelekassi, Aculus schlechtendali,* apple rust mite, *Amblyomma americanum,* lone star tick, *Boophilus* spp., *Brevipalpus obovatus,* privet mite, *Brevipalpus phoenicis,* red and black flat mite, *Demodex* spp., mange mites, *Dermacentor* spp., *Dermacentor variabilis,* american dog tick, *Dermatophagoides pteronyssinus,* house dust mite, *Eotetranycus* spp., *Eotetranychus carpini,* yellow spider mite, *Epitimerus* spp., *Eriophyes* spp., *L*̣ ; odes spp., *Metatetranycus* spp., *Notoedres cati, Oligonychus* spp., *Oligonychus* coffee, *Oligonychus ilicus,* southernred mite, *anonychus* spp., *Panonychus cirri,* citrus red mite, *Panonychus ulmi,* European red mite, *Phyllocoptruta oleivora,* citrus rust mite, *Polyphagotarsonemun latus,* broad mite, *Rhipicephalus sanguineus,* brown dog tick, *Rhizoglyphus* spp., bulb mite, *Sarcoptes scabiei,* itch mite, *Tegolophus perseaflorae, Tetranychus* spp., *Tetranychus urticae,* twospotted spider mite and *Varroa destructor.*

Nematoda, such as *Aphelenchoides* spp., bud and leaf & pine wood nematode, *Belonolaimus* spp., sting nematodes, *Criconemella* spp., ring nematodes, *Dirofilaria immitis,* dog heartworm, *Ditylenchus* spp., *Heterodera* spp., cyst nematode, *Heterodera zeae,* corn cyst nematode, *Hirschmanniella* spp., root nematodes, *Hoplolaimus* spp., lance nematodes, *Meloidogyne* spp., *Meloidogyne incognita, Onchocerca volvulus,* hook-tail worm, *PraLylenchus* spp., lesion nematode, *Radopholus* spp., burrowing nematode and *Rotylenchus reniformis,* kidney-shaped nematode.

Symphyla, such as *Scutigerella immaculata.*

Especially, the compound represented by the present invention provides great control effects against peach aphid, diamondback moth, armyworm, and carmine spider mite, and acquires great effects at a minimal dosage.

Due to their positive characteristics, the compounds mentioned above can be advantageously used in protecting crops of farming and gardening, domestic and breeding animals, as well as environments frequented by human beings, from pathogens, insects and pest mites.

In order to obtain desired effect, the dosage of the compound to be applied can vary with various factors, for example, the used compound, the protected crop, the type of harmful organism, the degree of infestation, the climatic conditions, the application method and the adopted formulation.

The dosage of compounds in the range of 10 g to 5 kg per hectare can provide a sufficient control.

A further object of the present invention also includes fungicidal, insecticidal/acaricidal compositions containing the compounds having general formula PY as active ingredient, and the weight percentage of the active ingredient in the composition is 0.1-99%. The fungicidal, insecticidal/acaricidal compositions also include the carrier being acceptable in agriculture, forestry, public health.

Especially, a preferred object of the present invention also includes fungicidal, insecticidal/acaricidal compositions containing the compounds and its salts/complexes having general formula I, II or III as active ingredient, wherein the weight percentage of the active ingredient in the composition is 0.1-99%.

The compositions of the present invention can be used in the form of various formulations. Usually, the compounds having general formula PY as active ingredient can be dissolved in or dispersed in carriers or made to a formulation so that they can be easily dispersed as an fungicide or insecticide. For example: these chemical formulations can be made into wettable powder, oil miscible flowable, aqueous suspension, aqueous emulsion, aqueous solution or emulsifiable concentrates. Therefore, in these compositions, at least a liquid or solid carrier is added, and usually suitable surfactant(s) can be added when needed.

Still also provided by the present invention are the application methods for controlling phytopathogenic fungi, insects, pest mites: which is to apply the compositions of the present invention to the phytopathogenic fungi, insects, pest mites as mentioned above or their growing loci. The suitable effective dosage of the compounds of the present invention is usually within a range of 10 g/ha to 1000 g/ha, preferably from 20 g/ha to 500 g/ha. For some applications, one or more other fungicides, insecticides/acaricides, herbicides, plant growth regulators or fertilizer can be added into the fungicidal, insecticidal/acaricidal compositions of the present invention to make additional merits and effects.

It should be noted that variations and changes are permitted within the claimed scopes in the present invention.

DETAILED DESCRIPTION OF THE INVENTION

The present invention is illustrated by the following examples, but without being restricted thereby. (All raw materials are commercially available unless otherwise specified.)

PREPARATION EXAMPLES

Example 1: The Preparation of Intermediate 4,5-dichloro-6-methylpyrimidine

1) The Preparation of 4-hydroxyl-5-chloro-6-methylpyrimidine

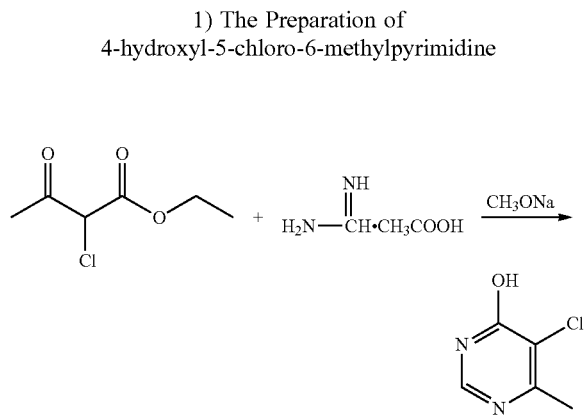

8.80 g (0.16 mol) of CH₃ONa in methanol was added slowly to a solution of 11.30 g (0.11 mol) of formimidamide in 50 mL of methanol at room temperature under stirring, the mixture was stirred for another 2 hrs after addition at room temperature. Followed by addition of 11.17 g (0.068 mol) of ethyl 2-chloro-3-oxobutanoate, the mixture was continued stirring for another 5-7 hrs at room temperature. After the reaction was over by Thin-Layer Chromatography monitoring, the reaction mixture was concentrated under reduced pressure and pH was adjusted to 5-6 with HCl, and then filtered to afford orange-yellow solid, the water phase was extracted with ethyl acetate (3×50 mL), dried over anhydrous magnesium sulfate, filtered and then concentrated under reduced pressure. The residue was dissolved to 50 ml of ethyl acetate, stand overnight to obtain 6.48 g as orange-yellow solid with yield of 66%. m.p. 181-184° C.

2) The Preparation of Intermediate 4,5-dichloro-6-methylpyrimidine

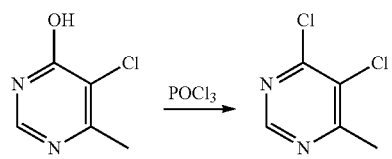

50 ml of POCl₃ was added dropwise to a solution of 14.5 g (0.1 mol) of 4-hydroxyl-5-chloro-6-methylpyrimidine in 50 mL of toluene, the mixture was refluxed for 5-7 hrs after addition. After the reaction was over by Thin-Layer Chromatography monitoring, the reaction mixture was concentrated under reduced pressure to remove toluene and extra POCl₃, and then poured into ice water. The water phase was extracted with ethyl acetate (3×50 mL), the organic phases were emerged, dried over anhydrous magnesium sulfate, filtered and then concentrated under reduced pressure. The residue was purified through silica column to give 14.43 g as yellow liquid with yield of 88.5%.

Example 2: The Preparation of Intermediate 4,5-dichloro-6-(difluoromethyl)pyrimidine 1) The Preparation of 2-dichloro-4,4-difluoro-3-oxobutanoate

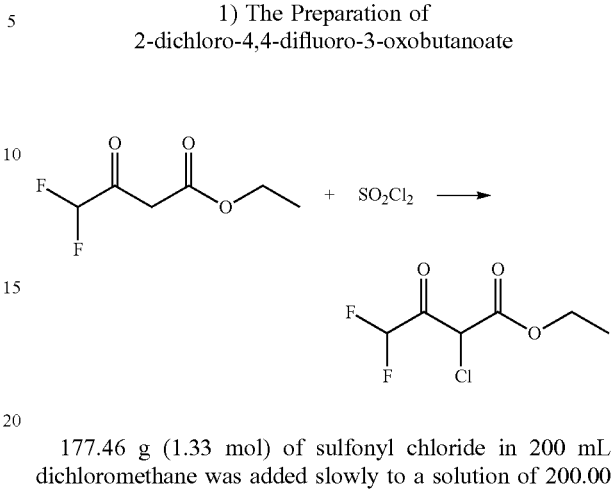

177.46 g (1.33 mol) of sulfonyl chloride in 200 mL dichloromethane was added slowly to a solution of 200.00 g (1.20 mol) of ethyl 4,4-difluoro-3-oxobutanoate in 300 mL of dichloromethane at room temperature under stirring for 3 hrs, then a lot of gas released out after addition, the mixture was continued stirring for another 5-7 hrs at room temperature. After the reaction was over by Thin-Layer Chromatography monitoring, the excess solvent and sulfonyl chloride were concentrated under reduced pressure to obtain 240 g as faint yellow liquid.

2) The Preparation of 4-hydroxyl-5-chloro-6-(difluoromethyl)pyrimidine

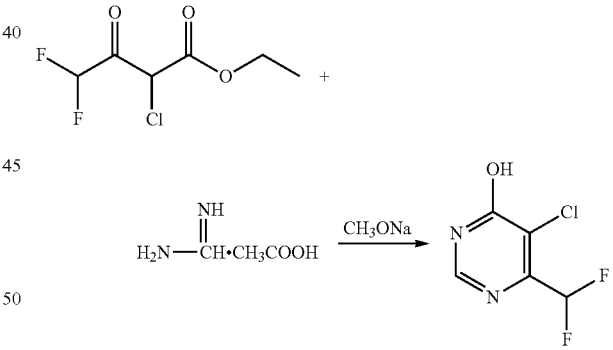

A solution of 71.9 g (0.70 mol) of formimidamide in 150 mL of methanol was stirred at 5-10° C., 64.6 g (1.20 mol) of CH₃ONa in methanol prepared and cooled to room temperature ahead of time was added slowly to the above solution under stirring, followed by addition of 100 g (0.50 mol) of ethyl 2-chloro-4,4-difluoro-3-oxobutanoate in 100 ml of methanol, the mixture was continued stirring for another 3-4 hrs at room temperature. After the reaction was over by Thin-Layer Chromatography monitoring, the reaction mixture was concentrated under reduced pressure and pH was adjusted to 5-6 with HCl, and then filtered to afford 65 g as white solid with yield of 73%. m.p. 204-206° C.

3) The Preparation of 4,5-dichloro-6-(difluoromethyl)pyrimidine

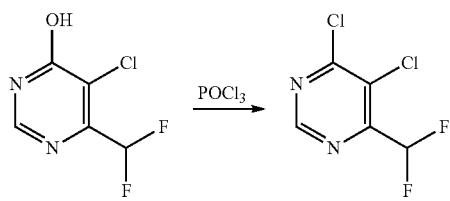

100 ml of POCl₃ was added dropwise to a solution of 65.0 g (0.36 mol) of 4-hydr oxyl-5-chloro-6-(difluoromethyl)pyrimidin in 150 mL of toluene, the mixture was refluxed for 3-5 hrs after addition. After the reaction was over by Thin-Layer Chromatography monitoring, the reaction mixture was concentrated under reduced pressure to remove toluene and extra POCl₃, and then poured into ice water. The water phase was extracted with ethyl acetate (3×50 mL), the organic phases were emerged, washed with saturated sodium bicarbonate, dried over anhydrous magnesium sulfate, filtered and then concentrated under reduced pressure. The residue was purified through silica column to give 64.5 g as yellow liquid, cooled to be solid in refrigerator with yield of 9 0%.

Example 3: The Preparation of 2-(4-(5-(trifluoromethyl)pyridin-2-yloxy)phenyl)ethanamine

1) The Preparation of 2-(4-(5-(trifluoromethyl)pyridin-2-yloxy)phenyl)acetonitrile

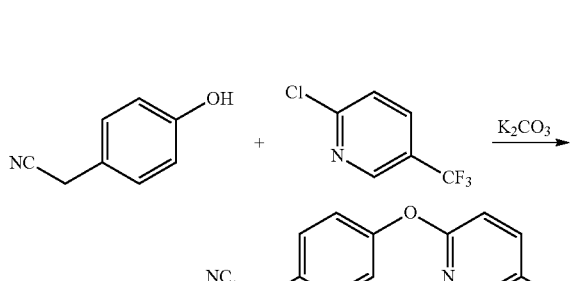

To a solution of 2-chloro-5-(trifluoromethyl)pyridine 18.15 g (0.1 mol) and 2-(4-hydroxyphenyl)acetonitrile 15.96 g (0.12 mol) in 200 mL butanone was added potassium carbonate 27.60 g (0.2 mol). The reaction mixture was continued stirring and heating to reflux for 4-10 hrs, and monitored by TLC (Thin-Layer Chromatography) until the reaction was over, the excessive solvent was evaporated under reduced pressure. Then the mixture was poured into 200 mL of ethyl acetate to separate the organic layer, the organic phase was washed with 50 mL of 5% aqueous solution of NaOH, and 50 mL of brine successively, dried and evaporated under reduced pressure, the residual was purified via silica column (ethyl acetate/petroleum ether (boiling point range 60-90° C.)=1:5, as an eluent) to obtain 22.50 g target intermediate as white solid with yield of 81.5%, m.p. 48-49 □.

2) The Preparation of 2-(4-(5-(trifluoromethyl)pyridin-2-yloxy)phenyl)ethanamine

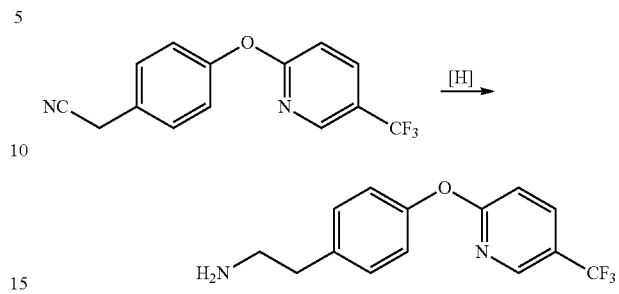

To a solution of 2-(4-(5-(trifluoromethyl)pyridin-2-yloxy)phenyl)acetonitrile 2.78 g (0.01 mol), Raney nickel (1.0 g) and 10 mL of 25% aqueous ammonia in 50 mL ethanol was filled with hydrogen, then the reaction mixture was continued stirring at room temperature for 3-15 hrs and monitored by TLC until the reaction was over, Raney nickel was filtered, the solution was concentrated under reduced pressure to give sticky oil cooled to obtain 2.20 g target intermediate as white solid with yield of 78%, m.p. 82-83° C.

Example 4: The Preparation of 4-(2-(5-chloro-6-methylpyrimidin-4-ylamino)ethyl)phenol

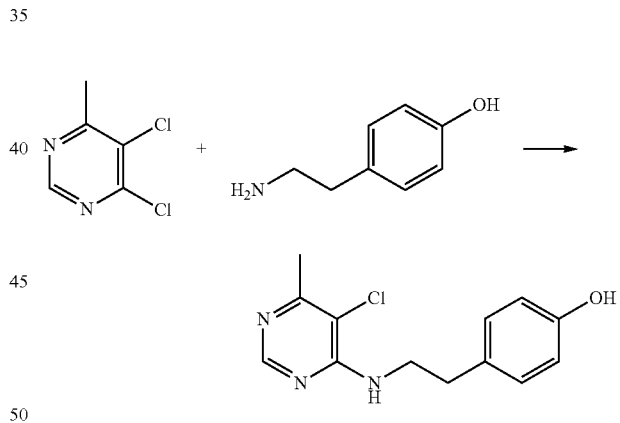

To a solution of 4-(2-aminoethyl)phenol 1.13 g (0.01 mol) and triethylamine 2.02 g (0.02 mol) in 50 mL toluene was dropwise added 4,5-dichloro-6-methylpyrimidine 1.63 g (0.01 mol). The reaction mixture was continued stirring for 4-10 hrs, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:3, as an eluent) to obtain 2.10 g target intermediate as white solid with yield of 88%, m.p. 177-179° C.

Example 5: The Preparation of Intermediate 2-(4-(3,5,6-trichloropyridin-2-yloxy)phenyl)ethanamine 1) tert-butyl 4-hydroxyphenethylcarbamate

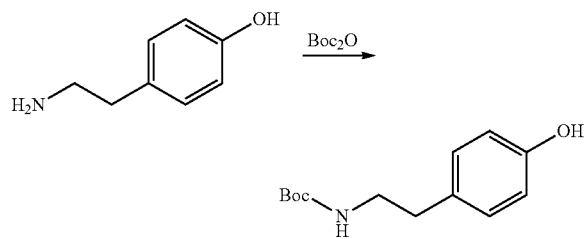

To a solution of 4-(2-aminoethyl)phenol 11.3 g (0.1 mol) and sodium bicarbonate 10.08 g (0.12 mol) in 80 mL tetrahydrofuran was dropwise added di-tert-butyl dicarbonate 21.80 g (0.1 mol) at room temperature, then the reaction mixture was continued stirring for 4-10 hrs, and monitored by TLC (Thin-Layer Chromatography) until the reaction was over, the excessive solvent was evaporated under reduced pressure. Then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:4, as an eluent) to obtain 17.15 g target intermediate as white solid with yield of 81%, m.p. 48-49° C.

2) The Preparation of tert-butyl 4-(3,5,6-trichloropyridin-2-yloxy)phenethylcarbamate

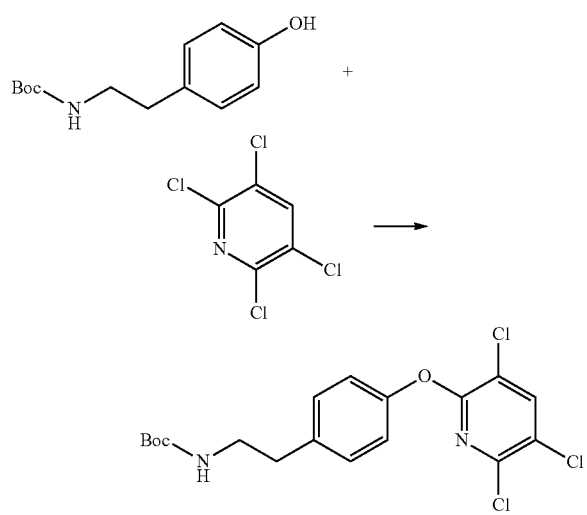

To a solution of tert-butyl 4-hydroxyphenethylcarbamate 2.37 g (0.01 mol) and 2,3,5,6-tetrachloropyridine 2.17 g (0.01 mol) in 50 mL butanone was added potassium carbonate 2.76 g (0.02 mol). The reaction mixture was continued stirring and heating to reflux for 4-10 hrs, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:5, as an eluent) to obtain 3.55 g target intermediate as white solid with yield of 82%, m.p. 48-49° C.

3) The Preparation of 2-(4-(3,5,6-trichloropyridin-2-yloxy)phenyl)ethanamine hydrochloride

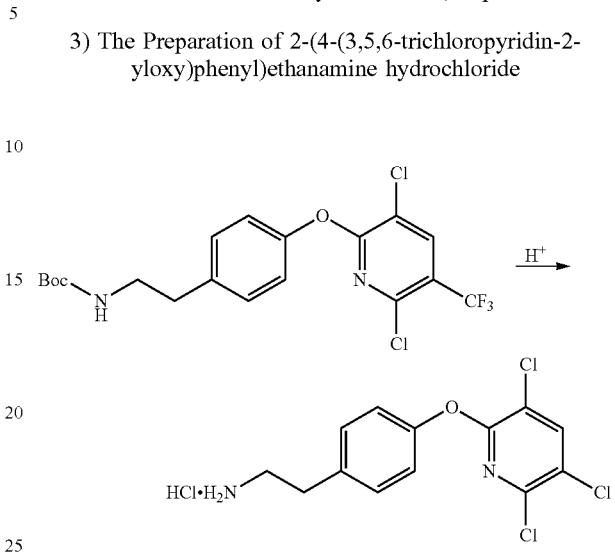

To a solution of tert-butyl 4-(3,5,6-trichloropyridin-2-yloxy)phenethylcarbamate 4.17 g (0.01 mol) in 50 mL ethyl acetate was dropwise added 15 mL concentrated hydrochloric acid. The reaction mixture was Gradually dissolved and continued stirring for 4-5 hrs, then a large amount of solid was precipitated and filtered, the filter cake was washed with 50 mL ethyl acetate to obtain 3.0 g target intermediate as white solid with yield of 88%, m.p. 48-49° C.

Example 6: The Preparation of Compound I-22

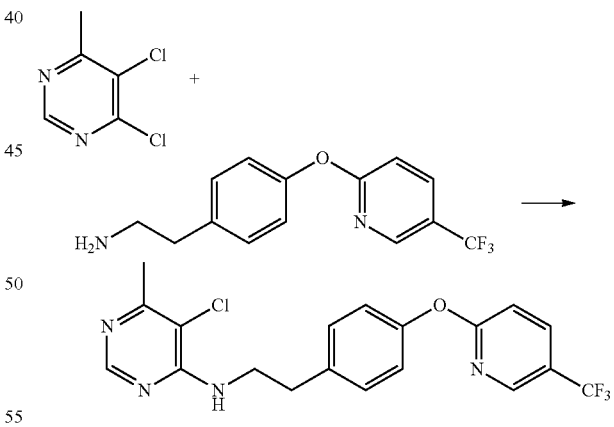

To a solution of 4,5-dichloro-6-methylpyrimidine 1.63 g (0.01 mol) and 2-(4-(5-(trifluoromethyl)pyridin-2-yloxy)phenyl)ethanamine 2.82 g (0.01 mol) in 50 mL toluene was added triethylamine 2.02 g (0.02 mol) after the reaction mixture was dissolved. The reaction mixture was continued stirring and heating to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:3, as an eluent) to obtain 3.25 g compound I-22 as white solid with yield of 80%, m.p. 98-99° C.

$^1$H-NMR (300 MHz, internal standard TMS, solvent CDCl$_3$) δ(ppm): 2.46 (3H, s), 2.97 (2H, t), 3.79 (2H, q), 5.47 (1H, t), 7.01 (1H, d), 7.12 (2H, d), 7.29 (2H, d), 7.90 (1H, d), 8.40 (1H, d), 8.44 (1H, s).

Example 7: The Preparation of Compound I-254

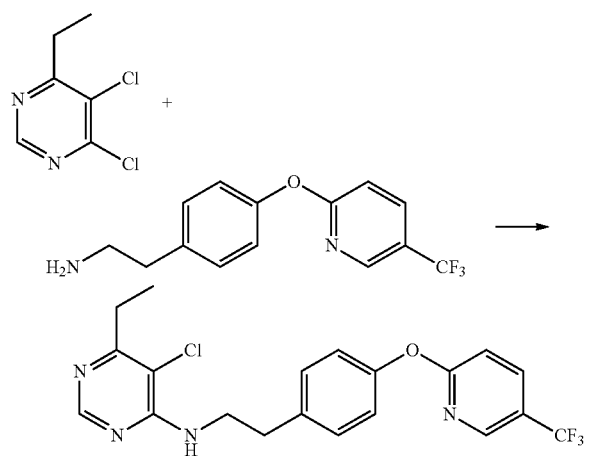

To a solution of 1.77 g (0.01 mol) 4,5-dichloro-6-ethyl-pyrimidine (the preparation refers to Example 1, the difference is replacing ethyl 2-chloro-3-oxobutanoate to ethyl 2-chloro-3-oxopentanoate) and 2-(4-(5-(trifluoromethyl) pyridin-2-yloxy)phenyl)ethanamine 2.82 g (0.01 mol) in 50 mL toluene was added triethylamine 2.02 g (0.02 mol). The reaction mixture was heated to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:3, as an eluent) to obtain 3.56 g compound I-254 as white solid with yield of 83%, m.p. 76~78° C.

$^1$H-NMR (300 MHz, internal standard TMS, solvent CDCl$_3$) δ(ppm): 1.26 (3H, t), 2.79 (2H, q), 2.77 (4H, m), 2.97 (2H, t), 3.79 (2H, q), 5.51 (1H, t), 7.00 (1H, d), 7.11 (2H, d), 7.29 (2H, d), 7.89 (1H, d), 8.44 (2H, m).

Example 8: The Preparation of Compound I-483

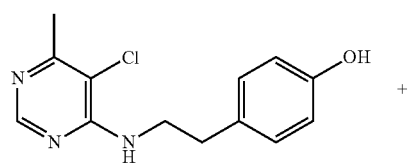

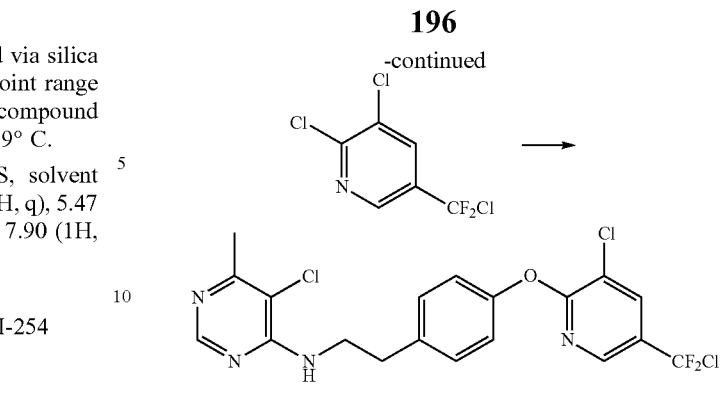

To a solution of 4-(2-(5-chloro-6-methylpyrimidin-4-ylamino)ethyl)phenol 2.64 g (0.01 mol) and 2-(4-(5-(trifluoromethyl)pyridin-2-yloxy)phenyl)ethanamine 2.33 g (0.01 mol) in 30 mL N,N-dimethyl formamide was added potassium carbonate 2.76 g (0.02 mol). The reaction mixture was heated to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:4, as an eluent) to obtain 3.77 g compound I-483 as colorless oil with yield of 82%.

$^1$H-NMR (300 MHz, internal standard TMS, solvent CDCl$_3$) δ (ppm): 2.45 (3H, s), 2.96 (2H, t), 3.72-3.84 (2H, q), 5.45 (1H, t), 7.13 (2H, d), 7.29 (2H, d), 7.99 (1H, d), 8.27 (1H, s), 8.40 (1H, s).

Example 9: The Preparation of Compound I-583

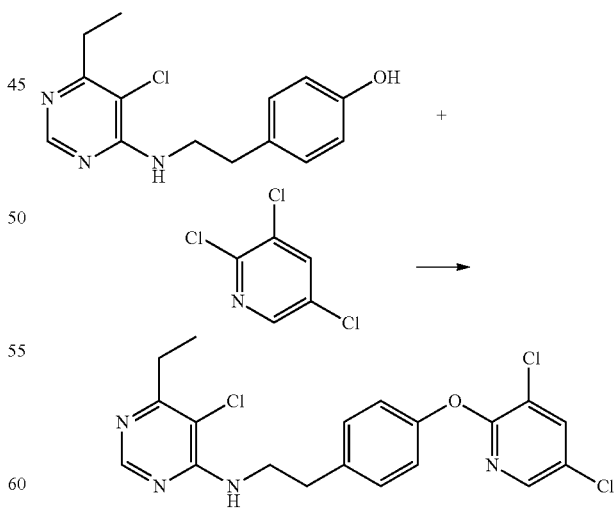

To a solution of 2.78 g (0.01 mol) 4-(2-(5-chloro-6-ethylpyrimidin-4-ylamino)ethyl)phenol (the preparation refers to Example 3, the difference is replacing 4,5-dichloro-6-methylpyrimidine to 4,5-dichloro-6-ethylpyrimidine) and 2,3,5-trichloropyridine 1.83 g (0.01 mol) in 30 mL N,N- dimethyl formamide was added potassium carbonate 2.76 g (0.02 mol). The reaction mixture was heated to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:3, as an eluent) to obtain 3.50 g compound I-583 as colorless oil with yield of 83%, m.p. 53-54° C.

$^1$H-NMR (300 MHz, internal standard TMS, solvent CDCl$_3$) δ (ppm): 1.26 (3H, t), 2.79 (2H, q), 2.96 (2H, q), 3.77 (2H, q), 5.47 (1H, t), 7.11 (2H, d), 7.28 (2H, d), 7.77 (1H, s), 8.45 (1H, s).

Example 10: The Preparation of Compound I-2342

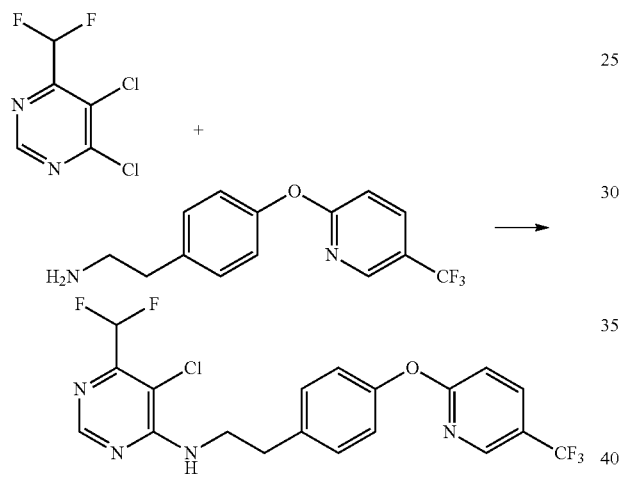

To a solution of 4,5-dichloro-6-(difluoromethyl)pyrimidine 1.99 g (0.01 mol) and 2-(4-(5-(trifluoromethyl)pyridin-2-yloxy)phenyl)ethanamine 2.82 g (0.01 mol) in 50 mL toluene was added triethylamine 2.02 g (0.02 mol) after the reaction mixture was dissolved. The reaction mixture was continued stirring and heating to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:4, as an eluent) to obtain 3.82 g compound I-2342 as white solid with yield of 86%, m.p. 102-103° C.

$^1$H-NMR (300 MHz, internal standard TMS, solvent CDCl$_3$) δ (ppm): 8.581 (s, 1H, pyrimidine-H), 8.439 (s, 1H, pyridine-6-H), 7.891-7.927 (d, 1H, pyridine-4-H), 7.008-7.037 (d, 1H, pyridine-3-H), 7.111-7.310 (dd, 4H, Ar—H), 6.547-6.904 (t, 1H, F$_2$C—H, 5.747 (s, 1H, NH), 3.815-3.882 (q, 2H, N—CH$_2$—C), 2.964-3.010 (t, 2H, C—CH$_2$—Ar).

Example 11: The Preparation of Compound I-2574

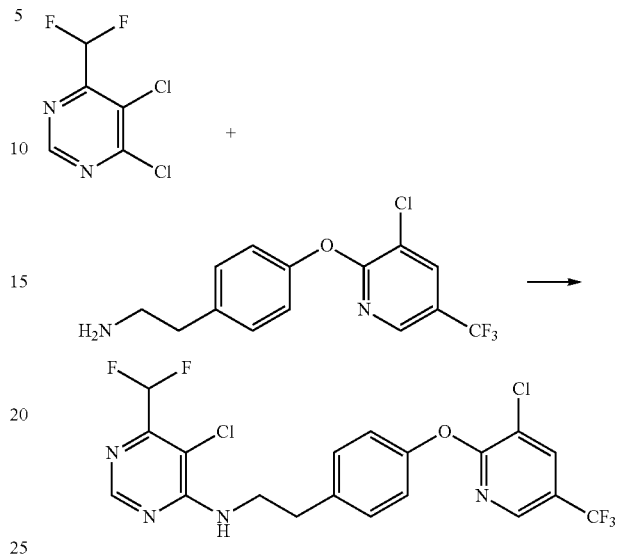

To a solution of 1.99 g (0.01 mol) 4,5-dichloro-6-(difluoromethyl)pyrimidine and 2.82 g (0.01 mol) 2-(4-(5-(trifluoromethyl)pyridin-2-yloxy)phenyl)ethanamine (the preparation refers to Example 3) in 50 mL toluene was added triethylamine 2.02 g (0.02 mol) after the reaction mixture was dissolved. The reaction mixture was heated to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:4, as an eluent) to obtain 4.16 g compound I-2574 as white solid with yield of 84%.

$^1$H-NMR (300 MHz, internal standard TMS, solvent CDCl$_3$) δ (ppm): δ 8.577 (s, 1H, pyrimidine-H), 8.270 (s, 1H, pyridine-6-H), 7.981-7.987 (d, 1H, pyridine-4-H), 7.128-7.319 (dd, 4H, Ar—H), 6.716 (t, 1H, F$_2$C—H), 3.843-3.864 (q, 2H, N—CH$_2$—C), 2.970-3.016 (t, 2H, C—CH$_2$—Ar).

Example 12: The Preparation of Compound I-2748

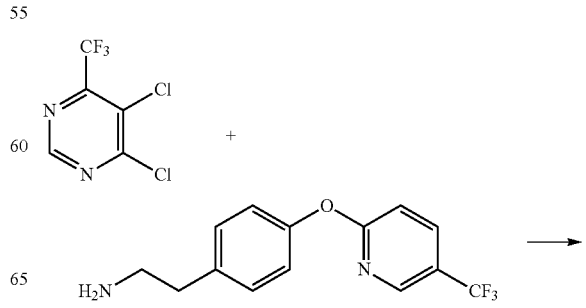

-continued

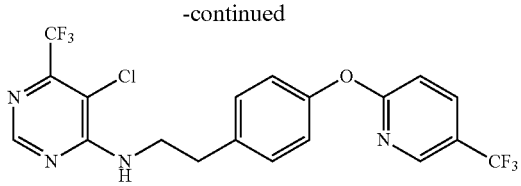

To a solution of 2.17 g (0.01 mol) 4,5-dichloro-6-(trifluoromethyl)pyrimidine (the preparation refers to Example 1) and 3.19 g (0.01 mol) 2-(4-(5-(trifluoromethyl)pyridin-2-yloxy)phenyl)ethanamine in 50 mL toluene was added triethylamine 2.02 g (0.02 mol). The reaction mixture was heated to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:4, as an eluent) to obtain 4.07 g compound I-2748 as white solid with yield of 88%, m.p. 96-97° C.

$^1$H-NMR (300 MHz, internal standard TMS, solvent CDCl$_3$) δ (ppm): 8.577 (s, 1H, pyrimidine-H), 8.436 (s, 1H, pyridine-6-H), 7.892-7.920 (d, 1H, pyridine-4-H), 7.010-7.039 (d, 1H, pyridine-3-H), 7.115-7.313 (dd, 4H, Ar—H), 5.898 (s, 1H, NH), 3.825-3.890 (q, 2H, N—CH$_2$—C), 2.966-3.014 (t, 2H, C—CH$_2$—Ar).

Example 13: The Preparation of Compound I-3309

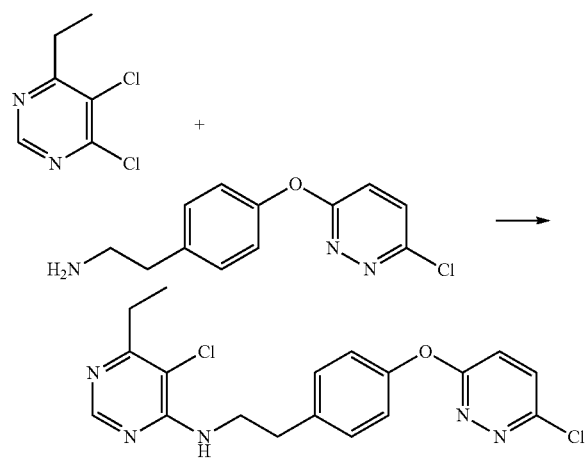

To a solution of 1.77 g (0.01 mol) 4,5-dichloro-6-ethylpyrimidine and 2.50 g (0.01 mol) 2-(4-(6-chloropyridazin-3-yloxy)phenyl)ethanamine (the preparation refers to Example 3, the difference is replacing 2-chloro-5-(trifluoromethyl)pyridine to 3,6-dichloropyridazine) in 50 mL toluene was added 2.02 g (0.02 mol)triethylamine after the reaction mixture was dissolved. The reaction mixture was heated to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:3, as an eluent) to obtain 3.40 g compound I-3309 as white solid with yield of 87%, m.p. 138-140° C.

$^1$H-NMR (300 MHz, internal standard TMS, solvent CDCl$_3$) δ (ppm): 1.25 (3H, t), 2.79 (2H, q), 2.96 (2H, t), 3.78 (2H, q), 5.50 (1H, s), 7.16 (3H, m), 7.26 (2H, m), 7.50 (1H, d), 8.45 (1H, s).

Example 14: The Preparation of Compound I-4757

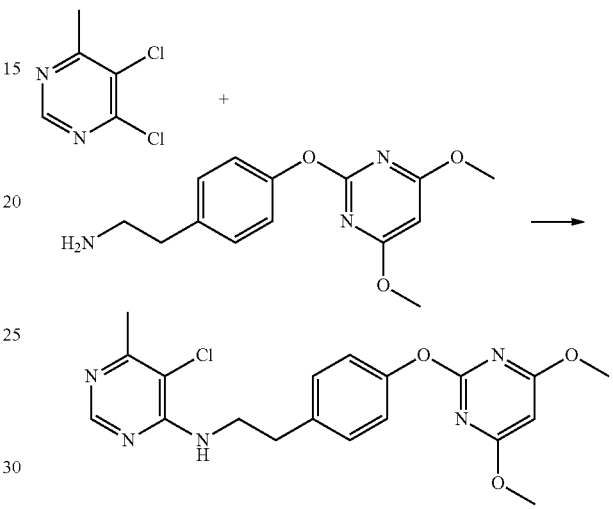

To a solution of 1.63 g (0.01 mol) 4,5-dichloro-6-methylpyrimidine and 2.75 g (0.01 mol) 2-(4-(4,6-dimethoxypyrimidin-2-yloxy)phenyl)ethanamine (the preparation refers to Example 3, the difference is replacing 2-chloro-5-(trifluoromethyl)pyridine to 4,6-dimethoxy-2-(methylsulfonyl) pyrimidine) in 50 mL toluene was added 2.02 g (0.02 mol)triethylamine after the reaction mixture was dissolved. The reaction mixture was heated to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:4, as an eluent) to obtain 3.24 g compound I-4757 as white solid with yield of 81%, m.p. 119-120° C.

$^1$H-NMR (300 MHz, internal standard TMS, solvent CDCl$_3$) δ (ppm): 2.46 (3H, s), 2.95 (2H, t), 3.82 (2H, m), 3.84 (6H, s), 5.43 (1H, s), 5.78 (1H, s), 7.26 (4H, m), 8.40 (1H, s).

Example 15: The Preparation of Compound I-6730

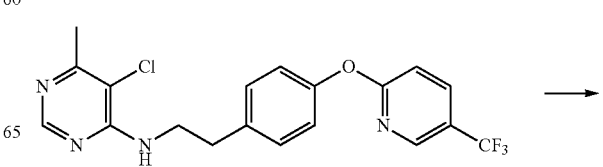

-continued

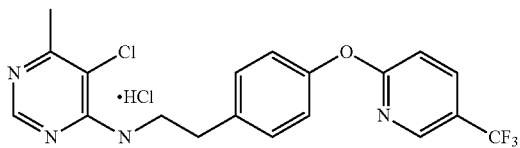

To a solution of compound I-22 0.41 g (0.01 mol) in 20 mL ethanol was dropwise added 10 mL of concentrated hydrochloric acid at room temperature, The reaction mixture was heated to reflux for 4-10 hours, and monitored by TLC (Thin-Layer Chromatography) until the reaction was over, the excessive solvent was evaporated under reduced pressure, the brown residue was washed with (3×50 mL) of acetone to obtain 0.33 g compound I-6730 as white solid with yield of 75%, m.p. 108-110° C.

$^1$H-NMR (300 MHz, internal standard TMS, solvent CDCl$_3$) δ(ppm): 2.49 (3H, s), 2.88 (2H, t), 3.64 (2H, m), 7.08 (2H, d), 7.17 (1H, d), 7.35 (2H, d), 7.37 (1H, m), 8.16 (1H, d), 8.25 (1H, s), 8.50 (1H, s).

Example 16: The Preparation of 2-(4-(2-chloro-4-(trifluoromethyl)phenoxy)phenyl)ethanamine 1) The Preparation of 2-(4-(2-chloro-4-(trifluoromethyl)phenoxy)phenyl)acetonitrile

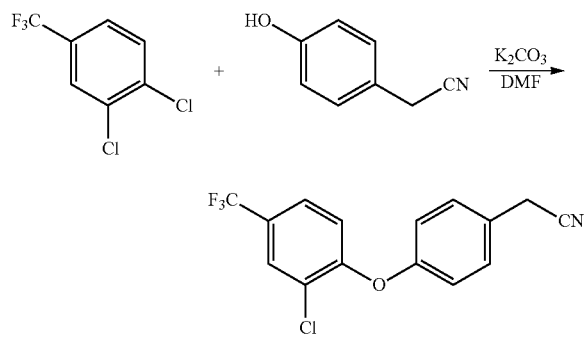

To a solution of 150 mL N,N-dimethyl formamide was added 1,2-dichloro-4-(trifluoromethyl)benzene 25.8 g (0.12 mol), 2-(4-hydroxyphenyl)acetonitrile 13.3 g (0.1 mol) and potassium carbonate 27.60 g (0.2 mol). The reaction mixture was continued stirring and heating to reflux overnight, and monitored by TLC (Thin-Layer Chromatography) until the reaction was over, the excessive solvent was evaporated under reduced pressure. Then the mixture was poured into 300 mL of ethyl acetate to separate the organic layer, the organic phase was washed with 50 mL of 5% aqueous solution of NaOH, and 50 mL of brine successively, dried and evaporated under reduced pressure, the residual was purified via silica column (ethyl acetate/petroleum ether (boiling point range 60-90° C.)=1:4, as an eluent) to obtain 14.55 g target intermediate as white solid with yield of 46.2%, m.p. 66.2° C.

2) The Preparation of 2-(4-(2-chloro-4-(trifluoromethyl)phenoxy)phenyl)ethanamine hydrochloride

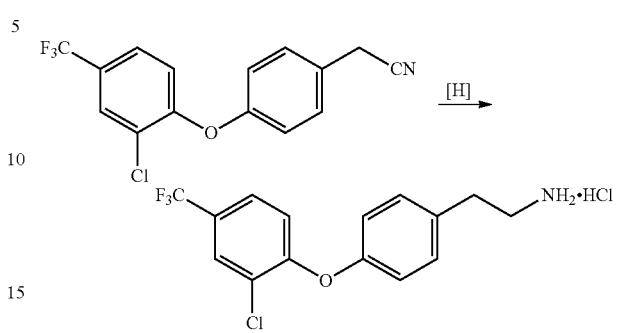

To a solution of 2-(4-(2-chloro-4-(trifluoromethyl)phenoxy)phenyl)acetonitrile 3.12 g (0.01 mol), Raney nickel (1.0 g) and 10 mL of 25% aqueous ammonia in 50 mL ethanol was filled with hydrogen at high pressure, then the reaction mixture was continued stirring at room temperature for 3 hours and monitored by TLC until the reaction was over, Raney nickel was filtered, the solution was concentrated under reduced pressure to give sticky liquid. To a solution of the residue was dropwise added 5 mL of concentrated hydrochloric acid and stirred for half an hour at room temperature until target intermediate precipitated, filtered to obtain 3.45 g white solid with yield of 97.9%, m.p. 155.7° C.

Example 17: The Preparation of 2-(4-(2,6-dichloro-4-nitrophenoxy)phenyl)ethanamine hydrochloride 1) The Preparation of tert-butyl 4-(2,6-dichloro-4-nitrophenoxy)phenethylcarbamate

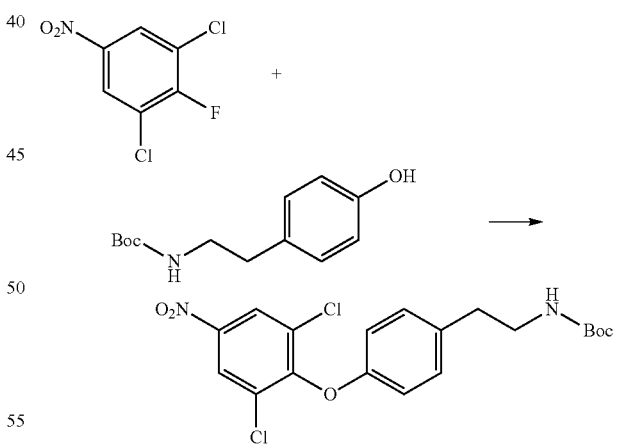

To a solution of tert-butyl 4-hydroxyphenethylcarbamate 2.10 g (0.01 mol) and 1,3-dichloro-2-fluoro-5-nitrobenzene 2.33 g (0.01 mol) in 50 mL butanone was added potassium carbonate 2.76 g (0.02 mol). The reaction mixture was continued stirring and heating to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:4, as an eluent) to obtain 3.73 g target intermediate as white solid with yield of 87.3%, m.p. 149-151° C.

2) The Preparation of 2-(4-(2,6-dichloro-4-nitrophenoxy)phenyl)ethanamine

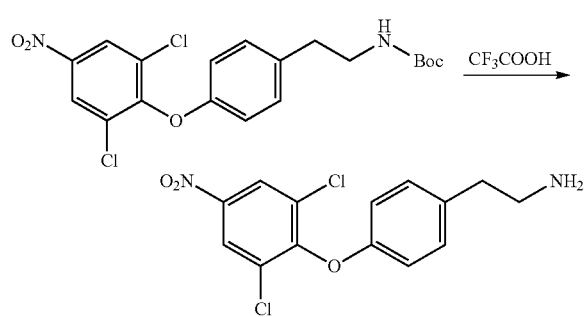

To a solution of tert-butyl 4-(2,6-dichloro-4-nitrophenoxy)phenethylcarbamate 4.27 g (0.01 mol) in 50 mL ethyl acetate was dropwise added 6 mL trifluoroacetic acid until the solid was dissolved at room temperature for 4-5 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure to give 3.03 g target intermediate as white solid with yield of 92.8%, m.p. 107-109° C.

Example 18: The Preparation of 2-(4-(4-(trifluoromethyl)phenoxy)phenyl)ethanamine 1) The Preparation of tert-butyl 4-(4-(trifluoromethyl)phenoxy)phenethylcarbamate

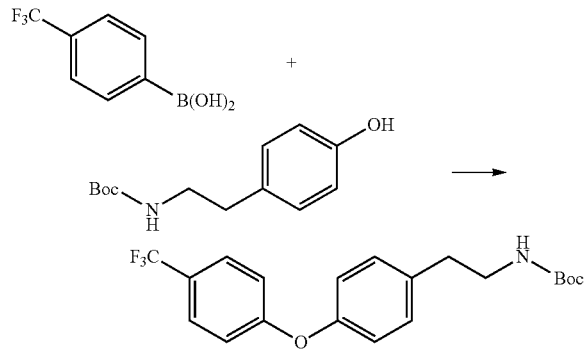

To a solution of 4-(trifluoromethyl)phenylboronic acid 4.56 g (0.024 mol) in 50 mL dichloromethane was added 4A molecular sieve powder, Cupric Acetate Anhydrous 3.82 g (0.021 mol), triethylamine 10.1 g (0.1 mol), and pyridine 7.9 g (0.1 mol) successively; The reaction mixture was continued to react overnight, and monitored by TLC (Thin-Layer Chromatography) until the reaction was over, filtered and the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:4, as an eluent) to obtain 5.95 g target intermediate as white solid with yield of 65.1%.

2) The Preparation of 2-(4-(4-(trifluoromethyl)phenoxy)phenyl)ethanamine hydrochloride

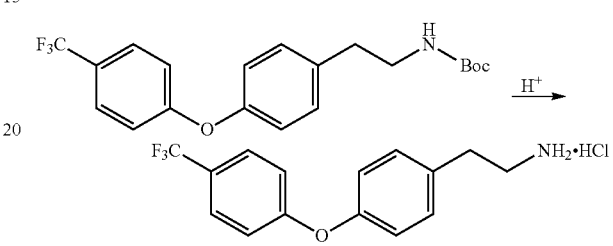

To a solution of tert-butyl 4-(4-(trifluoromethyl)phenoxy)phenethylcarbamate 3.81 g (0.01 mol) in 50 mL ethyl acetate was dropwise added 12 mL concentrated hydrochloric acid. The reaction mixture was continued to stir for 4-5 hours, and monitored by TLC (Thin-Layer Chromatography) until the reaction was over, the excessive solvent was evaporated under reduced pressure, then the mixture was poured into (3×50 mL) of ethyl acetate to react for half an hour and filtered to give 2.92 g target intermediate as white solid with yield of 91.9%.

Example 19: The Preparation of Compound II-69

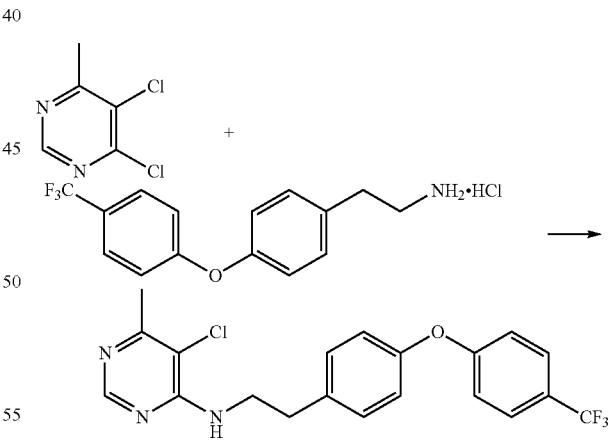

To a solution of 1.63 g (0.01 mol) 4,5-dichloro-6-methylpyrimidine and 3.18 g (0.01 mol) 2-(4-(4-(trifluoromethyl)phenoxy)phenyl)ethanamine hydrochloride in 50 mL toluene was added 4.45 g (0.022 mol) triethylamine. The reaction mixture was continued stirring and heating to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:2, as an eluent) to obtain 2.76 g compound II-69 as colourless oil with yield of 72.6%.

$^1$H-NMR (300 MHz, internal standard TMS, solvent CDCl$_3$) δ (ppm): 2.46 (3H, s), 2.94 (2H, t), 3.77 (2H, q), 5.42 (1H, s), 702 (4H, m), 7.25 (2H, m), 7.56 (2H, d), 8.39 (1H, s).

Example 20: The Preparation of Compound II-165

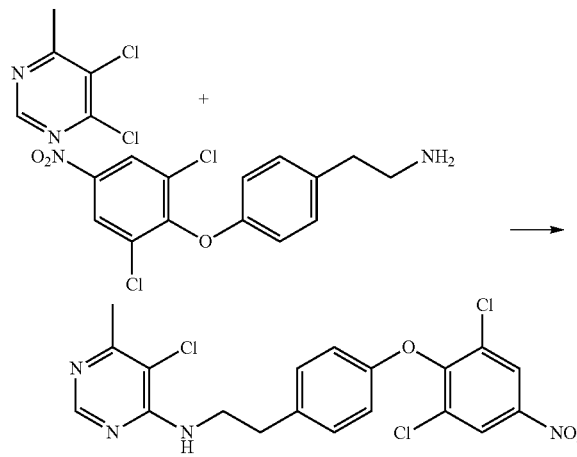

To a solution of 1.63 g (0.01 mol) 4,5-dichloro-6-methylpyrimidine and 3.26 g (0.01 mol) 2-(4-(2,6-dichloro-4-nitrophenoxy)phenyl)ethanamine in 50 mL toluene was added 4.45 g (0.022 mol)triethylamine. The reaction mixture was continued stirring and heating to reflux for 4-10 hours, and monitored by TLC (Thin-Layer Chromatography) until the reaction was over, the excessive solvent was evaporated under reduced pressure. Then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:2, as an eluent) to obtain 3.23 g compound II-165 as rufous solid with yield of 71.2%, m.p. 118-120° C.

$^1$H-NMR (300 MHz, internal standard TMS, solvent CDCl$_3$) δ (ppm): 2.45 (3H, s), 2.91 (2H, t), 3.70-3.85 (2H, q), 5.42 (1H, t), 6.80 (2H, d), 7.18 (2H, d), 8.31 (2H, s), 8.38 (1H, s).

Example 21: The Preparation of Compound II-297

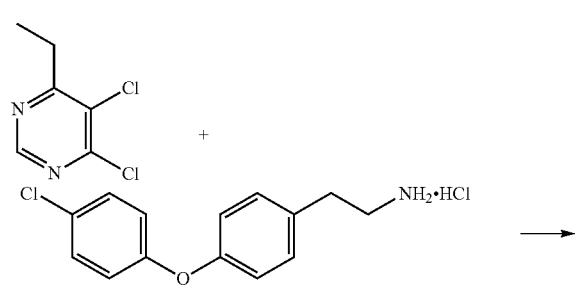

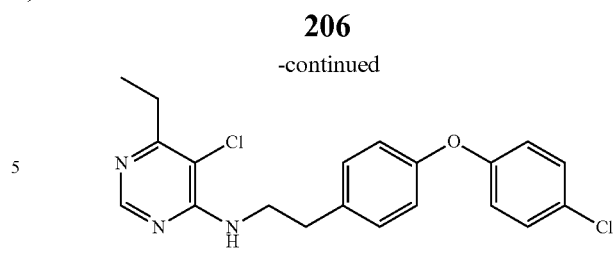

To a solution of 1.77 g (0.01 mol) 4,5-dichloro-6-ethylpyrimidine (the preparation refers to Example 1, the difference is replacing ethyl 2-chloro-3-oxobutanoate to ethyl 2-chloro-3-oxopentanoate) and 2.84 g (0.01 mol) 2-(4-(4-chlorophenoxy)phenyl)ethanamine hydrochloride (the preparation refers to Example 18, the difference is replacing 4-(trifluoromethyl)phenylboronic acid to 4-chlorophenylboronic acid) in 50 mL toluene was added 4.45 g (0.022 mol)triethylamine. The reaction mixture was continued stirring and heating to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:2, as an eluent) to obtain 3.16 g compound II-297 as rufous solid with yield of 81.6%, m.p. 84.7° C.

$^1$H-NMR (300 MHz, internal standard TMS, solvent CDCl$_3$) δ (ppm): 1.26 (3H, t), 2.78 (2H, dd), 2.92 (2H, t), 3.75 (2H, dd), 5.45 (1H, t), 6.84-7.00 (4H, m), 7.20 (2H, d), 7.29 (2H, d), 8.44 (1H, s).

Example 22: The Preparation of Compound II-303

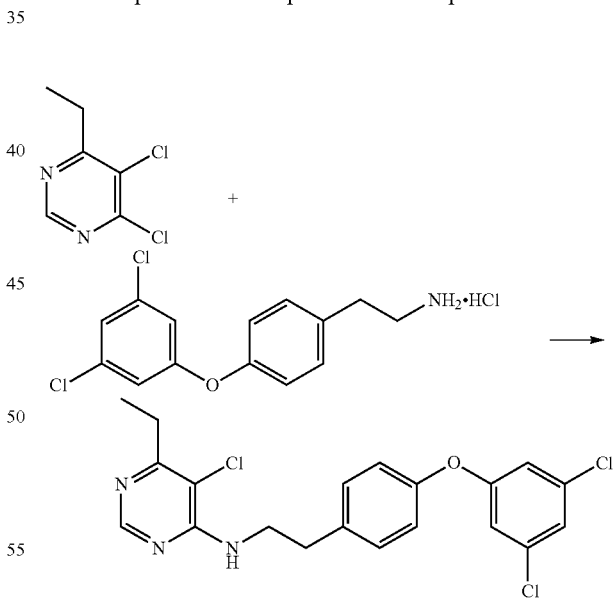

To a solution of 1.77 g (0.01 mol) 4,5-dichloro-6-ethylpyrimidine and 3.19 g (0.01 mol) 2-(4-(3,5-dichlorophenoxy)phenyl)ethanamine hydrochloride (the preparation refers to Example 18, the difference is replacing 4-(trifluoromethyl)phenylboronic acid to 3,5-dichlorophenylboronic acid) in 50 mL toluene was added 4.45 g (0.022 mol) triethylamine. The reaction mixture was continued stirring and heating to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:2, as an eluent) to obtain 3.17 g compound II-303 as pale rufous oil with yield of 75.1%.

¹H-NMR (300 MHz, internal standard TMS, solvent CDCl₃) δ (ppm): 1.26 (3H, t), 2.78 (2H, dd), 2.95 (2H, t), 3.72-3.84 (2H, q), 5.45 (1H, t), 6.85 (2H, d), 7.00 (2H, d), 7.25 (2H, d), 8.45 (1H, s).

Example 23: The Preparation of Compound II-347

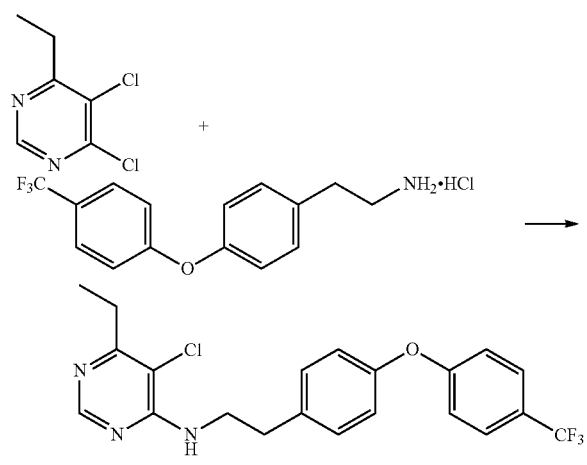

To a solution of 1.77 g (0.01 mol) 4,5-dichloro-6-ethyl-pyrimidine and 3.18 g (0.01 mol) 2-(4-(4-(trifluoromethyl)phenoxy)phenyl)ethanamine hydrochloride in 50 mL toluene was added 4.45 g (0.022 mol)triethylamine. The reaction mixture was continued stirring and heating to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:2, as an eluent) to obtain 3.15 g compound II-347 as white solid with yield of 74.8%, m.p. 52.6° C.

¹H-NMR (300 MHz, internal standard TMS, solvent CDCl₃) δ (ppm): 1.27 (3H, t), 2.78 (2H, q), 2.95 (2H, t), 3.78 (2H, q), 5.42 (1H, s), 7.01 (4H, m), 7.24 (2H, m), 7.58 (2H, d), 8.45 (1H, s).

Example 24: The Preparation of Compound II-8915

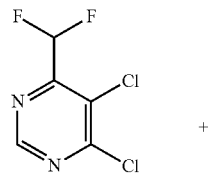

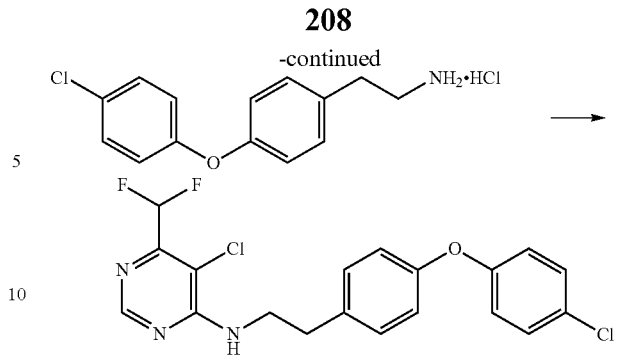

To a solution of 1.98 g (0.01 mol) 4,5-dichloro-6-(difluoromethyl)pyrimidine (the preparation refers to Example 1, the difference is replacing ethyl 2-chloro-3-oxobutanoate to ethyl 2-chloro-4,4-difluoro-3-oxobutanoate) and 2.84 g (0.01 mol) 2-(4-(4-chlorophenoxy)phenyl)ethanamine hydrochloride in 50 mL toluene was added 4.45 g (0.022 mol)triethylamine. The reaction mixture was continued stirring and heating to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:2, as an eluent) to obtain 2.89 g compound II-8915 as white solid with yield of 70.5%, m.p. 98.5° C.

¹H-NMR (300 MHz, internal standard TMS, solvent CDCl₃) δ (ppm): 2.94 (2H, t), 3.76-3.86 (2H, q), 5.71 (1H, s), 6.72 (1H, t), 6.90-7.05 (4H, m), 7.17-7.32 (4H, m), 8.57 (1H, s).

Example 25: The Preparation of Compound II-10583

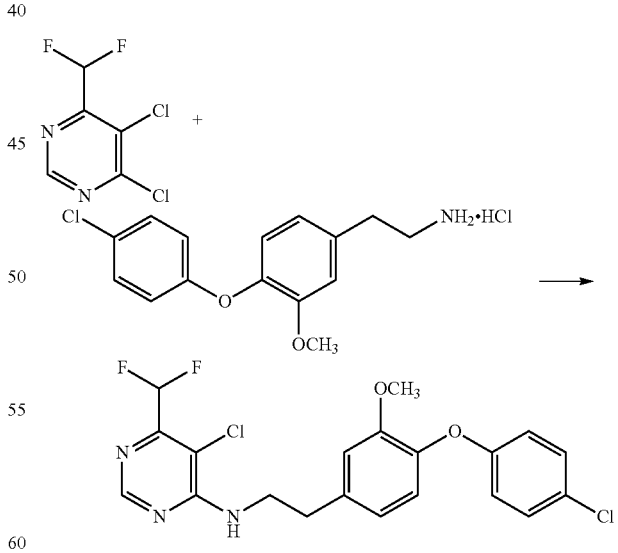

To a solution of 1.98 g (0.01 mol) 4,5-dichloro-6-(difluoromethyl)pyrimidine (the preparation refers to Example 1, the difference is replacing ethyl 2-chloro-3-oxobutanoate to ethyl 2-chloro-4,4-difluoro-3-oxobutanoate) and 3.14 g (0.01 mol) 2-(4-(4-chlorophenoxy)-3-methoxyphenyl)ethanamine hydrochloride in 50 mL toluene was added 4.45 g (0.022 mol)triethylamine. The reaction mixture was continued stirring and heating to reflux for 4-10 hours, and monitored by TLC (Thin-Layer Chromatography) until the reaction was over, the excessive solvent was evaporated under reduced pressure, then the mixture was poured into (3×50 mL) of ethyl acetate to separate the organic layer, the organic phase was washed with 50 mL of brine, dried and evaporated under reduced pressure, the residual was purified via silica column (ethyl acetate/petroleum ether (boiling point range 60-90° C.)=1:2, as an eluent) to obtain 2.89 g compound II-10583 as rufous oil with yield of 76.8%.

$^1$H-NMR (300 MHz, internal standard TMS, solvent CDCl$_3$) δ (ppm): 2.95 (2H, t), 3.80-3.92 (5H, m), 5.72 (1H, s), 6.72 (1H, t), 6.75-6.97 (5H, m), 7.20-7.26 (2H, m), 8.58 (1H, s).

Example 26: The Preparation of Compound II-19334

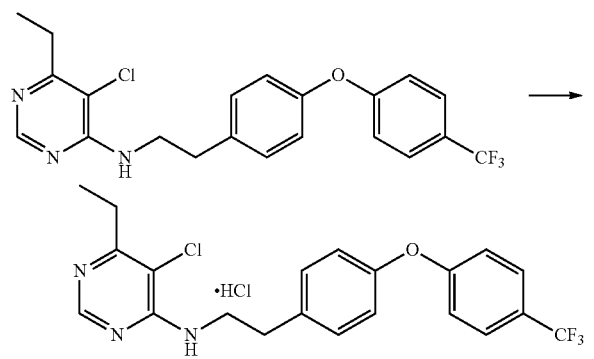

To a solution of compound II-347 0.42 g (0.01 mol) in 20 mL ethanol was dropwise added 10 mL of concentrated hydrochloric acid at room temperature. The reaction mixture was heated to reflux for 4-10 hours, and monitored by TLC (Thin-Layer Chromatography) until the reaction was over, the excessive solvent was evaporated under reduced pressure, the brown residue was washed with (3×10 mL) of ethyl acetate to obtain 0.36 g compound II-19334 as white solid with yield of 78.1%, m.p. 120.5° C.

$^1$H-NMR (300 MHz, internal standard TMS, solvent CDCl$_3$) δ (ppm): 1.27 (3H, t), 2.80-3.09 (4H, m), 3.80 (2H, d), 6.92-7.18 (4H, d), 7.31 (2H, d), 7.67 (2H, d), 8.71 (1H, d), 9.28 (1H, s).

Example 27: The Preparation of 2-(6-(4-chlorophenoxy)pyridin-3-yl)ethanamine

1) The Preparation of methyl 6-(4-chlorophenoxy)nicotinate

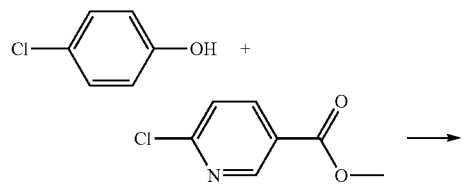

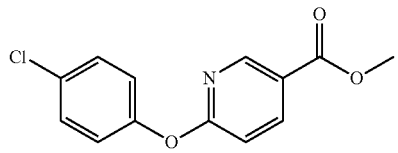

To a solution of 25.6 g (0.2 mol) 4-chlorophenol in 350 mL N,N-dimethylformamide was added 70% sodium hydride 103 g (3.0 mol) in batches. The reaction mixture was stirred for 4 hours at room temperature, then 34.2 g (0.2 mol) methyl 6-chloronicotinate was added in batches, then the reaction temperature was raised to 100° C. to react for 10 hours, and monitored by TLC (Thin-Layer Chromatography) until the reaction was over, the solution was poured into water, extracted with ethyl acetate, the organic phase was washed with water, saturated brine successively, dried, filtered and evaporated under reduced pressure, the cooled residual was filtered and washed with petroleum ether, to obtain 42.0 g air dried target intermediate as brown solid, m.p. 64-66° C. $^1$H-NMR (300 MHz, internal standard TMS, solvent CDCl$_3$) δ(ppm): 3.92 (3H, s), 6.75 (1H, d), 6.96 (1H, d), 7.11 (2H, d), 7.37 (2H, d), 8.30 (1H, d), 8.81 (1H, s).

2) The Preparation of (6-(4-chlorophenoxy)pyridin-3-yl)methanol

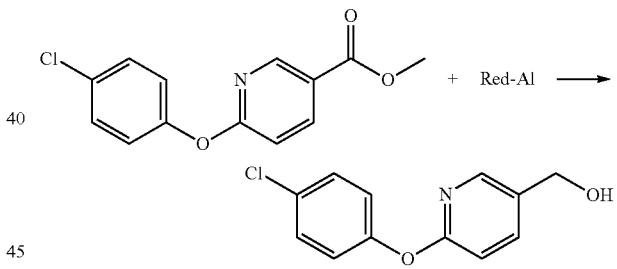

To a solution of 52.6 g (0.2 mol) methyl 6-(4-chlorophenoxy)nicotinate in 500 mL anhydrous ether was dropwise added 65% Red-Al 74.5 g (0.24 mol) in toluene at 0□. then the reaction mixture was stirred for 4 hours at room temperature, then at 0□, 10% sodium hydroxide solution prepared beforehand was dropwise added until the reaction solution was clarified, then the reaction temperature was raised to 35 □ to react for 2 hours, and monitored by TLC (Thin-Layer Chromatography) until the reaction was over, the solution was poured into water, extracted with ethyl acetate, the organic phase was washed with water, saturated brine successively, dried, filtered and evaporated under reduced pressure, the residual was purified via silica column (ethyl acetate/petroleum ether (boiling point range 60-90° C.)=1:3, as an eluent) to obtain 42.2 g target intermediate as white solid, m.p. 100-102° C. $^1$H-NMR (300 MHz, internal standard TMS, solvent CDCl$_3$) δ (ppm): 3.20 (1H, bs), 4.56 (2H, s), 6.87 (1H, d), 7.04 (2H, d), 7.33 (2H, d), 7.69 (1H, d), 8.06 (1H, s).

3) The Preparation of 5-(chloromethyl)-2-(4-chlorophenoxy)pyridine

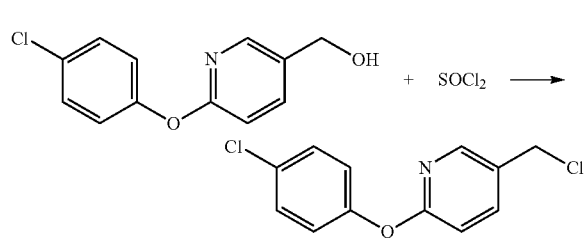

To a solution of 23.5 g (0.1 mol) (6-(4-chlorophenoxy)pyridin-3-yl)methanol in 350 mL dichloromethane was dropwise added 17.9 g (0.15 mol) sulfoxide chloride at 0° C. then the reaction mixture was stirred for 4 hours at room temperature, and monitored by TLC (Thin-Layer Chromatography) until the reaction was over, the excessive sulfoxide chloride was evaporated and the residual was poured into water, extracted with ethyl acetate, the organic phase was washed with water, saturated sodium bicarbonate solution, and saturated brine successively, dried, filtered and evaporated under reduced pressure, to obtain 22.8 g target intermediate as white solid, m.p. 78-80° C. $^1$H-NMR (300 MHz, internal standard TMS, solvent CDCl$_3$) δ(ppm): 4.55 (2H, s), 6.94 (1H, d), 7.09 (2H, d), 7.36 (2H, d), 7.75 (1H, d), 8.15 (1H, s).

4) The Preparation of 2-(6-(4-chlorophenoxy)pyridin-3-yl)acetonitrile

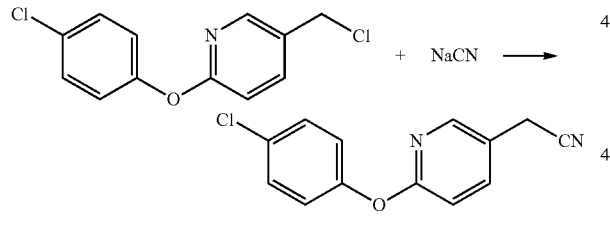

To a solution of 2.69 g (55 mmol) sodium cyanide dissolved in 300 mL dimethyl sulfoxide was added 13.9 g (50 mmol) 5-(chloromethyl)-2-(4-chlorophenoxy)pyridine and the catalytic amount of 18-Crown-6 at 40° C. then the reaction mixture was raised to 80° C. to react for 2 hours, and monitored by TLC (Thin-Layer Chromatography) until the reaction was over, the residual was poured into water, extracted with toluene, the organic phase was washed with water, and saturated brine successively, dried, filtered and evaporated under reduced pressure, the residual was purified via silica column (ethyl acetate/petroleum ether (boiling point range 60-90° C.)=1:3, as an eluent) to obtain 11.2 g target intermediate as white solid, m.p. 100-102° C. $^1$H-NMR (300 MHz, internal standard TMS, solvent CDCl$_3$) δ (ppm): 3.70 (2H, s), 6.97 (1H, d), 7.08 (2H, d), 7.37 (2H, d), 7.71 (1H, d), 8.10 (1H, s).

5) The Preparation of 2-(6-(4-chlorophenoxy)pyridin-3-yl)ethanamine

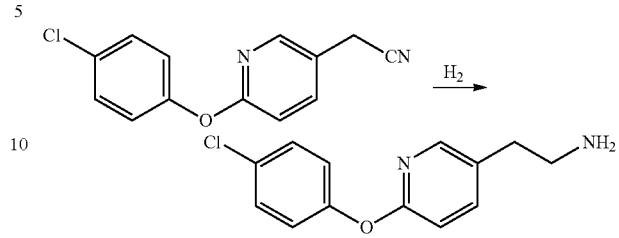

To a solution of 2-(6-(4-chlorophenoxy)pyridin-3-yl)acetonitrile 2.44 g (0.01 mol), Raney nickel (1.0 g) and 10 mL of 25% aqueous ammonia in 50 mL ethanol was filled with hydrogen, then the reaction mixture was continued stirring at room temperature for 3-15 hours and monitored by TLC until the reaction was over, Raney nickel was filtered, the solution was concentrated under reduced pressure to give 2.30 g jade-green sticky liquid with yield of 95.0%, colourless oil. $^1$H-NMR (300 MHz, internal standard TMS, solvent CDCl$_3$) δ(ppm): 1.46 (2H, bs), 2.70 (2H, t), 2.94 (2H, t), 6.87 (1H, d), 7.07 (2H, dd), 7.34 (2H, dd), 7.55 (1H, dd), 8.02 (1H, d).

Example 28: The Preparation of Compound III-7

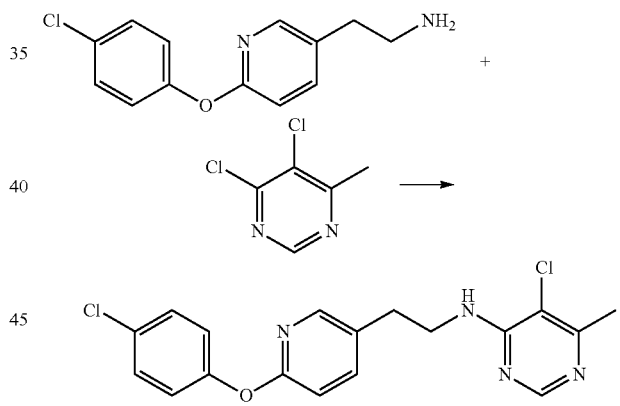

To a solution of 0.25 g (1.0 mmol) 2-(6-(4-chlorophenoxy)pyridin-3-yl)ethanamine and 0.21 g (1.5 mmol) potassium carbonate in 10 mL N,N-dimethylformamide was added 0.16 g (1.0 mmol) 4,5-dichloro-6-methylpyrimidine, then the reaction mixture was raised to 80° C. to react for 2 hours, and monitored by TLC (Thin-Layer Chromatography) until the reaction was over, the residual was poured into water, extracted with ethyl acetate, the organic phase was washed with water, and saturated brine successively, dried, filtered and evaporated under reduced pressure, the residual was purified via silica column (ethyl acetate/petroleum ether (boiling point range 60-90° C.)=1:4, as an eluent) to obtain 0.28 g compound III-7 as colourless oil. $^1$H-NMR (300 MHz, internal standard TMS, solvent CDCl$_3$) δ (ppm): 2.46 (3H, t), 2.91 (2H, t), 3.75 (2H, m), 5.43 (1H, bs), 6.89 (1H, d), 7.07 (2H, d), 7.35 (2H, d), 7.58 (1H, dd), 8.03 (1H, d), 8.39 (1H, s).

Example 29: The Preparation of Compound III-202

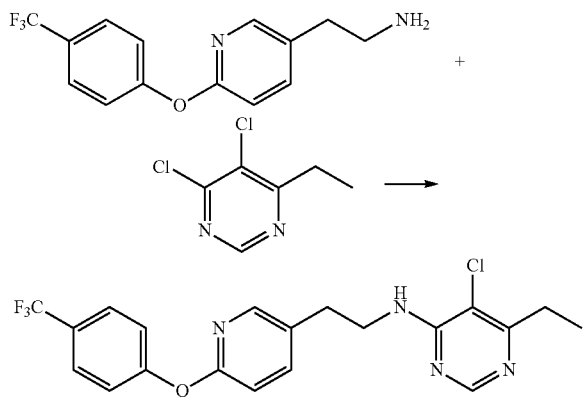

To a solution of 0.28 g (1.0 mmol) 2-(6-(4-(trifluoromethyl)phenoxy)pyridin-3-yl)ethanamine (the preparation refers to Example 27, the difference is replacing 4-chlorophenol to 4-(trifluoromethyl)phenol) and 0.21 g (1.5 mmol) potassium carbonate in 10 mL N,N-dimethylformamide was added 0.18 g (1.0 mmol) 4,5-dichloro-6-ethylpyrimidine (the preparation refers to Example 1, the difference is replacing ethyl 2-chloro-3-oxobutanoate to ethyl 2-chloro-3-oxopentanoate). then the reaction mixture was raised to 80° C. to react for 2 hours, and monitored by TLC (Thin-Layer Chromatography) until the reaction was over, the residual was poured into water, extracted with ethyl acetate, the organic phase was washed with water, and saturated brine successively, dried, filtered and evaporated under reduced pressure, the residual was purified via silica column (ethyl acetate/petroleum ether (boiling point range 60-90° C.)=1:4, as an eluent) to obtain 0.30 g compound III-202 as colourless oil.

$^1$H-NMR (300 MHz, internal standard TMS, solvent CDCl$_3$) δ (ppm): 1.28 (3H, t), 2.78 (2H, m), 2.93 (2H, t), 3.76 (2H, m), 5.43 (1H, bs), 6.96 (1H, d), 7.20-7.23 (2H, m), 7.61-7.66 (3H, m), 8.06 (1H, d), 8.44 (1H, s).

Example 30: The Preparation of Compound III-622

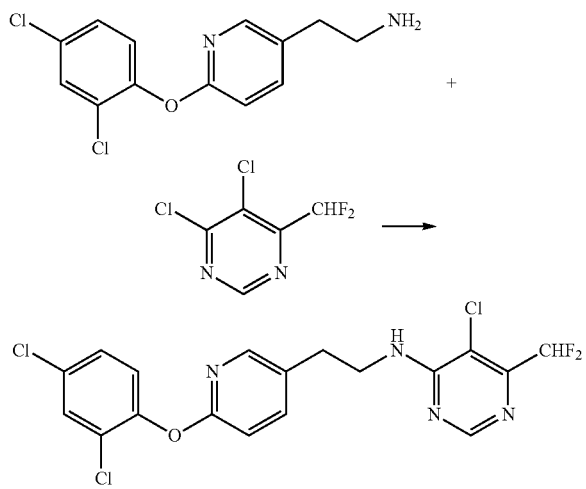

To a solution of 0.28 g (1.0 mmol) 2-(6-(2,4-dichlorophenoxy)pyridin-3-yl)ethanamine (the preparation refers to Example 27, the difference is replacing 4-chlorophenol to 2,4-dichlorophenol) and 0.21 g (1.5 mmol) potassium carbonate in 10 mL N,N-dimethylformamide was added 4,5-dichloro-6-(difluoromethyl)pyrimidine 0.20 g (1.0 mmol). then the reaction mixture was raised to 80° C. to react for 2 hours, and monitored by TLC (Thin-Layer Chromatography) until the reaction was over, the residual was poured into water, extracted with ethyl acetate, the organic phase was washed with water, and saturated brine successively, dried, filtered and evaporated under reduced pressure, the residual was purified via silica column (ethyl acetate/petroleum ether (boiling point range 60-90° C.)=1:4, as an eluent) to obtain 0.32 g compound III-622 as colourless oil. $^1$H-NMR (300 MHz, internal standard TMS, solvent CDCl$_3$) δ (ppm): 2.92 (2H, t), 3.80 (2H, m), 5.72 (1H, bs), 6.54, 6.72, 6.90 (1H, t), 6.89 (1H, s), 6.98 (1H, d), 7.14 (1H, d), 7.27-7.31 (2H, m), 7.48 (1H, d), 7.61 (1H, dd), 7.98 (1H, d), 8.56 (1H, s).

Example 31: The Preparation of Compound III-2630

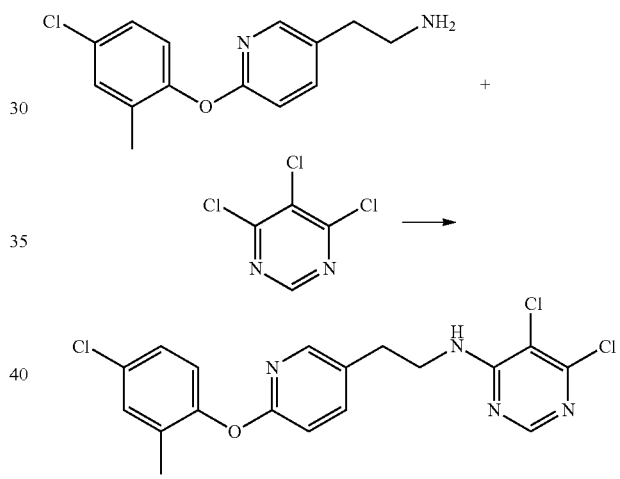

To a solution of 0.26 g (1.0 mmol) 2-(6-(4-chloro-2-methylphenoxy)pyridin-3-yl)ethanamine (the preparation refers to Example 27, the difference is replacing 4-chlorophenol to 4-chloro-2-methylphenol) and 0.21 g (1.5 mmol) potassium carbonate in 10 mL N,N-dimethylformamide was added 0.18 g (1.0 mmol) 4,5,6-trichloropyrimidine (the preparation refers to Example 1, the difference is replacing ethyl 2-chloro-3-oxobutanoate to diethyl 2-chloromalonate). then the reaction mixture was raised to 80° C. to react for 2 hours, and monitored by TLC (Thin-Layer Chromatography) until the reaction was over, the residual was poured into water, extracted with ethyl acetate, the organic phase was washed with water, and saturated brine successively, dried, filtered and evaporated under reduced pressure, the residual was purified via silica column (ethyl acetate/petroleum ether (boiling point range 60-90° C.)=1:4, as an eluent) to obtain 0.32 g compound III-2630 as colourless oil. $^1$H-NMR (300 MHz, internal standard TMS, solvent CDCl$_3$) δ (ppm): 2.15 (3H, s), 2.89 (2H, t), 3.73-3.79 (2H, m), 5.62 (1H, bs), 6.87 (1H, d), 6.98 (1H, d), 7.18-7.22 (2H, m), 7.54 (1H, dd), 8.00 (1H, d), 8.29 (1H, s).

Other compounds represented by the general formula PY of the present invention were prepared according to the above examples.

Physical properties and $^1$HNMR spectrum ($^1$HNMR, 300 MHz, internal standard: TMS, ppm) of some compounds of this invention are as follows:

Compound I-23: m.p. 147.5° C. δppm 2.46 (3H, s), 2.97 (2H, t), 3.78 (2H, q), 5.42 (1H, m), 7.01 (1H, d), 7.10 (2H, d), 7.30 (2H, d), 7.92 (1H, d), 8.40 (1H, s), 8.47 (1H, s).

Compound I-34: m.p. 109.0° C. δppm 2.46 (3H, s), 2.96 (2H, t), 3.79 (2H, q), 3.92 (3H, s), 5.43 (1H, m), 6.94 (1H, d), 7.12 (2H, d), 7.28 (2H, d), 8.28 (1H, d), 8.40 (1H, s), 8.82 (1H, s).

Compound I-35: yellow oil. δppm 1.38 (3H, t), 2.46 (3H, s), 2.96 (2H, t), 3.79 (2H, q), 4.38 (2H, q), 5.43 (1H, m), 6.93 (1H, d), 7.12 (2H, d), 7.28 (2H, d), 8.28 (1H, d), 8.40 (1H, s), 8.83 (1H, s).

Compound I-80: δppm 2.47 (3H, s), 2.95 (2H, t), 3.79 (2H, q), 5.55 (1H, m), 7.09 (1H, d), 7.18 (2H, m), 7.37 (1H, s), 7.93 (1H, m), 8.41 (2H, m).

Compound I-196: δppm 2.46 (3H, t), 2.96 (2H, t), 3.75 (3H, s), 3.80 (2H, dd), 5.49 (1H, t), 6.87 (2H, s), 7.02 (1H, d), 7.09 (1H, d), 7.88 (1H, d), 8.41 (2H, s).

Compound I-255: yellow oil. δppm 1.27 (3H, t), 2.79 (2H, q), 2.97 (2H, t), 3.80 (2H, q), 5.48 (1H, m), 7.02 (1H, d), 7.10 (2H, d), 7.30 (2H, d), 7.92 (1H, d), 8.46 (1H, s), 8.47 (1H, s).

Compound I-266: m.p. 102.2° C. δppm 1.26 (3H, t), 2.79 (2H, q), 2.97 (2H, t), 3.79 (2H, q), 3.92 (3H, s), 5.44 (1H, m), 6.94 (1H, d), 7.12 (2H, d), 8.29 (2H, d), 8.27 (1H, d), 8.45 (1H, s), 8.82 (1H, s).

Compound I-267: yellow oil. δppm 1.26 (3H, t), 1.38 (3H, t), 2.79 (2H, t), 2.98 (2H, t), 3.79 (2H, q), 4.38 (2H, q), 5.43 (1H, m), 6.93 (1H, d), 7.12 (2H, d), 7.29 (2H, d), 8.27 (1H, d), 8.45 (1H, s), 8.83 (1H, s).

Compound I-312: δppm 1.27 (3H, t), 2.80 (3H, q), 2.96 (2H, t), 3.80 (2H, q), 5.51 (1H, m), 7.09 (1H, d), 7.18 (2H, m), 7.37 (1H, s), 7.93 (1H, m), 8.40 (1H, s), 8.46 (1H, s).

Compound I-428: δppm 1.26 (3H, t), 2.79 (2H, dd), 2.96 (2H, t), 3.75 (3H, s), 3.81 (2H, dd), 5.50 (1H, t), 6.87 (2H, d), 7.02 (1H, d), 7.10 (1H, d), 7.88 (1H, s), 8.40 (1H, s), 8.45 (1H, s).

Compound I-467: m.p. 102-103° C. δppm 2.46 (3H, s), 2.96 (2H, t), 3.78 (2H, q), 5.43 (1H, s), 7.11 (2H, d), 7.27 (2H, d), 7.78 (1H, s), 7.97 (1H, s), 8.40 (1H, s).

Compound I-486: m.p. 92-93° C. δppm 2.47 (3H, s), 2.98 (2H, t), 3.80 (2H, q), 5.44 (1H, s), 7.13 (2H, d), 7.30 (2H, d), 7.98 (1H, s), 8.28 (1H, s), 8.41 (1H, s).

Compound I-502: m.p. 128.5° C. δppm 2.49 (3H, s), 2.89 (2H, t), 3.63 (2H, q), 5.34 (1H, m), 7.06 (2H, d), 7.28 (2H, d), 7.72 (2H, s), 8.24 (1H, s), 8.38 (1H, s), 8.46 (1H, s).

Compound I-602: colourless oil. Δppm 2.88 (2H, t), 4.06 (2H, q), 5.49 (s, 1H), 7.21 (4H, m,), 8.28 (1H, s), 8.28 (1H, s), 68.450 (1H, s).

Compound I-618: m.p. 168.9° C. δppm 1.26 (3H, t), 2.79 (2H, q), 2.97 (2H, t), 3.80 (2H, q), 5.47 (1H, m), 5.83 (2H, s), 7.13 (2H, d), 7.30 (2H, d), 8.28 (1H, s), 8.40 (1H, s), 8.44 (1H, s).

Compound I-699: m.p. 146-147° C. δppm 2.45 (3H, s), 2.96 (2H, t), 3.78 (2H, q), 5.45 (1H, s), 7.11 (2H, d), 7.28 (2H, d), 7.84 (1H, s), 8.41 (1H, s).

Compound I-815: m.p. 98-100° C. δppm 1.26 (3H, t), 2.79 (2H, q), 2.96 (2H, t), 3.79 (2H, q), 5.43 (1H, s), 7.11 (2H, d), 7.27 (2H, d), 7.84 (1H, s), 8.46 (1H, s).

Compound I-929: yellow oil. δppm 2.46 (3H, s), 2.96 (2H, t), 3.87 (2H, q), 5.47 (1H, m), 7.09 (1H, m), 7.14 (2H, d), 7.28 (2H, d), 7.98 (1H, d), 8.29 (1H, d), 8.40 (1H, s).

Compound I-987: yellow oil. δppm 1.26 (3H, t), 2.79 (2H, q), 2.96 (2H, t), 3.78 (2H, q), 5.46 (1H, m), 7.13 (1H, q), 7.15 (2H, d), 7.29 (2H, d), 8.00 (1H, d), 8.30 (1H, d), 8.45 (1H, s).

Compound I-1045: m.p. 80-83° C. δppm 1.39 (3H, t), 2.46 (3H, s), 2.94 (2H, t), 3.77 (2H, q), 5.47 (1H, s), 7.06 (1H, m), 7.12 (2H, d), 7.26 (2H, d), 8.27 (1H, m), 8.40 (1H, s).

Compound I-1199: m.p. 147-149° C. δppm 2.47 (3H, s), 2.97 (2H, t), 3.06 (3H, d), 3.62-3.79 (2H, q), 5.50 (1H, t), 7.12 (2H, d), 7.16 (1H, dd), 7.32 (2H, d), 7.86 (1H, s), 8.20 (1H, dd), 8.41 (1H, s), 8.64 (1H, dd).

Compound I-1219: m.p. 113-114° C. δppm 1.39 (3H, t), 2.79 (3H, s), 2.95 (2H, t), 3.78 (2H, q), 4.41 (2H, q), 5.49 (1H, t), 7.09 (3H, m), 7.27 (2H, m), 8.26 (2H, m), 8.45 (1H, s).

Compound I-1414: δppm 2.47 (3H, s), 2.96 (2H, t), 3.80 (2H, q), 5.46 (1H, m), 7.20 (2H, s), 7.37 (1H, s), 8.00 (1H, d), 8.24 (1H, d), 8.41 (1H, s).

Compound I-1472: δppm 1.27 (3H, t), 2.80 (2H, q), 2.97 (2H, t), 3.80 (2H, q), 5.47 (1H, m), 7.21 (2H, s), 7.37 (1H, s), 8.00 (1H, d), 8.25 (1H, d), 8.46 (1H, s).

Compound I-1646: δppm 2.46 (3H, t), 2.96 (2H, t), 3.74 (3H, s), 3.81 (2H, dd), 5.48 (1H, t), 6.89 (2H, t), 7.11 (1H, d), 7.96 (1H, d), 8.23 (1H, d), 8.41 (1H, s).

Compound I-1704: δppm 1.26 (3H, t), 2.79 (2H, dd), 2.96 (2H, t), 3.73 (3H, s), 3.79 (2H, dd), 5.48 (1H, t), 6.88 (2H, d), 7.12 (1H, d), 7.96 (1H, d), 8.23 (1H, s), 8.45 (1H, s).

Compound I-1762: δppm 2.50 (3H, s), 2.96 (2H, t), 3.78 (2H, q), 5.54 (1H, m), 7.01 (1H, d), 7.12 (1H, d), 7.30 (2H, d), 7.90 (1H, m), 8.41 (1H, s), 8.44 (1H, s).

Compound I-1820: δppm 1.26 (3H, t), 2.81 (3H, q), 2.97 (2H, t), 3.78 (2H, q), 5.55 (1H, m), 7.01 (1H, d), 7.11 (2H, d), 7.30 (2H, d), 7.90 (1H, m), 8.44 (1H, s).

Compound I-1878: δppm 2.50 (3H, s), 2.97 (2H, t), 3.79 (2H, q), 5.53 (1H, m), 7.14 (2H, d), 7.30 (3H, m), 7.99 (1H, s), 8.27 (1H, s), 8.40 (1H, s).

Compound I-1936: δppm 1.26 (3H, t), 2.81 (3H, q), 2.97 (2H, t), 3.79 (2H, q), 5.54 (1H, m), 7.13 (2H, d), 7.31 (2H, d), 7.98 (1H, m), 8.27 (1H, s), 8.44 (1H, s).

Compound I-2052: δppm 1.30 (3H, t), 2.83 (2H, q), 2.95 (2H, t), 3.79 (2H, q), 5.61 (1H, m), 7.09 (1H, d), 7.18 (2H, m), 7.33 (1H, s), 7.93 (1H, m), 8.43 (1H, d).

Compound I-2400: δppm 2.98 (3H, t), 3.85 (2H, q), 5.77 (1H, m), 6.73 (1H, d), 7.10 (1H, d), 7.19 (2H, m), 7.38 (1H, s), 7.94 (1H, m), 8.40 (1H, s), 8.59 (1H, s).

Compound I-2458: δppm 2.98 (2H, t), 3.75 (3H, s), 3.87 (2H, dd), 5.77 (1H, t), 6.72 (1H, t), 6.89 (2H, t), 7.03 (1H, d), 7.10 (1H, t), 7.88 (1H, dd), 8.40 (1H, s), 8.59 (1H, s).

Compound I-2555: brown oil. δppm 8.576 (s, 1H, pyrimidine-H), 7.965-7.972 (d, 1H, pyridine-6-H), 7.776-7.783 (d, 1H, pyridine-4-H), 7.128-7.294 (dd, 4H, Ar—H), 6.726-7.100 (t, 1H, F$_2$C—H), 3.828-3.849 (q, 2H, N—CH$_2$—C), 2.951-2.999 (t, 2H, C—CH$_2$—Ar).

Compound I-2611: m.p. 156-157° C. δppm 8.583 (s, 1H, pyrimidine-H), 8.337-8.393 (m, 3H, pyridine-H), 7.164-7.322 (dd, 4H, Ar—H), 6.550-6.909 (t, 1H, F$_2$C—H), 5.739 (s, 1H, NH), 3.816-3.883 (q, 2H, N—CH$_2$—C), 2.968-3.015 (t, 2H, C—CH$_2$—Ar).

Compound I-2690: δppm 2.98 (2H, t), 3.74 (3H, s), 3.86 (2H, dd), 5.76 (1H, t), 6.72 (1H, t), 6.88 (2H, d), 7.13 (1H, d), 7.96 (1H, d), 8.23 (1H, s), 8.58 (1H, s).

Compound I-2787: δppm 8.575 (s, 1H, pyrimidine-H), 7.965-7.972 (d, 1H, pyridine-6-H), 7.775-7.782 (d, 1H, pyridine-4-H), 7.105-7.295 (dd, 4H, Ar—H), 5.882 (s, 1H, NH), 3.815-3.881 (q, 2H, N—CH$_2$—C), 2.955-3.001 (t, 2H, C—CH$_2$—Ar).

Compound I-2843: m.p. 123-124° C. δppm 8.577 (s, 1H, pyrimidine-H), 8.336-8.394 (m, 3H, pyridine-H), 7.152-7.325 (dd, 4H, Ar—H), 5.917 (s, 1H, NH), 3.826-3.917 (q, 2H, N—CH$_2$—C), 2.972-3.020 (t, 2H, C—CH$_2$—Ar).

Compound I-3077: m.p. 130-132° C. δppm 2.46 (3H, s), 2.95 (2H, t), 3.77 (2H, q), 5.50 (1H, s), 7.16 (3H, m), 7.27 (2H, m), 7.48 (1H, d), 8.40 (1H, s).

Compound I-4121: δppm 2.50 (3H, s), 2.95 (2H, t), 3.77 (2H, q), 5.57 (1H, m), 7.16 (3H, m), 7.29 (2H, m), 7.49 (1H, d), 8.40 (1H, s).

Compound I-5221: m.p. 121-124° C. δppm 1.26 (3H, t), 2.78 (2H, q), 2.95 (2H, t), 3.78 (2H, m), 3.84 (6H, s), 5.44 (1H, s), 5.78 (1H, s), 7.20 (4H, m), 8.45 (1H, s).

Compound I-6729: m.p. 102.8° C. δppm 2.49 (3H, s), 2.88 (2H, t), 3.81 (2H, m), 7.11 (2H, d), 18 (1H, d), 7.30 (2H, d), 7.52 (1H, d), 8.17 (1H, d), 8.50 (1H, s), 8.78 (1H, s), 9.40 (1H, s).

Compound I-6731: m.p. 148.6° C. δppm 2.30 (3H, s), 2.49 (3H, s), 2.93 (2H, t), 3.81 (2H, m), 7.27-7.05 (8H, m), 7.29 (2H, d), 7.51 (1H, d), 8.14 (1H, d), 8.47 (1H, s), 8.77 (1H, s), 9.33 (1H, s).

Compound I-6732: m.p. 164.6° C. δppm 2.50 (3H, s), 2.94 (2H, t), 3.81 (2H, m), 7.09 (2H, d), 7.18 (1H, d), 7.30 (2H, d), 8.18 (1H, d), 8.50 (1H, s), 8.81 (1H, s), 9.28 (1H, s).

Compound I-6733: m.p. 113.7° C. δppm 2.35 (3H, s), 2.89 (2H, t), 3.64 (2H, m), 7.09 (2H, d), 7.16 (1H, d), 7.30 (2H, d), 7.37 (1H, m), 8.15 (1H, d), 8.19 (1H, d), 8.51 (1H, s).

Compound I-6734: m.p. 56.9° C. δppm 2.37 (3H, s), 2.90 (2H, t), 3.66 (2H, m), 7.09 (2H, d), 7.16 (1H, d), 7.29 (2H, d), 7.49 (1H, m), 8.16 (1H, d), 8.30 (1H, s), 8.50 (1H, s).

Compound I-6735: m.p.>300° C. δppm 2.35 (3H, s), 2.88 (2H, t), 3.62 (2H, m), 7.08 (2H, d), 7.15 (1H, d), 7.36 (1H, m), 8.15 (1H, d), 7.32 (2H, d), 8.20 (1H, s), 8.48 (1H, s).

Compound I-6790: δppm 1.23 (3H, t), 2.51 (3H, s), 2.74 (2H, q), 2.94 (2H, t), 3.77 (2H, q), 5.40 (1H, m), 7.11 (2H, d), 7.26 (2H, d), 7.84 (1H, s).

Compound I-6791: yellow oil. δppm 1.23 (3H, t), 2.50 (3H, s), 2.74 (2H, q), 2.96 (2H, t), 3.79 (2H, q), 5.39 (1H, m), 5.83 (2H, s), 7.13 (2H, d), 7.30 (2H, d), 8.26 (1H, s), 8.40 (1H, s).

Compound I-6793: m.p. 116.0° C. δppm 1.23 (3H, t), 2.51 (3H, s), 2.74 (2H, q), 2.94 (2H, t), 3.77 (2H, q), 5.40 (1H, m), 7.10 (1H, m), 7.14 (2H, d), 7.29 (2H, d), 8.00 (1H, d), 8.31 (1H, d).

Compound I-6795: yellow oil. δppm 1.24 (3H, t), 2.46 (3H, s), 2.74 (2H, q), 2.96 (2H, t), 3.78 (2H, q), 5.40 (1H, m), 7.01 (1H, d), 7.10 (2H, d), 7.30 (2H, d), 7.91 (1H, d), 8.47 (1H, s).

Compound I-6796: m.p. 90.8° C. δppm 1.23 (3H, t), 1.38 (3H, t), 2.51 (3H, s), 2.74 (2H, q), 2.95 (2H, t), 3.78 (2H, q), 4.38 (2H, q), 5.38 (1H, m), 6.93 (1H, d), 7.11 (2H, d), 7.29 (2H, d), 8.28 (1H, d), 8.83 (1H, s).

Compound I-6797: yellow oil. δppm 1.23 (3H, t), 2.49 (3H, s), 2.74 (2H, q), 2.95 (2H, t), 3.78 (2H, q), 3.92 (3H, s), 5.39 (1H, m), 6.93 (1H, d), 7.11 (2H, d), 7.29 (2H, d), 8.28 (1H, d), 8.82 (1H, s).

Compound I-6806: δppm 1.24 (3H, t), 2.51 (3H, s), 2.75 (2H, q), 2.94 (2H, t), 3.79 (2H, q), 5.40 (1H, m), 7.09 (1H, d), 7.17 (2H, m), 7.33 (1H, s), 7.93 (1H, m), 8.41 (1H, s).

Compound II-19: δppm 2.52 (3H, s), 2.92 (2H, t), 3.75 (2H, dd), 5.43 (1H, t), 6.81-7.01 (4H, m), 7.19 (2H, d), 7.28 (2H, d), 8.39 (1H, s).

Compound II-21: δppm 2.46 (3H, s), 2.92 (2H, t), 3.75 (2H, dd), 5.42 (1H, t), 6.89 (1H, t), 6.92 (2H, d), 7.15-7.22 (3H, m), 7.47 (1H, d), 8.39 (1H, s).

Compound II-25: δppm 2.45 (3H, s), 2.95 (2H, t), 3.70-3.83 (2H, q), 5.44 (1H, t), 6.84 (2H, d), 7.00 (2H, d), 7.06 (1H, s), 7.26 (2H, d), 8.40 (1H, s).

Compound II-53: m.p. 140-142° C. δppm 2.65 (3H, s), 3.13 (2H, t), 3.65-3.76 (2H, q), 6.93 (1H, d), 7.17 (2H, d), 7.35 (2H, d), 8.31 (1H, d), 8.47 (1H, s), 8.62 (1H, t), 9.14 (1H, d).

Compound II-154: δppm 2.46 (3H, s), 2.95 (2H, t), 3.77 (2H, dd), 5.42 (1H, t), 6.92 (1H, d), 7.00 (2H, d), 7.25 (2H, d), 7.43 (1H, d), 7.75 (1H, s), 8.39 (1H, s).

Compound II-204: δppm 2.47 (3H, s), 2.96 (2H, t), 3.77 (2H, dd), 5.43 (1H, t), 6.93 (1H, t), 7.02 (2H, d), 7.26 (2H, d), 7.37 (1H, dd), 7.48 (1H, dd), 8.40 (1H, s).

Compound II-235: m.p. 140-142° C. δppm 1.25 (3H, s), 2.45 (3H, s), 2.86 (2H, t), 3.72 (2H, q), 5.41 (1H, s), 6.79 (2H, d), 7.08 (2H, d), 8.39 (2H, m).

Compound II-236: δppm 2.25 (3H, s), 2.45 (3H, s), 2.90 (2H, t), 3.62-3.81 (2H, q), 5.43 (1H, t), 6.74 (2H, d), 7.14 (2H, d), 7.40 (1H, d), 7.77 (1H, d), 8.38 (1H, s).

Compound II-254: m.p. 183-185° C. δppm 2.45 (3H, s), 2.86 (2H, t), 3.66-3.83 (2H, q), 5.43 (1H, t), 6.80 (2H, d), 7.08 (2H, d), 8.39 (1H, s).

Compound II-274: m.p. 130-132° C. δppm 2.929-2.953 (t, 2H), 3.744-3.765 (q, 2H), 5.65 (s, 1H), 6.830-7.230 (dd, 4H), 8.392 (s, 1H).

Compound II-299: δppm 1.23 (3H, t), 2.78 (2H, dd), 2.92 (2H, t), 3.75 (2H, dd), 5.44 (1H, t), 6.85 (1H, d), 6.91 (2H, d), 7.17-7.23 (3H, m), 7.46 (1H, d), 8.44 (1H, s).

Compound II-432: δppm 1.26 (3H, t), 2.78 (2H, dd), 2.95 (2H, t), 3.77 (2H, dd), 5.44 (1H, t), 6.92 (1H, d), 7.00 (2H, d), 7.25 (2H, d), 7.42 (1H, d), 7.73 (1H, s), 8.44 (1H, s).

Compound II-443: m.p. 101.0° C. δppm 1.25 (3H, t), 2.77 (2H, dd), 2.92 (2H, t), 3.74 (2H, dd), 5.42 (1H, t), 6.79 (2H, d), 7.18 (2H, d), 8.32 (2H, s), 8.43 (1H, s).

Compound II-482: δppm 1.26 (3H, t), 2.78 (2H, dd), 2.98 (2H, t), 3.78 (2H, dd), 5.44 (1H, t), 6.93 (1H, t), 7.08 (2H, d), 7.27 (2H, d), 7.37 (1H, dd), 7.48 (1H, dd), 8.44 (1H, s).

Compound II-1687: δppm 2.46 (3H, s), 2.93 (2H, t), 3.75-3.96 (5H, m), 5.43 (1H, t), 6.77-6.87 (4H, m), 6.93 (1H, d), 7.23 (2H, d), 8.40 (1H, s).

Compound II-1737: δppm 2.47 (3H, s), 2.95 (2H, t), 3.75-3.91 (5H, m), 5.42 (1H, t), 6.80-7.04 (5H, m), 7.53 (2H, d), 8.41 (1H, s).

Compound II-1965: δppm 1.26 (3H, t), 2.79 (2H, dd), 2.95 (2H, t), 3.72-3.95 (5H, m), 5.45 (1H, t), 6.78-6.90 (4H, m), 6.94 (1H, d), 7.24 (2H, d), 8.45 (1H, s).

Compound II-2015: δppm 1.26 (3H, t), 2.79 (2H, dd), 2.95 (2H, t), 3.75-3.95 (5H, m), 5.48 (1H, t), 6.80-6.88 (2H, q), 6.93 (2H, d), 7.01 (1H, d), 7.53 (2H, d), 8.45 (1H, s).

Compound II-8917: m.p. 93.3° C. δppm 2.94 (2H, t), 3.81 (2H, dd), 5.70 (1H, t), 6.72 (1H, t), 6.90-6.97 (3H, q), 7.16-7.23 (3H, q), 7.47 (1H, d), 8.57 (1H, s).

Compound II-8921: m.p. 106-107° C. δppm 2.945-2.992 (2H, t), 3.797-3.864 (2H, q), 5.717 (1H, s), 6.549-6.848 (1H, t), 6.854-7.237 (7H, m), 8.583 (1H, s).

Compound II-8965: m.p. 109-110° C. δppm 2.944-2.990 (2H, t), 3.798-3.865 (2H, q), 5.717 (1H, s), 6.542-6.900 (1H, t), 7.010-7.588 (8H, m), 8.574 (1H, s).

Compound II-9058: δppm 2.938-2.984 (2H, t), 3.790-3.858 (2H, q), 6.545-6.903 (1H, t), 6.992-7.458 (4H, dd), 6.930-6.959 (1H, d), 7.478-7.487 (1H, d), 7.952-7.960 (1H, s), 8.571 (1H, s).

Compound II-9073: m.p. 77-78° C. δppm 2.970-3.016 (2H, t), 3.812-3.878 (2H, q), 5.738 (1H, s), 6.549-6.906 (1H, t), 7.061-7.319 (4H, dd), 7.005-7.035 (1H, d), 7.698-7.727 (1H, d), 8.233 (1H, s), 8.575 (1H, s).

Compound 物 II-9170: m.p. 154-158° C. δppm 2.951-2.975 (2H, t), 3.800-3.821 (2H, q), 6.714-6.874 (1H, t), 6.844-7.233 (4H, dd), 8.569 (1H, s).

Compound II-9336: m.p. 130-131° C. δppm 2.942-2.989 (2H, t), 3.799-3.866 (2H, q), 6.994-7.459 (4H, dd), 6.936-6.965 (1H, d), 7.480-7.488 (1H, d), 7.593-7.961 (1H, d), 8.571 (1H, s).

Compound II-9351: m.p. 128-129° C. δppm 2.975-3.021 (2H, t), 3.820-3.887 (2H, q), 5.875 (1H, s), 7.066-7.322 (4H, dd), 7.009-7.039 (1H, d), 7.704-7.731 (1H, d), 8.238 (1H, s), 8.580 (1H, s).

Compound II-10633: δppm 2.98 (2H, t), 3.79 (3H, t), 3.86 (2H, dd) 5.74 (1H, s), 6.72 (1H, t), 6.84-7.05 (5H, m), 7.53 (2H, d), 8.58 (1H, s).

Compound III-1: colourless oil. δppm 2.50 (3H, s), 2.88 (2H, t), 3.74 (2H, m), 5.45 (1H, bs), 6.87 (1H, d), 7.09-7.22 (3H, m), 7.36-7.42 (2H, m), 7.56 (1H, dd), 8.05 (1H, d), 8.38 (1H, s).

Compound III-5: colourless oil.

Compound III-6: colourless oil. δppm 2.46 (3H, s), 2.92 (2H, t), 3.75 (2H, m), 5.42 (1H, bs), 6.90 (1H, d), 7.03 (1H, dd), 7.13-7.18 (2H, m), 7.29 (1H, d), 7.59 (1H, dd), 8.05 (1H, d), 8.39 (1H, s).

Compound III-16: colourless oil. δppm 2.35 (3H, s), 2.52 (3H, s), 2.88 (2H, t), 3.70-3.77 (2H, m), 5.42 (1H, bs), 6.85 (1H, d), 7.01 (2H, d), 7.19 (2H, d), 7.53 (1H, dd), 8.03 (1H, d), 8.38 (1H, s).

Compound III-19: colourless oil. δppm 2.46 (3H, s), 2.89 (2H, t), 3.70-3.77 (2H, m), 3.82 (3H, s), 5.42 (1H, bs), 6.83 (1H, d), 6.92 (2H, d), 7.06 (2H, d), 7.53 (1H, dd), 8.03 (1H, d), 8.38 (1H, s).

Compound III-21: colourless oil.

Compound III-22: colourless oil. δppm 2.46 (3H, t), 2.93 (2H, t), 3.76 (2H, m), 5.43 (1H, bs), 6.95 (1H, d), 7.20-7.28 (2H, m), 7.60-7.66 (3H, m), 8.06 (1H, d), 8.39 (1H, s).

Compound III-82: colourless oil. δppm 2.46 (3H, s), 2.90 (2H, t), 3.74 (2H, m), 5.42 (1H, bs), 6.97 (1H, d), 7.14 (1H, d), 7.28 (1H, d), 7.49 (1H, d), 7.62 (1H, dd), 7.97 (1H, d), 8.38 (1H, s).

Compound III-83: colourless oil. δppm 2.46 (3H, s), 2.91 (2H, t), 3.75 (2H, m), 5.42 (1H, bs), 6.97 (1H, d), 7.16 (1H, dd), 7.22 (1H, d), 7.40 (1H, d), 7.61 (1H, dd), 7.99 (1H, d), 8.39 (1H, s).

Compound III-110: colourless oil. δppm 2.14 (3H, t), 2.46 (3H, t), 2.89 (2H, t), 3.73 (2H, m), 5.42 (1H, bs), 6.86 (1H, d), 6.97 (1H, d), 7.17-7.25 (2H, m), 7.56 (1H, dd), 7.99 (1H, d), 8.38 (1H, s).

Compound III-121: colourless oil.

Compound III-181: colourless oil. δppm 1.26 (3H, t), 2.78 (2H, m), 2.90 (2H, t), 3.75 (2H, m), 5.45 (1H, bs), 6.87 (1H, d), 7.11-7.22 (3H, m), 7.36-7.42 (2H, m), 7.56 (1H, dd), 8.05 (1H, d), 8.43 (1H, s).

Compound III-185: colourless oil. δppm 1.26 (3H, t), 2.78 (2H, m), 2.88 (2H, t), 3.74 (2H, m), 5.43 (1H, bs), 6.94 (1H, d), 7.20 (2H, d), 7.28-7.32 (1H, m), 7.47 (1H, d), 7.59 (1H, dd), 8.00 (1H, d), 8.43 (1H, s).

Compound III-186: colourless oil. δppm 1.26 (3H, t), 2.75-2.83 (2H, m), 2.89-2.96 (2H, m), 3.72-3.79 (2H, m), 5.47 (1H, bs), 6.91 (1H, d), 7.03 (1H, d), 7.13-7.19 (2H, m), 7.29-7.34 (1H, m), 7.60 (1H, dd), 8.06 (1H, s), 8.44 (1H, s).

Compound III-187: colourless oil. δppm 1.26 (3H, t), 2.79 (2H, m), 2.91 (2H, t), 3.75 (2H, m), 5.43 (1H, bs), 6.89 (1H, d), 7.07 (1H, d), 7.35 (1H, d), 7.58 (1H, dd), 8.03 (1H, dd), 8.43 (1H, s).

Compound III-196: colourless oil. δppm 1.23 (3H, t), 2.35 (3H, s), 2.74-2.91 (5H, m), 3.70-3.77 (2H, m), 5.46 (1H, bs), 6.85 (1H, d), 6.99 (2H, d), 7.19 (2H, d), 7.54 (1H, dd), 8.03 (1H, d), 8.43 (1H, s).

Compound III-199: colourless oil. δppm 1.26 (3H, t), 2.75-2.82 (2H, m), 2.88 (2H, t), 3.70-3.77 (2H, m), 3.82 (3H, s), 5.42 (1H, bs), 6.83 (1H, d), 6.92 (2H, d), 7.06 (2H, d), 7.54 (1H, dd), 8.03 (1H, d), 8.43 (1H, s).

Compound III-201: colourless oil.

Compound III-262: colourless oil. δppm 1.26 (3H, t), 2.79 (2H, m), 2.90 (2H, t), 3.74 (2H, m), 5.42 (1H, bs), 6.97 (1H, d), 7.14 (1H, d), 7.29 (1H, d), 7.48 (1H, d), 7.61 (1H, dd), 7.97 (1H, d), 8.43 (1H, s).

Compound III-263: colourless oil. δppm 1.26 (3H, t), 2.81 (2H, m), 2.91 (2H, t), 3.75 (2H, m), 5.43 (1H, bs), 6.98 (1H, d), 7.14-7.22 (2H, m), 7.40 (2H, d), 7.63 (1H, dd), 7.99 (1H, s), 8.44 (1H, s).

Compound III-290: colourless oil. δppm 1.26 (3H, t), 2.14 (3H, s), 2.78 (2H, m), 2.89 (2H, t), 3.74 (2H, m), 5.42 (1H, bs), 6.86 (1H, d), 6.97 (1H, d), 7.19 (1H, dd), 7.25 (1H, d), 7.57 (1H, dd), 8.00 (1H, d), 8.43 (1H, s).

Compound III-301: colourless oil.

Compound III-541: colourless oil. δppm 2.91 (2H, t), 3.81 (2H, m), 5.73 (1H, bs), 6.54, 6.71, 6.83 (1H, t), 6.88 (1H, d), 7.09-7.18 (2H, m), 7.22 (1H, t), 7.36-7.42 (2H, m), 7.56 (1H, dd), 8.07 (1H, d), 8.56 (1H, s).

Compound III-545: colourless oil. δppm 2.92 (2H, t), 3.80 (2H, m), 5.71 (1H, bs), 6.53, 6.71, 6.89 (1H, t), 6.95 (1H, d), 7.18-7.32 (3H, m), 7.47 (1H, d), 7.59 (1H, dd), 8.00 (1H, d), 8.56 (1H, s).

Compound III-546: colourless oil. δppm 2.94 (2H, t), 3.77-3.82 (2H, m), 5.74 (1H, bs), 6.54, 6.72, 6.89 (1H, t), 6.91 (1H, d), 7.02 (1H, d), 7.13-7.18 (2H, m), 7.29-7.35 (1H, m), 7.61 (1H, dd), 8.06 (1H, d), 8.61 (1H, s).

Compound III-547: colourless oil. δppm 2.93 (2H, t), 3.80 (2H, m), 5.72 (1H, bs), 6.53, 6.72, 6.89 (1H, t), 6.92 (1H, d), 7.07 (2H, d), 7.35 (2H, d), 7.58 (1H, dd), 8.03 (1H, s), 8.56 (1H, s).

Compound III-556: colourless oil. δppm 2.35 (3H, t), 2.91 (2H, t), 3.76-3.84 (2H, m), 5.73 (1H, bs), 6.54, 6.72, 6.84 (1H, t), 6.89 (1H, d), 7.01 (1H, d), 7.19 (1H, d), 7.55 (1H, dd), 8.04 (1H, d), 8.56 (1H, s).

Compound III-559: colourless oil. δppm 2.91 (2H, t), 3.76-3.81 (5H, m), 5.73 (1H, bs), 6.54, 6.72, 6.84 (1H, t), 6.91 (1H, d), 6.94 (1H, dd), 7.06 (1H, dd), 7.54 (1H, dd), 8.03 (1H, d), 8.56 (1H, s).

Compound III-561: colourless oil. δppm 2.95 (2H, t), 3.81 (2H, m), 5.74 (1H, bs), 6.54, 6.72, 6.89 (1H, t), 6.95 (1H, d), 7.32 (1H, d), 7.39 (1H, s), 7.44-7.54 (2H, m), 7.62 (1H, dd), 8.05 (1H, d), 8.57 (1H, s).

Compound III-562: colourless oil. δppm 2.95 (2H, t), 3.81 (2H, m), 5.74 (1H, bs), 6.54, 6.72, 6.89 (1H, t), 6.97 (1H, d), 7.21-7.24 (2H, m), 7.61-7.67 (3H, m), 8.06 (1H, d), 8.57 (1H, s).

Compound III-623: colourless oil. δppm 2.92 (2H, t), 3.80 (2H, m), 5.72 (1H, bs), 6.54, 6.72, 6.89 (1H, t), 6.91 (1H, s), 6.99 (1H, d), 7.15-7.22 (2H, m), 7.40 (1H, d), 7.61 (1H, dd), 8.00 (1H, d), 8.57 (1H, s).

Compound III-650: colourless oil. δppm 2.13 (3H, s), 2.91 (2H, t), 3.79 (2H, m), 5.66 (1H, bs), 6.53, 6.72, 6.86 (1H, t), 6.89 (1H, s), 6.97 (1H, d), 7.17-7.25 (2H, m), 7.57 (1H, dd), 8.01 (1H, d), 8.56 (1H, s).

Compound III-661: colourless oil.

Compound III-2521: colourless oil. δppm 2.90 (2H, t), 3.74-3.81 (2H, m), 5.60 (1H, bs), 6.83-6.89 (1H, m), 7.09-7.11 (2H, m), 7.13-7.22 (1H, m), 7.37-7.42 (2H, m), 7.49-7.56 (1H, m), 8.15 (1H, d), 8.29 (1H, s).

Compound III-2526: colourless oil. δppm 2.92 (2H, t), 3.74-3.81 (2H, m), 5.62 (1H, bs), 6.91 (1H, d), 7.02 (1H, d), 7.14-7.18 (2H, m), 7.29-7.34 (1H, m), 7.57-7.60 (1H, m), 8.05 (1H, d), 8.32 (1H, s).

Compound III-2527: colourless oil. δppm 2.91 (2H, t), 3.74-3.81 (2H, m), 5.60 (1H, bs), 6.90 (1H, d), 7.07 (2H, dd), 7.35 (2H, dd), 7.54 (1H, dd), 8.03 (1H, d), 8.29 (1H, s).

Compound III-2536: colourless oil. δ(CDCl$_3$): 2.36 (3H, s), 2.89 (2H, t), 3.73-3.79 (2H, m), 5.62 (1H, bs), 6.85 (1H, d), 6.98-7.02 (2H, m), 7.20 (2H, d), 7.54 (1H, dd), 8.03 (1H, d), 8.29 (1H, s).

Compound III-2539: colourless oil. δppm 2.89 (2H, t), 3.73-3.79 (2H, m), 3.81 (3H, t), 5.61 (1H, bs), 6.83 (1H, d), 6.92 (2H, dd), 7.05 (2H, dd), 7.52 (1H, dd), 8.03 (1H, d), 8.29 (1H, s).

Compound III-2541: colourless oil. δppm 2.93 (2H, t), 3.75-3.82 (2H, m), 5.62 (1H, bs), 6.94 (1H, d), 7.32 (1H, d), 7.40-7.51 (3H, m), 7.60 (1H, dd), 8.04 (1H, d), 8.30 (1H, s).

Biological Testing

The compounds of the present invention exhibit both excellent fungicidal activity against many fungi in agricultural field and better insecticidal and acaricidal activities.

Except for the controls CK1-CK21 (known compounds illustrated in background technology) listed in following Table 303-310, according to the prior art, the following compounds CK22-CK84, diflumetorim and flufenerim were also prepared as controls, all the controls were self-made, they are listed in Table 302.

TABLE 302

| No. | Structure |
|---|---|
| CK22 | 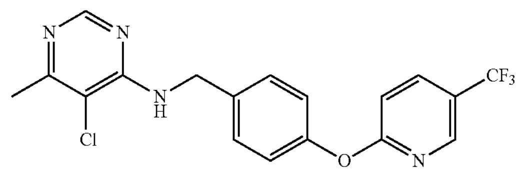 [SMILES: Cc1ncnc(NCc2ccc(Oc3ccc(C(F)(F)F)cn3)cc2)c1Cl] |
| CK23 | 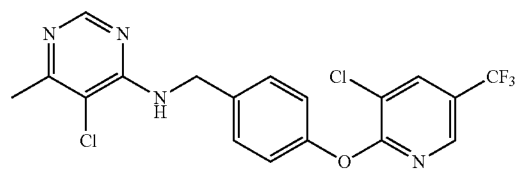 [SMILES: Cc1ncnc(NCc2ccc(Oc3ncc(C(F)(F)F)cc3Cl)cc2)c1Cl] |
| CK24 | 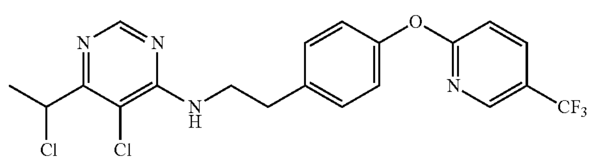 [SMILES: CC(Cl)c1ncnc(NCCc2ccc(Oc3ccc(C(F)(F)F)cn3)cc2)c1Cl] |
| CK25 | 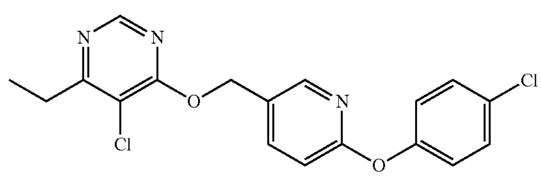 [SMILES: CCc1ncnc(OCc2ccc(Oc3ccc(Cl)cc3)nc2)c1Cl] |
| CK26 | 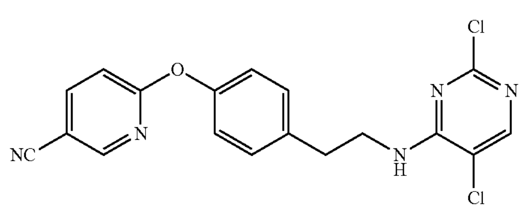 [SMILES: N#Cc1ccc(Oc2ccc(CCNc3nc(Cl)ncc3Cl)cc2)nc1] |
| CK27 | 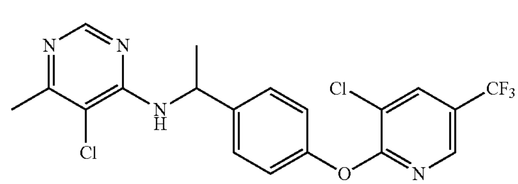 [SMILES: Cc1ncnc(NC(C)c2ccc(Oc3ncc(C(F)(F)F)cc3Cl)cc2)c1Cl] |

TABLE 302-continued

| No. | Structure |
|---|---|
| CK28 | (structure) |
| CK29 | (structure) |
| CK30 | (structure) |
| CK31 | (structure) |
| CK32 | (structure) |
| CK33 | (structure) |
| CK34 | (structure) |

TABLE 302-continued the structure of controls

| No. | Structure |
|---|---|
| CK35 | 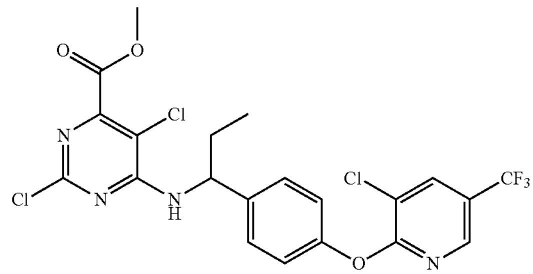 [SMILES: CCC(Nc1nc(Cl)nc(C(=O)OC)c1Cl)c1ccc(Oc2ncc(C(F)(F)F)cc2Cl)cc1] |
| CK36 | 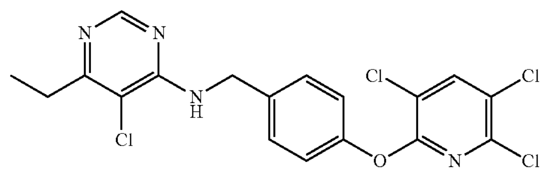 [SMILES: CCc1ncnc(NCc2ccc(Oc3nc(Cl)c(Cl)cc3Cl)cc2)c1Cl] |
| CK37 | 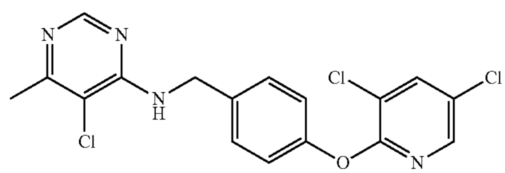 [SMILES: Cc1ncnc(NCc2ccc(Oc3ncc(Cl)cc3Cl)cc2)c1Cl] |
| CK38 | 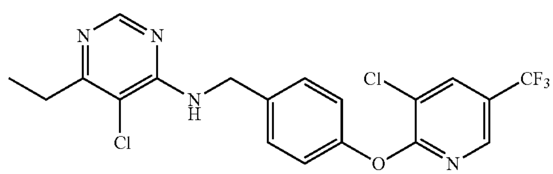 [SMILES: CCc1ncnc(NCc2ccc(Oc3ncc(C(F)(F)F)cc3Cl)cc2)c1Cl] |
| CK39 | 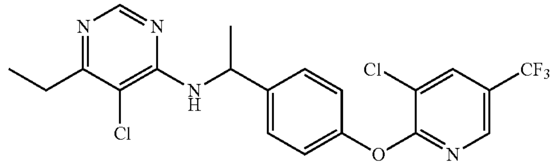 [SMILES: CCc1ncnc(NC(C)c2ccc(Oc3ncc(C(F)(F)F)cc3Cl)cc2)c1Cl] |
| CK40 | 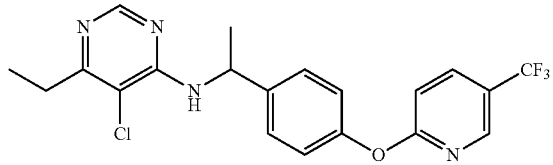 [SMILES: CCc1ncnc(NC(C)c2ccc(Oc3ccc(C(F)(F)F)cn3)cc2)c1Cl] |
| CK41 | 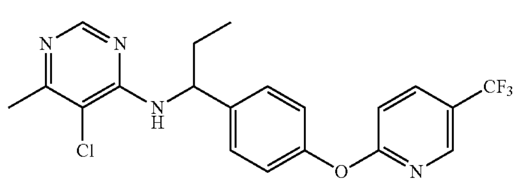 [SMILES: CCC(Nc1ncnc(C)c1Cl)c1ccc(Oc2ccc(C(F)(F)F)cn2)cc1] |
| CK42 | 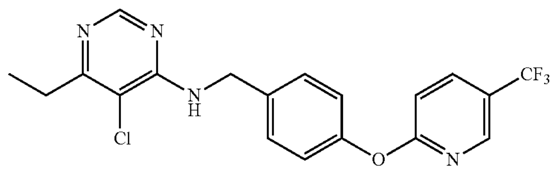 [SMILES: CCc1ncnc(NCc2ccc(Oc3ccc(C(F)(F)F)cn3)cc2)c1Cl] |

TABLE 302-continued the structure of controls

| No. | Structure |
|---|---|
| CK43 | 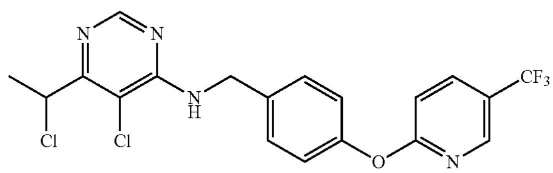 [SMILES: CC(Cl)c1ncnc(NCc2ccc(Oc3ccc(C(F)(F)F)cn3)cc2)c1Cl] |
| CK44 | 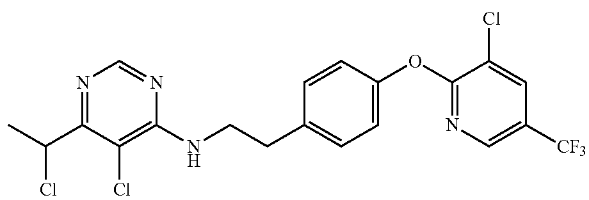 [SMILES: CC(Cl)c1ncnc(NCCc2ccc(Oc3ncc(C(F)(F)F)cc3Cl)cc2)c1Cl] |
| CK45 | 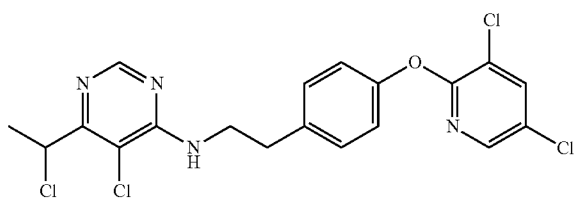 [SMILES: CC(Cl)c1ncnc(NCCc2ccc(Oc3ncc(Cl)cc3Cl)cc2)c1Cl] |
| CK46 | 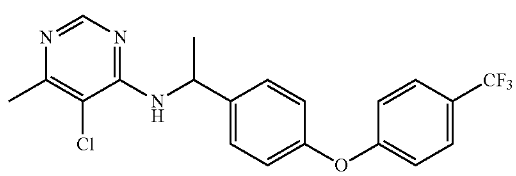 [SMILES: Cc1ncnc(NC(C)c2ccc(Oc3ccc(C(F)(F)F)cc3)cc2)c1Cl] |
| CK47 | 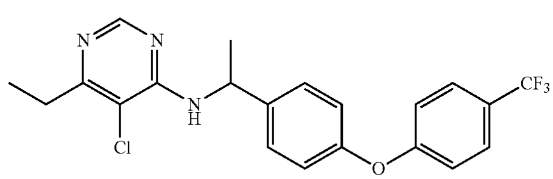 [SMILES: CCc1ncnc(NC(C)c2ccc(Oc3ccc(C(F)(F)F)cc3)cc2)c1Cl] |
| CK48 | 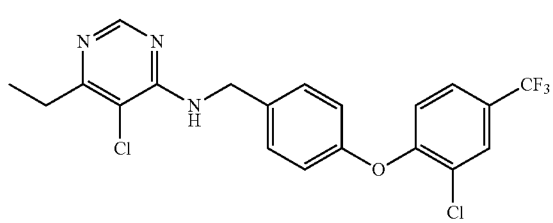 [SMILES: CCc1ncnc(NCc2ccc(Oc3ccc(C(F)(F)F)cc3Cl)cc2)c1Cl] |
| CK49 | 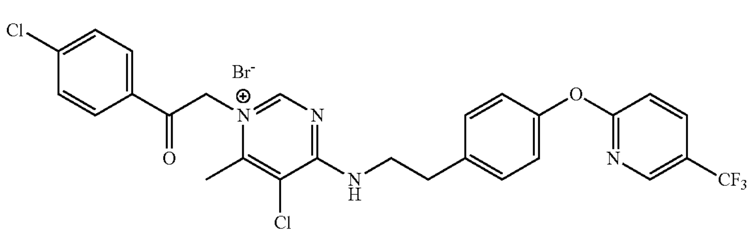 [SMILES: Cc1c(Cl)c(NCCc2ccc(Oc3ccc(C(F)(F)F)cn3)cc2)nc[n+]1CC(=O)c1ccc(Cl)cc1 ; [Br-]] |

TABLE 302-continued the structure of controls

| No. | Structure |
|---|---|
| CK50 | 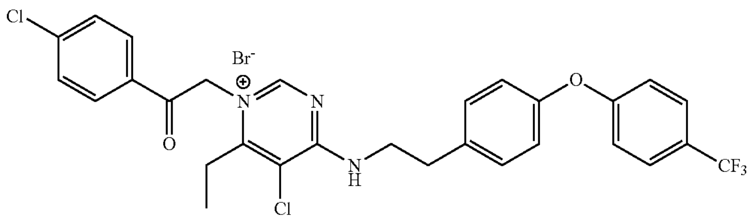 [SMILES: CCc1c(Cl)c(NCCc2ccc(Oc3ccc(C(F)(F)F)cc3)cc2)nc[n+]1CC(=O)c1ccc(Cl)cc1 ; [Br-]] |
| CK51 | 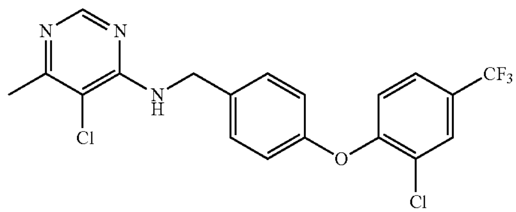 [SMILES: Cc1ncnc(NCc2ccc(Oc3ccc(C(F)(F)F)cc3Cl)cc2)c1Cl] |
| CK52 | 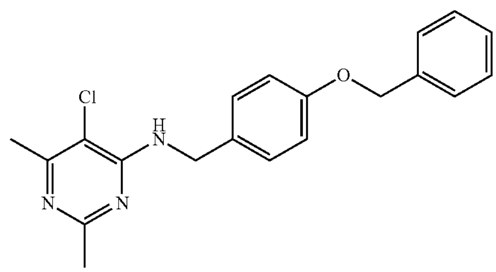 [SMILES: Cc1nc(C)c(Cl)c(NCc2ccc(OCc3ccccc3)cc2)n1] |
| CK53 | 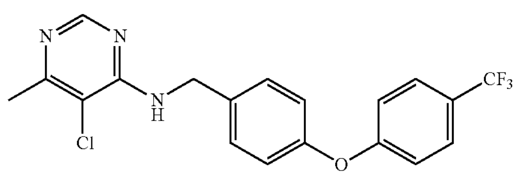 [SMILES: Cc1ncnc(NCc2ccc(Oc3ccc(C(F)(F)F)cc3)cc2)c1Cl] |
| CK54 | 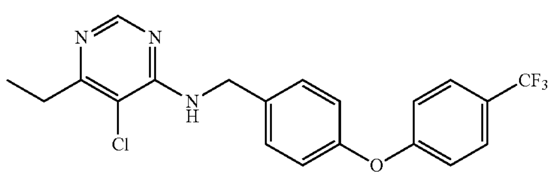 [SMILES: CCc1ncnc(NCc2ccc(Oc3ccc(C(F)(F)F)cc3)cc2)c1Cl] |
| CK55 | 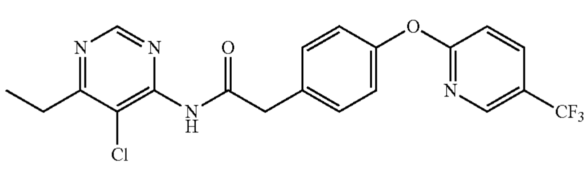 [SMILES: CCc1ncnc(NC(=O)Cc2ccc(Oc3ccc(C(F)(F)F)cn3)cc2)c1Cl] |
| CK56 | 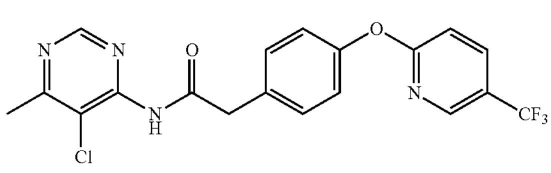 [SMILES: Cc1ncnc(NC(=O)Cc2ccc(Oc3ccc(C(F)(F)F)cn3)cc2)c1Cl] |

TABLE 302-continued

| | the structure of controls |
|---|---|
| No. | Structure |
| CK57 | 6-ethyl-5-chloro-pyrimidin-4-yl-NH-C(O)-CH₂-(4-phenoxy)-(2-chloro-4-trifluoromethylphenyl) |
| CK58 | 6-methyl-5-chloro-pyrimidin-4-yl-NH-C(O)-CH₂-(4-phenoxy)-(2-chloro-4-trifluoromethylphenyl) |
| CK59 | 6-ethyl-5-chloro-pyrimidin-4-yl-NH-C(O)-CH₂-(4-phenoxy)-(4-trifluoromethylphenyl) |
| CK60 | 6-methyl-5-chloro-pyrimidin-4-yl-NH-C(O)-CH₂-(4-phenoxy)-(3-chloro-5-trifluoromethylpyridin-2-yl) |
| CK61 | 6-methyl-5-chloro-pyrimidin-4-yl-NH-C(O)-CH₂-(4-phenoxy)-(4-trifluoromethylphenyl) |
| CK62 | 6-(1-chloroethyl)-5-chloro-pyrimidin-4-yl-NH-CH₂CH₂-(4-phenoxy)-(6-chloropyridazin-3-yl) |
| CK63 | 6-(1-chloroethyl)-5-chloro-pyrimidin-4-yl-NH-CH₂CH₂-(4-phenoxy)-(3,5,6-trichloropyridin-2-yl) |
| CK64 | 6-ethyl-5-chloro-pyrimidin-4-yl-NH-CH₂-(4-phenoxy)-(3,5-dichloropyridin-2-yl) |

TABLE 302-continued the structure of controls

| No. | Structure |
|---|---|
| CK65 | 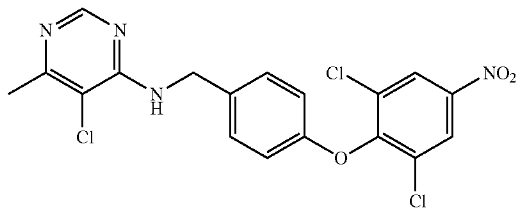 [SMILES: Cc1ncnc(NCc2ccc(Oc3c(Cl)cc([N+](=O)[O-])cc3Cl)cc2)c1Cl] |
| CK66 | 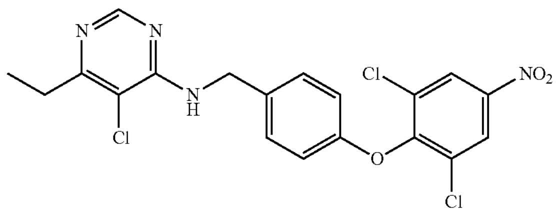 [SMILES: CCc1ncnc(NCc2ccc(Oc3c(Cl)cc([N+](=O)[O-])cc3Cl)cc2)c1Cl] |
| CK67 | 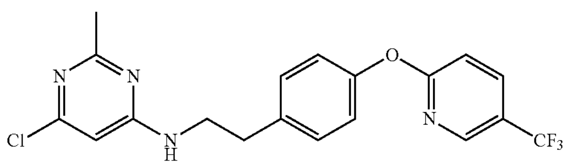 [SMILES: Cc1nc(Cl)cc(NCCc2ccc(Oc3ccc(C(F)(F)F)cn3)cc2)n1] |
| CK68 | 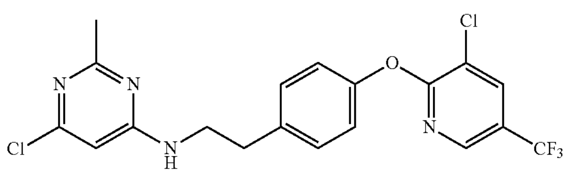 [SMILES: Cc1nc(Cl)cc(NCCc2ccc(Oc3ncc(C(F)(F)F)cc3Cl)cc2)n1] |
| CK69 | 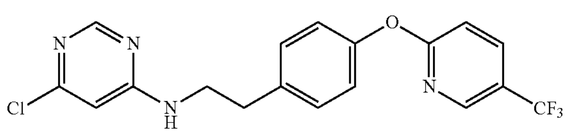 [SMILES: FC(F)(F)c1ccc(Oc2ccc(CCNc3cc(Cl)ncn3)cc2)nc1] |
| CK70 | 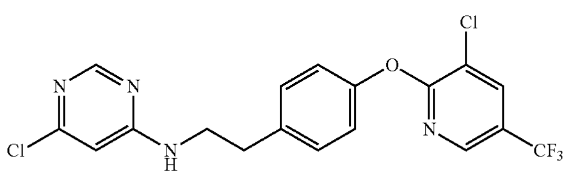 [SMILES: FC(F)(F)c1cnc(Oc2ccc(CCNc3cc(Cl)ncn3)cc2)c(Cl)c1] |
| CK71 | 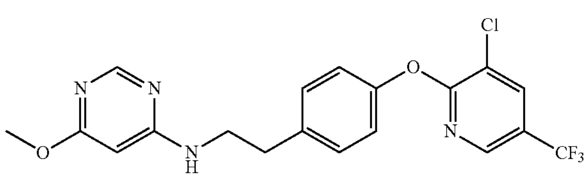 [SMILES: COc1cc(NCCc2ccc(Oc3ncc(C(F)(F)F)cc3Cl)cc2)ncn1] |
| CK72 | 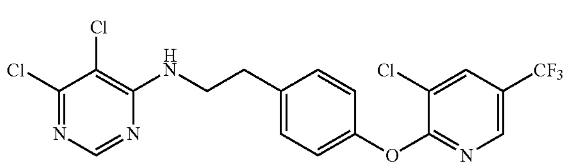 [SMILES: FC(F)(F)c1cnc(Oc2ccc(CCNc3ncnc(Cl)c3Cl)cc2)c(Cl)c1] |

TABLE 302-continued the structure of controls

| No. | Structure |
|---|---|
| CK73 | 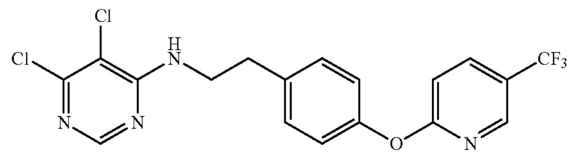 [SMILES: FC(F)(F)c1ccc(Oc2ccc(CCNc3ncnc(Cl)c3Cl)cc2)nc1] |
| CK74 | 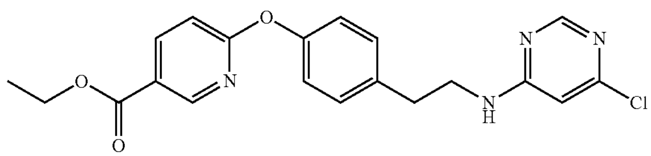 [SMILES: CCOC(=O)c1ccc(Oc2ccc(CCNc3cc(Cl)ncn3)cc2)nc1] |
| CK75 | 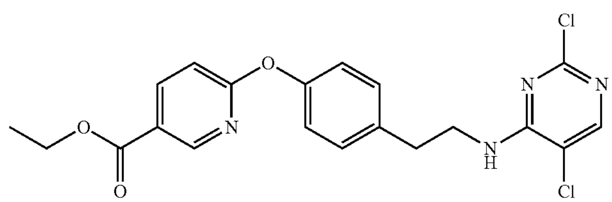 [SMILES: CCOC(=O)c1ccc(Oc2ccc(CCNc3nc(Cl)ncc3Cl)cc2)nc1] |
| CK76 | 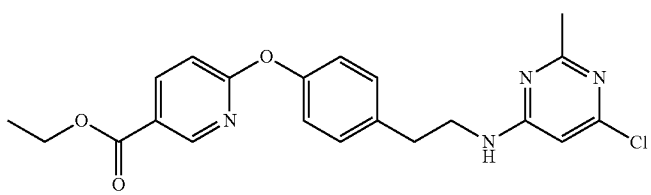 [SMILES: CCOC(=O)c1ccc(Oc2ccc(CCNc3cc(Cl)nc(C)n3)cc2)nc1] |
| CK77 | 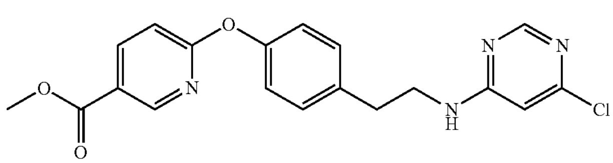 [SMILES: COC(=O)c1ccc(Oc2ccc(CCNc3cc(Cl)ncn3)cc2)nc1] |
| CK78 | 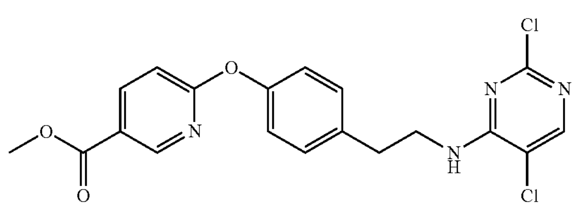 [SMILES: COC(=O)c1ccc(Oc2ccc(CCNc3nc(Cl)ncc3Cl)cc2)nc1] |
| CK79 | 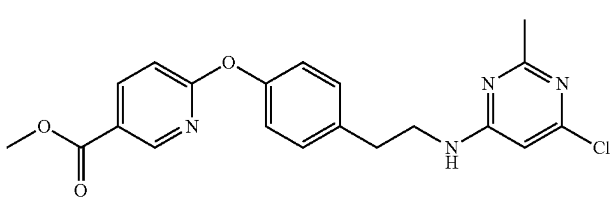 [SMILES: COC(=O)c1ccc(Oc2ccc(CCNc3cc(Cl)nc(C)n3)cc2)nc1] |
| CK80 | 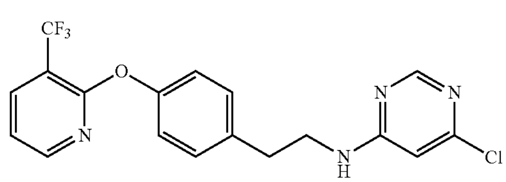 [SMILES: FC(F)(F)c1cccnc1Oc1ccc(CCNc2cc(Cl)ncn2)cc1] |

TABLE 302-continued the structure of controls

| No. | Structure |
|-----|-----------|
| CK81 | 3-CF3-pyridin-2-yl-O-phenyl-CH2CH2-NH-(2,5-dichloropyrimidin-4-yl) |
| CK82 | 3-CF3-pyridin-2-yl-O-phenyl-CH2CH2-NH-(2,6-dichloropyrimidin-4-yl) |
| CK83 | 5-cyano-pyridin-2-yl-O-phenyl-CH2CH2-NH-(6-chloropyrimidin-4-yl) |
| CK84 | 5-cyano-pyridin-2-yl-O-phenyl-CH2CH2-NH-(2-methyl-6-chloropyrimidin-4-yl) |

Example 32: Fungicidal Testing (1) The Determination of Protectant Activity In Vivo The method is as follows: The whole plant is used in this test. The compound is dissolved in a proper solvent to get mother solution. The proper solvent is selected from acetone, methanol, DMF and so on according to their dissolving capability to the sample. The volume rate of solvent and testing solution (v/v) is equal to or less than 5%. The mother solution is diluted with water containing 0.1% tween-80 to get the testing solution whose concentration is designed. The testing solution is sprayed to the host plant by a special plant sprayer. The plant is inoculated with fungus after 24 hours. According to the infecting characteristic of fungus, the plant is stored in a humidity chamber and then transferred into greenhouse after infection is finished. And the other plants are placed in greenhouse directly. The activity of compound is obtained by eyeballing after 7 days in common.

The protectant activities in vivo of some compounds are as follows:

The protectant activity against cucumber downy mildew in vivo:

At the dosage of 400 ppm, the protectant activity of compounds I-22, I-35, I-254, I-255, I-467, I-483, I-486, I-502, I-583, I-602, I-699, I-815, I-987, I-1762, I-1878, I-2555, I-2574, I-2748, I-2611, I-3077, I-3309, I-4757, I-5221, I-6730, I-6732, I-6740, I-6765, I-6790, I-6796, II-21, II-25, II-69, II-154, II-204, II-236, II-254, II-297, II-299, II-303, II-347, II-432, II-482, II-1687, II-1965, II-8915, II-8917, II-8921, II-8965, II-9058, II-10583, III-1, III-5, III-7, III-16, III-19, III-22, III-82, III-110, III-121, III-181, III-187, III-196, III-199, III-201, II-202, III-262, III-263, III-290, III-301, III-541, III-547, III-556, III-562, III-622, III-623, III-650, III-2521, III-2526, III-2527, III-2536, III-2539, III-2541, III-2630 and so on was 100%, the protectant activity of compounds I-618, I-1199, I-2787, I-2843, I-6793, I-6797, II-235, II-274, II-9073, II-9170, II-9336, II-19334 and so on was between 80%-99%;

At the dosage of 100 ppm, the protectant activity of compounds I-22, I-254, I-255, I-467, I-583, I-602, I-699, I-987, I-1199, I-2748, I-3077, I-4757, I-6730, I-6732, I-6740, I-6765, II-21, II-204, II-236, II-297, II-299, II-482, II-1687, II-8915, II-8917, II-8921, II-8965, II-10583, III-1, III-5, III-7, III-16, III-19, III-22, III-82, III-110, III-121, III-181, III-187, III-196, III-199, III-201, III-202, III-262, III-263, III-301, III-541, III-547, III-556, III-562, III-622, III-623, III-650, III-2521, III-2526, III-2527, III-2536, III-2539, III-2541 and so on was 100%, the protectant activity of compounds I-35, I-502, I-987, I-2555, I-2611, I-3309, I-5221, I-6790, I-6796, II-25, II-69, II-303, II-347, II-9058, III-290, III-2630 and so on was between 80%-99%;

At the dosage of 50 ppm, the protectant activity of compounds I-22, I-254, I-255, I-467, I-2748, I-3077, I-6730, I-6765, II-21, II-204, II-236, II-297, II-482, II-1687, II-8917, II-8965, III-1, III-5, III-7, III-16, III-19, III-22, III-82, III-110, III-121, III-181, III-187, III-196, III-201, III-202, III-262, III-263, III-301, III-541, III-547, III-556, III-562, III-622, III-623, III-650, III-2521, III-2526, III-2527, III-2536, III-2539, III-2541 and so on was 100%, the protectant activity of compounds I-583, I-602, I-699, I-987, I-1199, I-2611, I-3309, I-5221, I-6790, I-6796, II-25, II-299, II-8915, II-8921, II-9058, II-10583, III-199, III-2630 and so on was between 80%-99%;

At the dosage of 25 ppm, the protectant activity of compounds I-22, I-255, I-467, I-583, I-699, I-3077, I-6730, I-6732, I-6765, II-204, II-236, II-297, II-482, II-8917, III-1, III-5, III-7, III-16, III-19, III-22, III-82, III-110, III-121, III-181, III-187, III-196, III-201, III-202, III-262, III-263, III-301, III-541, III-547, III-556, III-562, III-622, III-623, III-2521, III-2526, III-2527, III-2539 and so on was 100%, the protectant activity of compounds I-602, I-699, I-3309, I-6790, II-25, II-1687, II-8915, II-8921, II-8965, II-10583, III-199, III-650, III-2536, III-2541 and so on was between 80%-99%;

At the dosage of 12.5 ppm, the protectant activity of compounds I-22, III-1, III-7, III-16, III-22, III-187, III-202, III-301, III-541, III-556, III-562, III-622, III-2521, III-2527 and so on was 100%, the protectant activity of compounds I-255, I-3077, I-6765, II-204, II-482, II-8915, II-8917, II-10583, III-19, III-82, III-196, III-201, III-263, III-623, III-650, III-2536, III-2539 and so on was between 80%-99%;

At the dosage of 6.25 ppm, the protectant activity of compounds I-22, III-7, III-16, III-22, III-187, III-202, III-301, III-541, III-562 and so on was 100%, the protectant activity of compounds I-6765, II-8915, II-8917, II-10583, III-19, III-196, III-556, III-622 and so on was between 80%-99%.

The protectant activity against wheat powdery mildew in vivo:

At the dosage of 400 ppm, the protectant activity of compounds I-22, I-23, I-34, I-35, I-254, I-255, I-266, I-267, I-467, I-486, I-502, I-602, I-815, I-929, I-987, I-1219, I-1414, I-1472, I-1762, I-2342, I-2555, I-2574, I-3309, I-4121, I-4757, I-6729, I-6730, I-6731, I-6732, I-6733, I-6734, I-6735, I-6739, I-6740, I-6741, I-6742, I-6756, I-6757, I-6758, I-6763, I-6765, I-6790, I-6793, I-6795, I-6796, II-19, II-25, II-69, II-154, II-204, II-297, II-299, II-303, II-347, II-432, II-482, II-1687, II-1965, II-8917, II-8921, II-8965, II-9058, II-9073, II-10583, II-19334, III-1, III-5, III-6, III-7, III-16, III-19, III-21, III-22, III-82, III-83, III-110, III-121, III-181, III-185, III-186, III-187, III-196, III-199, III-201, III-202, III-262, III-263, III-301, III-541, III-545, III-546, III-547, III-556, III-559, III-561, III-562, III-622, III-623, III-650, III-2536, III-2541 and so on was 100%; compounds I-483, I-583, I-2748, I-2787, I-2922, I-3077, I-5221, I-6797, II-53, II-9351, III-2539 and so on was between 80%-99%.

At the dosage of 100 ppm, the protectant activity of compounds I-22, I-254, I-255, I-267, I-467, I-486, I-602, I-987, I-1414, I-1472, I-2342, I-2555, I-2574, I-6729, I-6730, I-6739, I-6740, I-6741, I-6742, I-6756, I-6757, I-6758, I-6763, I-6765, I-6793, II-154, II-204, II-297, II-303, II-347, II-432, II-482, II-1687, II-8921, II-8965, II-10583, II-19334, III-121, III-202, III-301 and so on was 100%; compounds I-23, I-483, I-502, I-583, I-6731, I-6732, I-6733, I-6735, II-19, II-25, II-299, II-8917, II-9058, II-9073, III-1, III-5, III-7, III-22, III-82, III-110, III-181, III-541, III-545, III-562, III-2541 and so on was between 80%-99%.

At the dosage of 25 ppm, the protectant activity of compounds I-22, I-254, I-255, I-2342, I-2555, I-2574, I-6730, I-6739, I-6740, I-6742, I-6765, I-6793, II-204, II-297, II-303, II-347, II-432, II-482, II-1687, II-8921, II-10583, II-19334, III-202 and so on was 100%; compounds I-23, I-254, I-502, I-602, I-987, I-6729, I-6731, I-6732, I-6733, I-6735, I-6756, I-6763, II-19, II-299, II-8917, II-8965, II-9058, II-9073, III-121, III-301 and so on was between 80%-99%.

At the dosage of 6.25 ppm, the protectant activity of compounds I-22, I-2342, I-2574, I-6765, II-204, II-432, II-10583 and II-19334 and so on was 100%; compounds I-23, I-255, I-502, I-2555, I-6730, I-6739, I-6742, II-19, II-297, II-303, II-482, II-1687, II-8921, III-202 and so on was between 80%-99%.

The protectant activity against corn rust in vivo:

At the dosage of 400 ppm, the protectant activity of compounds I-22, I-35, I-254, I-266, I-267, I-467, I-483, I-486, I-583, I-815, I-929, I-987, I-1045, I-1199, I-1219, I-1472, I-1762, I-1878, I-2342, I-2555, I-2574, I-2922, I-3077, I-4121, I-4757, I-5221, I-6729, I-6730, I-6731, I-6732, I-6733, I-6734, I-6735, I-6739, I-6740, I-6741, I-6742, I-6756, I-6757, I-6758, I-6763, I-6765, I-6790, I-6791, I-6793, I-6795, I-6796, II-19, II-21, II-53, II-69, II-154, II-165, II-204, II-297, II-299, II-303, II-347, II-432, II-482, II-1687, II-1965, II-8915, II-8917, II-8921, II-8965, II-10583, II-19334, III-1, III-6, III-7, III-16, III-19, III-21, III-82, III-83, III-110, III-181, III-185, III-186, III-196, III-199, III-201, III-202, III-262, III-301, III-541, III-545, III-546, III-547, III-556, III-559, III-561, III-622, III-623, III-661, III-2521, III-2526, III-2536, III-2539, III-2630 and so on was 100%; compounds I-1627, I-2748, II-25, II-236, II-254, III-5, III-22, III-650, III-2527, III-2541 and so on was between 80%-99%.

At the dosage of 100 ppm, the protectant activity of compounds I-22, I-35, I-254, I-467, I-486, I-583, I-987, I-2342, I-2574, I-2922, I-4757, I-5221, I-6729, I-6731, I-6732, I-6733, I-6734, I-6735, I-6739, I-6740, I-6741, I-6742, I-6756, I-6757, I-6758, I-6763, I-6765, I-6796, II-21, II-69, II-154, II-204, II-297, II-299, II-303, II-347, II-432, II-482, II-1687, II-8915, II-8917, II-8965, II-10583, III-6, III-7, III-21, III-110, III-201, III-202, III-262, III-301, III-545, III-546, III-559, III-561, III-622, III-661 and so on was 100%; compounds I-267, I-815, I-1199, I-1219, I-3077, I-3309, I-6730, I-6791, II-19, II-165, II-8921, II-19334, III-19, III-82, III-181, III-185, III-186, III-196, III-199, III-547, III-556, III-623, III-2526 and so on was between 80%-99%.

At the dosage of 25 ppm, the protectant activity of compounds I-22, I-254, I-583, I-2342, I-6729, I-6742, II-69, II-154, II-204, II-303, II-432, II-482, II-8915, II-8917, II-8965, III-7, III-262, III-561, III-622 and so on was 100%; compounds I-35, I-266, I-467, I-987, I-1219, I-2574, I-4757, I-5221, I-6730, I-6731, I-6732, I-6733, I-6734, I-6735, I-6739, I-6740, I-6765, I-6757, I-6796, II-21, II-297, II-299, II-347, II-8921, II-10583, III-199, III-201, III-545, III-546, III-559 was between 80%-99%.

At the dosage of 6.25 ppm, the protectant activity of compounds I-22, I-254, I-2342, I-6742, II-154, II-303, II-432, II-482, II-8915, II-8917 and so on was 100%; compounds I-266, I-987, I-2574, I-6732, I-6733, I-6796, II-21, II-204, II-297, II-299, II-347, II-8921, II-8965, III-262, III-559, III-561, III-622 was between 80%-99%.

(2) Determination of Fungicidal Activity In Vitro

The method is as followed: High Through Put is used in the test. The compound is dissolved in a proper solvent to become a testing solution whose concentration is designed. The solvent is selected from acetone, methanol, DMF and so on according to their dissolving capability to the sample. In a no animalcule condition, the testing solution and pathogens suspension are added into the cells of 96 cells culture board, which then should be placed in the constant temperature box. 24 hours later, pathogen germination or growth can be investigated by eyeballing, and the activity in vitro of the compound is evaluated based on germination or growth of control treatment.

The activities in vitro (inhibition rate) of some compounds are as follows:

The inhibition rate against rice blast:

At the dosage of 25 ppm, the inhibition rate of compounds I-22, I-483, I-929, I-987, I-1762, I-2574, I-2922, I-6757, I-6758, I-6763, II-53, II-165, II-274, II-1965, III-7, III-121, III-301, III-661 and so on was 100%; compounds I-23, I-35, I-254, I-255, I-266, I-618, I-1199, I-1219, I-1878, I-2342, I-3077, I-3309, I-4121, I-4757, I-5221, I-6729, I-6730, I-6731, I-6732, I-6733, I-6734, I-6735, I-6742, I-6758, I-6791, I-6793, I-6795, I-6796, I-6797, II-19, II-25, II-69, II-204, II-347, II-482, II-1687, II-9336, II-10583, III-1, III-5, III-6, III-7, III-16, III-19, III-21, III-22, III-82, III-83, III-110, III-181, III-186, III-187, III-196, III-199, III-201, III-202, III-262, III-541, III-545, III-546, III-547, III-556, III-559, III-561, III-562, III-622, III-623, III-661, III-2521, III-2526, III-2536, III-2539, III-2541, III-2630 was between 80%-99%, contrast compounds CK4, CK5, CK6, CK10, CK20, CK32, CK33, CK35, CK37, CK40, CK41, CK43, CK46, CK47, CK48, CK49, CK50, CK55, CK56 and CK58 was less than 50%, contrast compounds CK1, CK2, CK3, CK7, CK11, CK13, CK15, CK16, CK21, CK38, CK39, CK44, CK45, CK59, CK60, CK61 and CK63 was all 0;

At the dosage of 8.3 ppm, the inhibition rate of compounds I-483, I-2574, I-2922, II-53, II-165, III-7, III-661 and so on was 100%; compounds I-22, I-929, I-987, I-6758 and II-274 was between 80%-99%, contrast compound CK17 was 50%; contrast compounds CK5, CK6, CK14, CK18, CK19, CK46, CK47, CK48, CK49, CK50, CK51, CK52 and diflumetorim was all 0;

At the dosage of 2.8 ppm, the inhibition rate of compounds I-483, I-2922, II-53, II-165, III-7 and so on was 100%; compound II-274 was between 80%-99%, contrast compound CK17 was 0;

At the dosage of 0.9 ppm, the inhibition rate of compounds I-483, I-2922, II-53, II-165, III-7 and so on was 100%;

At the dosage of 0.3 ppm, the inhibition rate of compounds I-483, I-2922, II-53, II-165 and III-7 was 100%;

At the dosage of 0.1 ppm, the inhibition rate of compounds I-483, I-2922, II-165 and III-7 was 100%;

The inhibition rate against cucumber gray mold:

At the dosage of 25 ppm, the inhibition rate of compounds I-486, I-1045, I-2342, I-4757, II-303, II-1965, II-8921, III-82 and so on was 100%; compounds I-1199, I-3309, II-69, II-347, III-7, III-199, III-202, III-262, III-545, III-547, III-559, III-622 was between 80%-99%, contrast compounds CK20, CK21, CK24, CK25, CK44, CK45, CK56, CK57, CK62 was less than 50%, contrast compounds CK1, CK2, CK3, CK4, CK6, CK7, CK8, CK9, CK10, CK13, CK14, CK15, CK16, CK17, CK22, CK26, CK32, CK33, CK34, CK35, CK46, CK47, CK48, CK51, CK52, CK53, CK54, CK55, CK58, CK59, CK60, CK61, CK63, CK67, CK68, CK70, CK73, CK74, CK75, CK76, CK77, CK78, CK79, CK80, CK81, CK82, CK83, CK84, diflumetorim and flufenerim was all 0;

(2) The Contrastive Test Results of Some Compounds and Contrasts

Contrastive tests were carried out between some compounds and contrasts. The test results are listed in table 303-table 305 ("///" in the following tables means no test).

TABLE 303

The comparative test of protectant activity against cucumber downy mildew

| Compound No. | control effect against cucumber downy mildew (%) | | | | | | |
|---|---|---|---|---|---|---|---|
| | 400 mg/L | 100 mg/L | 50 mg/L | 25 mg/L | 12.5 mg/L | 6.25 mg/L | 3.125 mg/L |
| I-22 | 100 | 100 | 100 | 100 | 100 | 100 | 85 |
| I-3309 | 100 | 90 | 90 | 90 | 70 | 60 | 50 |
| II-236 | 100 | 100 | 100 | 100 | /// | /// | /// |
| II-297 | 100 | 100 | 100 | 100 | /// | /// | /// |
| II-8915 | 100 | 100 | 100 | 99 | 95 | 90 | 20 |
| II-8917 | 100 | 100 | 100 | 100 | 95 | 85 | /// |
| II-10583 | 100 | 100 | 100 | 95 | 95 | 95 | /// |
| III-1 | 100 | 100 | 100 | 100 | 100 | /// | /// |
| III-5 | 100 | 100 | 100 | 100 | /// | /// | /// |
| III-7 | 100 | 100 | 100 | 100 | 100 | 100 | 100 |
| III-16 | 100 | 100 | 100 | 100 | 100 | 100 | /// |
| III-19 | 100 | 100 | 100 | 100 | 98 | 95 | /// |
| III-22 | 100 | 100 | 100 | 100 | 100 | 100 | /// |
| III-82 | 100 | 100 | 100 | 100 | 98 | /// | /// |
| III-110 | 100 | 100 | 100 | 100 | /// | /// | /// |
| III-121 | 100 | 100 | 100 | 100 | /// | /// | /// |
| III-181 | 100 | 100 | 100 | 100 | /// | /// | /// |
| III-187 | 100 | 100 | 100 | 100 | 100 | 100 | /// |
| III-196 | 100 | 100 | 100 | 100 | 85 | 85 | /// |
| III-201 | 100 | 100 | 100 | 100 | 98 | /// | /// |
| III-202 | 100 | 100 | 100 | 100 | 100 | 100 | /// |
| III-262 | 100 | 100 | 100 | 100 | /// | /// | /// |
| III-263 | 100 | 100 | 100 | 100 | 98 | 70 | /// |
| III-301 | 100 | 100 | 100 | 100 | 100 | 100 | /// |
| III-541 | 100 | 100 | 100 | 100 | 100 | 100 | 95 |
| III-547 | 100 | 100 | 100 | 100 | /// | /// | /// |
| III-556 | 100 | 100 | 100 | 100 | 100 | 95 | /// |
| III-562 | 100 | 100 | 100 | 100 | 100 | 100 | /// |
| III-622 | 100 | 100 | 100 | 100 | 100 | 98 | /// |
| III-623 | 100 | 100 | 100 | 100 | 98 | 70 | /// |
| III-650 | 100 | 100 | 100 | 98 | 95 | /// | /// |
| III-2521 | 100 | 100 | 100 | 100 | 100 | /// | /// |
| III-2527 | 100 | 100 | 100 | 100 | 100 | 75 | /// |
| III-2536 | 100 | 100 | 100 | 98 | 90 | /// | /// |
| III-2539 | 100 | 100 | 100 | 100 | 85 | /// | /// |
| CK1 | 100 | 100 | 100 | 100 | 50 | 30 | 20 |
| CK3 | 80 | /// | /// | /// | /// | /// | /// |
| CK6 | 70 | /// | /// | /// | /// | /// | /// |
| CK7 | 70 | 30 | 0 | 0 | /// | /// | /// |
| CK8 | 98 | 95 | 80 | 75 | /// | /// | /// |
| CK9 | 100 | 98 | 90 | 70 | /// | /// | /// |
| CK10 | 100 | 82 | 40 | 20 | /// | /// | /// |
| CK11 | 85 | 30 | 0 | 0 | /// | /// | /// |
| CK13 | 85 | 25 | 0 | 0 | /// | /// | /// |
| CK14 | 98 | 40 | 0 | 0 | /// | /// | /// |
| CK15 | 95 | 15 | 0 | 0 | /// | /// | /// |
| CK16 | 85 | /// | /// | /// | /// | /// | /// |
| CK17 | 100 | 40 | 10 | 0 | /// | /// | /// |
| CK20 | 100 | 10 | 0 | 0 | /// | /// | /// |
| CK22 | 100 | 98 | 75 | 60 | /// | /// | /// |
| CK23 | 100 | 0 | 0 | 0 | /// | /// | /// |
| CK25 | 100 | 0 | 0 | 0 | /// | /// | /// |
| CK26 | 100 | 60 | 40 | 0 | /// | /// | /// |
| CK27 | 100 | 0 | 0 | 0 | /// | /// | /// |
| CK28 | 100 | 40 | 20 | 0 | /// | /// | /// |
| CK29 | 98 | 98 | 90 | 25 | /// | /// | /// |
| CK32 | 60 | /// | /// | /// | /// | /// | /// |
| CK33 | 0 | /// | /// | /// | /// | /// | /// |
| CK34 | 85 | /// | /// | /// | /// | /// | /// |
| CK35 | 60 | /// | /// | /// | /// | /// | /// |
| CK37 | 100 | 20 | 10 | 0 | /// | /// | /// |
| CK42 | 100 | 100 | 100 | 20 | 0 | 0 | 0 |
| CK43 | 100 | 40 | 20 | 0 | /// | /// | /// |
| CK52 | 100 | 98 | 90 | 70 | /// | /// | /// |
| CK53 | 100 | 90 | 85 | 60 | /// | /// | /// |
| CK54 | 100 | 90 | 80 | 65 | /// | /// | /// |
| CK55 | 100 | 0 | 0 | 0 | /// | /// | /// |
| CK56 | 100 | 10 | 0 | 0 | /// | /// | /// |
| CK57 | 50 | /// | /// | /// | /// | /// | /// |
| CK58 | 0 | /// | /// | /// | /// | /// | /// |
| CK59 | 80 | /// | /// | /// | /// | /// | /// |
| CK60 | 100 | 10 | 0 | 0 | /// | /// | /// |

TABLE 303-continued

The comparative test of protectant activity against cucumber downy mildew control effect against cucumber downy mildew (%)

| Compound No. | 400 mg/L | 100 mg/L | 50 mg/L | 25 mg/L | 12.5 mg/L | 6.25 mg/L | 3.125 mg/L |
|---|---|---|---|---|---|---|---|
| CK61 | 100 | 90 | 85 | 30 | /// | /// | /// |
| CK62 | 80 | /// | /// | /// | /// | /// | /// |
| CK63 | 70 | /// | /// | /// | /// | /// | /// |
| CK65 | 0 | /// | /// | /// | /// | /// | /// |
| CK66 | 0 | /// | /// | /// | /// | /// | /// |
| CK67 | 100 | 60 | 20 | 0 | /// | /// | /// |
| CK68 | 0 | /// | /// | /// | /// | /// | /// |
| CK69 | 100 | 100 | 98 | 50 | /// | /// | /// |
| CK70 | 100 | 60 | 30 | 0 | /// | /// | /// |
| CK71 | 80 | /// | /// | /// | /// | /// | /// |
| CK72 | 100 | 100 | 40 | 20 | /// | /// | /// |
| CK73 | 98 | 98 | 95 | 60 | /// | /// | /// |
| CK74 | 50 | /// | /// | /// | /// | /// | /// |
| CK75 | 60 | /// | /// | /// | /// | /// | /// |
| CK76 | 0 | /// | /// | /// | /// | /// | /// |
| CK77 | 0 | /// | /// | /// | /// | /// | /// |
| CK78 | 0 | /// | /// | /// | /// | /// | /// |
| CK79 | 85 | /// | /// | /// | /// | /// | /// |
| CK80 | 85 | /// | /// | /// | /// | /// | /// |
| CK83 | 100 | 100 | 98 | 85 | /// | /// | /// |
| CK84 | 100 | 100 | 100 | 85 | /// | /// | /// |
| diflumetorim | 100 | 100 | 100 | 70 | 15 | 0 | /// |
| flufenerim | 0 | /// | /// | /// | /// | /// | /// |

TABLE 304

The comparative test of protectant activity against wheat powdery mildew control effect against wheat powdery mildew (%)

| Compound No. | 400 mg/L | 100 mg/L | 25 mg/L | 6.25 mg/L | 1.6 mg/L | 0.4 mg/L |
|---|---|---|---|---|---|---|
| I-22 | 100 | 100 | 100 | 100 | 15 | /// |
| I-254 | 100 | 100 | 100 | 100 | 20 | /// |
| I-2342 | 100 | 100 | 100 | 100 | 95 | 60 |
| I-2574 | 100 | 100 | 100 | 100 | 75 | 20 |
| I-6765 | 100 | 100 | 100 | 100 | /// | /// |
| II-204 | 100 | 100 | 100 | 100 | /// | /// |
| II-297 | 100 | 100 | 100 | 90 | 40 | 30 |
| II-303 | 100 | 100 | 100 | 90 | 80 | 25 |
| II-432 | 100 | 100 | 100 | 100 | 80 | 50 |
| II-482 | 100 | 100 | 100 | 98 | /// | /// |
| II-8921 | 100 | 100 | 100 | 90 | 40 | /// |
| II-10583 | 100 | 100 | 100 | 100 | /// | /// |
| II-19334 | 100 | 100 | 100 | 100 | 60 | /// |
| III-1 | 100 | 98 | 98 | 98 | /// | /// |
| III-202 | 100 | 100 | 100 | 95 | /// | /// |
| CK1 | 100 | 100 | 100 | 80 | /// | /// |
| CK2 | 100 | 100 | 80 | 0 | /// | /// |
| CK4 | 40 | 0 | /// | /// | /// | /// |
| CK6 | 100 | 100 | 90 | 85 | 0 | 0 |
| CK8 | 0 | /// | /// | /// | /// | /// |
| CK9 | 100 | 0 | 0 | 0 | /// | /// |
| CK10 | 50 | /// | /// | /// | /// | /// |
| CK11 | 100 | 60 | 40 | 0 | /// | /// |
| CK12 | 80 | 30 | 0 | 0 | /// | /// |
| CK13 | 40 | 0 | 0 | 0 | /// | /// |
| CK14 | 85 | 10 | 0 | 0 | /// | /// |
| CK15 | 95 | 85 | 10 | 0 | /// | /// |
| CK16 | 70 | /// | /// | /// | /// | /// |
| CK17 | 100 | 75 | 70 | 50 | /// | /// |
| CK19 | 50 | 0 | /// | /// | /// | /// |
| CK20 | 100 | 30 | 0 | 0 | /// | /// |
| CK21 | 0 | /// | /// | /// | /// | /// |
| CK22 | 100 | 90 | 50 | 0 | /// | /// |
| CK23 | 100 | 0 | 0 | 0 | /// | /// |
| CK24 | 0 | 0 | /// | /// | /// | /// |

TABLE 304-continued

The comparative test of protectant activity against wheat powdery mildew control effect against wheat powdery mildew (%)

| Compound No. | 400 mg/L | 100 mg/L | 25 mg/L | 6.25 mg/L | 1.6 mg/L | 0.4 mg/L |
|---|---|---|---|---|---|---|
| CK25 | 0 | /// | /// | /// | /// | /// |
| CK26 | 70 | /// | /// | /// | /// | /// |
| CK27 | 80 | /// | /// | /// | /// | /// |
| CK29 | 100 | 80 | 50 | 40 | /// | /// |
| CK30 | 100 | 80 | 20 | 0 | /// | /// |
| CK31 | 0 | 0 | 0 | 0 | /// | /// |
| CK32 | 0 | /// | /// | /// | /// | /// |
| CK33 | 0 | /// | /// | /// | /// | /// |
| CK34 | 0 | /// | /// | /// | /// | /// |
| CK35 | 0 | /// | /// | /// | /// | /// |
| CK36 | 100 | 80 | 60 | 0 | /// | /// |
| CK37 | 0 | /// | /// | /// | /// | /// |
| CK41 | 100 | 70 | 50 | 0 | /// | /// |
| CK42 | 100 | 70 | 60 | 50 | /// | /// |
| CK43 | 20 | /// | /// | /// | /// | /// |
| CK44 | 0 | /// | /// | /// | /// | /// |
| CK45 | 0 | /// | /// | /// | /// | /// |
| CK48 | 30 | 0 | 0 | 0 | /// | /// |
| CK51 | 100 | 80 | 40 | 0 | /// | /// |
| CK53 | 100 | 80 | 0 | 0 | /// | /// |
| CK52 | 0 | /// | /// | /// | /// | /// |
| CK55 | 60 | /// | /// | /// | /// | /// |
| CK56 | 70 | /// | /// | /// | /// | /// |
| CK57 | 0 | /// | /// | /// | /// | /// |
| CK58 | 0 | /// | /// | /// | /// | /// |
| CK59 | 0 | /// | /// | /// | /// | /// |
| CK60 | 0 | /// | /// | /// | /// | /// |
| CK61 | 70 | /// | /// | /// | /// | /// |
| CK63 | 50 | /// | /// | /// | /// | /// |
| CK65 | 0 | /// | /// | /// | /// | /// |
| CK66 | 0 | /// | /// | /// | /// | /// |
| CK67 | 0 | /// | /// | /// | /// | /// |
| CK68 | 0 | /// | /// | /// | /// | /// |
| CK69 | 100 | 0 | 0 | 0 | /// | /// |
| CK70 | 98 | 0 | 0 | 0 | /// | /// |
| CK71 | 100 | /// | /// | /// | /// | /// |
| CK72 | 100 | 70 | 60 | 50 | /// | /// |
| CK73 | 40 | /// | /// | /// | /// | /// |
| CK74 | 0 | /// | /// | /// | /// | /// |
| CK75 | 0 | /// | /// | /// | /// | /// |
| CK76 | 75 | /// | /// | /// | /// | /// |
| CK77 | 100 | 100 | 80 | 70 | /// | /// |
| CK78 | 0 | /// | /// | /// | /// | /// |
| CK79 | 0 | /// | /// | /// | /// | /// |
| CK80 | 100 | 80 | 0 | 0 | /// | /// |
| CK81 | 40 | /// | /// | /// | /// | /// |
| CK82 | 100 | 80 | 0 | 0 | /// | /// |
| CK83 | 100 | 100 | 70 | 40 | /// | /// |
| diflumetorim | 100 | 95 | 95 | 90 | /// | /// |

TABLE 305

The comparative test of protectant activity against corn rust control effect against corn rust (%)

| Compound No. | 400 mg/L | 100 mg/L | 25 mg/L | 6.25 mg/L | 1.6 mg/L | 0.4 mg/L |
|---|---|---|---|---|---|---|
| I-22 | 100 | 100 | 100 | 100 | 50 | 20 |
| I-254 | 100 | 100 | 100 | 100 | 95 | 40 |
| II-154 | 100 | 100 | 100 | 100 | 50 | /// |
| II-303 | 100 | 100 | 100 | 100 | 80 | 50 |
| II-432 | 100 | 100 | 100 | 100 | 75 | 15 |
| II-482 | 100 | 100 | 100 | 100 | /// | /// |
| II-8915 | 100 | 100 | 100 | 100 | 80 | 30 |
| II-8917 | 100 | 100 | 100 | 100 | 60 | 10 |
| II-8965 | 100 | 100 | 100 | 95 | 85 | 30 |
| III-7 | 100 | 100 | 100 | /// | /// | /// |

TABLE 305-continued

The comparative test of protectant activity against corn rust

| Compound No. | control effect against corn rust (%) | | | | | |
|---|---|---|---|---|---|---|
| | 400 mg/L | 100 mg/L | 25 mg/L | 6.25 mg/L | 1.6 mg/L | 0.4 mg/L |
| III-262 | 100 | 100 | 100 | 90 | 90 | 60 |
| III-561 | 100 | 100 | 100 | 95 | 80 | 40 |
| CK2 | 100 | 100 | 100 | 85 | /// | /// |
| CK4 | 0 | 0 | /// | /// | /// | /// |
| CK5 | 95 | 98 | 40 | 30 | /// | /// |
| CK6 | 100 | 100 | 100 | 80 | 30 | 0 |
| CK8 | 50 | /// | /// | /// | /// | /// |
| CK9 | 100 | 100 | 20 | 0 | /// | /// |
| CK10 | 50 | /// | /// | /// | /// | /// |
| CK12 | 100 | 100 | 85 | 75 | /// | /// |
| CK13 | 100 | 0 | 0 | 0 | /// | /// |
| CK14 | 100 | 20 | 0 | 0 | /// | /// |
| CK15 | 95 | 85 | 30 | 0 | /// | /// |
| CK16 | 0 | /// | /// | /// | /// | /// |
| CK17 | 100 | 0 | 0 | 0 | //// | /// |
| CK18 | 80 | 30 | 0 | /// | /// | /// |
| CK19 | 70 | 0 | /// | /// | /// | /// |
| CK20 | 100 | 70 | 0 | 0 | /// | /// |
| CK21 | 85 | /// | /// | /// | /// | /// |
| CK22 | 100 | 100 | 40 | 0 | /// | /// |
| CK23 | 100 | 0 | 0 | 0 | /// | /// |
| CK24 | 100 | 50 | 20 | 0 | /// | /// |
| CK25 | 0 | /// | /// | /// | /// | /// |
| CK26 | 100 | 0 | 0 | 0 | /// | /// |
| CK27 | 100 | 100 | 90 | 30 | /// | /// |
| CK28 | 100 | 100 | 100 | 95 | 0 | 0 |
| CK29 | 100 | 95 | 85 | 30 | /// | /// |
| CK30 | 0 | 0 | 0 | 0 | /// | /// |
| CK31 | 0 | 0 | 0 | 0 | /// | /// |
| CK33 | 0 | /// | /// | /// | /// | /// |
| CK34 | 0 | /// | /// | /// | /// | /// |
| CK35 | 0 | /// | /// | /// | /// | /// |
| CK36 | 100 | 60 | 40 | 0 | /// | /// |
| CK37 | 0 | /// | /// | /// | /// | /// |
| CK38 | 0 | /// | /// | /// | /// | /// |
| CK39 | 100 | 100 | 80 | 50 | 10 | 0 |
| CK40 | 100 | 100 | 90 | 70 | 30 | 0 |
| CK41 | 100 | 100 | 90 | 80 | 20 | 0 |
| CK42 | 70 | /// | /// | /// | /// | /// |
| CK43 | 85 | /// | /// | /// | /// | /// |
| CK44 | 85 | /// | /// | /// | /// | /// |
| CK45 | 80 | /// | /// | /// | /// | /// |
| CK46 | 40 | 0 | 0 | 0 | /// | /// |
| CK47 | 80 | 30 | 0 | 0 | /// | /// |
| CK48 | 60 | 20 | 0 | 0 | /// | /// |
| CK49 | 85 | 30 | 0 | 0 | /// | /// |
| CK50 | 80 | 0 | 0 | 0 | /// | /// |
| CK51 | 80 | 20 | 0 | 0 | /// | /// |
| CK52 | 85 | /// | /// | /// | /// | /// |
| CK53 | 0 | /// | /// | /// | /// | /// |
| CK54 | 100 | 60 | 30 | 0 | /// | /// |
| CK55 | 0 | /// | /// | /// | /// | /// |
| CK56 | 70 | /// | /// | /// | /// | /// |
| CK57 | 0 | /// | /// | /// | /// | /// |
| CK58 | 0 | /// | /// | /// | /// | /// |
| CK59 | 0 | /// | /// | /// | /// | /// |
| CK60 | 0 | /// | /// | /// | /// | /// |
| CK61 | 0 | /// | /// | /// | /// | /// |
| CK63 | 100 | 30 | 0 | 0 | /// | /// |
| CK65 | 0 | /// | /// | /// | /// | /// |
| CK66 | 0 | /// | /// | /// | /// | /// |
| CK67 | 0 | /// | /// | /// | /// | /// |
| CK68 | 0 | /// | /// | /// | /// | /// |
| CK69 | 100 | 90 | 50 | 0 | /// | /// |
| CK70 | 100 | 30 | 10 | 0 | /// | /// |
| CK71 | 0 | /// | /// | /// | /// | /// |
| CK72 | 100 | 80 | 20 | 0 | /// | /// |
| CK73 | 100 | 90 | 10 | 0 | /// | /// |
| CK74 | 100 | 100 | 90 | 85 | /// | /// |
| CK75 | 0 | /// | /// | /// | /// | /// |
| CK76 | 70 | /// | /// | /// | /// | /// |
| CK77 | 100 | 60 | 40 | 0 | /// | /// |
| CK78 | 0 | /// | /// | /// | /// | /// |
| CK79 | 0 | /// | /// | /// | /// | /// |
| CK80 | 100 | 85 | 20 | 0 | /// | /// |
| CK81 | 80 | /// | /// | /// | /// | /// |
| CK82 | 100 | 30 | 0 | 0 | /// | /// |
| CK83 | 30 | /// | /// | /// | /// | /// |
| CK84 | 100 | 90 | 60 | 0 | /// | /// |
| diflumetorim | 100 | 80 | 10 | 0 | /// | /// |

Example 33: Bioactivity Test Against Insects and Mites

Determination of insecticidal activity of compounds of the present invention against a few insects were carried out by the following procedures:

Compounds were dissolved in mixed solvent (acetone:methanol=1:1), and diluted to required concentration with water containing 0.1% of tween 80.

Diamond back moth, armyworm, peach aphid and carmine spider mite were used as targets and the method of spraying by airbrush was used for determination of insecticidal biassays.

(1) Bioactivity Test Against Diamond Back Moth (1) Determination of Insecticidal Activity Against Diamond Back Moth The method of spraying by airbrush: The cabbage leaves were made into plates of 2 cm diameter by use of punch. A test solution (0.5 ml) was sprayed by airbrush at the pressure of 0.7 kg/cm$^2$ to both sides of every plate. 10 Second instar larvae were put into the petri-dishes after the leaf disc air-dried and 3 replicates were set for each treatment. Then the insects were maintained in observation room (25° C., 60~70% R.H.). Scores were conducted and mortalities were calculated after 72 hrs.

Part of Test Results Against Diamond Back Moth:

At the dosage of 600 ppm, compounds I-22, I-254, I-255, I-467, I-583, I-815, I-3077, I-3309, I-4121, I-6729, I-6731, I-6732, I-6733, I-6734, I-6735, I-6739, I-6740, I-6742, I-6756, I-6757, I-6758, I-6765, II-19, II-154, II-204, II-297, II-347, II-482, II-1687, II-1965, II-8915, II-8965, II-10583, II-19334, III-1, III-6, III-7, III-16, III-19, III-21, III-22, III-110, III-181, III-185, III-187, III-196, III-199, III-201, III-202, III-541, III-546, III-547, II-556, III-559, III-562, III-622 and III-2527 showed 100% control against carmine spider mite; compounds II-21, II-274, II-303, II-432, II-8917, II-9170, III-83, III-262, III-545, II-561, III-2526 and III-2539 showed 80%-99% control.

At the dosage of 100 ppm, compounds I-254, I-255, I-6739, I-6740, I-6742, I-6756, I-6757, I-6758, I-6765, I-3309, II-19, II-204, II-482, II-19334, III-196, III-546, III-547 and III-556 showed 100% control against carmine spider mite; compounds II-1965, II-8965, II-9170, III-7, III-22, III-187 and III-202 showed 80%-99% control.

(2) Bioactivity Test Against Armyworm

The method of spraying by airbrush: The corn leaves were made into plates of 2 cm diameter by use of punch. A test solution (0.5 ml) was sprayed by airbrush at the pressure of 0.7 kg/cm$^2$ to both sides of every plate. 10 Second instar larvae were put into the petri-dishes after the leaf disc air-dried and 3 replicates were set for each treatment. Then the insects were maintained in observation room (25□, 60~70% R.H.). Scores were conducted and mortalities were calculated after 72 h.

Part of Test Results Against Armyworm:

At the dosage of 600 ppm, compounds I-255, I-467, I-486, I-583, I-1472, I-2342, I-3309, I-4121, I-6729, I-6731, I-6732, I-6733, I-6734, I-6735, I-6739, I-6740, I-6741, I-6756, I-6757, I-6758, I-6763, I-6765, II-19, II-21, II-69, II-204, II-297, II-299, II-347, II-482, II-1965, II-8915, II-8917, II-8965, II-10583, II-19334, III-1, III-6, III-7, III-16, III-19, III-21, III-22, III-181, III-187, III-196, III-199, III-201, III-202, III-541, III-546, III-547, III-556, II-559, III-561, III-562 and III-2527 showed 100% control against carmine spider mite; compounds I-254, I-1762, I-2748, I-6742, II-303, II-432, III-110, III-650 and III-2541 showed 80%-99% control.

At the dosage of 100 ppm, compounds I-255, I-3309, I-6739, I-6740, I-6741, I-6756, I-6757, I-6758, I-6763, I-6765, II-204, II-482, II-8965, III-22, III-187, III-199, III-202, III-547, III-559, III-561 and III-562 showed 100% control against carmine spider mite; compounds I-1472, II-69, II-297, II-1965, II-8915, II-19334, III-196, III-201 and III-650 showed 80%-99% control.

At the dosage of 10 ppm, compounds II-482, III-187, III-547 and III-562 showed 80%-99% control.

(3) Bioactivity Test Against Green Peach Aphid

Method: Filter papers were put in culture dishes (Diameter=6 cm), and water was dripped on filter papers for preserving moisture. Green peach aphids (*Myzus Persicae* Sulzer) were maintained on cabbage. Leaves (Diameter=3 cm) of approximately 15-30 aphids were put in the culture dishes. Bioactivity tests were used the method of Airbrush Foliar Spray, pressure=10 psi (0.7 kg/cm2), spray volume=0.5 mL. The studies were conducted at three constant temperatures 25±1 C in incubator cabinets with 60±5% RH. Survey the survival aphids after 48 hrs and calculate the death rates.

Part of Test Results Against Green Peach Aphid:

At the dosage of 600 ppm, compounds I-22, I-23, I-34, I-35, I-254, I-255, I-266, I-267, I-467, I-483, I-486, I-502, I-583, I-602, I-815, I-929, I-987, I-1414, I-1472, I-1762, I-1878, I-2342, I-2555, I-2748, I-3077, I-3309, I-4121, I-6729, I-6730, I-6731, I-6732, I-6733, I-6734, I-6735, I-6739, I-6740, I-6741, I-6742, I-6756, I-6757, I-6758, I-6763, I-6765, I-6790, I-6793, I-6795, I-6796, I-6797, II-19, II-21, II-25, II-69, II-154, II-204, II-236, II-297, II-299, II-303, II-347, II-432, II-443, II-482, II-1687, II-1965, II-8915, II-8917, II-8921, II-8965, II-9073, II-10583, II-19334, III-1, III-5, III-6, III-7, III-16, III-19, III-21, III-22, III-82, III-83, III-110, III-121, III-181, III-185, III-186, III-187, III-196, III-199, III-201, III-202, III-262, III-263, III-301, III-541, III-545, III-546, III-547, III-556, III-559, III-561, III-562, III-622, III-623, III-650, III-661, III-2527, III-2536 and III-2539 showed 100% control against carmine spider mite; compounds I-699, I-1199, I-5221, III-2526 and III-2541 showed 80%-99% control.

At the dosage of 100 ppm, compounds I-22, I-23, I-34, I-35, I-254, I-255, I-266, I-267, I-483, I-486, I-583, I-602, I-815, I-987, I-1414, I-1472, I-1762, I-1878, I-2342, I-2555, I-3077, I-3309, I-4121, I-6729, I-6731, I-6732, I-6733, I-6734, I-6735, I-6739, I-6740, I-6741, I-6742, I-6756, I-6757, I-6758, I-6763, I-6765, I-6793, I-6796, I-6797, II-19, II-69, II-154, II-204, II-297, II-299, II-303, II-347, II-432, II-443, II-482, II-1687, II-1965, II-8915, II-8917, II-8965, II-10583, II-19334, III-7, III-16, II-22, III-110, III-121, III-181, III-185, III-186, III-187, III-196, III-199, III-201, III-202, III-262, III-301, III-541, III-547, III-556, III-559, III-561, III-562, III-650 and III-661 showed 100% control against carmine spider mite; compounds I-467, I-5221, II-21, II-25, II-8921, II-9073, III-1, III-5, III-6, III-21, III-545 and III-546 showed 80%-99% control.

At the dosage of 10 ppm, compounds I-22, I-34, I-35, I-254, I-255, I-266, I-267, I-987, I-1472, I-1762, I-1878, I-2342, I-3309, I-4121, I-6729, I-6731, I-6732, I-6733, I-6734, I-6735, I-6739, I-6740, I-6741, I-6742, I-6756, I-6757, I-6758, I-6763, I-6765, I-6796, II-19, II-69, II-204, II-297, II-347, II-482, II-1687, II-1965, II-8915, II-8917, II-8965, II-10583, II-19334, III-22, III-181, III-187, III-202, III-301, III-547 and III-562 showed 100% control against carmine spider mite; compounds I-23, I-583, I-602, I-3077, I-6793, I-6797, II-21, II-299, III-7, III-186, III-196 and III-541 showed 80%-99% control.

At the dosage of 5 ppm, compounds I-254, I-1762, I-6731, I-6735, I-6739, I-6740, I-6741, I-6742, I-6756, I-6757, I-6758, I-6763, I-6765, II-69, II-204, II-297, II-347, II-482 and II-8915 showed 100% control against carmine spider mite; compounds II-299, II-8917, II-8965 and II-19334 showed 80%-99% control.

At the dosage of 2.5 ppm, compounds I-254, I-6739, I-6756, I-6757, I-6758, I-6765, II-297, II-347, II-482 and II-8915 showed 100% control against carmine spider mite; compounds II-69, II-204 and II-19334 showed 80%-99% control.

(4) Bioactivity Test Against Carmine Spider Mite

The method: Broadbean shoots with two true leaves in pot were taken, the healthy adults of carmine spider mite were inoculated to the leaves. The adults were counted and then sprayed with airbrush at the pressure of 0.7 kg/cm² and at dose of 0.5 ml. 3 replicates were set for each treatment. And then they were maintained in standard observation room. Scores were conducted and mortalities were calculated after 72 hrs.

Parts of the Test Results Against Carmine Spider Mite are as Follows:

At the dosage of 600 ppm, compounds I-22, I-23, I-254, I-255, I-266, I-267, I-483, I-583, I-602, I-929, I-987, I-1472, I-1762, I-2342, I-6729, I-6730, I-6731, I-6732, I-6733, I-6734, I-6735, I-6739, I-6740, I-6741, I-6742, I-6756, I-6757, I-6758, I-6763, I-6765, I-6795, I-6797, II-19, II-21, II-69, II-154, II-204, II-297, II-299, II-303, II-347, II-432, II-443, II-482, II-1687, II-1965, II-8915, II-8917, II-8965, II-10583, II-19334, III-1, III-5, III-7, III-16, III-19, III-21, III-22, III-110, III-181, III-185, III-187, III-196, III-199, III-201, III-202, III-541, III-545, III-547, III-556, III-559, III-561, III-562 and III-2539 showed 100% control against carmine spider mite; compounds I-1414, I-2555, I-3077, I-3309, I-6796, II-165, III-83, III-546 and III-623 showed 80%-99% control.

At the dosage of 100 ppm, compounds I-22, I-254, I-255, I-266, I-987, I-1762, I-2342, I-6729, I-6731, I-6732, I-6733, I-6734, I-6735, I-6739, I-6740, I-6741, I-6756, I-6757, I-6758, I-6763, I-6765, I-6795, I-6797, II-19, II-21, II-69, II-154, II-204, II-297, II-299, II-347, II-432, II-443, II-482, II-1965, II-8915, II-8917, II-8965, II-19334, III-7, III-16, III-22, III-181, III-187, III-199, III-202, III-547, III-556, III-559 and III-562 showed 100% control against carmine spider mite; compounds I-23, I-483, I-602, I-3309, III-1, III-19, III-196, III-541 and III-2539 showed 80%-99% control.

At the dosage of 10 ppm, compounds I-254, I-6739, I-6756, I-6765, II-204, II-347, II-482, II-8965 and II-19334 showed 100% control against carmine spider mite; compounds I-6740, I-6741, I-6757, I-6758, II-69, II-443, III-199 and III-562 showed 80%-99% control.

At the dosage of 5 ppm, compounds II-482 and II-19334 showed 100% control against carmine spider mite; compounds II-204, II-347 and II-8965 showed 80%-99% control.

At the dosage of 2.5 ppm, compounds II-482, II-8965 and II-19334 showed 80%-99% control.

(5) The Contrastive Test Results of Some Compounds and Contrasts

Contrastive tests were carried out between some compounds and contrasts. The test results are listed in table 306 to table 310 ("///" in the following tables means no test).

TABLE 306 contrastive tests against diamond back moth

| Compound No. | Insecticidal activity against diamond back moth (%) | | |
|---|---|---|---|
| | 600 mg/L | 100 mg/L | 10 mg/L |
| I-255 | 100 | 100 | 43 |
| I-3309 | 100 | 100 | 60 |
| I-6733 | 100 | 68 | 40 |
| I-6734 | 100 | 52 | 40 |
| I-6742 | 100 | 75 | 47 |
| II-19 | 100 | 100 | 50 |
| II-204 | 100 | 100 | 20 |
| II-347 | 100 | 70 | 65 |
| II-482 | 100 | 100 | 60 |
| II-8965 | 100 | 80 | 40 |
| III-196 | 100 | 100 | /// |
| III-546 | 100 | 100 | /// |
| III-547 | 100 | 100 | 57 |
| III-556 | 100 | 100 | 77 |
| CK4 | 0 | /// | /// |
| CK6 | 86 | 16 | 0 |
| CK7 | 85 | 16 | 0 |
| CK8 | 33 | /// | /// |
| CK9 | 100 | 45 | 25 |
| CK10 | 33 | /// | /// |
| CK11 | 86 | 55 | 5 |
| CK12 | 100 | 35 | 0 |
| CK13 | 67 | 16 | 0 |
| CK14 | 67 | 10 | 0 |
| CK15 | 17 | 15 | 0 |
| CK16 | 0 | /// | /// |
| CK17 | 0 | /// | /// |
| CK20 | 57 | /// | /// |
| CK21 | 80 | 25 | 10 |
| CK22 | 0 | /// | /// |
| CK23 | 0 | /// | /// |
| CK25 | 0 | /// | /// |
| CK26 | 0 | /// | /// |
| CK27 | 0 | /// | /// |
| CK28 | 0 | /// | /// |
| CK29 | 0 | /// | /// |
| CK30 | 0 | /// | /// |
| CK32 | 0 | /// | /// |
| CK33 | 29 | /// | /// |
| CK34 | 0 | /// | /// |
| CK35 | 0 | /// | /// |
| CK36 | 20 | 0 | 0 |
| CK37 | 0 | /// | /// |
| CK38 | 100 | 21 | 5 |
| CK39 | 80 | 20 | 0 |
| CK40 | 100 | 29 | 13 |
| CK41 | 86 | 53 | 0 |
| CK42 | 0 | /// | /// |
| CK43 | 0 | /// | /// |
| CK44 | 80 | 25 | 10 |
| CK45 | 86 | 12 | 0 |
| CK46 | 100 | 10 | 0 |
| CK48 | 40 | /// | /// |
| CK51 | 57 | /// | /// |
| CK52 | 20 | /// | /// |
| CK53 | 0 | /// | /// |
| CK55 | 0 | /// | /// |
| CK56 | 0 | /// | /// |

TABLE 306-continued contrastive tests against diamond back moth

| Compound No. | Insecticidal activity against diamond back moth (%) | | |
|---|---|---|---|
| | 600 mg/L | 100 mg/L | 10 mg/L |
| CK57 | 0 | /// | /// |
| CK58 | 0 | /// | /// |
| CK59 | 57 | /// | /// |
| CK60 | 86 | 25 | 15 |
| CK61 | 0 | /// | /// |
| CK63 | 57 | /// | /// |
| CK65 | 86 | 35 | 5 |
| CK66 | 0 | /// | /// |
| CK67 | 14 | /// | /// |
| CK68 | 14 | /// | /// |
| CK69 | 100 | 5 | 0 |
| CK70 | 0 | /// | /// |
| CK71 | 0 | /// | /// |
| CK72 | 0 | /// | /// |
| CK74 | 0 | /// | /// |
| CK75 | 0 | /// | /// |
| CK76 | 0 | /// | /// |
| CK77 | 0 | /// | /// |
| CK78 | 0 | /// | /// |
| CK79 | 0 | /// | /// |
| CK80 | 0 | /// | /// |
| CK81 | 0 | /// | /// |
| CK82 | 17 | /// | /// |
| CK83 | 17 | /// | /// |
| CK84 | 0 | /// | /// |
| diflumetorim | 0 | /// | /// |

TABLE 307 contrastive tests against armyworm

| Compound No. | Insecticidal activity against armyworm (%) | | |
|---|---|---|---|
| | 600 mg/L | 100 mg/L | 10 mg/L |
| I-255 | 100 | 100 | 25 |
| I-3309 | 100 | 100 | 60 |
| I-6756 | 100 | 100 | 28 |
| I-6757 | 100 | 100 | 28 |
| II-204 | 100 | 100 | 47 |
| II-297 | 100 | 95 | 30 |
| II-482 | 100 | 100 | 80 |
| II-8915 | 100 | 95 | 44 |
| II-8965 | 100 | 100 | 69 |
| II-19334 | 100 | 84 | 44 |
| III-22 | 100 | 100 | 71 |
| III-187 | 100 | 100 | 95 |
| III-199 | 100 | 100 | 64 |
| III-202 | 100 | 100 | 65 |
| III-547 | 100 | 100 | 95 |
| III-556 | 100 | 75 | 45 |
| III-562 | 100 | 100 | 83 |
| CK4 | 40 | /// | /// |
| CK5 | 100 | 56 | 0 |
| CK6 | 29 | /// | /// |
| CK7 | 100 | 0 | 0 |
| CK8 | 17 | /// | /// |
| CK9 | 40 | /// | /// |
| CK10 | 0 | /// | /// |
| CK11 | 29 | /// | /// |
| CK12 | 86 | 20 | 0 |
| CK13 | 86 | 0 | 0 |
| CK14 | 0 | /// | /// |
| CK15 | 0 | /// | /// |
| CK16 | 0 | /// | /// |
| CK17 | 0 | /// | /// |
| CK18 | 100 | 43 | 14 |
| CK19 | 86 | 25 | 7 |
| CK20 | /// | /// | 0 |

TABLE 307-continued contrastive tests against armyworm

| Compound No. | Insecticidal activity against armyworm (%) | | |
|---|---|---|---|
| | 600 mg/L | 100 mg/L | 10 mg/L |
| CK21 | 0 | /// | /// |
| CK22 | 0 | /// | /// |
| CK23 | 0 | /// | /// |
| CK24 | /// | /// | 0 |
| CK25 | 0 | /// | /// |
| CK26 | 0 | /// | /// |
| CK27 | 29 | /// | /// |
| CK28 | 29 | /// | /// |
| CK29 | 14 | /// | /// |
| CK30 | 57 | /// | /// |
| CK32 | 0 | /// | /// |
| CK33 | 100 | 0 | 0 |
| CK34 | 0 | /// | /// |
| CK35 | 0 | /// | /// |
| CK36 | 0 | /// | /// |
| CK37 | 0 | /// | /// |
| CK38 | 0 | /// | /// |
| CK39 | 0 | /// | /// |
| CK40 | 43 | 6 | 0 |
| CK41 | 100 | 0 | 0 |
| CK42 | 0 | /// | /// |
| CK43 | 0 | /// | /// |
| CK44 | 0 | /// | /// |
| CK45 | 0 | /// | /// |
| CK46 | 71 | 0 | 0 |
| CK47 | 86 | 25 | 0 |
| CK48 | 50 | /// | /// |
| CK49 | 17 | /// | /// |
| CK51 | 43 | /// | /// |
| CK52 | 0 | /// | /// |
| CK53 | 0 | /// | /// |
| CK54 | 67 | /// | /// |
| CK55 | 0 | /// | /// |
| CK56 | 0 | /// | /// |
| CK57 | 0 | /// | /// |
| CK58 | 0 | /// | /// |
| CK59 | 14 | /// | /// |
| CK60 | 0 | /// | /// |
| CK61 | 0 | /// | /// |
| CK63 | 71 | /// | /// |
| CK64 | 0 | /// | /// |
| CK65 | 0 | /// | /// |
| CK66 | 0 | /// | /// |
| CK67 | 0 | /// | /// |
| CK68 | 0 | /// | /// |
| CK70 | 0 | /// | /// |
| CK71 | 86 | /// | /// |
| CK72 | 71 | /// | /// |
| CK73 | 100 | 50 | 0 |
| CK74 | 0 | /// | /// |
| CK75 | 0 | /// | /// |
| CK76 | 0 | /// | /// |
| CK77 | 0 | /// | /// |
| CK78 | 0 | /// | /// |
| CK79 | 0 | /// | /// |
| CK80 | 0 | /// | /// |
| CK81 | 14 | /// | /// |
| CK82 | 0 | /// | /// |
| CK83 | 29 | /// | /// |
| CK84 | 0 | /// | /// |
| diflumetorim | 0 | /// | /// |

TABLE 308 contrastive tests against peach aphid

| Compound No. | Insecticidal activity against peach aphid (%) | | | | | |
|---|---|---|---|---|---|---|
| | 600 mg/L | 100 mg/L | 10 mg/L | 5 mg/L | 2.5 mg/L | 1.25 mg/L |
| I-22 | 100 | 100 | 100 | 100 | 100 | 100 |
| I-254 | 100 | 100 | 100 | 100 | 100 | 100 |
| I-3309 | 100 | 100 | 100 | 100 | 96 | 48 |
| I-6731 | 100 | 100 | 100 | 100 | 93 | 60 |
| I-6735 | 100 | 100 | 100 | 100 | 80 | 67 |
| I-6739 | 100 | 100 | 100 | 100 | 100 | 100 |
| I-6756 | 100 | 100 | 100 | 100 | 100 | 100 |
| I-6757 | 100 | 100 | 100 | 100 | 100 | 100 |
| I-6758 | 100 | 100 | 100 | 100 | 100 | 89 |
| I-6765 | 100 | 100 | 100 | 100 | 100 | 84 |
| II-19 | 100 | 100 | 100 | /// | /// | /// |
| II-69 | 100 | 100 | 100 | 100 | 81 | /// |
| II-204 | 100 | 100 | 100 | 100 | 97 | 60 |
| II-297 | 100 | 100 | 100 | 100 | 100 | 93 |
| II-347 | 100 | 100 | 100 | 100 | 100 | 81 |
| II-482 | 100 | 100 | 100 | 100 | 100 | 100 |
| II-1687 | 100 | 100 | 100 | /// | /// | /// |
| II-1965 | 100 | 100 | 100 | /// | /// | /// |
| II-8915 | 100 | 100 | 100 | 100 | 100 | 100 |
| II-8917 | 100 | 100 | 100 | 83 | /// | /// |
| II-8965 | 100 | 100 | 100 | 91 | /// | /// |
| II-10583 | 100 | 100 | 100 | /// | /// | /// |
| II-19334 | 100 | 100 | 100 | 96 | 83 | 67 |
| III-7 | 100 | 100 | 90 | 88 | /// | /// |
| III-22 | 100 | 100 | 100 | 100 | 98 | 67 |
| III-181 | 100 | 100 | 100 | /// | /// | /// |
| III-187 | 100 | 100 | 100 | /// | /// | /// |
| III-202 | 100 | 100 | 100 | 100 | 100 | 94 |
| III-301 | 100 | 100 | 100 | /// | /// | /// |
| III-547 | 100 | 100 | 100 | /// | /// | /// |
| III-562 | 100 | 100 | 100 | /// | /// | /// |
| CK2 | 100 | 100 | 95 | 37 | 23 | 0 |
| CK4 | 100 | 100 | 64 | 41 | 0 | /// |
| CK6 | 100 | 76 | 0 | /// | /// | /// |
| CK7 | 100 | 100 | 59 | /// | /// | /// |
| CK8 | 0 | /// | /// | /// | /// | /// |
| CK9 | 100 | 79 | 23 | /// | /// | /// |
| CK10 | 100 | 91 | 23 | /// | /// | /// |
| CK11 | 100 | 98 | 85 | 25 | 0 | /// |
| CK12 | 100 | 100 | 73 | /// | /// | /// |
| CK13 | 100 | 98 | 83 | 0 | /// | /// |
| CK14 | 100 | 70 | 0 | /// | /// | /// |
| CK15 | 69 | 40 | 0 | /// | /// | /// |
| CK16 | 64 | /// | /// | /// | /// | /// |
| CK17 | 0 | /// | /// | /// | /// | /// |
| CK18 | 100 | 71 | 51 | 7 | 0 | /// |
| CK19 | 100 | 86 | 33 | /// | /// | /// |
| CK21 | 100 | 98 | 35 | 19 | 0 | /// |
| CK22 | 0 | /// | /// | /// | /// | /// |
| CK23 | 0 | /// | /// | /// | /// | /// |
| CK24 | 100 | 100 | 89 | 28 | 0 | /// |
| CK25 | 0 | /// | /// | /// | /// | /// |
| CK26 | 100 | 48 | 45 | /// | /// | /// |
| CK27 | 0 | /// | /// | /// | /// | /// |
| CK28 | 100 | 100 | 43 | /// | /// | /// |
| CK29 | 0 | /// | /// | /// | /// | /// |
| CK30 | 93 | 50 | 0 | /// | /// | /// |
| CK32 | 0 | /// | /// | /// | /// | /// |
| CK33 | 0 | /// | /// | /// | /// | /// |
| CK34 | 65 | /// | /// | /// | /// | /// |
| CK35 | 0 | /// | /// | /// | /// | /// |
| CK36 | 90 | 14 | 0 | /// | /// | /// |
| CK37 | 100 | 16 | 0 | /// | /// | /// |
| CK38 | 100 | 24 | 0 | /// | /// | /// |
| CK39 | 100 | 86 | 2 | 0 | /// | /// |
| CK40 | 100 | 100 | 72 | 27 | 0 | /// |
| CK41 | 100 | 97 | 23 | 15 | 0 | /// |
| CK42 | 100 | 67 | 20 | 17 | 0 | /// |
| CK43 | 0 | /// | /// | /// | /// | /// |
| CK44 | 100 | 98 | 35 | 19 | 0 | /// |
| CK45 | 100 | 98 | 55 | 39 | 26 | 0 |
| CK46 | 100 | 5 | 0 | /// | /// | /// |
| CK48 | 100 | 87 | 0 | /// | /// | /// |

TABLE 308-continued contrastive tests against peach aphid

| Compound No. | Insecticidal activity against peach aphid (%) | | | | | |
|---|---|---|---|---|---|---|
| | 600 mg/L | 100 mg/L | 10 mg/L | 5 mg/L | 2.5 mg/L | 1.25 mg/L |
| CK51 | 100 | 50 | 0 | /// | /// | /// |
| CK52 | 88 | 0 | 0 | /// | /// | /// |
| CK53 | 84 | 66 | 34 | /// | /// | /// |
| CK54 | 100 | 100 | 34 | /// | /// | /// |
| CK55 | 0 | /// | /// | /// | /// | /// |
| CK56 | 100 | 0 | 0 | /// | /// | /// |
| CK57 | 61 | /// | /// | /// | /// | /// |
| CK58 | 100 | 0 | 0 | /// | /// | /// |
| CK59 | 75 | 15 | 0 | /// | /// | /// |
| CK60 | 81 | 0 | 0 | /// | /// | /// |
| CK61 | 88 | 0 | 0 | /// | /// | /// |
| CK63 | 100 | 0 | 0 | /// | /// | /// |
| CK65 | 0 | /// | /// | /// | /// | /// |
| CK66 | 0 | /// | /// | /// | /// | /// |
| CK67 | 86 | 54 | 0 | /// | /// | /// |
| CK68 | 0 | /// | /// | /// | /// | /// |
| CK69 | 100 | 100 | 70 | /// | /// | /// |
| CK70 | 81 | 0 | 0 | /// | /// | /// |
| CK72 | 55 | /// | /// | /// | /// | /// |
| CK73 | 100 | 100 | 0 | /// | /// | /// |
| CK74 | 100 | 100 | 26 | /// | /// | /// |
| CK75 | 100 | 0 | 0 | /// | /// | /// |
| CK76 | 52 | /// | /// | /// | /// | /// |
| CK77 | 72 | /// | /// | /// | /// | /// |
| CK78 | 0 | /// | /// | /// | /// | /// |
| CK79 | 100 | 16 | 0 | /// | /// | /// |
| CK80 | 87 | 40 | 16 | /// | /// | /// |
| CK81 | 75 | /// | /// | /// | /// | /// |
| CK82 | 86 | 130 | 0 | /// | /// | /// |
| CK83 | 100 | 100 | 11 | /// | /// | /// |
| CK84 | 100 | 43 | 7 | /// | /// | /// |
| diflumetorim | 100 | 35 | 0 | /// | /// | /// |
| flufenerim | 100 | 100 | 100 | 100 | 90 | 37 |

TABLE 309 contrastive tests against carmine spider mite

| Compound No. | Insecticidal activity against carmine spider mite (%) | | |
|---|---|---|---|
| | 600 mg/L | 100 mg/L | 10 mg/L |
| I-22 | 100 | 100 | 74 |
| I-254 | 100 | 100 | 97 |
| I-255 | 100 | 100 | 85 |
| I-987 | 100 | 100 | 80 |
| I-6729 | 100 | 100 | 87 |
| I-6734 | 100 | 100 | 82 |
| I-6757 | 100 | 100 | 97 |
| I-6758 | 100 | 100 | 99 |
| I-6739 | 100 | 100 | 100 |
| I-6756 | 100 | 100 | 100 |
| I-6741 | 100 | 100 | 85 |
| I-6765 | 100 | 100 | 100 |
| I-6740 | 100 | 100 | 85 |
| II-69 | 100 | 100 | 90 |
| II-204 | 100 | 100 | 100 |
| II-297 | 100 | 100 | 74 |
| II-299 | 100 | 100 | 72 |
| II-347 | 100 | 100 | 100 |
| II-432 | 100 | 100 | 76 |
| II-443 | 100 | 100 | 83 |
| II-482 | 100 | 100 | 100 |
| II-8965 | 100 | 100 | 100 |
| II-19334 | 100 | 100 | 100 |
| III-7 | 100 | 100 | /// |
| III-16 | 100 | 100 | /// |
| III-22 | 100 | 100 | 72 |
| III-181 | 100 | 100 | /// |
| III-199 | 100 | 100 | 87 |
| III-547 | 100 | 100 | /// |
| III-556 | 100 | 100 | /// |
| III-559 | 100 | 100 | /// |
| III-562 | 100 | 100 | 88 |
| CK2 | 100 | 100 | 32 |
| CK4 | 75 | /// | /// |
| CK6 | 100 | 53 | 5 |
| CK7 | 100 | 96 | 36 |
| CK8 | 54 | /// | /// |
| CK12 | 100 | 41 | /// |
| CK13 | 100 | 0 | 0 |
| CK14 | 100 | 33 | 6 |
| CK15 | 59 | 0 | 0 |
| CK16 | 0 | /// | /// |
| CK17 | 40 | /// | /// |
| CK20 | 100 | 72 | /// |
| CK21 | 0 | /// | /// |
| CK23 | 64 | /// | /// |
| CK24 | 100 | 100 | 85 |
| CK25 | 0 | /// | /// |
| CK26 | 0 | /// | /// |
| CK27 | 100 | 100 | 18 |
| CK28 | 100 | 100 | 22 |
| CK30 | 100 | 100 | 28 |
| CK32 | 91 | 22 | 0 |
| CK33 | 41 | /// | /// |
| CK34 | 0 | /// | /// |
| CK35 | 0 | /// | /// |
| CK36 | 0 | /// | /// |
| CK37 | 0 | /// | /// |
| CK38 | 99 | 37 | 14 |
| CK39 | 100 | 37 | 16 |
| CK41 | 100 | 99 | 0 |
| CK43 | 74 | 29 | 16 |
| CK44 | 0 | /// | /// |
| CK45 | 0 | /// | /// |
| CK46 | 100 | 63 | 28 |
| CK52 | 44 | /// | /// |
| CK53 | 100 | 100 | 12 |
| CK55 | 0 | /// | /// |
| CK56 | 32 | 25 | 0 |
| CK57 | 33 | /// | /// |
| CK58 | 0 | /// | /// |
| CK59 | 0 | /// | /// |
| CK60 | 0 | /// | /// |
| CK61 | 0 | /// | /// |
| CK62 | 0 | /// | /// |
| CK63 | 0 | /// | /// |
| CK64 | 56 | /// | /// |
| CK65 | 0 | /// | /// |
| CK66 | 0 | /// | /// |
| CK67 | 61 | /// | /// |
| CK68 | 4 | /// | /// |
| CK69 | 100 | 100 | 4 |
| CK70 | 13 | /// | /// |
| CK72 | 13 | /// | /// |
| CK73 | 100 | 85 | 24 |
| CK74 | 0 | /// | /// |
| CK75 | 0 | /// | /// |
| CK76 | 41 | /// | /// |
| CK77 | 56 | /// | /// |
| CK78 | 17 | /// | /// |
| CK79 | 27 | /// | /// |
| CK80 | 6 | /// | /// |
| CK81 | 0 | /// | /// |
| CK82 | 23 | /// | /// |
| CK84 | 100 | 0 | 0 |
| diflumetorim | 100 | 100 | 73 |
| flufenerim | 100 | 100 | 72 |

Further contrastive tests were carried out between the compounds with better activities, such as compound I-22, I-254, I-255, I-6729, I-6734, I-6739, I-6756, I-6757, I-6758, II-204, II-347, II-482, II-8965 and II-19334, and the contrast CK24 at a low dosage. The test results are listed in table 310.

TABLE 310

| Compound No. | Insecticidal activity against carmine spider mite (%) | |
|---|---|---|
| | 5 mg/L | 2.5 mg/L |
| I-22 | 59 | /// |
| I-254 | 93 | 79 |
| I-255 | 84 | 72 |
| I-6729 | 78 | 64 |
| I-6734 | 57 | 51 |
| I-6739 | 93 | 76 |
| I-6756 | 88 | 71 |
| I-6757 | 80 | 75 |
| I-6758 | 82 | 79 |
| II-204 | 80 | 60 |
| II-347 | 90 | 75 |
| II-482 | 100 | 93 |
| II-8965 | 92 | 82 |
| II-19334 | 100 | 87 |
| CK24 | 15 | 5 |

We claim:
1. A substituted pyrimidine compound represented by formula PY:

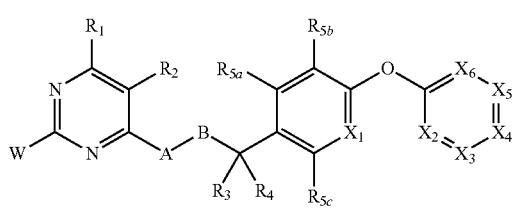

wherein
$R_1$ is cyano, $C_1$-$C_{12}$alkyl, $C_3$-$C_{12}$cycloalkyl, cyano$C_1$-$C_{12}$alkyl, cyano$C_1$-$C_{12}$alkoxy, $C_2$-$C_{12}$alkenyl, halo$C_2$-$C_{12}$alkenyl, $C_2$-$C_{12}$alkynyl, halo$C_2$-$C_{12}$alkynyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkoxycarbonyl$C_1$-$C_{12}$alkyl, $C_1$-$C_{12}$alkylaminocarbonyl$C_1$-$C_{12}$alkyl, or di($C_1$-$C_{12}$alkyl)aminocarbonyl$C_1$-$C_{12}$alkyl;
$R_2$ is halo, cyano, $C_3$-$C_{12}$cycloalkyl, $C_1$-$C_{12}$alkyl, or halo$C_1$-$C_{12}$alkoxy;
$R_3$ and $R_4$, may be the same or different, and are each selected independently from the group consisting of H, halo, OH, amino, $C_1$-$C_{12}$alkyl, $C_1$-$C_{12}$alkoxy, $C_3$-$C_{12}$cycloalkyl, $C_2$-$C_{12}$alkenyl, $C_2$-$C_{12}$alkynyl, halo$C_2$-$C_{12}$alkenyl, halo$C_2$-$C_{12}$alkynyl, $C_1$-$C_{12}$alkoxy$C_1$-$C_{12}$alkyl, unsubstituted or further substituted aryl$C_1$-$C_6$alkyl or heteroaryl$C_1$-$C_6$alkyl by 1 to 5 following groups: halo, $C_1$-$C_6$alkyl, halo$C_1$-$C_6$alkyl, $C_1$-$C_6$alkoxy, and halo$C_1$-$C_6$alkoxy; or $R_3$, $R_4$ and conjoint carbon can also form a $C_3$-$C_8$ cycle;
$R_{5a}$, $R_{5b}$, and $R_{5c}$, may be the same or different, and are each selected independently from the group consisting of H, OH, $C_3$-$C_{12}$cycloalkyl, $C_1$-$C_{12}$alkylthio, halo$C_1$-$C_{12}$alkylthio, $C_3$-$C_{12}$alkenoxy, halo$C_3$-$C_{12}$alkenoxy, $C_3$-$C_{12}$alkynoxy, halo$C_3$-$C_{12}$alkynoxy, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylcarbonyl, halo$C_1$-$C_{12}$alkylcarbonyl, $C_1$-$C_{12}$alkylcarbonyloxy, $C_1$-$C_{12}$alkylcarbonylamino, $C_1$-$C_{12}$alkylsulfonyloxy, $C_1$-$C_{12}$alkoxycarbonyl, $C_1$-$C_{12}$alkoxycarbonyl$C_1$-$C_{12}$alkyl, $C_1$-$C_{12}$alkoxycarbonylamino, $C_1$-$C_{12}$alkoxy$C_1$-$C_{12}$alkoxy, and $C_1$-$C_{12}$alkoxycarbonyl$C_1$-$C_{12}$alkoxy;
$X_1$ is N or $CR_6$; $X_2$ is N or $CR_7$; $X_3$ is N or $CR_8$; $X_4$ is N or $CR_9$; $X_5$ is N or $CR_{10}$; $X_6$ is N or $CR_{11}$; however, $X_2$, $X_3$, $X_4$, $X_5$, $X_6$ are not simultaneously N;
$R_6$ is selected from H, OH, HO(C=O), amino, $C_3$-$C_{12}$cycloalkyl, $C_2$-$C_{12}$alkenoxy, halo$C_2$-$C_{12}$alkenoxy, $C_2$-$C_{12}$alkynoxy, halo$C_2$-$C_{12}$alkynoxy, $C_1$-$C_{12}$alkylthio, halo$C_1$-$C_{12}$alkylthio, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, $C_1$-$C_{12}$alkylamino, halo$C_1$-$C_{12}$alkylamino, di($C_1$-$C_{12}$alkyl)amino, halodi($C_1$-$C_{12}$alkyl)amino, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, di($C_1$-$C_{12}$alkyl)amino($C_1$-$C_{12}$alkyl), $CONH_2$, $CONHNH_2$, $CON(C_1$-$C_{12}$alkyl)$NH_2$, $CONHNH(C_1$-$C_{12}$alkyl), $CONHN(di(C_1$-$C_{12}$alkyl))$, $CONHNHCO(C_1$-$C_{12}$alkyl), $CONHNHCO_2(C_1$-$C_{12}$alkyl), $CONHNH(phenyl)$, $C_1$-$C_{12}$alkylaminocarbonyl, di($C_1$-$C_{12}$alkyl)aminocarbonyl, halodi($C_1$-$C_{12}$alkyl)aminocarbonyl, $C_1$-$C_{12}$alkylsulfonylamino, $C_1$-$C_{12}$alkylsulfonyl($C_1$-$C_{12}$alkyl)amino, halo$C_1$-$C_{12}$alkylsulfonylamino, $C_1$-$C_{12}$alkoxyamino, $C_1$-$C_{12}$alkoxycarbonylamino, $C_1$-$C_{12}$alkoxyaminocarbonyl, cyano$C_1$-$C_{12}$alkyl, cyano$C_1$-$C_{12}$alkoxy, $C_1$-$C_{12}$alkoxycarbonyl$C_1$-$C_{12}$alkyl, halo$C_1$-$C_{12}$alkoxycarbonyl$C_1$-$C_{12}$alkyl, $C_1$-$C_{12}$alkylaminocarbonyl$C_1$-$C_{12}$alkyl, di($C_1$-$C_{12}$alkyl)aminocarbonyl$C_1$-$C_{12}$alkyl, $C_1$-$C_{12}$alkylthiocarbonyl$C_1$-$C_{12}$alkyl, halo$C_1$-$C_{12}$alkylthiocarbonyl$C_1$-$C_{12}$alkyl, $C_1$-$C_{12}$alkylcarbonyloxy, halo$C_1$-$C_{12}$alkylcarbonyloxy, $C_1$-$C_{12}$alkoxycarbonyloxy, halo$C_1$-$C_{12}$alkoxycarbonyloxy, $C_1$-$C_{12}$alkylaminocarbonyloxy, halo$C_1$-$C_{12}$alkylaminocarbonyloxy, $C_1$-$C_{12}$alkylsulfonyloxy, halo$C_1$-$C_{12}$alkylsulfonyloxy, $C_1$-$C_{12}$alkoxy$C_1$-$C_{12}$alkoxy, halo$C_1$-$C_{12}$alkoxy$C_1$-$C_{12}$alkoxy, $C_1$-$C_{12}$alkoxycarbonyl$C_1$-$C_{12}$alkoxy or halo$C_1$-$C_{12}$alkoxycarbonyl$C_1$-$C_{12}$alkoxy;
$R_7$, $R_8$, $R_9$, $R_{10}$, and $R_{11}$, may be the same or different, and are each selected independently from the group consisting of H, halo, OH, cyano, HO(C=O), amino, $NO_2$, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_2$-$C_{12}$alkenyl, $C_2$-$C_{12}$alkynyl, $C_2$-$C_{12}$alkenoxy, halo$C_2$-$C_{12}$alkenoxy, $C_2$-$C_{12}$alkynoxy, halo$C_2$-$C_{12}$alkynoxy, $C_1$-$C_{12}$alkylthio, halo$C_1$-$C_{12}$alkylthio, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, $C_1$-$C_{12}$alkylamino, halo$C_1$-$C_{12}$alkylamino, di($C_1$-$C_{12}$alkyl)amino, halodi($C_1$-$C_{12}$alkyl)amino, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, di($C_1$-$C_{12}$alkyl)amino($C_1$-$C_{12}$alkyl), $CONH_2$, $CONHNH_2$, $CON(C_1$-$C_{12}$alkyl)$NH_2$, $CONHNH(C_1$-$C_{12}$alkyl), $CONHN(di(C_1$-$C_{12}$alkyl))$, $CONHNHCO$ (C$_1$-C$_{12}$alkyl), CONHNHCO$_2$(C$_1$-C$_{12}$alkyl), CONHNH(phenyl), C$_1$-C$_{12}$alkylaminocarbonyl, di(C$_1$-C$_{12}$alkyl)aminocarbonyl, halodi(C$_1$-C$_{12}$alkyl)aminocarbonyl, C$_1$-C$_{12}$alkylsulfonylamino, C$_1$-C$_{12}$alkylsulfonyl(C$_1$-C$_{12}$alkyl)amino, haloC$_1$-C$_{12}$alkylsulfonylamino, C$_1$-C$_{12}$alkoxyamino, C$_1$-C$_{12}$alkoxycarbonylamino, C$_1$-C$_{12}$alkoxyaminocarbonyl, cyanoC$_1$-C$_{12}$alkyl, cyanoC$_1$-C$_{12}$alkoxy, C$_1$-C$_{12}$alkoxycarbonylC$_1$-C$_{12}$alkyl, haloC$_1$-C$_{12}$alkoxycarbonylC$_1$-C$_{12}$alkyl, C$_1$-C$_{12}$alkylaminocarbonylC$_1$-C$_{12}$alkyl, di(C$_1$-C$_{12}$alkyl)aminocarbonylC$_1$-C$_{12}$alkyl, C$_1$-C$_{12}$alkylthiocarbonylC$_1$-C$_{12}$alkyl, haloC$_1$-C$_{12}$alkylthiocarbonylC$_1$-C$_{12}$alkyl, C$_1$-C$_{12}$alkylcarbonyloxy, haloC$_1$-C$_{12}$alkylcarbonyloxy, C$_1$-C$_{12}$alkoxycarbonyloxy, haloC$_1$-C$_{12}$alkoxycarbonyloxy, C$_1$-C$_{12}$alkylaminocarbonyloxy, haloC$_1$-C$_{12}$alkylaminocarbonyloxy, C$_1$-C$_{12}$alkyl sulfonyloxy, haloC$_1$-C$_{12}$alkyl sulfonyloxy, C$_1$-C$_{12}$alkoxyC$_1$-C$_{12}$alkoxy, haloC$_1$-C$_{12}$alkoxyC$_1$-C$_{12}$alkoxy, C$_1$-C$_{12}$alkoxycarbonylC$_1$-C$_{12}$alkoxy, and haloC$_1$-C$_{12}$alkoxycarbonylC$_1$-C$_{12}$alkoxy;

W is H, halo, C$_1$-C$_{12}$alkyl, C$_1$-C$_{12}$alkylthio, or C$_1$-C$_{12}$alkylsulfonyl;

A is NR$_{12}$;

B is —CH$_2$— or —CH$_2$CH$_2$—; and

R$_{12}$ is H, OH, H(C)=O, C$_1$-C$_{12}$alkyl, haloC$_1$-C$_{12}$alkyl, C$_1$-C$_{12}$alkoxy, haloC$_1$-C$_{12}$alkoxy, C$_3$-C$_{12}$cycloalkyl, C$_1$-C$_{12}$alkylthio, C$_2$-C$_{12}$alkenylthio, C$_2$-C$_{12}$alkenyl, C$_2$-C$_{12}$alkynyl, haloC$_2$-C$_{12}$alkenyl, haloC$_2$-C$_{12}$alkynyl, C$_1$-C$_{12}$alkoxyC$_1$-C$_{12}$alkyl, haloC$_1$-C$_{12}$alkoxyC$_1$-C$_{12}$alkyl, C$_1$-C$_{12}$alkylthioC$_1$-C$_{12}$alkyl, haloC$_1$-C$_{12}$alkylthioC$_1$-C$_{12}$alkyl, C$_1$-C$_{12}$alkylsulfinyl, haloC$_1$-C$_{12}$alkylsulfinyl, C$_1$-C$_{12}$alkylsulfonyl, haloC$_1$-C$_{12}$alkylsulfonyl, C$_1$-C$_{12}$alkylaminosulfonyl, di(C$_1$-C$_{12}$alkyl)aminosulfonyl, C$_1$-C$_{12}$alkylsulfonylaminocarbonyl, C$_1$-C$_{12}$alkylcarbonylaminosulfonyl, C$_3$-C$_{12}$cycloalkyloxycarbonyl, C$_1$-C$_{12}$alkylcarbonyl, haloC$_1$-C$_{12}$alkylcarbonyl, C$_1$-C$_{12}$alkoxycarbonyl, haloC$_1$-C$_{12}$alkoxycarbonyl, C$_1$-C$_{12}$alkylcarbonylC$_1$-C$_{12}$alkyl, C$_1$-C$_{12}$alkoxycarbonylC$_1$-C$_{12}$alkyl, C$_1$-C$_{12}$alkylaminocarbonyl, di(C$_1$-C$_{12}$alkyl)aminocarbonyl, C$_2$-C$_{12}$alkenoxycarbonyl, C$_2$-C$_{12}$alkynoxycarbonyl, C$_1$-C$_{12}$alkoxyC$_1$-C$_{12}$alkoxycarbonyl, C$_1$-C$_{12}$alkylaminothio, di(C$_1$-C$_{12}$alkyl)aminothio, unsubstituted or further substituted (hetero)arylcarbonylC$_1$-C$_6$alkyl, (hetero)arylcarbonyl, (hetero)aryloxycarbonyl, or (hetero)arylC$_1$-C$_6$alkyloxycarbonyl by 1 to 5 following groups: halo, NO$_2$, cyano, C$_1$-C$_6$alkyl, haloC$_1$-C$_6$alkyl, C$_1$-C$_6$alkoxy, or haloC$_1$-C$_6$alkoxy;

or a salt thereof formed with an acid selected from the group consisting of hydrochloric acid, sulfuric acid, nitric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid, and citric acid.

2. The substituted pyrimidine compound according to claim 1, wherein the substituted pyrimidine compound is represented by formula I:

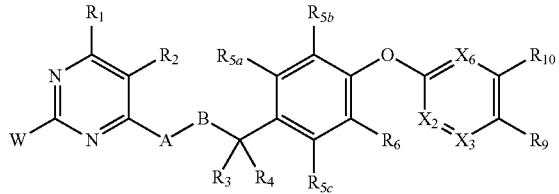

wherein

R$_1$ is cyano, C$_3$-C$_{12}$cycloalkyl, C$_1$-C$_{12}$alkyl, cyanoC$_1$-C$_{12}$alkyl, cyanoC$_1$-C$_{12}$alkoxy, C$_1$-C$_{12}$alkoxycarbonylC$_1$-C$_{12}$alkyl, C$_1$-C$_{12}$alkylaminocarbonylC$_1$-C$_{12}$alkyl, or di(C$_1$-C$_{12}$alkyl)aminocarbonylC$_1$-C$_{12}$alkyl;

R$_2$ is halo, cyano, C$_3$-C$_{12}$cycloalkyl, or C$_1$-C$_{12}$alkyl;

R$_3$ and R$_4$, may be the same or different, and are each selected independently from the group consisting of H, halo, OH, amino, C$_1$-C$_{12}$alkyl, and C$_1$-C$_{12}$alkoxy;

R$_{5a}$, R$_{5b}$, and R$_{5c}$, may be the same or different, and are each selected independently from the group consisting of H or OH;

X$_2$ is N or CR$_7$, X$_3$ is N or CR$_8$, X$_6$ is N or CR$_{11}$, within X$_2$, X$_3$, X$_6$, at least one substituent is N;

R$_9$ is H, halo, OH, cyano, HO(C=O), amino, NO$_2$, C$_1$-C$_{12}$alkyl, haloC$_1$-C$_{12}$alkyl, C$_1$-C$_{12}$alkoxy, haloC$_1$-C$_{12}$alkoxy, C$_3$-C$_{12}$cycloalkyl, C$_2$-C$_{12}$alkenyl, C$_2$-C$_{12}$alkynyl, C$_2$-C$_{12}$alkenoxy, haloC$_2$-C$_{12}$alkenoxy, C$_2$-C$_{12}$alkynoxy, haloC$_2$-C$_{12}$alkynoxy, C$_1$-C$_{12}$alkylthio, haloC$_1$-C$_{12}$alkylthio, C$_1$-C$_{12}$alkoxyC$_1$-C$_{12}$alkyl, haloC$_1$-C$_{12}$alkoxyC$_1$-C$_{12}$alkyl, C$_1$-C$_{12}$alkylthioC$_1$-C$_{12}$alkyl, haloC$_1$-C$_{12}$alkylthioC$_1$-C$_{12}$alkyl, C$_1$-C$_{12}$alkylsulfinyl, haloC$_1$-C$_{12}$alkylsulfinyl, C$_1$-C$_{12}$alkylsulfonyl, haloC$_1$-C$_{12}$alkylsulfonyl, C$_1$-C$_{12}$alkylaminosulfonyl, C$_1$-C$_{12}$alkylamino, haloC$_1$-C$_{12}$alkylamino, di(C$_1$-C$_{12}$alkyl)amino, C$_1$-C$_{12}$alkoxycarbonyl, di(C$_1$-C$_{12}$alkyl)amino(C$_1$-C$_{12}$alkyl), haloC$_1$-C$_{12}$alkoxycarbonyl, CONH$_2$, CON(C$_1$-C$_{12}$alkyl)NH$_2$, CONHNH(C$_1$-C$_{12}$alkyl), CONHN(di(C$_1$-C$_{12}$alkyl)), CONHNHCO(C$_1$-C$_{12}$alkyl), CONHNHCO$_2$(C$_1$-C$_{12}$alkyl), CONHNH(phenyl), C$_1$-C$_{12}$alkylaminocarbonyl, di(C$_1$-C$_{12}$alkyl)aminocarbonyl, C$_1$-C$_{12}$alkylsulfonylamino, C$_1$-C$_{12}$alkylsulfonyl(C$_1$-C$_{12}$alkyl)amino, haloC$_1$-C$_{12}$alkylsulfonylamino, C$_1$-C$_{12}$alkoxyamino, C$_1$-C$_{12}$alkoxycarbonylamino, C$_1$-C$_{12}$alkoxyaminocarbonyl, cyanoC$_1$-C$_{12}$alkyl, cyanoC$_1$-C$_{12}$alkoxy, C$_1$-C$_{12}$alkoxycarbonylC$_1$-C$_{12}$alkyl, C$_1$-C$_{12}$alkylaminocarbonylC$_1$-C$_{12}$alkyl, or di(C$_1$-C$_{12}$alkyl)aminocarbonylC$_1$-C$_{12}$alkyl;

R$_6$ is selected from H, OH, HO(C=O), amino, C$_3$-C$_{12}$cycloalkyl, C$_2$-C$_{12}$alkenoxy, haloC$_2$-C$_{12}$alkenoxy, C$_2$-C$_{12}$alkynoxy, haloC$_2$-C$_{12}$alkynoxy, C$_1$-C$_{12}$alkylthio, haloC$_1$-C$_{12}$alkylthio, C$_1$-C$_{12}$alkoxyC$_1$-C$_{12}$alkyl, haloC$_1$-C$_{12}$alkoxyC$_1$-C$_{12}$alkyl, C$_1$-C$_{12}$alkylthioC$_1$-C$_{12}$alkyl, haloC$_1$-C$_{12}$alkylthioC$_1$-C$_{12}$alkyl, C$_1$-C$_{12}$alkylsulfinyl, haloC$_1$-C$_{12}$alkylsulfinyl, C$_1$-C$_{12}$alkylsulfonyl, C$_1$-C$_{12}$alkylamino, haloC$_1$-C$_{12}$alkylamino, di(C$_1$-C$_{12}$alkyl)amino, C$_1$-C$_{12}$alkoxycarbonyl, CONH$_2$, C$_1$-C$_{12}$alkylaminocarbonyl or di(C$_1$-C$_{12}$alkyl)aminocarbonyl;

$R_7$, $R_8$, $R_{10}$, and $R_{11}$, may be the same or different, and are each selected independently from the group consisting of H, OH, cyano, HO(C=O), amino, $NO_2$, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_2$-$C_{12}$alkenyl, $C_2$-$C_{12}$alkynyl, $C_2$-$C_{12}$alkenoxy, halo$C_2$-$C_{12}$alkenoxy, $C_2$-$C_{12}$alkynoxy, halo$C_2$-$C_{12}$alkynoxy, $C_1$-$C_{12}$alkylthio, halo$C_1$-$C_{12}$alkylthio, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylamino, halo$C_1$-$C_{12}$alkylamino, di($C_1$-$C_{12}$alkyl)amino, $C_1$-$C_{12}$alkoxycarbonyl, $CONH_2$, $C_1$-$C_{12}$alkylaminocarbonyl, and di($C_1$-$C_{12}$alkyl)aminocarbonyl;

W is H or $C_1$-$C_{12}$alkyl;

A is $NR_{12}$;

B is —$CH_2$— or —$CH_2CH_2$—; and $R_{12}$ is H, OH, H(C)=O, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_1$-$C_{12}$alkylthio, $C_2$-$C_{12}$alkenylthio, $C_2$-$C_{12}$alkenyl, $C_2$-$C_{12}$alkynyl, halo$C_2$-$C_{12}$alkenyl, halo$C_2$-$C_{12}$alkynyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, di($C_1$-$C_{12}$alkyl)aminosulfonyl, $C_1$-$C_{12}$alkylsulfonylaminocarbonyl, $C_1$-$C_{12}$alkylcarbonylaminosulfonyl, $C_3$-$C_{12}$cycloalkyloxycarbonyl, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, $C_1$-$C_{12}$alkylcarbonyl$C_1$-$C_{12}$alkyl, $C_1$-$C_{12}$alkoxycarbonyl$C_1$-$C_{12}$alkyl, $C_1$-$C_{12}$alkylaminocarbonyl, di($C_1$-$C_{12}$alkyl)aminocarbonyl, $C_2$-$C_{12}$alkenoxycarbonyl, $C_2$-$C_{12}$alkynoxycarbonyl, $C_1$-$C_{12}$alkoxy$C_1$-$C_{12}$alkoxycarbonyl, $C_1$-$C_{12}$alkylaminothio, di($C_1$-$C_{12}$alkyl)aminothio, unsubstituted or further substituted (hetero)arylcarbonyl$C_1$-$C_6$alkyl, (hetero)arylcarbonyl, (hetero)aryloxycarbonyl, or (hetero)aryl$C_1$-$C_6$alkyloxycarbonyl by 1 to 5 following groups: halo, $NO_2$, cyano, $C_1$-$C_6$alkyl, halo$C_1$-$C_6$alkyl, $C_1$-$C_6$alkoxy, or halo$C_1$-$C_6$alkoxy;

or a salt thereof formed with an acid selected from the group consisting of hydrochloric acid, sulfuric acid, nitric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid, and citric acid.

3. The substituted pyrimidine compound according to claim 2, wherein $R_1$ is cyano, $C_3$-$C_6$cycloalkyl, $C_1$-$C_6$alkyl, cyano$C_1$-$C_6$alkyl, cyano$C_1$-$C_6$alkoxy, $C_1$-$C_6$alkoxycarbonyl$C_1$-$C_6$alkyl, $C_1$-$C_6$alkylaminocarbonyl$C_1$-$C_6$alkyl, or di($C_1$-$C_6$alkyl)aminocarbonyl$C_1$-$C_6$alkyl;

$R_2$ is halo, cyano, $C_3$-$C_6$cycloalkyl, or $C_1$-$C_6$alkyl;

$R_3$ and $R_4$, may be the same or different, and are each selected independently from the group consisting of H, halo, OH, amino, $C_1$-$C_6$alkyl, and $C_1$-$C_6$alkoxy;

$R_{5a}$, $R_{5b}$, and $R_{5c}$, may be the same or different, selected independently from H or OH;

$X_2$ is N or $CR_7$, $X_3$ is N or $CR_8$, $X_6$ is N or $CR_{11}$, within $X_2$, $X_3$, $X_6$, at least one substituent is N;

$R_6$ is H;

$R_7$ is H, halo, cyano, or $C_1$-$C_6$alkyl;

$R_8$ is selected from the group consisting of H, halo, cyano, $C_1$-$C_6$alkyl, and $C_1$-$C_6$alkoxy;

$R_9$ is H, halo, OH, cyano, HO(C=O), amino, $NO_2$, $C_1$-$C_6$alkyl, halo$C_1$-$C_6$alkyl, $C_1$-$C_6$alkoxy, halo$C_1$-$C_6$alkoxy, $C_3$-$C_6$cycloalkyl, $C_2$-$C_6$alkenyl, $C_2$-$C_6$alkynyl, $C_2$-$C_6$alkenoxy, halo$C_2$-$C_6$alkenoxy, $C_2$-$C_6$alkynoxy, halo$C_2$-$C_6$alkynoxy, $C_1$-$C_6$alkylthio, halo$C_1$-$C_6$alkylthio, $C_1$-$C_6$alkoxy$C_1$-$C_6$alkyl, halo$C_1$-$C_6$alkoxy$C_1$-$C_6$alkyl, $C_1$-$C_6$alkylthio$C_1$-$C_6$alkyl, halo$C_1$-$C_6$alkylthio$C_1$-$C_6$alkyl, $C_1$-$C_6$alkylsulfinyl, halo$C_1$-$C_6$alkylsulfinyl, $C_1$-$C_6$alkylsulfonyl, halo$C_1$-$C_6$alkylsulfonyl, $C_1$-$C_6$alkylaminosulfonyl, $C_1$-$C_6$alkylamino, halo$C_1$-$C_6$alkylamino, di($C_1$-$C_6$alkyl)amino, $C_1$-$C_6$alkoxycarbonyl, $CONH_2$, $C_1$-$C_6$alkylaminocarbonyl, di($C_1$-$C_6$alkyl)aminocarbonyl, cyano$C_1$-$C_6$alkoxy, $C_1$-$C_6$alkoxycarbonyl$C_1$-$C_6$alkyl, $C_1$-$C_6$alkylaminocarbonyl$C_1$-$C_6$alkyl, or di($C_1$-$C_6$alkyl)aminocarbonyl$C_1$-$C_6$alkyl;

$R_{10}$ is H, halo, OH, cyano, HO(C=O), amino, $NO_2$, $C_1$-$C_6$alkyl, halo$C_1$-$C_6$alkyl, $C_1$-$C_6$alkoxy, halo$C_1$-$C_6$alkoxy, $C_3$-$C_6$cycloalkyl, $C_2$-$C_6$alkenyl, $C_2$-$C_6$alkynyl, $C_2$-$C_6$alkenoxy, halo$C_2$-$C_6$alkenoxy, $C_2$-$C_6$alkynoxy, halo$C_2$-$C_6$alkynoxy, $C_1$-$C_6$alkylthio, halo$C_1$-$C_6$alkylthio, $C_1$-$C_6$alkoxy$C_1$-$C_6$alkyl, halo$C_1$-$C_6$alkoxy$C_1$-$C_6$alkyl, $C_1$-$C_6$alkylthio$C_1$-$C_6$alkyl, halo$C_1$-$C_6$alkylthio$C_1$-$C_6$alkyl, $C_1$-$C_6$alkylsulfinyl, halo$C_1$-$C_6$alkylsulfinyl, $C_1$-$C_6$alkylsulfonyl, halo$C_1$-$C_6$alkylsulfonyl, $C_1$-$C_6$alkylamino, halo$C_1$-$C_6$alkylamino, di($C_1$-$C_6$alkyl)amino, $C_1$-$C_6$alkoxycarbonyl, $CONH_2$, $C_1$-$C_6$alkylaminocarbonyl, or di($C_1$-$C_6$alkyl)aminocarbonyl;

$R_{11}$ is H, halo, OH, cyano, HO(C=O), amino, $NO_2$, $C_1$-$C_6$alkyl, halo$C_1$-$C_6$alkyl, $C_1$-$C_6$alkoxy, halo$C_1$-$C_6$alkoxy, $C_1$-$C_6$alkoxycarbonyl, $CONH_2$, $C_1$-$C_6$alkylaminocarbonyl, or di($C_1$-$C_6$alkyl)aminocarbonyl;

W is H or $C_1$-$C_6$alkyl;

A is $NR_{12}$;

B is —$CH_2$— or —$CH_2CH_2$—; and $R_{12}$ is H, OH, H(C)=O, $C_1$-$C_6$alkyl, $C_1$-$C_6$alkylcarbonyl, or $C_1$-$C_6$alkylsulfonyl;

or wherein the salt of formula I is formed with hydrochloric acid, sulfuric acid, nitric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid, or citric acid.

4. The substituted pyrimidine compound according to claim 3, wherein the substituted pyrimidine compound is represented by formula I-A, I-B, I-C, I-D, I-E, I-F, I-G, or I-H:

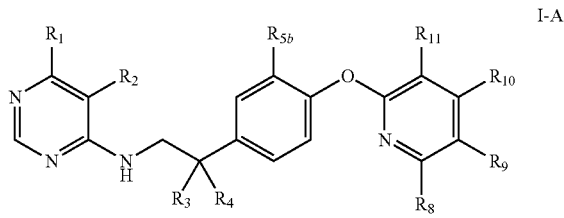

-continued

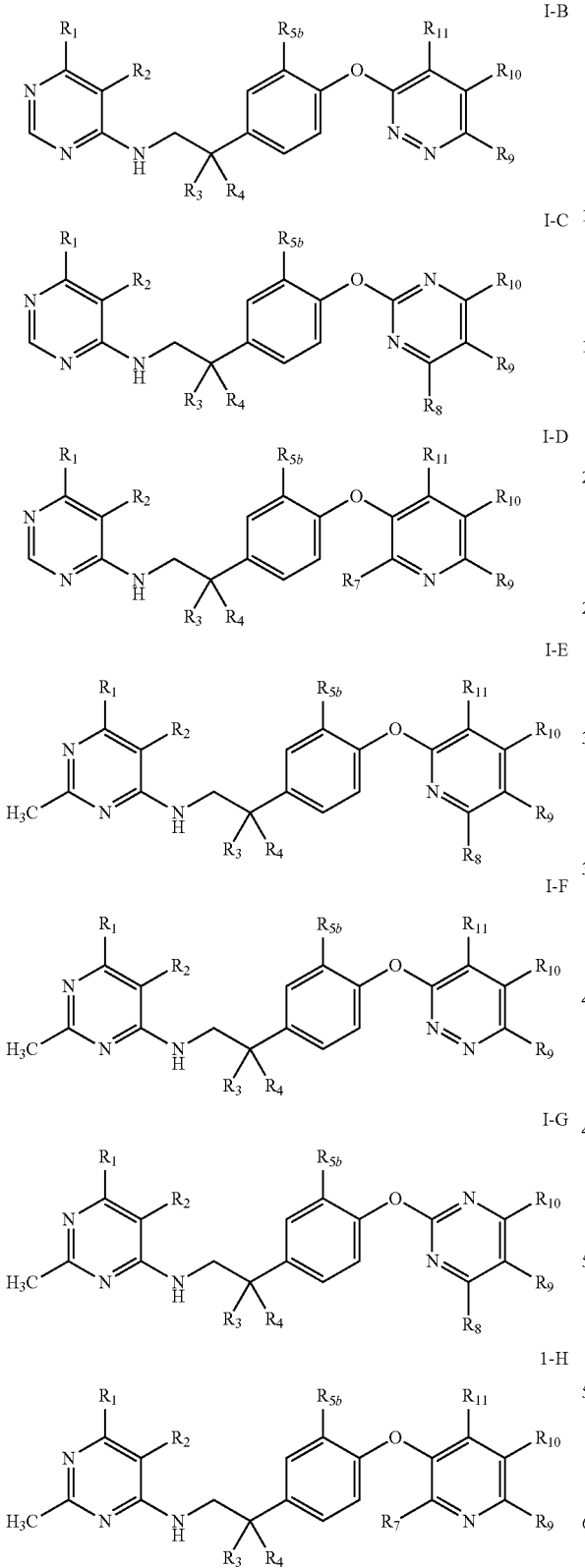

wherein
R₁ is cyano or $C_1$-$C_4$alkyl;
R₂ is halo, cyano, $C_3$-$C_4$cycloalkyl, or $C_1$-$C_4$alkyl;
R₃ and R₄, may be the same or different, and are each selected independently from the group consisting of H, halo, OH, amino, $C_1$-$C_4$alkyl, and $C_1$-$C_4$alkoxy;
$R_{5b}$ is H or OH;
R₇ is H, halo, cyano, or $C_1$-$C_4$alkyl;
R₈ is H, halo, cyano, $C_1$-$C_4$alkyl, or $C_1$-$C_4$alkoxy;
R₉ is H, halo, OH, cyano, HO(C=O), amino, $NO_2$, $C_1$-$C_4$alkyl, halo$C_1$-$C_4$alkyl, $C_1$-$C_4$alkoxy, halo$C_1$-$C_4$alkoxy, $C_1$-$C_4$alkylthio, halo$C_1$-$C_4$alkylthio, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkylsulfinyl, halo$C_1$-$C_4$alkylsulfinyl, $C_1$-$C_4$alkylsulfonyl, halo$C_1$-$C_4$alkylsulfonyl, $C_1$-$C_4$alkylaminosulfonyl, $C_1$-$C_4$alkylamino, halo$C_1$-$C_4$alkylamino, di($C_1$-$C_4$alkyl)amino, $C_1$-$C_4$alkoxycarbonyl, $CONH_2$, $C_1$-$C_4$alkylaminocarbonyl, di($C_1$-$C_4$alkyl)aminocarbonyl, cyano$C_1$-$C_4$alkoxy, $C_1$-$C_4$alkoxycarbonyl$C_1$-$C_4$alkyl, $C_1$-$C_4$alkylaminocarbonyl$C_1$-$C_4$alkyl, or di($C_1$-$C_4$alkyl)aminocarbonyl$C_1$-$C_4$alkyl;
$R_{10}$ is H, halo, OH, cyano, HO(C=O), amino, $NO_2$, $C_1$-$C_4$alkyl, halo$C_1$-$C_4$alkyl, $C_1$-$C_4$alkoxy, halo$C_1$-$C_4$alkoxy, $C_3$-$C_4$cycloalkyl, $C_2$-$C_4$alkenyl, $C_2$-$C_4$alkynyl, $C_2$-$C_4$alkenoxy, halo$C_2$-$C_4$alkenoxy, $C_2$-$C_4$alkynoxy, halo$C_2$-$C_4$alkynoxy, $C_1$-$C_4$alkylthio, halo$C_1$-$C_4$alkylthio, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkylsulfinyl, halo$C_1$-$C_4$alkylsulfinyl, $C_1$-$C_4$alkylsulfonyl, halo$C_1$-$C_4$alkylsulfonyl, $C_1$-$C_4$alkylamino, halo$C_1$-$C_4$alkylamino, di($C_1$-$C_4$alkyl)amino, $C_1$-$C_4$alkoxycarbonyl, $CONH_2$, $C_1$-$C_4$alkylaminocarbonyl, or di($C_1$-$C_4$alkyl)aminocarbonyl; and
$R_{11}$ is H, halo, OH, cyano, HO(C=O), amino, $NO_2$, $C_1$-$C_4$alkyl, halo$C_1$-$C_4$alkyl, $C_1$-$C_4$alkoxy, halo$C_1$-$C_4$alkoxy, $C_1$-$C_4$alkoxycarbonyl, $CONH_2$, $C_1$-$C_4$alkylaminocarbonyl, or di($C_1$-$C_4$alkyl)aminocarbonyl;
or the salt of formula I-A, I-B, I-C, I-D, I-E, I-F, I-G, or I-H is formed with hydrochloric acid, sulfuric acid, nitric acid, phosphoric acid, acetic acid, trifluoroacetic acid, oxalic acid, methylsulfonic acid, p-toluenesulfonic acid, benzoic acid, maleic acid, sorbic acid, malic acid, or citric acid.

5. The substituted pyrimidine compound according to claim 4, wherein
R₁ is cyano, $CH_3$, $C_2H_5$, n-$C_3H_7$, i-$C_3H_7$, n-$C_4H_9$, s-$C_4H_9$, i-$C_4H_9$, or t-$C_4H_9$;
R₂ is F, Cl, Br, cyano, $CH_3$, or $C_2H_5$;
R₃ and R₄, may be the same or different, and are each selected independently from the group consisting of H, Cl, Br, OH, amino, $CH_3$, $C_2H_5$, $OCH_3$, and $OC_2H_5$;
$R_{5b}$ is H or OH;
R₇ is H, Cl, or cyano;
R₈ is H, Cl, Br, cyano, $CH_3$, or $OCH_3$;
R₉ is H, F, Cl, Br, cyano, HO(C=O), amino, $NO_2$, $CH_3$, $C_2H_5$, $CF_3$, $CClF_2$, $OCH_3$, $OC_2H_5$, $OCF_3$, $COOCH_3$, $COOC_2H_5$, $CONH_2$, $CONHCH_3$, $CONHC_2H_5$, $CON(CH_3)_2$, $SO_2CH_3$, or $SO_2NHCH_3$;
$R_{10}$ is H, Cl, cyano, $CH_3$, $C_2H_5$, $OCH_3$, or $OC_2H_5$; and
$R_{11}$ is H, F, Cl, Br, cyano, HO(C=O), amino, $NO_2$, $CH_3$, $C_2H_5$, $CF_3$, $CClF_2$, $OCH_3$, $OC_2H_5$, $OCF_3$, $COOCH_3$, $COOC_2H_5$, $CONH_2$, $CONHCH_3$, $CONHC_2H_5$, or $CON(CH_3)_2$;
or the salt of formula I-A, I-B, I-C, I-D, I-E, I-F, I-G, or I—H is formed with hydrochloric acid, sulfuric acid, nitric acid, phosphoric acid, acetic acid, trifluoroacetic acid, oxalic acid, methylsulfonic acid, p-toluenesulfonic acid, maleic acid, or benzoic acid.

6. The substituted pyrimidine compound according to claim 5, wherein the substituted pyrimidine compound is represented by formula I-A and wherein
   $R_1$ is $CH_3$ or $C_2H_5$;
   $R_2$ is Cl, Br, or cyano;
   $R_3$, $R_4$, and $R_{10}$ are H;
   $R_{5b}$ is H;
   $R_8$ is H or Cl;
   $R_9$ is H, Cl, cyano, $CF_3$, $CClF_2$, $COOCH_3$, $COOC_2H_5$, or $CONH_2$; and
   $R_{11}$ is H, Cl, $NO_2$, $CF_3$, $COOCH_3$, or $CONHCH_3$;
or wherein the substituted pyrimidine compound is represented by formula I-B and
   $R_1$ is $CH_3$, $C_2H_5$, or $CHF_2$;
   $R_2$ is Cl, Br, or cyano;
   $R_9$ is Cl, Br, cyano, or $CF_3$; and
   $R_3$, $R_4$, $R_{5b}$, $R_{10}$, and $R_{11}$ are H;
or wherein the substituted pyrimidine compound is represented by formula I-C and
   $R_1$ is $CH_3$, $C_2H_5$, or $CHF_2$;
   $R_2$ is Cl, Br, or cyano;
   $R_3$, $R_4$, $R_{5b}$, and $R_9$ are H; and
   $R_8$ and $R_{10}$ are $CH_3$ or $OCH_3$;
or wherein the substituted pyrimidine compound is represented by formula I-D and
   $R_1$ is $CH_3$, $C_2H_5$, or $CHF_2$;
   $R_2$ is Cl, Br, or cyano;
   $R_3$, $R_4$, $R_{5b}$, $R_8$, and $R_{10}$ are H;
   $R_9$ is H, Cl, cyano, $CF_3$, $COOCH_3$, $COOC_2H_5$, or $CONH_2$; and
   $R_{11}$ is H, Cl, or $CF_3$;
or wherein the salt of formula I-A, I-B, I-C, or I-D is formed with hydrochloric acid, sulfuric acid, nitric acid, phosphoric acid, acetic acid, trifluoroacetic acid, oxalic acid, methylsulfonic acid, p-toluenesulfonic acid, maleic acid, or benzoic acid.

7. The substituted pyrimidine compound according to claim 6, wherein
   the substituted pyrimidine compound is represented by formula I-A and wherein
   $R_1$ is $CH_3$ or $C_2H_5$;
   $R_2$ is Cl, Br, or cyano;
   $R_3$, $R_4$, $R_{5b}$, and $R_{10}$ are H;
   $R_9$ is Cl, cyano, or $CF_3$; and
   $R_8$ and $R_{11}$ are H or Cl;
or wherein the substituted pyrimidine compound is represented by formula I-B and
   $R_1$ is $CH_3$, $C_2H_5$, or $CHF_2$;
   $R_2$ and $R_9$ are Cl, Br, or cyano; and
   $R_3$, $R_4$, $R_{5b}$, $R_{10}$, and $R_{11}$ are H;
or wherein the salt of formula I-A or I-B is formed with hydrochloric acid, sulfuric acid, nitric acid, phosphoric acid, acetic acid, trifluoroacetic acid, oxalic acid, methylsulfonic acid, p-toluenesulfonic acid, maleic acid, or benzoic acid.

8. A substituted pyrimidine compound represented by formula II:

II wherein
$R_1$ is $C_1$-$C_{12}$alkyl or $C_3$-$C_8$cycloalkyl;
$R_2$ is halo or cyano;
$R_3$ and $R_4$, may be the same or different, and are each selected independently from the group consisting of H, halo, $C_1$-$C_{12}$alkyl, $C_1$-$C_{12}$alkoxy, and $C_3$-$C_{12}$cycloalkyl; or $R_3$, $R_4$ and conjoint carbon can also form a $C_3$-$C_8$ cycle;
$R_{5a}$, $R_{5b}$, and $R_{5c}$, may be the same or different, and are each selected independently from the group consisting of H or OH;
$R_6$ is selected from H, OH, amino, $C_3$-$C_{12}$ cycloalkyl, $C_1$-$C_{12}$alkylamino, halo$C_1$-$C_{12}$alkylamino, di($C_1$-$C_{12}$alkyl)amino, halodi($C_1$-$C_{12}$alkyl)amino, $C_1$-$C_{12}$alkylaminocarbonyl, di($C_1$-$C_{12}$alkyl)aminocarbonyl, halodi($C_1$-$C_{12}$alkyl)aminocarbonyl, $CONH_2$, $C_1$-$C_{12}$alkylthio, halo$C_1$-$C_{12}$alkylthio, $C_2$-$C_{12}$alkenoxy, halo$C_2$-$C_{12}$alkenoxy, $C_2$-$C_{12}$alkynoxy, halo$C_2$-$C_{12}$alkynoxy, $C_1$-$C_{12}$alkylsulfonyl, halo$C_1$-$C_{12}$alkylsulfonyl, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkoxycarbonyl$C_1$-$C_{12}$alkyl, halo$C_1$-$C_{12}$alkoxycarbonyl$C_1$-$C_{12}$alkyl, $C_1$-$C_{12}$alkylthiocarbonyl$C_1$-$C_{12}$alkyl, halo$C_1$-$C_{12}$alkylthiocarbonyl$C_1$-$C_{12}$alkyl,
$C_1$-$C_{12}$alkylcarbonyloxy, halo$C_1$-$C_{12}$alkylcarbonyloxy, $C_1$-$C_{12}$alkoxycarbonyloxy, halo$C_1$-$C_{12}$alkoxycarbonyloxy,
$C_1$-$C_{12}$alkylaminocarbonyloxy, halo$C_1$-$C_{12}$alkylaminocarbonyloxy, $C_1$-$C_{12}$alkylsulfonyloxy, halo$C_1$-$C_{12}$alkylsulfonyloxy, $C_1$-$C_{12}$alkoxy$C_1$-$C_{12}$alkoxy, halo$C_1$-$C_{12}$alkoxy$C_1$-$C_{12}$alkoxy, $C_1$-$C_{12}$alkoxycarbonyl$C_1$-$C_{12}$alkoxy or halo$C_1$-$C_{12}$alkoxycarbonyl$C_1$-$C_{12}$alkoxy;
$R_7$, $R_8$, $R_9$, $R_{10}$, and $R_{11}$, may be the same or different, and are each selected independently from the group consisting of H, halo, OH, amino, cyano, $NO_2$, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$ cycloalkyl, $C_1$-$C_{12}$alkylamino, halo$C_1$-$C_{12}$alkylamino, di($C_1$-$C_{12}$alkyl)amino, halodi($C_1$-$C_{12}$alkyl)amino, $C_1$-$C_{12}$alkylaminocarbonyl, di($C_1$-$C_{12}$alkyl)aminocarbonyl, halodi($C_1$-$C_{12}$alkyl)aminocarbonyl, $CONH_2$, $C_1$-$C_{12}$alkylthio, halo$C_1$-$C_{12}$alkylthio, $C_2$-$C_{12}$alkenyl, $C_2$-$C_{12}$alkynyl, $C_2$-$C_{12}$alkenoxy, halo$C_2$-$C_{12}$alkenoxy, $C_2$-$C_{12}$alkynoxy, halo$C_2$-$C_{12}$alkynoxy, $C_1$-$C_{12}$alkylsulfonyl, halo$C_1$-$C_{12}$alkylsulfonyl, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkoxycarbonyl$C_1$-

$C_{12}$alkyl, haloC$_1$-C$_{12}$alkoxycarbonylC$_1$-C$_{12}$alkyl, C$_1$-C$_{12}$alkylthiocarbonylC$_1$-C$_{12}$alkyl, haloC$_1$-C$_{12}$alkylthiocarbonylC$_1$-C$_{12}$alkyl, C$_1$-C$_{12}$alkylcarbonyloxy, haloC$_1$-C$_{12}$alkylcarbonyloxy, C$_1$-C$_{12}$alkoxycarbonyloxy, haloC$_1$-C$_{12}$alkoxycarbonyloxy, C$_1$-C$_{12}$alkylaminocarbonyloxy, haloC$_1$-C$_{12}$alkylaminocarbonyloxy, C$_1$-C$_{12}$alkyl sulfonyloxy, haloC$_1$-C$_{12}$alkyl sulfonyloxy, C$_1$-C$_{12}$alkoxyC$_1$-C$_{12}$alkoxy, haloC$_1$-C$_{12}$alkoxyC$_1$-C$_{12}$alkoxy, C$_1$-C$_{12}$alkoxycarbonylC$_1$-C$_{12}$alkoxy, and haloC$_1$-C$_{12}$alkoxycarbonylC$_1$-C$_{12}$alkoxy;

W is H or C$_1$-C$_{12}$alkyl;

A is NR$_{12}$;

B is —CH$_2$— or —CH$_2$CH$_2$—; and

R$_{12}$ is H, OH, H(C)=O, C$_1$-C$_{12}$alkyl, haloC$_1$-C$_{12}$alkyl, C$_1$-C$_{12}$alkoxy, haloC$_1$-C$_{12}$alkoxy, C$_3$-C$_{12}$cycloalkyl, C$_1$-C$_{12}$alkylthio, C$_2$-C$_{12}$alkenylthio, C$_2$-C$_{12}$alkenyl, C$_2$-C$_{12}$alkynyl, haloC$_2$-C$_{12}$alkenyl, haloC$_2$-C$_{12}$alkynyl, C$_1$-C$_{12}$alkoxyC$_1$-C$_{12}$alkyl, haloC$_1$-C$_{12}$alkoxyC$_1$-C$_{12}$alkyl, C$_1$-C$_{12}$alkylthioC$_1$-C$_{12}$alkyl, haloC$_1$-C$_{12}$alkylthioC$_1$-C$_{12}$alkyl, C$_1$-C$_{12}$alkylsulfinyl, haloC$_1$-C$_{12}$alkylsulfinyl, C$_1$-C$_{12}$alkylsulfonyl, haloC$_1$-C$_{12}$alkylsulfonyl, C$_1$-C$_{12}$alkylaminosulfonyl, di(C$_1$-C$_{12}$alkyl)aminosulfonyl, C$_1$-C$_{12}$alkylsulfonylaminocarbonyl, C$_1$-C$_{12}$alkylcarbonylaminosulfonyl, C$_3$-C$_{12}$cycloalkyloxycarbonyl, C$_1$-C$_{12}$alkylcarbonyl, haloC$_1$-C$_{12}$alkylcarbonyl, C$_1$-C$_{12}$alkoxycarbonyl, haloC$_1$-C$_{12}$alkoxycarbonyl, C$_1$-C$_{12}$alkylcarbonylC$_1$-C$_{12}$alkyl, C$_1$-C$_{12}$alkoxycarbonylC$_1$-C$_{12}$alkyl, C$_1$-C$_{12}$alkylaminocarbonyl, di(C$_1$-C$_{12}$alkyl)aminocarbonyl, C$_2$-C$_{12}$alkenoxycarbonyl, C$_2$-C$_{12}$alkynoxycarbonyl, C$_1$-C$_{12}$alkoxyC$_1$-C$_{12}$alkoxycarbonyl, C$_1$-C$_{12}$alkylaminothio, di(C$_1$-C$_{12}$alkyl)aminothio, unsubstituted or further substituted (hetero)arylcarbonylC$_1$-C$_6$alkyl, (hetero)arylcarbonyl, (hetero)aryloxycarbonyl, or (hetero)arylC$_1$-C$_6$alkyloxycarbonyl by 1 to 5 following groups: halo, NO$_2$, cyano, C$_1$-C$_6$alkyl, haloC$_1$-C$_6$alkyl, C$_1$-C$_6$alkoxy, or haloC$_1$-C$_6$alkoxy;

or a salt thereof formed with an acid selected from the group consisting of hydrochloric acid, sulfuric acid, nitric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid, and citric acid.

9. The substituted pyrimidine compound according to claim 8, wherein

R$_1$ is C$_1$-C$_6$alkyl or C$_3$-C$_6$cycloalkyl;

R$_2$ is halo or cyano;

R$_3$ and R$_4$, may be the same or different, and are each selected independently from the group consisting of H, halo, C$_1$-C$_6$alkyl, C$_1$-C$_6$alkoxy, and C$_3$-C$_6$cycloalkyl; or R$_3$, R$_4$ and conjoint carbon can also form a C$_3$-C$_8$ cycle;

R$_{5a}$, R$_{5b}$, and R$_{5c}$, may be the same or different, selected independently from H or OH;

R$_6$ is H or OH;

R$_7$, R$_8$, R$_9$, R$_{10}$, and R$_{11}$, may be the same or different, and are each selected independently from the group consisting of H, halo, OH, amino, cyano, NO$_2$, C$_1$-C$_6$alkyl, haloC$_1$-C$_6$alkyl, C$_1$-C$_6$alkoxy, haloC$_1$-C$_6$alkoxy, C$_3$-C$_6$cycloalkyl, C$_1$-C$_6$alkylamino, haloC$_1$-C$_6$alkylamino, di(C$_1$-C$_6$alkyl)amino, halodi(C$_1$-C$_6$alkyl)amino, C$_1$-C$_6$alkylaminocarbonyl, di(C$_1$-C$_6$alkyl)aminocarbonyl, halodi(C$_1$-C$_6$alkyl)aminocarbonyl, CONH$_2$, C$_1$-C$_6$alkylthio, haloC$_1$-C$_6$alkylthio, C$_2$-C$_6$alkenyl, C$_2$-C$_6$alkynyl, C$_2$-C$_6$alkenoxy, haloC$_2$-C$_6$alkenoxy, C$_2$-C$_6$alkynoxy, haloC$_2$-C$_6$alkynoxy, C$_1$-C$_6$alkylsulfonyl, haloC$_1$-C$_6$alkylsulfonyl, C$_1$-C$_6$alkylcarbonyl, haloC$_1$-C$_6$alkylcarbonyl, C$_1$-C$_6$alkoxycarbonyl, haloC$_1$-C$_6$alkoxycarbonyl, C$_1$-C$_6$alkoxyC$_1$-C$_6$alkyl, haloC$_1$-C$_6$alkoxyC$_1$-C$_6$alkyl, C$_1$-C$_6$alkylthioC$_1$-C$_6$alkyl, haloC$_1$-C$_6$alkylthioC$_1$-C$_6$alkyl, C$_1$-C$_6$alkoxycarbonylC$_1$-C$_6$alkyl, haloC$_1$-C$_6$alkoxycarbonylC$_1$-C$_6$alkyl, C$_1$-C$_6$alkylthiocarbonylC$_1$-C$_6$alkyl, haloC$_1$-C$_6$alkylthiocarbonylC$_1$-C$_6$alkyl, C$_1$-C$_6$alkylcarbonyloxy, haloC$_1$-C$_6$alkylcarbonyloxy, C$_1$-C$_6$alkoxycarbonyloxy, haloC$_1$-C$_6$alkoxycarbonyloxy, C$_1$-C$_6$alkylaminocarbonyloxy, haloC$_1$-C$_6$alkylaminocarbonyloxy, C$_1$-C$_6$alkylsulfonyloxy, haloC$_1$-C$_6$alkylsulfonyloxy, C$_1$-C$_6$alkoxyC$_1$-C$_6$alkoxy, haloC$_1$-C$_6$alkoxyC$_1$-C$_6$alkoxy, C$_1$-C$_6$alkoxycarbonylC$_1$-C$_6$alkoxy, and haloC$_1$-C$_6$alkoxycarbonylC$_1$-C$_6$alkoxy;

W is H or C$_1$-C$_3$alkyl;

A is NR$_{12}$;

B is —CH$_2$— or —CH$_2$CH$_2$—; and

R$_{12}$ is H, OH, H(C)=O, C$_1$-C$_6$alkyl, C$_1$-C$_6$alkylsulfonyl or C$_1$-C$_6$alkylcarbonyl;

or wherein the salt is formed with hydrochloric acid, sulfuric acid, nitric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid, or citric acid.

10. The substituted pyrimidine compound according to claim 9, wherein

R$_1$ is C$_1$-C$_4$alkyl or C$_3$-C$_4$cycloalkyl;

R$_2$ is F, Cl, Br, or cyano;

R$_3$ and R$_4$, may be the same or different, and are each selected independently from the group consisting of H, halo, C$_1$-C$_4$alkyl, C$_1$-C$_4$alkoxy, and C$_3$-C$_6$cycloalkyl; or R$_3$, R$_4$ and conjoint carbon can also form a C$_3$-C$_8$ cycle;

R$_{5a}$, R$_{5b}$, and R$_{5c}$, may be the same or different, selected independently from H or OH;

R$_6$ is H or OH;

R$_7$, R$_8$, R$_9$, R$_{10}$, and R$_{11}$, may be the same or different, and are each selected independently from the group consisting of H, halo, OH, amino, cyano, NO$_2$, C$_1$-C$_4$alkyl, haloC$_1$-C$_4$alkyl, C$_1$-C$_4$alkoxy, haloC$_1$-C$_4$alkoxy, C$_3$-C$_4$cycloalkyl, C$_1$-C$_4$alkylamino, haloC$_1$-C$_4$alkylamino, di(C$_1$-C$_4$alkyl)amino, halodi(C$_1$-C$_4$alkyl)amino, C$_1$-C$_4$alkylaminocarbonyl, di(C$_1$-C$_4$alkyl)aminocarbonyl, halodi(C$_1$-C$_4$alkyl)aminocarbonyl, CONH$_2$, C$_1$-C$_4$alkylthio, haloC$_1$-C$_4$alkylthio, C$_2$-C$_4$alkenyl, C$_2$-C$_4$alkynyl, C$_2$-C$_4$alkenoxy, haloC$_2$-C$_4$alkenoxy, C$_2$-C$_4$alkynoxy, haloC$_2$-C$_4$alkynoxy, C$_1$-C$_4$alkylsulfonyl, haloC$_1$-C$_4$alkylsulfonyl, C$_1$-C$_4$alkylcarbonyl, haloC$_1$-C$_4$alkylcarbonyl, C$_1$-C$_4$alkoxycarbonyl, haloC$_1$-C$_4$alkoxycarbonyl, C$_1$-C$_4$alkoxyC$_1$-C$_4$alkyl, haloC$_1$-C$_4$alkoxyC$_1$-C$_4$alkyl, C$_1$-C$_4$alkylthioC$_1$-C$_4$alkyl, haloC$_1$-C$_4$alkylthioC$_1$-C$_4$alkyl, C$_1$-C$_4$alkoxycarbonylC$_1$-C$_4$alkyl, haloC$_1$-C$_4$alkoxycarbonylC$_1$-C$_4$alkyl, C$_1$-C$_4$alkylthiocarbonylC$_1$-C$_4$alkyl, haloC$_1$-C$_4$alkylthiocarbonylC$_1$-C$_4$alkyl, C$_1$-C$_4$alkylcarbonyloxy, haloC$_1$-C$_4$alkylcarbonyloxy, C$_1$-C$_4$alkoxycarbonyloxy, haloC$_1$-

C₄alkoxycarbonyloxy, C₁-C₄alkylaminocarbonyloxy, haloC₁-C₄alkylaminocarbonyloxy, C₁-C₄alkylsulfonyloxy, haloC₁-C₄alkylsulfonyloxy, C₁-C₄alkoxyC₁-C₄alkoxy, haloC₁-C₄alkoxyC₁-C₄alkoxy, C₁-C₄alkoxycarbonylC₁-C₄alkoxy, and haloC₁-C₄alkoxycarbonylC₁-C₄alkoxy;

W is H or CH₃;

A is NR₁₂;

B is —CH₂— or —CH₂CH₂—; and

R₁₂ is H, OH, H(C)=O, C₁-C₄alkyl, C₁-C₄alkylsulfonyl, or C₁-C₄alkylcarbonyl;

or wherein the salt is formed with hydrochloric acid, sulfuric acid, nitric acid, phosphoric acid, acetic acid, trifluoroacetic acid, oxalic acid, methylsulfonic acid, p-toluenesulfonic acid, benzoic acid, maleic acid, sorbic acid, malic acid, or citric acid.

11. The substituted pyrimidine compound according to claim 10, wherein

R₁ is CH₃, C₂H₅, n-C₃H₇, i-C₃H₇, n-C₄H₉, s-C₄H₉, i-C₄H₉, t-C₄H₉, cyclopropyl or cyclobutyl;

R₂ is F, Cl, Br, or cyano;

R₃ and R₄, may be the same or different, and are each selected independently from the group consisting of H, F, Cl, Br, I, CH₃, C₂H₅, n-C₃H₇, i-C₃H₇, n-C₄H₉, s-C₄H₉, i-C₄H₉, t-C₄H₉, OCH₃, OC₂H₅, OC₃H₇-n, OC₃H₇-i, OC₄H₉-n, OC₄H₉-s, OC₄H₉-i, and OC₄H₉-t;

R₅ₐ, R₅ᵦ, and R₅c, may be the same or different, selected independently from H or OH;

R₆ is H or OH;

R₇, R₈, R₉, R₁₀, and R₁₁, may be the same or different, and are each selected independently from the group consisting of H, F, Cl, Br, I, cyano, amino, NO₂, CH₃, C₂H₅, n-C₃H₇, i-C₃H₇, n-C₄H₉, s-C₄H₉, i-C₄H₉, t-C₄H₉, CF₃, CCl₃, CClF₂, CCl₂F, CHCl₂, CH₂F, CHF₂, OCH₃, OC₂H₅, OC₃H₇-n, OC₃H₇-i, OC₄H₉-n, OC₄H₉-s, OC₄H₉-i, OC₄H₉-t, OCF₃, OCH₂CF₃, COOCH₃, COOC₂H₅, CONH₂, CONHCH₃, CONHC₂H₅, CONH(CH₃)₂, methylsulfonyl, and trifluoromethylsulfonyl;

W is H or CH₃;

A is NR₁₂;

B is —CH₂— or —CH₂CH₂—; and

R₁₂ is H;

or wherein the salt is formed with hydrochloric acid, sulfuric acid, nitric acid, phosphoric acid, acetic acid, trifluoroacetic acid, oxalic acid, methylsulfonic acid, p-toluenesulfonic acid, maleic acid, or benzoic acid.

12. The substituted pyrimidine compound according to claim 11, wherein

R₁ is CH₃, C₂H₅, n-C₃H₇, i-C₃H₇, n-C₄H₉, s-C₄H₉, i-C₄H₉, t-C₄H₉, cyclopropyl or cyclobutyl;

R₂ is F, Cl, Br, or cyano;

R₃ and R₄, may be the same or different, and are each selected independently from the group consisting of H, F, Cl, Br, I, CH₃, C₂H₅, n-C₃H₇, i-C₃H₇, OCH₃, OC₂H₅, OC₃H₇-n, and OC₃H₇-i;

R₅ₐ, R₅ᵦ, and R₅c, are H;

R₆ is H;

R₇, R₈, R₉, R₁₀, and R₁₁, may be the same or different, and are each selected independently from the group consisting of H, F, Cl, Br, I, cyano, NO₂, CH₃, C₂H₅, n-C₃H₇, i-C₃H₇, n-C₄H₉, s-C₄H₉, i-C₄H₉, t-C₄H₉, OCH₃, OCF₃, CF₃, CCl₃, CClF₂, CCl₂F, CHCl₂, CH₂F, CHF₂, methylsulfonyl, and trifluoromethylsulfonyl;

W is H or CH₃;

A is NH;

B is —CH₂— or —CH₂CH₂—; and or wherein the salt is formed with hydrochloric acid, sulfuric acid, nitric acid, phosphoric acid, acetic acid, trifluoroacetic acid, oxalic acid, methylsulfonic acid, p-toluenesulfonic acid, maleic acid, or benzoic acid.

13. The substituted pyrimidine compound according to claim 12, wherein

R₁ is CH₃ or C₂H₅;

R₂ is Cl or cyano;

R₃ and R₄ are H;

R₅ₐ, R₅ᵦ, and R₅c, are H;

R₆ is H;

W is H or CH₃;

R₇, R₈, R₉, R₁₀, and R₁₁, may be the same or different, and are each selected independently from the group consisting of H, F, Cl, cyano, NO₂, CH₃, OCH₃, OCF₃, CF₃, and methylsulfonyl;

A is NH; and

B is —CH₂— or —CH₂CH₂—;

or wherein the salt is formed with hydrochloric acid, sulfuric acid, nitric acid, phosphoric acid, acetic acid, or trifluoroacetic acid.

14. A substituted pyrimidine compound represented by formula III:

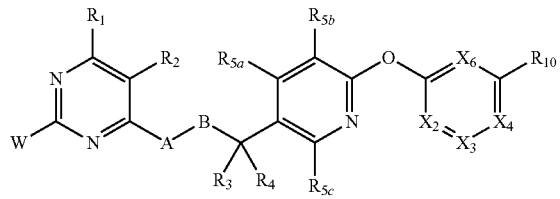

wherein

R₁ is C₁-C₁₂alkyl, C₃-C₁₂cycloalkyl, C₂-C₁₂alkenyl, haloC₂-C₁₂alkenyl, C₂-C₁₂alkynyl, haloC₂-C₁₂alkynyl, C₁-C₁₂alkoxyC₁-C₁₂alkyl, or haloC₁-C₁₂alkoxyC₁-C₁₂alkyl;

R₂ is halo, cyano, C₁-C₁₂alkyl, or haloC₁-C₁₂alkoxy;

W is H, halo, C₁-C₁₂alkyl, C₁-C₁₂alkylthio, or C₁-C₁₂alkylsulfonyl;

R₃ and R₄, may be the same or different, and are each selected independently from the group consisting of H, C₁-C₁₂alkyl, C₃-C₁₂cycloalkyl, C₂-C₁₂alkenyl, C₂-C₁₂alkynyl, haloC₂-C₁₂alkenyl, haloC₂-C₁₂alkynyl, C₁-C₁₂alkoxyC₁-C₁₂alkyl, unsubstituted or further substituted arylC₁-C₆alkyl or heteroarylC₁-C₆alkyl by 1 to 5 following groups: halo, C₁-C₆alkyl, haloC₁-C₆alkyl, C₁-C₆alkoxy, and haloC₁-C₆alkoxy; or R₃, R₄ and conjoint carbon can also form a C₃-C₅₈ cycle;

R₅ₐ, R₅ᵦ, and R₅c, may be the same or different, and are each selected independently from the group consisting of H, C₃-C₁₂cycloalkyl, C₁-C₁₂alkylthio, haloC₁-C₁₂alkylthio, C₃-C₁₂alkenoxy, haloC₃-C₁₂alkenoxy, C₃-C₁₂alkynoxy, haloC₃-C₁₂alkynoxy, C₁-C₁₂alkylsulfinyl, haloC₁-C₁₂alkylsulfinyl, C₁-C₁₂alkylsulfonyl, haloC₁-C₁₂alkylsulfonyl, C₁-C₁₂alkylcarbonyl, haloC₁-C₁₂alkylcarbonyl, C₁-C₁₂alkylcarbonyloxy, C₁-C₁₂alkylcarbonylamino, C₁-C₁₂alkylsulfonyloxy, C₁-C₁₂alkoxycarbonyl, C₁-C₁₂alkoxycarbonylC₁-C₁₂alkyl, C₁-C₁₂alkoxycarbonylamino, C₁-C₁₂alkoxyC₁-C₁₂alkoxy, and C₁-C₁₂alkoxycarbonylC₁-C₁₂alkoxy;

$X_2$ is N or $CR_7$;

$X_3$ is N or $CR_8$;

$X_4$ is N or $CR_9$;

$X_6$ is N or $CR_{11}$; however, $X_2$, $X_3$, $X_4$, and $X_6$ are not simultaneously N;

$R_7$, $R_8$, $R_9$, and $R_{11}$, may be the same or different, and are each selected independently from the group consisting of H, halo, OH, cyano, HO(C=O), amino, $NO_2$, $C_1$-$C_{12}$alkyl, halo$C_1$-$C_{12}$alkyl, $C_1$-$C_{12}$alkoxy, halo$C_1$-$C_{12}$alkoxy, $C_1$-$C_{12}$alkoxycarbonyl, $CONH_2$, $C_1$-$C_{12}$alkylaminocarbonyl, di($C_1$-$C_{12}$alkyl)aminocarbonyl, $C_1$-$C_{12}$alkylsulfonyl, and halo$C_1$-$C_{12}$alkylsulfonyl;

$R_{10}$ is H, halo, OH, cyano, HO(C=O), amino, $NO_2$, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_2$-$C_{12}$alkenyl, $C_2$-$C_{12}$alkynyl, $C_2$-$C_{12}$alkenoxy, halo$C_2$-$C_{12}$alkenoxy, $C_2$-$C_{12}$alkynoxy, halo$C_2$-$C_{12}$alkynoxy, $C_1$-$C_{12}$alkylthio, halo$C_1$-$C_{12}$alkylthio, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, $C_1$-$C_{12}$alkylamino, halo$C_1$-$C_{12}$alkylamino, di($C_1$-$C_{12}$alkyl)amino, $C_1$-$C_{12}$alkoxycarbonyl, $CONH_2$, $C_1$-$C_{12}$alkylaminocarbonyl, di($C_1$-$C_{12}$alkyl)aminocarbonyl, cyano$C_1$-$C_{12}$alkoxy, $C_1$-$C_{12}$alkoxycarbonyl$C_1$-$C_{12}$alkyl, $C_1$-$C_{12}$alkylaminocarbonyl$C_1$-$C_{12}$alkyl, or di($C_1$-$C_{12}$alkyl)aminocarbonyl$C_1$-$C_{12}$alkyl;

A is $NR_{12}$;

B is —$CH_2$— or —$CH_2CH_2$—; and $R_{12}$ is H, OH, H(C)=O, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_1$-$C_{12}$alkylthio, $C_2$-$C_{12}$alkenylthio, $C_2$-$C_{12}$alkenyl, $C_2$-$C_{12}$alkynyl, halo$C_2$-$C_{12}$alkenyl, halo$C_2$-$C_{12}$alkynyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, di($C_1$-$C_{12}$alkyl)aminosulfonyl, $C_1$-$C_{12}$alkylsulfonylaminocarbonyl, $C_1$-$C_{12}$alkylcarbonylaminosulfonyl, $C_3$-$C_{12}$cycloalkyloxycarbonyl, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, $C_1$-$C_{12}$alkylcarbonyl$C_1$-$C_{12}$alkyl, $C_1$-$C_{12}$alkoxycarbonyl$C_1$-$C_{12}$alkyl, $C_1$-$C_{12}$alkylaminocarbonyl, di($C_1$-$C_{12}$alkyl)aminocarbonyl, $C_2$-$C_{12}$alkenoxycarbonyl, $C_2$-$C_{12}$alkynoxycarbonyl, $C_1$-$C_{12}$alkoxy$C_1$-$C_{12}$alkoxycarbonyl, $C_1$-$C_{12}$alkylaminothio, di($C_1$-$C_{12}$alkyl)aminothio, unsubstituted or further substituted (hetero)arylcarbonyl$C_1$-$C_6$alkyl, (hetero)arylcarbonyl, (hetero)aryloxycarbonyl, or (hetero)aryl$C_1$-$C_6$alkyloxycarbonyl by 1 to 5 following groups: halo, $NO_2$, cyano, $C_1$-$C_6$alkyl, halo$C_1$-$C_6$alkyl, $C_1$-$C_6$alkoxy, or halo$C_1$-$C_6$alkoxy;

or a salt thereof formed with an acid selected from the group consisting of hydrochloric acid, sulfuric acid, nitric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid, and citric acid.

15. The substituted pyrimidine compound according to claim 14, wherein $R_1$ is $C_1$-$C_8$alkyl, $C_3$-$C_8$cycloalkyl, $C_2$-$C_8$alkenyl, halo$C_2$-$C_8$alkenyl, $C_2$-$C_8$alkynyl, halo$C_2$-$C_8$alkynyl, $C_1$-$C_8$alkoxy$C_1$-$C_8$alkyl, or halo$C_1$-$C_8$alkoxy$C_1$-$C_8$alkyl;

$R_2$ is halo, cyano, $C_1$-$C_8$alkyl, or halo$C_1$-$C_8$alkoxy;

W is H, halo, $C_1$-$C_8$alkyl, $C_1$-$C_8$alkylthio, or $C_1$-$C_8$alkylsulfonyl;

$R_3$ and $R_4$, may be the same or different, and are each selected independently from the group consisting of H, $C_1$-$C_8$alkyl, $C_3$-$C_8$cycloalkyl, $C_2$-$C_8$alkenyl, $C_2$-$C_8$alkynyl, halo$C_2$-$C_8$alkenyl, halo$C_2$-$C_8$alkynyl, $C_1$-$C_8$alkoxy$C_1$-$C_8$alkyl, unsubstituted or further substituted aryl$C_1$-$C_4$alkyl or heteroaryl$C_1$-$C_4$alkyl by 1 to 3 following groups: halo, $C_1$-$C_4$alkyl, halo$C_1$-$C_4$alkyl, $C_1$-$C_4$alkoxy, and halo$C_1$-$C_4$alkoxy; or $R_3$, $R_4$ and conjoint carbon can also form a $C_3$-$C_8$ cycle;

$R_{5a}$, $R_{5b}$, and $R_{5c}$, may be the same or different, and are each selected independently from the group consisting of H, $C_3$-$C_6$cycloalkyl, $C_1$-$C_8$alkylthio, halo$C_1$-$C_8$alkylthio $C_3$-$C_8$alkenoxy, halo$C_3$-$C_8$alkenoxy, $C_3$-$C_8$alkynoxy, halo$C_3$-$C_8$alkynoxy, $C_1$-$C_8$alkylsulfinyl, halo$C_1$-$C_8$alkylsulfinyl, $C_1$-$C_8$alkylsulfonyl, halo$C_1$-$C_8$alkylsulfonyl, $C_1$-$C_8$alkylcarbonyl, halo$C_1$-$C_8$alkylcarbonyl, $C_1$-$C_8$alkylcarbonyloxy, $C_1$-$C_8$alkylcarbonylamino, $C_1$-$C_8$alkylsulfonyloxy, $C_1$-$C_8$alkoxycarbonyl, $C_1$-$C_8$alkoxycarbonyl$C_1$-$C_8$alkyl, $C_1$-$C_8$alkoxycarbonylamino, $C_1$-$C_8$alkoxy$C_1$-$C_8$alkoxy, and $C_1$-$C_8$alkoxycarbonyl$C_1$-$C_8$alkoxy;

$X_2$ is N or $CR_7$;

$X_3$ is N or $CR_8$;

$X_4$ is N or $CR_9$;

$X_6$ is N or $CR_{11}$; however, $X_2$, $X_3$, $X_4$, and $X_6$ are not simultaneously N;

$R_7$, $R_8$, $R_9$, and $R_{11}$, may be the same or different, and are each selected independently from the group consisting of H, halo, OH, cyano, HO(C=O), amino, $NO_2$, $C_1$-$C_8$alkyl, halo$C_1$-$C_8$alkyl, $C_1$-$C_8$alkoxy, halo$C_1$-$C_8$alkoxy, $C_1$-$C_8$alkoxycarbonyl, $CONH_2$, $C_1$-$C_8$alkylaminocarbonyl, di($C_1$-$C_8$alkyl)aminocarbonyl, $C_1$-$C_8$alkylsulfonyl, and halo$C_1$-$C_8$alkylsulfonyl;

$R_{10}$ is H, halo, OH, cyano, HO(C=O), amino, $NO_2$, $C_1$-$C_8$alkyl, halo$C_1$-$C_8$alkyl, $C_1$-$C_8$alkoxy, halo$C_1$-$C_8$alkoxy, $C_3$-$C_8$cycloalkyl, $C_2$-$C_8$alkenyl, $C_2$-$C_8$alkynyl, $C_2$-$C_8$alkenoxy, halo$C_2$-$C_8$alkenoxy, $C_2$-$C_8$alkynoxy, halo$C_2$-$C_8$alkynoxy, $C_1$-$C_8$alkylthio, halo$C_1$-$C_8$alkylthio, $C_1$-$C_8$alkoxy$C_1$-$C_8$alkyl, halo$C_1$-$C_8$alkoxy$C_1$-$C_8$alkyl, $C_1$-$C_8$alkylthio$C_1$-$C_8$alkyl, halo$C_1$-$C_8$alkylthio$C_1$-$C_8$alkyl, $C_1$-$C_8$alkylsulfinyl, halo$C_1$-$C_8$alkylsulfinyl, $C_1$-$C_8$alkylsulfonyl, halo$C_1$-$C_8$alkylsulfonyl, $C_1$-$C_8$alkylaminosulfonyl, $C_1$-$C_8$alkylamino, halo$C_1$-$C_8$alkylamino, di($C_1$-$C_8$alkyl)amino, $C_1$-$C_8$alkoxycarbonyl, $CONH_2$, $C_1$-$C_8$alkylaminocarbonyl, di($C_1$-$C_8$alkyl)aminocarbonyl, cyano$C_1$-$C_8$alkoxy, $C_1$-$C_8$alkoxycarbonyl$C_1$-$C_8$alkyl, $C_1$-$C_8$alkylaminocarbonyl$C_1$-$C_8$alkyl, and di($C_1$-$C_8$alkyl)aminocarbonyl$C_1$-$C_8$alkyl;

A is $NR_{12}$;

B is —$CH_2$— or —$CH_2CH_2$—; and $R_{12}$ is H, OH, H(C)=O, $C_1$-$C_8$alkyl, halo$C_1$-$C_8$alkyl, $C_1$-$C_8$alkoxy, halo$C_1$-$C_8$alkoxy, $C_3$-$C_8$cycloalkyl, $C_1$-$C_8$alkylthio, $C_2$-$C_8$alkenylthio, $C_2$-$C_8$alkenyl, $C_2$-$C_8$alkynyl, halo$C_2$-$C_8$alkenyl, halo$C_2$-$C_8$alkynyl, $C_1$-$C_8$alkoxy$C_1$-$C_8$alkyl, halo$C_1$-$C_8$alkoxy$C_1$-$C_8$alkyl, $C_1$-$C_8$alkylthio$C_1$-$C_8$alkyl, halo$C_1$-$C_8$alkylthio$C_1$-$C_8$alkyl, $C_1$-$C_8$alkylsulfinyl, halo$C_1$-$C_8$alkylsulfinyl, $C_1$-$C_8$alkylsulfonyl, halo$C_1$-$C_8$alkylsulfonyl, $C_1$-$C_8$alkylaminosulfonyl, di($C_1$-$C_8$alkyl)aminosulfonyl, $C_1$-$C_8$alkylsulfonylaminocarbonyl, $C_1$-$C_8$alkylcarbonylaminosulfonyl, $C_3$-$C_8$cycloalkyloxycarbonyl, $C_1$-$C_8$alkylcarbonyl, halo$C_1$-$C_8$alkylcarbonyl, $C_1$-$C_8$alkoxycarbonyl, halo$C_1$-$C_8$alkoxycarbonyl, $C_1$-$C_8$alkylcarbonyl$C_1$-$C_8$alkyl, $C_1$-$C_8$alkoxycarbonyl$C_1$-$C_8$alkyl, $C_1$-$C_8$alkylaminocarbonyl, di($C_1$-$C_8$alkyl)aminocarbonyl, $C_2$-$C_8$alkenoxycarbonyl, $C_2$-$C_8$alkynoxycarbonyl, $C_1$-$C_8$alkoxy$C_1$-$C_8$alkoxycarbonyl, $C_1$-$C_8$alkylaminothio, di($C_1$-$C_8$alkyl)aminothio, unsubstituted or further substituted (hetero)arylcarbonyl$C_1$-$C_6$alkyl, (hetero)arylcarbonyl, (hetero)aryloxycarbonyl, or (hetero)aryl$C_1$-$C_6$alkyloxycarbonyl by 1 to 3 following groups: halo, $NO_2$, cyano, $C_1$-$C_4$alkyl, halo$C_1$-$C_4$alkyl, $C_1$-$C_4$alkoxy, or halo$C_1$-$C_4$alkoxy;

or a salt thereof formed with an acid selected from the group consisting of hydrochloric acid, sulfuric acid, nitric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid, and citric acid.

16. The substituted pyrimidine compound according to claim 15, wherein $R_1$ is $C_1$-$C_4$alkyl, $C_3$-$C_6$cycloalkyl, $C_2$-$C_4$alkenyl, halo$C_2$-$C_4$alkenyl, $C_2$-$C_4$alkynyl, halo$C_2$-$C_4$alkynyl, $C_1$-$C_4$alkoxy$C_1$-$C_4$alkyl, or halo$C_1$-$C_4$alkoxy$C_1$-$C_4$alkyl;

$R_2$ is halo or cyano;

W is H or $CH_3$;

$R_3$ and $R_4$ are H, $CH_3$, or $C_2H_5$;

$R_{5a}$, $R_{5b}$, and $R_{5c}$, may be the same or different, and are each selected independently from the group consisting of H, $C_3$-$C_6$cycloalkyl, $C_1$-$C_4$alkylthio, halo$C_1$-$C_4$alkylthio, $C_1$-$C_4$alkylsulfinyl, $C_1$-$C_4$alkylsulfonyl, $C_1$-$C_4$alkylcarbonyl, and $C_1$-$C_4$alkoxy$C_1$-$C_4$alkoxy;

$X_2$ is N or $CR_7$;

$X_3$ is N or $CR_8$;

$X_4$ is N or $CR_9$;

$X_6$ is N or $CR_{11}$; however, $X_2$, $X_3$, $X_4$, and $X_6$ are not simultaneously N;

$R_7$, $R_8$, $R_9$, and $R_{11}$, may be the same or different, and are each selected independently from the group consisting of H, halo, OH, cyano, HO(C=O), amino, $NO_2$, $C_1$-$C_4$alkyl, halo$C_1$-$C_4$alkyl, $C_1$-$C_4$alkoxy, halo$C_1$-$C_4$alkoxy, $C_1$-$C_4$alkoxycarbonyl, $CONH_2$, $C_1$-$C_4$alkylaminocarbonyl, di($C_1$-$C_4$alkyl)aminocarbonyl, $C_1$-$C_4$alkylsulfonyl, and halo$C_1$-$C_4$alkylsulfonyl;

$R_{10}$ is H, halo, OH, cyano, HO(C=O), amino, $NO_2$, $C_1$-$C_4$alkyl, halo$C_1$-$C_4$alkyl, $C_1$-$C_4$alkoxy, halo$C_1$-$C_4$alkoxy, $C_3$-$C_4$cycloalkyl, $C_2$-$C_4$alkenyl, $C_2$-$C_4$alkynyl, $C_2$-$C_4$alkenoxy, halo$C_2$-$C_4$alkenoxy, $C_2$-$C_4$alkynoxy, halo$C_2$-$C_4$alkynoxy, $C_1$-$C_4$alkylthio, halo$C_1$-$C_4$alkylthio, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkylsulfinyl, halo$C_1$-$C_4$alkylsulfinyl, $C_1$-$C_4$alkylsulfonyl, halo$C_1$-$C_4$alkylsulfonyl, $C_1$-$C_4$alkylaminosulfonyl, $C_1$-$C_4$alkylamino, halo$C_1$-$C_4$alkylamino, di($C_1$-$C_4$alkyl)amino, $C_1$-$C_4$alkoxycarbonyl, $CONH_2$, $C_1$-$C_4$alkylaminocarbonyl, di($C_1$-$C_4$alkyl)aminocarbonyl, cyano$C_1$-$C_{12}$alkoxy, $C_1$-$C_4$alkoxycarbonyl$C_1$-$C_4$alkyl, $C_1$-$C_4$alkylaminocarbonyl$C_1$-$C_4$alkyl, or di($C_1$-$C_4$alkyl)aminocarbonyl$C_1$-$C_4$alkyl;

A is NH; and

B is —$CH_2$— or —$CH_2CH_2$—;

or wherein the salt is formed with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid, or citric acid.

17. The substituted pyrimidine compound according to claim 16, wherein the substituted pyrimidine compound is represented by formula III-A, III-B, III-C, III-D, III-E, III-F, III-G, III-H, III-I, or III-J:

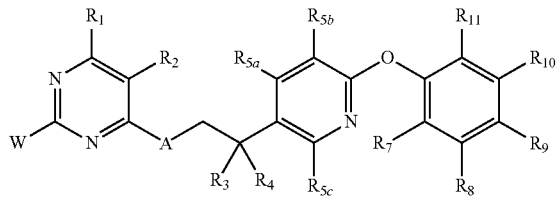

III-A

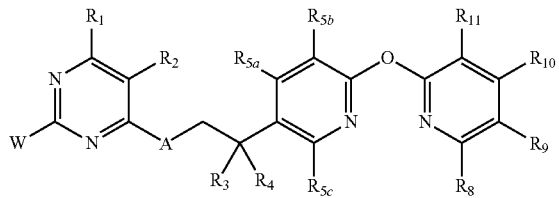

III-B

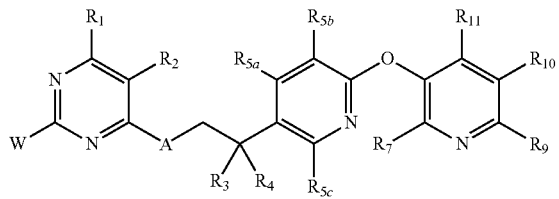

III-C

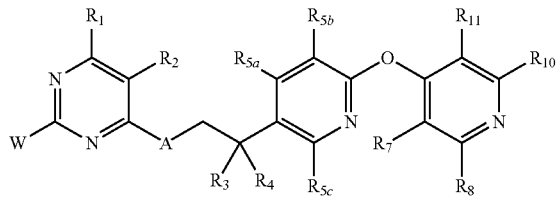

III-D

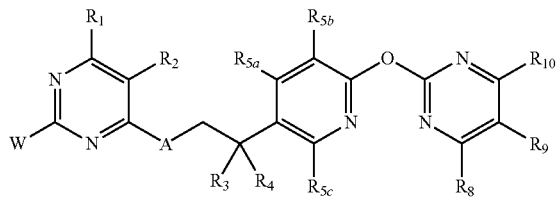

III-E

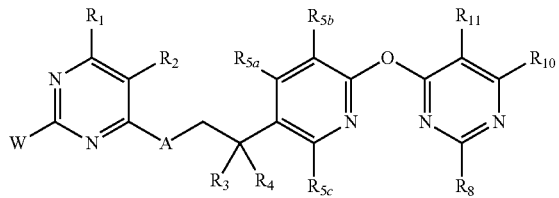

III-F

-continued

III-G

III-H

III-I

III-J wherein
$R_1$ is $C_1$-$C_4$alkyl, $C_3$-$C_6$cycloalkyl, $C_2$-$C_4$alkenyl, $C_2$-$C_4$alkynyl, $C_1$-$C_4$alkoxy$C_1$-$C_4$alkyl, or halo$C_1$-$C_4$alkoxy$C_1$-$C_4$alkyl;
$R_2$ is halo or cyano;
W is H or $CH_3$;
$R_3$ and $R_4$ is H, $CH_3$, or $C_2H_5$;
$R_{5a}$, $R_{5b}$, and $R_{5c}$, may be the same or different, and are each selected independently from the group consisting of H and $C_1$-$C_4$alkylcarbonyl;
$R_7$, $R_8$, $R_9$, and $R_{11}$, may be the same or different, and are each selected independently from the group consisting of H, F, Cl, Br, I, cyano, HO(C═O), $NO_2$, $C_1$-$C_4$alkyl, halo$C_1$-$C_4$alkyl, $C_1$-$C_4$alkoxy, halo$C_1$-$C_4$alkoxy, $C_1$-$C_4$alkoxycarbonyl, $C_1$-$C_4$alkylaminocarbonyl, di($C_1$-$C_4$alkyl)aminocarbonyl, $C_1$-$C_4$alkylsulfonyl, and halo$C_1$-$C_4$alkylsulfonyl;
$R_{10}$ is H, F, Cl, Br, I, cyano, $NO_2$, $C_1$-$C_4$alkyl, halo$C_1$-$C_4$alkyl, $C_1$-$C_4$alkoxy, halo$C_1$-$C_4$alkoxy, $C_1$-$C_4$alkylsulfonyl, or halo$C_1$-$C_4$alkylsulfonyl; and
A is NH;
or wherein the salt of formula III-A, III-B, III-C, III-D, III-E, III-F, III-G, III-H, III-I, or III-J is formed with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid, or citric acid.

18. The substituted pyrimidine compound according to claim 17, wherein
the substituted pyrimidine compound is represented by formula III-A and wherein
$R_1$ is $CH_3$, or $C_2H_5$;
$R_2$ is halo or cyano;
W is H or $CH_3$;
$R_3$ and $R_4$ are H;
$R_{5a}$ and $R_{5c}$ are H;
$R_{5b}$ is H;
$R_7$, $R_8$, $R_9$, and $R_{11}$, may be the same or different, and are each selected independently from the group consisting of H, F, Cl, Br, cyano, $NO_2$, $C_1$-$C_4$alkyl, halo$C_1$-$C_4$alkyl, $C_1$-$C_4$alkoxy, halo$C_1$-$C_4$alkoxy, $C_1$-$C_4$alkoxycarbonyl, $C_1$-$C_4$alkylaminocarbonyl, di($C_1$-$C_4$alkyl)aminocarbonyl, $C_1$-$C_4$alkylsulfonyl, and halo$C_1$-$C_4$alkylsulfonyl;
$R_{10}$ is H, F, Cl, Br, I, cyano, $NO_2$, methylsulfonyl, $C_1$-$C_4$alkyl, halo$C_1$-$C_4$alkyl, $C_1$-$C_4$alkoxy, or halo$C_1$-$C_4$alkoxy; and
A is NH;
or wherein the salt of formula III-A is formed with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid, or citric acid.

19. The substituted pyrimidine compound according to claim 18, wherein $R_1$ is Cl, $CH_3$ or $C_2H_5$;
$R_2$ is cyano;
W is H or $CH_3$;
$R_3$ and $R_4$ are H;
$R_{5a}$ and $R_{5c}$ are H;
$R_{5b}$ is H;
$R_7$, $R_8$, $R_9$, and $R_{11}$, may be the same or different, and are each selected independently from the group consisting of H, F, Cl, $CH_3$, cyano, $NO_2$, $CF_3$, $CClF_2$, $CCl_3$, $OCH_3$, $OCF_3$, $OCH_2CF_3$, methylsulfonyl, and trifluorosulfonyl;
$R_{10}$ is H, F, Cl, $CH_3$, cyano, $NO_2$, methylsulfonyl, $CF_3$, $CClF_2$, $OCH_3$, $OCF_3$, or $OCH_2CF_3$; and
A is NH;
or wherein the salt of formula III-A is formed with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid, or citric acid.

20. A fungicidal, insecticidal, or acaricidal composition comprising one or more compounds according to claim 1 as an active ingredient, wherein the weight percentage of the active ingredient in the composition is 0.1-99%.

21. A fungicidal, insecticidal, or acaricidal composition comprising one or more compounds according to claim 2 as an active ingredient, wherein the weight percentage of the active ingredient in the composition is 0.1-99%.

22. A method to control fungus, insects, and/or mites which comprises contacting an effective dose of the composition of claim 20 with the fungus, insects, and/or mites, or its growth medium.

23. A method to control fungus, insects, and/or mites which comprises contacting an effective dose of the composition of claim 21 with the fungus, insects, and/or mites, or its growth medium.

24. A fungicidal, insecticidal, or acaricidal composition comprising one or more compounds according to claim 8 as an active ingredient, wherein the weight percentage of the active ingredient in the composition is 0.1-99%.

25. A method to control fungus, insects, and/or mites which comprises contacting an effective dose of the composition of claim 24 with the fungus, insects, and/or mites, or its growth medium.

26. A fungicidal, insecticidal, or acaricidal composition comprising one or more compounds according to claim 14 as an active ingredient, wherein the weight percentage of the active ingredient in the composition is 0.1-99%.

27. A method to control fungus, insects, and/or mites which comprises contacting an effective dose of the composition of claim 26 with the fungus, insects, and/or mites, or its growth medium.

* * * * *